United States Patent
Huber et al.

(10) Patent No.: US 11,965,163 B2
(45) Date of Patent: Apr. 23, 2024

(54) HNF4A SARNA COMPOSITIONS AND METHODS OF USE

(71) Applicant: MiNA THERAPEUTICS LIMITED, London (GB)

(72) Inventors: Hans E. Huber, Lansdale, PA (US); David Blakey, London (GB); Jon Voutila, London (GB); Monika Krampert, Bamberg (DE); Markus Hossbach, Kulmbach (DE)

(73) Assignee: MiNA Therapeutics Limited, London (GB)

( * ) Notice: Subject to any disclaimer, the term of this patent is extended or adjusted under 35 U.S.C. 154(b) by 33 days.

(21) Appl. No.: 17/487,664

(22) Filed: Sep. 28, 2021

(65) Prior Publication Data

US 2022/0090074 A1 Mar. 24, 2022
US 2024/0035026 A9 Feb. 1, 2024

Related U.S. Application Data

(62) Division of application No. 16/645,012, filed as application No. PCT/EP2018/074191 on Sep. 7, 2018, now Pat. No. 11,162,099.

(60) Provisional application No. 62/555,937, filed on Sep. 8, 2017, provisional application No. 62/555,951, filed on Sep. 8, 2017.

(30) Foreign Application Priority Data

Sep. 22, 2017 (WO) ................ PCT/EP2017/074130

(51) Int. Cl.
C07H 21/04 (2006.01)
A61P 3/06 (2006.01)
C12N 15/113 (2010.01)
A61K 31/496 (2006.01)

(52) U.S. Cl.
CPC ............ C12N 15/113 (2013.01); A61P 3/06 (2018.01); A61K 31/496 (2013.01); *C12N 2310/11* (2013.01); *C12N 2310/14* (2013.01); *C12N 2310/315* (2013.01); *C12N 2310/317* (2013.01); *C12N 2310/321* (2013.01); *C12N 2310/322* (2013.01); *C12N 2310/3515* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 7,452,987 B2 | 11/2008 | Giese et al. | |
| 7,820,809 B2 | 10/2010 | Khvorova et al. | |
| 9,745,579 B2 | 8/2017 | Saetrom | |
| 9,944,930 B2 | 4/2018 | Saetrom | |
| 10,758,624 B2 | 9/2020 | Kortylewski et al. | |
| 2005/0137155 A1* | 6/2005 | McSwiggen ........ H01L 29/7371 257/E29.189 |

FOREIGN PATENT DOCUMENTS

| | | |
|---|---|---|
| WO | 2012/175958 A1 | 12/2012 |
| WO | 2015/162422 A1 | 10/2015 |
| WO | 2016170349 A1 | 10/2016 |
| WO | 2016205410 A2 | 12/2016 |

OTHER PUBLICATIONS

International Search Report issued Nov. 29, 2018 in corresponding international application No. PCT/EP2018/074191 entitled, "HNF4A SARNA Compositions and Methods of Use".
Kamiyama et al. ("Role of human hepatocyte nuclear factor 4a in the expression of drug-metabolizing enzymes and transporters in human hepatocytes assessed by use of small interfering RNA." Drug metabolism and pharmacokinetics 22.4 (2007): 287-298).
Rae, James M., et al. ("Rifampin is a selective, pleiotropic inducer of drug metabolism genes in human hepatocytes: studies with cDNA and oligonucleotide expression arrays." Journal of Pharmacology and Experimental Therapeutics 299.3 (2001): 849-857).
Communication pursuant to Article 94(3) EPC issued Feb. 11, 2021 in corresponding Europe application No. 18 765 123.7 entitled HNF4A SARNA Compositions and Methods of Use.
European Extended Search Report issued in EP Application No. 22204866.2 on Apr. 25, 2023; 6 pages.
PCT International Search Report and Written Opinion issued in PCT Application No. PCT/EP2018/074192 on Nov. 29, 2018; 12 pages.
PCT International Search Report and Written Opinion issued in PCT/EP2017/074130 on Feb. 12, 2018; 15 pages.
Place et al., Current Pharmaceutical Biotechnology; 11, 5, pp. 518-526 (2010).
Xia et al., Cancer Gene Therapy, 23; pp. 333-340 (2016).

* cited by examiner

*Primary Examiner* — Kimberly Chong
(74) *Attorney, Agent, or Firm* — McNeill Baur PLLC

(57) ABSTRACT

The invention relates to saRNA targeting an HNF4a transcript and therapeutic compositions comprising said saRNA. Methods of using the therapeutic compositions are also provided.

12 Claims, 35 Drawing Sheets

Specification includes a Sequence Listing.

SEQUENCE LISTING

<160> NUMBER OF SEQ ID NOS: 144

<210> SEQ ID NO 1
<211> LENGTH: 4001
<212> TYPE: DNA
<213> ORGANISM: Homo sapiens

<400> SEQUENCE: 1

```
tctttctggt tccagagctg gaggtggtct tgtctttggg actcccagtt caggggcttg      60
gcctctgcct caggagcaca cagttcctgg gcttggaaaa agtgatgggg gcggggagca     120
gcccagggca gggcagtggt cctcgtgggg ccacacaaca ctccacctag tgcagcagca     180
gcttgtttgc tatctctggt gtgtttttgc cttgcgctcc tggcgtggtc ctcagacagg     240
cctaaaagcc gtccagccag caggcctggg ggaatgaagc ctgttttgta gaagatacag     300
aagccaggat aggggaggtg acatgcccaa ggtcacacgt gactggacgg caggggcagg     360
tgagcacctg ctgagctgac aacaagcagt gcccagcagc tgcctcctca ccctagctga     420
gctgaccaca agattccaga cctcagctgg agctgcagcc tcatactggc tgagtggctc     480
caagacacag aaggaagcag ggtggcaggc tgacctcagc cagctgcctg cccctctcc      540 tctgaggctg gcctgggacc gatgggctc ttccctccag gaggggttc cgggcctcct       600 cttttcccct acctccctgt ggagaactgt ccacccctcc agatatgctc cagtgatgtc     660 ggagggatg cctcaatctg gcgagacgca gcggcaacaa aatctgctca gagacaaacg      720
gacatgttgc tgatatgaat ctcacttggt gagtggcaac aacagagtcc tgcatttggg     780
tctgtgcagt cgtgcacacc agagaccgct gaccccgcc cgcagcacag ggaactgcat      840
atatacacag caggtacaaa tatgggcaca cgacaaaacg cccatacagg ataaagatgc     900
aggaagaaca gggcactcca acaggtccgc atgcacaaac gcatgtgctc tatgacccgc     960
```

-continued

| | |
|---|---|
| acacacagca cacatgtaca aacatccaca gacacaagta cacacacata cacacttaca | 1020 |
| tacataagca agatcaacac gggcaactcc taagacacaa acacagaccc actcaatgaa | 1080 |
| tacaaaggaa aatagaccca gaactcacac acagagacaa atgaacacac atatgcaaat | 1140 |
| gggttcctga aggcatcacc ccacccatac aacctacatg gaaactcact atcacacacg | 1200 |
| aacgcacaca caacacacac agtgctgagt tggcttcgta gttagcaaaa cttccctgag | 1260 |
| agctccattt tccctaagtg ccaatttcat ttccctagga aagtcccaaa gacaccgaga | 1320 |
| aatgcggtta tgtctccaac caccatctcc agggatacaa catcccttgc cgtctctctg | 1380 |
| aacctaggcc caaggggttc acgaaggggc cgtgctgggc tgaatcgctg agctgggca | 1440 |
| ccaaggggga gctcaccatc acgtcactgt gccaagcgcc aagcagagcc actgtgaggc | 1500 |
| agtgaggact ggaagggcct gggaggaata gccgggatcg acttttgctg gaaattggcc | 1560 |
| cttgcaggcc tcccttcacc cagaatgcct gtgatcactg tgcctgggca catgggcttc | 1620 |
| acttggcaac acctgtgctg gcctgtagga ccaacctacc attttgtatc attctcctcc | 1680 |
| cacccccaaag ttgagtgcca aagatctgct cctggaccca ggcacacctg cccccactgg | 1740 |
| cacacctggg cacatctgcc cccacctacc attgcccatc gtcaacacct gcacattctc | 1800 |
| aaattccagg gtggtgtagg ctgggtccag tgcagcactg tagtcggcca tgtccatgtc | 1860 |
| gacgagggtt ttggagagtc gcattctccc tgcctccacg ccgcggccac ctgccctacc | 1920 |
| ctgggcgccc accccgaagg cccccgccct ccgccctccc actgcctcct cccagtgccc | 1980 |
| tctctgcctt cctttcaaac cgtcctctgg gaagatctgc tgggagtctt ggcctagcct | 2040 |
| ctgtgaaggg gtgtgaggctc tgccggggag gggtggggt taatggttaa tcggtccccc | 2100 |
| gccggtggat aggctgggcg gggctgcagg gatttggctg tttgttggtt tctggctgac | 2160 |
| acccggggtg ctaattacaa ctgctggggc cctaactcac cgatgttcag ttatcaattg | 2220 |
| tacaaggcag gcatcatgac tcacgggcac tcatttgacc cttgactcac ccacccctcc | 2280 |
| aagccattgt caccccaagt caggcattct aactgtatact atcaggcact gacagcctac | 2340 |
| ctccgagatc ccctaattca ataacttccc aaatcattga cttctaccct caatgctttt | 2400 |
| gcagagataa ggctgcccca tggcccacga tttagaaacc taaatcccag gccccagatg | 2460 |
| ccaatcttct ggatccttgt tctgggagct cccttccagt tccccgcag tttcccggtt | 2520 |
| cccctgggag cagaatggac tggaagtttg ggagggccag attcacctcc aattccccgc | 2580 |
| tcctgctccc tgtgatccca ccctgcccct ctccgtctcc cacagctccc agtgtttctg | 2640 |
| gcccaggctg gctccatctc ggattttccc atcacattct cctgtttccc tcaccccac | 2700 |
| cccctcccgg agcaggcaga gacctggatt tacattcagg cacctaccgt ctactaactg | 2760 |
| ggaccttggg taaatgattc tcctctccga gcctcagttt cctttctgt aaaatgtaca | 2820 |
| atcaacttca aagggtggtt tgagaaggaa atgagatggc ataaatcaag caccaagtgg | 2880 |
| ggcctggtag acgtccatcc tcttcccct cctccctctc cctgtttcgt atccccttg | 2940 |
| ccatccccct gtttctctcc acccgtctcc taccttcaga gtgggctttg tgggggtatc | 3000 |
| gccagtgcag tcacaggcaa cccaaccctt agaaagtcct ggttcctggt tcagtgctct | 3060 |
| gctgtggttg tcctaaaatt catcatgact tttgaacaag ggattgtgca ttttttgtttt | 3120 |
| ggacggggcc ctgaaaatta cacagctggt cctggctgtc tgaagctcat ggtgcactct | 3180 |
| gttcttctca ctccctccag ccctcattgc cttctgtgca gacattttca agggctgcca | 3240 |
| atcaatctgg ggaagtaaag tcttgatgta aaggcagag agtgagggca gaggaagaaa | 3300 |
| agcctgagac ttgggaggcc tgggagcctg tcctccactg ctggctggaa gggcaggttg | 3360 |

| | | | |
|---|---|---|---|
| gagggcctcg | gtgacacctg | tgagcaagag | tgggcgaatt agtgggagca ccaattaatg | 3420 |
| agtgagtgtg | tgggggaatt | gatgagtggg | tgaattagga gtgagtgaat tagagacagg | 3480 |
| gagaattaat | gagtgagttg | agtgaatgca | tgaatgagtg agtgaatgaa cgaatgaggg | 3540 |
| taaattactg | agtaagtgag | caaatgggtg | ggtgaattaa tgagtgaatg ggtgggtgaa | 3600 |
| ttaatgagtg | agtgaatgag | tgaatgtgtg | ggtggattaa tgagtgagca aatcgggagt | 3660 |
| cagggcatgt | gtgttcgagt | ggtatgagga | ggcatcttca tgttctttcc actgctagaa | 3720 |
| gccctttctc | tgccctgctt | agctttattc | tgtccacttg atctgacctc tgaagctgag | 3780 |
| atgactgggg | agtgctattg | cctgtaggga | aaggggagag ggagcaactg ttgtggagga | 3840 |
| caagagaggc | tagatttgat | gtcaggagac | ctggggttag gaactagctc agtcactatt | 3900 |
| ccgataactt | tatttacatc | gtctcttctc | agggcttcaa tttctccctc tgtaaaatag | 3960 |
| aaagatgatc | ctggctcagt | tttctgttag | ccaggacaag a | 4001 |

<210> SEQ ID NO 2
<211> LENGTH: 4001
<212> TYPE: DNA
<213> ORGANISM: Homo sapiens

<400> SEQUENCE: 2

| | | | |
|---|---|---|---|
| caatattatt | tatctcagac | agccgtttgg | aaaatgaaac agctgtctga gagataatag | 60 |
| tagaacattc | actaacccat | tcatccatcc | attcacccac ctacctgtcg atagaagcaa | 120 |
| ccattctaat | aattgctgaa | tgtttgctat | ataatgagta tgacacagga gcagagatga | 180 |
| agagacatga | ggacatccta | caaggtgcag | agacgtggga gacagtgaaa ggctgtcagg | 240 |
| ttatattatt | gtatcatcct | ttaagagaca | ctgtggggcc ttctgttcac ccctagctta | 300 |
| gccttatgac | ctgggctgtc | cttccccaga | agctgtctgg cccctttgag agacaatgtc | 360 |
| ttcccctagc | cacaggttca | accaagtcat | ccattggcat ctatactcca ggtcttaaaa | 420 |
| ttgtggatta | agggtggcct | caccttaat | ctcctctatg ctatctcctc taatctcccc | 480 |
| gctctctggg | agataggtcc | tgttgttatc | ttcattttac agatgaggaa ataggttcag | 540 |
| agagggaaa | tgtcttgccc | aaggtcacac | agctggtgtg tgggatgggt tcccaggctg | 600 |
| ttggtttctt | cagcctctgc | catttccagt | gcatcacata ttcctgtttg atggggggtca | 660 |
| aagcaaagaa | gattcttcct | gactagagtc | aggagatcag gccctgattc tgtcattccc | 720 |
| tggccctctg | tcctcagcaa | ttgatgacat | aaatgttgat tgtgtctttg caatgcacgt | 780 |
| ggtatcaagg | gctttacatc | cttgttcccc | acggcatcca ccatgatctt aagacacatc | 840 |
| ctagtcctgt | ctccacttca | gaaagaaagc | aagaggcacg tgaatgttga gccgtgtgac | 900 |
| agagtcacaa | ctagaccccg | aggtctgctg | gattccagag accaagttct gtgcgggtgt | 960 |
| gtgatttgaa | caggtttata | aaaggcaccc | aacttttaaa aaatccaaaa tgtgtcccca | 1020 |
| aaagataaaa | cattctcttg | aatttccctc | ctcagaaaca aacctgtcac caattttatt | 1080 |
| gtgtcattcc | acgaattttc | tatgcgtgga | atgtacacgt atacgcgtgt gtacatatat | 1140 |
| acatctatat | ccgtttcgct | atcagcaact | acacagttct tcagtgtacc gttttcactt | 1200 |
| aatttaactg | agaggttctt | ccctgtcaca | cacagatgtg cgttgtttcc ttgaacaatg | 1260 |
| ggatagcatt | ccactgtaaa | gacgtctcac | gctttattta cccgtcttcc ctctgctgag | 1320 |
| ggacattggg | ttgcttccaa | tgtgggggtc | accctaagga gtgagcctga gccttttcact | 1380 |
| ctcagtaaca | catgctttct | agccctgcat | ctgagtttca cacgtccgca caagatattc | 1440 |

```
tcattttcca acgctccacc ctgcgcggcg ctttctacct cctccccatt atccagagcc    1500
aacggaggtg cggagcgacc gagctgcccg gtcccacgcc cagcttgata atgcaccagc    1560
aacgtgacct aggcccagca agcctctcct ggtggacctc aatttgcccc gcatcgaaac    1620
aggacggtgc ttccaagccc caccctctgt ggggttttgg aaagacccct gagatgcatt    1680
cccaggaagg cctctggaca gacaaaatga gccaagcctc tgccccaggg cttctcggcc    1740
cctcccagca cttctcgcac caagcaggcc atgccccggc ttgagagctt agggaagcgg    1800
tcacattgcc tccgtggggc ttcctgccct tccagaggag ctccaggagg agctttgggc    1860
ccgtaagaaa cacacgggga ggtgtcccat ggcctcccaa agctgaccgc agtcccgccc    1920
tgtccagtct tcccccagcc ccacttaccg taagaactct ccactggagc cccgaggggc    1980
gcgttcacgc tgaccatggc caagcccacc cagccggaga gctggggggca tggaggagca    2040 ggggcccgct cacagcagca gcacagccac caggagcccg tccaccagga aggcggtgag    2100
tgcggccagc tgccaccgcc cggttatctt attgattctt ctaatcaccc aaggtgggtg    2160
gatacgttaa agagtaacca gtcacttagg gaacccgcgg ctggggactg ttgctgtctc    2220
catggcaatg gcgacctggc cagacctgag gtccactcgg gtcctagtcc tgcactctgg    2280
ggttagggga acccagagcc aggtgtatgg ggacatcagc cccccaattt gaggacaggg    2340
ccggagcaga aggggctgga gaggtgagag tccaacctgg gttgggtttt atggctccaa    2400
actatgggtg tgtcaccatg caggaagtag tgggaaaacc gagggagggg cagaggaaaa    2460
aaggagggtg gagaactgtg tttagtgagt gcctactgga tgctgggagt tgcatacagg    2520
cgttaccata tttaaattaa accttgagat gaagggactg aaggacagag agaaattgca    2580
tgcctggagt ctcactgcta gtacatagag gtgttatctt cctttcatct aacatattta    2640
ttgagcacct actatgtacc aggccttgtg ctagactctg gggatatgga aatgagcaaa    2700
gtagatgtac ccccgaaact tgtggactaa tggaggagac ggaccttaat cagatcgtca    2760
ttcaaagata ctattacaaa ctggtgagtg atatgagggg tggagaaaca tggggctgcc    2820
tccaggccaa tgggacaaag tcatcctgtc tggcgtctcc tctggtctcc ttccccattc    2880
taaattcaac ctgctgctga aactcacaca ctctgtttta gctccctggc atgttagaca    2940
cctgccacct agcttttttt ttggaacagc cccgtttctt ttgtctcagt tttggatctc    3000
accacctgct tggggattct gaaatcaagg tcattcatcc tgttagagag agctgaaatg    3060
agaacagtga acaaattct ggactcagaa aaatcagaaa actccagctc tattattttc    3120
ttgctgtatg ttttttagta aattatttca tttccttata ggaataccta gctcatagtt    3180
tgccctgctt ctaaaatagc taattgataa tattcctctt ctcttcccat agtctctttt    3240
ttcagcttta tcaatcacct cagagggacc ttcagcccct acagatgggc atgggttgca    3300
ttaaaatgtc ctttctttc taaaacaaca gtgataacaa acgttagatt ttggggccgg    3360
gtgcagtggc tcacgcctgt aaccccagca ttttgggagg ccgaggcgca ccgatcacga    3420
ggtcaggagt ttgaggccag cctgaccaac atggtgaaac cccgtctcta ccaaaaataa    3480
aaaaattagc cgggcatggt ggcaaacggg aggctgaggc aagagaatcg tttgaaccag    3540
ggggacagag gttgcagtga gccaagatcg tgccactgca ctccagcctg gcaacagag    3600 agagactcca tctcaaaata aataaataaa taaataaata aataaataaa taataacttt    3660
cgatattttt taaaaaaaag tattaatatt cttggtcggg tgtagtggct catgcctgta    3720
atcccagcag tttgggaggc tgaggcaggt ggatcacttg aggtcaggag tttgagacca    3780
ggctggccaa cacggtgtaa tcccatctct actaaaaata caaaaattag ctgggtgtgg    3840
```

-continued

```
cagcgagcac ctgtaatctc agctactcgg gaggctgaag gaggagaatc gtttcaacct    3900
aggaggcaaa tgttgcagtg agccaagatt gcactactgc actgcagcct tggcgacaga    3960
gccagactcc atctcagaaa aaaaaaaagt attaatattt t                        4001
```

<210> SEQ ID NO 3
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3

```
gagcuuuggg cccguaaga                                                   19
```

<210> SEQ ID NO 4
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4

```
ucuuacgggc ccaaagcuc                                                   19
```

<210> SEQ ID NO 5
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5

```
gguggauacg uuaaagagu                                                   19
```

<210> SEQ ID NO 6
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6

```
acucuuuaac guauccacc                                                   19
```

<210> SEQ ID NO 7
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7

```
cccagaaugc cugugauca                                                   19
```

<210> SEQ ID NO 8
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 8
ugaucacagg cauucuggg                                                        19

<210> SEQ ID NO 9
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
ccgauguuca guuaucaau                                                        19

<210> SEQ ID NO 10
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
auugauaacu gaacaucgg                                                        19

<210> SEQ ID NO 11
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
gaagauugcu cgugcaaau                                                        19

<210> SEQ ID NO 12
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
auuugcacga gcaaucuuc                                                        19

<210> SEQ ID NO 13
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
cagauaugcu ccagugaug                                                        19

<210> SEQ ID NO 14
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 14
caucacugga gcauaucug                                              19

<210> SEQ ID NO 15
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
auaccacucg aacacacau                                              19

<210> SEQ ID NO 16
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
auguguguuc gagugguau                                              19

<210> SEQ ID NO 17
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
uacucaguaa uuuacccuc                                              19

<210> SEQ ID NO 18
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
gaggguaaau uacugagua                                              19

<210> SEQ ID NO 19
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
ucauaucagc aacaugucc                                              19

<210> SEQ ID NO 20
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 20
ggacauguug cugauauga                                                  19

<210> SEQ ID NO 21
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
ucuccugaca ucaaaucua                                                  19

<210> SEQ ID NO 22
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
uagauuugau gucaggaga                                                  19

<210> SEQ ID NO 23
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
ucacucacuc cuaauucac                                                  19

<210> SEQ ID NO 24
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
gugaauuagg agugaguga                                                  19

<210> SEQ ID NO 25
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
agacauaacc gcauuucuc                                                  19

<210> SEQ ID NO 26
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
```
gagaaaugcg guuaugucu                    19

<210> SEQ ID NO 27
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
aacacaccag agauagcaa                    19

<210> SEQ ID NO 28
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
uugcuaucuc ugguguguu                    19

<210> SEQ ID NO 29
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
ucgaucccgg cuauuccuc                    19

<210> SEQ ID NO 30
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
gaggaauagc cgggaucga                    19

<210> SEQ ID NO 31
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
uuuggcacuc aacuuuggg                    19

<210> SEQ ID NO 32
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
cccaaaguug agugccaaa                                              19

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (7)..(7)
<223> OTHER INFORMATION: 2'-OMe modified nucleotide
<220> FEATURE:
<221> NAME/KEY: modified_base
<222> LOCATION: (11)..(11)
<223> OTHER INFORMATION: 2'-OMe modified nucleotide
<220> FEATURE:
<221> NAME/KEY: modified_base
<222> LOCATION: (16)..(16)
<223> OTHER INFORMATION: 2'-OMe modified nucleotide
<220> FEATURE:
<221> NAME/KEY: modified_base
<222> LOCATION: (20)..(21)
<223> OTHER INFORMATION: Phosphorothioate linkage

<400> SEQUENCE: 33
ucgaaguacu uagcguaagt t                                           21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(3)
<223> OTHER INFORMATION: 2'-OMe modified nucleotide
<220> FEATURE:
<221> NAME/KEY: modified_base
<222> LOCATION: (5)..(5)
<223> OTHER INFORMATION: 2'-OMe modified nucleotide
<220> FEATURE:
<221> NAME/KEY: modified_base
<222> LOCATION: (7)..(8)
<223> OTHER INFORMATION: 2'-OMe modified nucleotide
<220> FEATURE:
<221> NAME/KEY: modified_base
<222> LOCATION: (12)..(12)
<223> OTHER INFORMATION: 2'-OMe modified nucleotide
<220> FEATURE:
<221> NAME/KEY: modified_base
<222> LOCATION: (14)..(17)
<223> OTHER INFORMATION: 2'-OMe modified nucleotide
<220> FEATURE:
<221> NAME/KEY: modified_base
<222> LOCATION: (20)..(21)
<223> OTHER INFORMATION: Phosphorothioate linkage

<400> SEQUENCE: 34
cuuacgcuga guacuucgat t                                           21

<210> SEQ ID NO 35
<211> LENGTH: 21
<212> TYPE: RNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe modified nucleotide

<400> SEQUENCE: 35
uucauuaagc cuugagacau u                                            21

<210> SEQ ID NO 36
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe modified nucleotide

<400> SEQUENCE: 36
ugucucaagg cuuaaugaau u                                            21

<210> SEQ ID NO 37
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
auugacuucu acccucaauu u                                            21

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
auugagggua gaagucaauu u                                            21

<210> SEQ ID NO 39
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
ugggugaauu aaugagugau u                                            21

<210> SEQ ID NO 40
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
```

-continued ucacucauua auucacccau u                                       21

<210> SEQ ID NO 41
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
cagggauuug gcuguuuguu u                                       21

<210> SEQ ID NO 42
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
acaaacagcc aaaucccugu u                                       21

<210> SEQ ID NO 43
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
gcccgguuau cuuauugauu u                                       21

<210> SEQ ID NO 44
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
aucaauaaga uaaccggcu u                                        21

<210> SEQ ID NO 45
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
guggauacgu uaaagaguau u                                       21

<210> SEQ ID NO 46
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
uacucuuuaa cguauccacu u                                       21

```
<210> SEQ ID NO 47
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
acgcgugugu acauauauau u                                            21

<210> SEQ ID NO 48
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
uauauaugua cacacgcguu u                                            21

<210> SEQ ID NO 49
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 49
auaccacucg aacacacauu u                                            21

<210> SEQ ID NO 50
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 50
auguguguuc gagugguauu u                                            21

<210> SEQ ID NO 51
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 51
uacucaguaa uuuacccucu u                                            21
```

```
<210> SEQ ID NO 52
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 52
gaggguaaau uacugaguau u                                              21

<210> SEQ ID NO 53
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 53
ucauaucagc aacauguccu u                                              21

<210> SEQ ID NO 54
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 54
ggacauguug cugauaugau u                                              21

<210> SEQ ID NO 55
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 55
ucuccugaca ucaaaucuau u                                              21

<210> SEQ ID NO 56
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide
```

```
<400> SEQUENCE: 56
uagauuugau gucaggagau u                                              21

<210> SEQ ID NO 57
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 57
ucacucacuc cuaauucacu u                                              21

<210> SEQ ID NO 58
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 58
gugaauuagg agugagugau u                                              21

<210> SEQ ID NO 59
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 59
agacauaacc gcauuucucu u                                              21

<210> SEQ ID NO 60
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 60
gagaaaugcg guuaugucuu u                                              21

<210> SEQ ID NO 61
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 61
aacacaccag agauagcaau u                                              21

<210> SEQ ID NO 62
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 62
uugcuaucuc uggguguguuu u                                             21

<210> SEQ ID NO 63
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 63
ucgaucccgg cuauuccucu u                                              21

<210> SEQ ID NO 64
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 64
gaggaauagc cgggaucgau u                                              21

<210> SEQ ID NO 65
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 65
uuuggcacuc aacuuugggu u                                              21
```

<210> SEQ ID NO 66
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 66
cccaaaguug agugccaaau u                                          21

<210> SEQ ID NO 67
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 67
aaaugucugc acagaaggcu u                                          21

<210> SEQ ID NO 68
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 68
gccuucugug cagacauuuu u                                          21

<210> SEQ ID NO 69
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 69
cuacaucaag acuuuacuuu u                                          21

<210> SEQ ID NO 70
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)

<223> OTHER INFORMATION: 2'-O-Methyl nucleotide

<400> SEQUENCE: 70
aaguaaaguc uugauguagu u                                         21

<210> SEQ ID NO 71
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 71
gauuugcuca cucauuaauu u                                         21

<210> SEQ ID NO 72
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 72
auuaaugagu gagcaaaucu u                                         21

<210> SEQ ID NO 73
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 73
cacuuacuca guaauuuacu u                                         21

<210> SEQ ID NO 74
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 74
guaaauuacu gaguaagugu u                                         21

<210> SEQ ID NO 75
<211> LENGTH: 21
<212> TYPE: RNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 75
gacucccagc agaucuuccu u                                                21

<210> SEQ ID NO 76
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 76
ggaagaucug cugggagucu u                                                21

<210> SEQ ID NO 77
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 77
aauucaccca cccauucacu u                                                21

<210> SEQ ID NO 78
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 78
gugaaugggu gggugaauuu u                                                21

<210> SEQ ID NO 79
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 79
aucuucccag aggacgguuu u                                                21
```

```
<210> SEQ ID NO 80
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 80
aaccguccuc ugggaagauu u                                                 21

<210> SEQ ID NO 81
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 81
acacucacuc auuaauuggu u                                                 21

<210> SEQ ID NO 82
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 82
ccaauuaaug agugaguguu u                                                 21

<210> SEQ ID NO 83
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 83
cccagaaugc cugugaucau u                                                 21

<210> SEQ ID NO 84
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

```
<222> LOCATION: (20)..(21)
<223> OTHER INFORMATION: 2'-O-Methyl nucleotide

<400> SEQUENCE: 84
ugaucacagg cauucugggu u                                              21

<210> SEQ ID NO 85
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Inverted abasic capped nucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 85
cugugaucac ugugccuggu u                                              21

<210> SEQ ID NO 86
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 86
ucaggcacag ugaucacagu u                                              21

<210> SEQ ID NO 87
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Inverted abasic capped nucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 87
ccugugauca cugugccugu u                                              21

<210> SEQ ID NO 88
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide
```

```
<400> SEQUENCE: 88
uaggcacagu gaucacaggu u                                              21

<210> SEQ ID NO 89
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Inverted abasic capped nucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 89
gccugugauc acugugccuu u                                              21

<210> SEQ ID NO 90
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 90
uggcacagug aucacaggcu u                                              21

<210> SEQ ID NO 91
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Inverted abasic capped nucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 91
ugccugugau cacugugccu u                                              21

<210> SEQ ID NO 92
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 92
ugcacaguga ucacaggcau u                                              21
```

```
<210> SEQ ID NO 93
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Inverted abasic capped nucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 93
augccuguga ucacugugcu u                                              21

<210> SEQ ID NO 94
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 94
ucacagugau cacaggcauu u                                              21

<210> SEQ ID NO 95
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Inverted abasic capped nucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 95
aaugccugug aucacugugu u                                              21

<210> SEQ ID NO 96
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 96
uacagugauc acaggcauuu u                                              21

<210> SEQ ID NO 97
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Inverted abasic capped nucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 97
gaaugccugu gaucacuguu u                                            21

<210> SEQ ID NO 98
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 98
ucagugauca caggcauucu u                                            21

<210> SEQ ID NO 99
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Inverted abasic capped nucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 99
agaaugccug ugaucacugu u                                            21

<210> SEQ ID NO 100
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 100
uagugaucac aggcauucuu u                                            21

<210> SEQ ID NO 101
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Inverted abasic capped nucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 101
cagaaugccu gugaucacuu u                                              21

<210> SEQ ID NO 102
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 102
ugugaucaca ggcauucugu u                                              21

<210> SEQ ID NO 103
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Inverted abasic capped nucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 103
ccagaaugcc ugugaucacu u                                              21

<210> SEQ ID NO 104
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 104
uugaucacag gcauucuggu u                                              21

<210> SEQ ID NO 105
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

-continued

```
<220> FEATURE:
<221> NAME/KEY: modified_base
<222> LOCATION: (1)..(1)
<223> OTHER INFORMATION: Inverted abasic capped nucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 105
cccagaaugc cugugaucau u                                              21

<210> SEQ ID NO 106
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 106
ugaucacagg cauucugggu u                                              21

<210> SEQ ID NO 107
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Inverted abasic capped nucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 107
acccagaaug ccugugaucu u                                              21

<210> SEQ ID NO 108
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 108
uaucacaggc auucuggguu u                                              21

<210> SEQ ID NO 109
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
```

<223> OTHER INFORMATION: Inverted abasic capped nucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 109
cacccagaau gccugugauu u                                              21

<210> SEQ ID NO 110
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 110
uucacaggca uucuggugu u                                               21

<210> SEQ ID NO 111
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Inverted abasic capped nucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 111
ucacccagaa ugccugugau u                                              21

<210> SEQ ID NO 112
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 112
ucacaggcau ucugggugau u                                              21

<210> SEQ ID NO 113
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Inverted abasic capped nucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 113
uucacccaga augccugugu u                                               21

<210> SEQ ID NO 114
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 114
uacaggcauu cugggugaau u                                               21

<210> SEQ ID NO 115
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Inverted abasic capped nucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 115
cuucacccag aaugccuguu u                                               21

<210> SEQ ID NO 116
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 116
ucaggcauuc ugggugaagu u                                               21

<210> SEQ ID NO 117
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Inverted abasic capped nucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 117
ccuucaccca gaaugccugu u                                              21

<210> SEQ ID NO 118
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 118
uaggcauucu gggugaaggu u                                              21

<210> SEQ ID NO 119
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Inverted abasic capped nucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 119
cccuucaccc agaaugccuu u                                              21

<210> SEQ ID NO 120
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 120
uggcauucug ggugaagggu u                                              21

<210> SEQ ID NO 121
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Inverted abasic capped nucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 121
ucccuucacc cagaaugccu u                                              21

```
<210> SEQ ID NO 122
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 122
ugcauucugg gugaagggau u                                               21

<210> SEQ ID NO 123
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Inverted abasic capped nucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 123
cucccuucac ccagaaugcu u                                               21

<210> SEQ ID NO 124
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 124
ucauucuggg ugaagggagu u                                               21

<210> SEQ ID NO 125
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Inverted abasic capped nucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 125
ccucccuuca cccagaaugu u                                               21

<210> SEQ ID NO 126
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 126
uauucugggu gaagggaggu u                                            21

<210> SEQ ID NO 127
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Inverted abasic capped nucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 127
cccagaaugc cugugaucuu u                                            21

<210> SEQ ID NO 128
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 128
ugaucacagg cauucugggu u                                            21

<210> SEQ ID NO 129
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Inverted abasic capped nucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 129
ucacccagaa ugccuguguu u                                            21

<210> SEQ ID NO 130
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 130
ucacaggcau ucugggugau u                                              21

<210> SEQ ID NO 131
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Inverted abasic capped nucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 131
ccagaaugcc ugugaucaau u                                              21

<210> SEQ ID NO 132
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 132
uugaucacag gcauucuggu u                                              21

<210> SEQ ID NO 133
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA molecule:
      Synthetic oligonucleotide
<220> FEATURE:
<223> OTHER INFORMATION: 5' NH2-(C6H12)-linker
<220> FEATURE:
<221> NAME/KEY: modified_base
<222> LOCATION: (1)..(1)
<223> OTHER INFORMATION: 2'-fluoro nucleotide
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: modified_base
<222> LOCATION: (3)..(3)
<223> OTHER INFORMATION: 2'-fluoro nucleotide
<220> FEATURE:
<221> NAME/KEY: modified_base
<222> LOCATION: (4)..(4)
<223> OTHER INFORMATION: 2'-O-Methyl nucleotide
```

```
<220> FEATURE:
<221> NAME/KEY: modified_base
<222> LOCATION: (5)..(5)
<223> OTHER INFORMATION: 2'-fluoro nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(9)
<223> OTHER INFORMATION: 2'-fluoro nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-fluoro nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-fluoro nucleotide
<220> FEATURE:
<221> NAME/KEY: modified_base
<222> LOCATION: (14)..(14)
<223> OTHER INFORMATION: 2'-O-Methyl nucleotide
<220> FEATURE:
<221> NAME/KEY: modified_base
<222> LOCATION: (15)..(15)
<223> OTHER INFORMATION: 2'-fluoro nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-fluoro nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-fluoro nucleotide
<220> FEATURE:
<221> NAME/KEY: modified_base
<222> LOCATION: (20)..(21)
<223> OTHER INFORMATION: 2'-O-Methyl nucleotide
<220> FEATURE:
<221> NAME/KEY: modified_base
<222> LOCATION: (22)..(22)
<223> OTHER INFORMATION: Inverted nucleotide

<400> SEQUENCE: 133
cccagaaugc cugugaucau ut                                             22

<210> SEQ ID NO 134
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: modified_base
```

```
<222> LOCATION: (2)..(2)
<223> OTHER INFORMATION: 2'-fluoro nucleotide
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-fluoro nucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-fluoro nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-fluoro nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-fluoro nucleotide
<220> FEATURE:
<221> NAME/KEY: modified_base
<222> LOCATION: (11)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-fluoro nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-fluoro nucleotide
<220> FEATURE:
<221> NAME/KEY: modified_base
<222> LOCATION: (19)..(21)
<223> OTHER INFORMATION: 2'-O-Methyl nucleotide
<220> FEATURE:
<221> NAME/KEY: misc_feature
<222> LOCATION: (19)..(21)
<223> OTHER INFORMATION: Phosphorothioate linkage

<400> SEQUENCE: 134
ugaucacagg cauucggggu u                                           21

<210> SEQ ID NO 135
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

-continued

```
<220> FEATURE:
<221> NAME/KEY: modified_base
<222> LOCATION: (1)..(1)
<223> OTHER INFORMATION: Inverted abasic capped nucleotide
<220> FEATURE:
<221> NAME/KEY: modified_base
<222> LOCATION: (1)..(2)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-O-Methyl nucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 135
cccagaaugc cugugaucau u                                              21

<210> SEQ ID NO 136
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 136
ugaucacagg cauucgggu u                                               21

<210> SEQ ID NO 137
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Inverted abasic capped nucleotide
<220> FEATURE:
<221> NAME/KEY: modified_base
<222> LOCATION: (1)..(3)
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-O-Methyl nucleotide
<220> FEATURE:
<221> NAME/KEY: modified_base
<222> LOCATION: (10)..(12)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-O-Methyl nucleotide
<220> FEATURE:
<221> NAME/KEY: modified_base
<222> LOCATION: (17)..(18)
<223> OTHER INFORMATION: 2'-O-Methyl nucleotide
<220> FEATURE:
```

```
<221> NAME/KEY: modified_base
<222> LOCATION: (20)..(20)
<223> OTHER INFORMATION: 2'-O-Methyl nucleotide

<400> SEQUENCE: 137
cccagaaugc cugugaucau                                          20

<210> SEQ ID NO 138
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-O-Methyl nucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 138
ugaucacagg cauucugggu u                                        21

<210> SEQ ID NO 139
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5' NH2-(C6H12)-linker
<220> FEATURE:
<221> NAME/KEY: modified_base
<222> LOCATION: (1)..(1)
<223> OTHER INFORMATION: 2'-fluoro nucleotide
<220> FEATURE:
<221> NAME/KEY: modified_base
<222> LOCATION: (2)..(2)
<223> OTHER INFORMATION: 2'-O-Methyl nucleotide
<220> FEATURE:
<221> NAME/KEY: modified_base
<222> LOCATION: (3)..(3)
<223> OTHER INFORMATION: 2'-fluoro nucleotide
<220> FEATURE:
<221> NAME/KEY: modified_base
<222> LOCATION: (4)..(4)
<223> OTHER INFORMATION: 2'-O-Methyl nucleotide
<220> FEATURE:
<221> NAME/KEY: modified_base
<222> LOCATION: (5)..(5)
<223> OTHER INFORMATION: 2'-fluoro nucleotide
<220> FEATURE:
<221> NAME/KEY: modified_base
<222> LOCATION: (6)..(6)
<223> OTHER INFORMATION: 2'-O-Methyl nucleotide
<220> FEATURE:
<221> NAME/KEY: modified_base
<222> LOCATION: (7)..(9)
<223> OTHER INFORMATION: 2'-fluoro nucleotide
<220> FEATURE:
```

```
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (11)..(11)
<223> OTHER INFORMATION: 2'-fluoro nucleotide
<220> FEATURE:
<221> NAME/KEY: modified_base
<222> LOCATION: (12)..(12)
<223> OTHER INFORMATION: 2'-O-Methyl nucleotide
<220> FEATURE:
<221> NAME/KEY: modified_base
<222> LOCATION: (13)..(13)
<223> OTHER INFORMATION: 2'-fluoro nucleotide
<220> FEATURE:
<221> NAME/KEY: modified_base
<222> LOCATION: (14)..(14)
<223> OTHER INFORMATION: 2'-O-Methyl nucleotide
<220> FEATURE:
<221> NAME/KEY: modified_base
<222> LOCATION: (15)..(15)
<223> OTHER INFORMATION: 2'-fluoro nucleotide
<220> FEATURE:
<221> NAME/KEY: modified_base
<222> LOCATION: (16)..(16)
<223> OTHER INFORMATION: 2'-O-Methyl nucleotide
<220> FEATURE:
<221> NAME/KEY: modified_base
<222> LOCATION: (17)..(17)
<223> OTHER INFORMATION: 2'-fluoro nucleotide
<220> FEATURE:
<221> NAME/KEY: modified_base
<222> LOCATION: (18)..(18)
<223> OTHER INFORMATION: 2'-O-Methyl nucleotide
<220> FEATURE:
<221> NAME/KEY: modified_base
<222> LOCATION: (19)..(19)
<223> OTHER INFORMATION: 2'-fluoro nucleotide
<220> FEATURE:
<221> NAME/KEY: modified_base
<222> LOCATION: (20)..(21)
<223> OTHER INFORMATION: 2'-O-Methyl nucleotide
<220> FEATURE:
<221> NAME/KEY: modified_base
<222> LOCATION: (22)..(22)
<223> OTHER INFORMATION: Inverted nucleotide

<400> SEQUENCE: 139
ccagaaugcc ugugaucaau ut                                              22

<210> SEQ ID NO 140
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-Methyl nucleotide
<220> FEATURE:
<221> NAME/KEY: modified_base
<222> LOCATION: (2)..(2)
<223> OTHER INFORMATION: 2'-fluoro nucleotide
<220> FEATURE:
<221> NAME/KEY: modified_base
<222> LOCATION: (3)..(3)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-fluoro nucleotide
<220> FEATURE:
<221> NAME/KEY: modified_base
<222> LOCATION: (5)..(5)
```

```
<223> OTHER INFORMATION: 2'-O-Methyl nucleotide
<220> FEATURE:
<221> NAME/KEY: modified_base
<222> LOCATION: (6)..(6)
<223> OTHER INFORMATION: 2'-fluoro nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (8)..(8)
<223> OTHER INFORMATION: 2'-fluoro nucleotide
<220> FEATURE:
<221> NAME/KEY: modified_base
<222> LOCATION: (9)..(9)
<223> OTHER INFORMATION: 2'-O-Methyl nucleotide
<220> FEATURE:
<221> NAME/KEY: modified_base
<222> LOCATION: (10)..(10)
<223> OTHER INFORMATION: 2'-fluoro nucleotide
<220> FEATURE:
<221> NAME/KEY: modified_base
<222> LOCATION: (11)..(13)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-fluoro nucleotide
<220> FEATURE:
<221> NAME/KEY: modified_base
<222> LOCATION: (15)..(15)
<223> OTHER INFORMATION: 2'-O-Methyl nucleotide
<220> FEATURE:
<221> NAME/KEY: modified_base
<222> LOCATION: (16)..(16)
<223> OTHER INFORMATION: 2'-fluoro nucleotide
<220> FEATURE:
<221> NAME/KEY: modified_base
<222> LOCATION: (17)..(17)
<223> OTHER INFORMATION: 2'-O-Methyl nucleotide
<220> FEATURE:
<221> NAME/KEY: modified_base
<222> LOCATION: (18)..(18)
<223> OTHER INFORMATION: 2'-fluoro nucleotide
<220> FEATURE:
<221> NAME/KEY: modified_base
<222> LOCATION: (19)..(21)
<223> OTHER INFORMATION: 2'-O-Methyl nucleotide
<220> FEATURE:
<221> NAME/KEY: misc_feature
<222> LOCATION: (19)..(21)
<223> OTHER INFORMATION: Phosphorothioate linkage

<400> SEQUENCE: 140
uugaucacag gcauucuggu u                                        21

<210> SEQ ID NO 141
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Inverted abasic capped nucleotide
<220> FEATURE:
<221> NAME/KEY: modified_base
<222> LOCATION: (1)..(2)
<223> OTHER INFORMATION: 2'-O-Methyl nucleotide
<220> FEATURE:
<221> NAME/KEY: modified_base
<222> LOCATION: (4)..(4)
<223> OTHER INFORMATION: 2'-O-Methyl nucleotide
<220> FEATURE:
```

```
<221> NAME/KEY: modified_base
<222> LOCATION: (10)..(10)
<223> OTHER INFORMATION: 2'-O-Methyl nucleotide
<220> FEATURE:
<221> NAME/KEY: modified_base
<222> LOCATION: (14)..(14)
<223> OTHER INFORMATION: 2'-O-Methyl nucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 141
ccagaaugcc ugugaucaau u                                              21

<210> SEQ ID NO 142
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 142
uugaucacag gcauucuggu u                                              21

<210> SEQ ID NO 143
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Inverted abasic capped nucleotide
<220> FEATURE:
<221> NAME/KEY: modified_base
<222> LOCATION: (1)..(2)
<223> OTHER INFORMATION: 2'-O-Methyl nucleotide
<220> FEATURE:
<221> NAME/KEY: modified_base
<222> LOCATION: (7)..(7)
<223> OTHER INFORMATION: 2'-O-Methyl nucleotide
<220> FEATURE:
<221> NAME/KEY: modified_base
<222> LOCATION: (9)..(11)
<223> OTHER INFORMATION: 2'-O-Methyl nucleotide
<220> FEATURE:
<221> NAME/KEY: modified_base
<222> LOCATION: (13)..(14)
<223> OTHER INFORMATION: 2'-O-Methyl nucleotide
<220> FEATURE:
<221> NAME/KEY: modified_base
<222> LOCATION: (16)..(17)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide

<400> SEQUENCE: 143
ccagaaugcc ugugaucaau u                                              21

<210> SEQ ID NO 144
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-O-Methyl nucleotide

<400> SEQUENCE: 144
uugaucacag gcauucuggu u                                              21
```

HNF4A SARNA COMPOSITIONS AND METHODS OF USE

CROSS-REFERENCE TO RELATED APPLICATIONS

This application is a divisional application of U.S. application Ser. No. 16/645,012 filed Mar. 6, 2020, entitled "HNF4A SARNA COMPOSITIONS AND METHODS OF USE", which is a 35 U.S.C. § 371 U.S. National Stage Entry of International Application No. PCT/EP2018/074191 filed Sep. 7, 2018, entitled "HNF4A SARNA COMPOSITIONS AND METHODS OF USE", which claims the benefit of priority to International Application No. PCT/EP2017/074130 filed Sep. 22, 2017, entitled "HNF4A SARNA COMPOSITIONS AND METHODS OF USE", which claims the benefit of priority to U.S. Provisional Patent Application No. 62/555,951, filed Sep. 8, 2017, entitled "STABILIZED SARNA COMPOSITIONS AND METHODS OF USE", and U.S. Provisional Patent Application No. 62/555,937, filed Sep. 8, 2017, entitled "HNF4A SARNA COMPOSITIONS AND METHODS OF USE", the contents of each of which are herein incorporated by reference in their entirety.

REFERENCE TO SEQUENCE LISTING

The present application is being filed along with a Sequence Listing in electronic format. The sequence listing filed, entitled 2058_1020PCT1_SL.txt, was created on Sep. 4, 2018 and is 62,809 bytes in size. The information in electronic format of the Sequence Listing is incorporated herein by reference in its entirety.

FIELD OF THE DISCLOSURE

The invention relates to polynucleotide, specifically saRNA, compositions for the modulating HNF4a and HNF4a pathways and to the methods of using the compositions in therapeutic applications such as treating metabolic disorders, hyperproliferative diseases, and regulating stem cell linage.

BACKGROUND

Hepatocyte Nuclear Factor 4 Alpha (HNF4a, also known as NR2A1) is a member of the superfamily of nuclear receptors. HNF4A has been widely associated with the transcriptional regulation of hepatocyte genes specifically implicated in lipid metabolism, glucose metabolism, differentiation and morphogenesis. HNF4a modulates the expression of several genes, including hepatocyte nuclear factor 1 alpha, a transcription factor which regulates the expression of several hepatic genes. Diseases associated with HNF4A include monogenic autosomal dominant non-insulin-dependent diabetes mellitus type I; mody, type I; and fanconi renotubular syndrome 4, with maturity-onset diabetes of the young. HNF4a is encoded by HNF4a gene. There is a need for targeted modulation of HNF4a for therapeutic purposes with saRNA.

SUMMARY

The present invention provides compositions, methods and kits for the design, preparation, manufacture, formulation and/or use of short activating RNA (saRNA) molecules that modulate HNF4a gene expression and/or function for therapeutic purposes, including diagnosing and prognosis.

The details of various embodiments of the invention are set forth in the description below. Other features, objects, and advantages of the invention will be apparent from the description and the drawings, and from the claims.

The patent or application file contains at least one drawing executed in color. Copies of this patent or patent application publication with color drawing(s) will be provided by the Office upon request and payment of the necessary fee.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead being placed upon illustrating the principles of various embodiments of the invention.

FIG. 2A: HEPG2 cells; FIG. 2B: HEP3B cells; FIG. 2C: PLCPRF5 cells; and FIG. 2D: SNU475 cells. HNF4a gene expression is up-regulated by HNF4a-saRNA.

FIG. 3A (HEPG2 cells), FIG. 3C (HEP3B), and FIG. 3E (PLCPRF5) are WST-1 relative proliferation assay results. FIG. 3B (HEPG2 cells), FIG. 3D (HEP3B), and FIG. 3F (PLCPRF5) are absolute cell numbers.

Family 3 Subfamily A Member 43 (CYP3A43), ALBUMIN, HNF4A and HSP90 expression. HSP90 was used a house keeping gene (HKG).

Figure 12A:
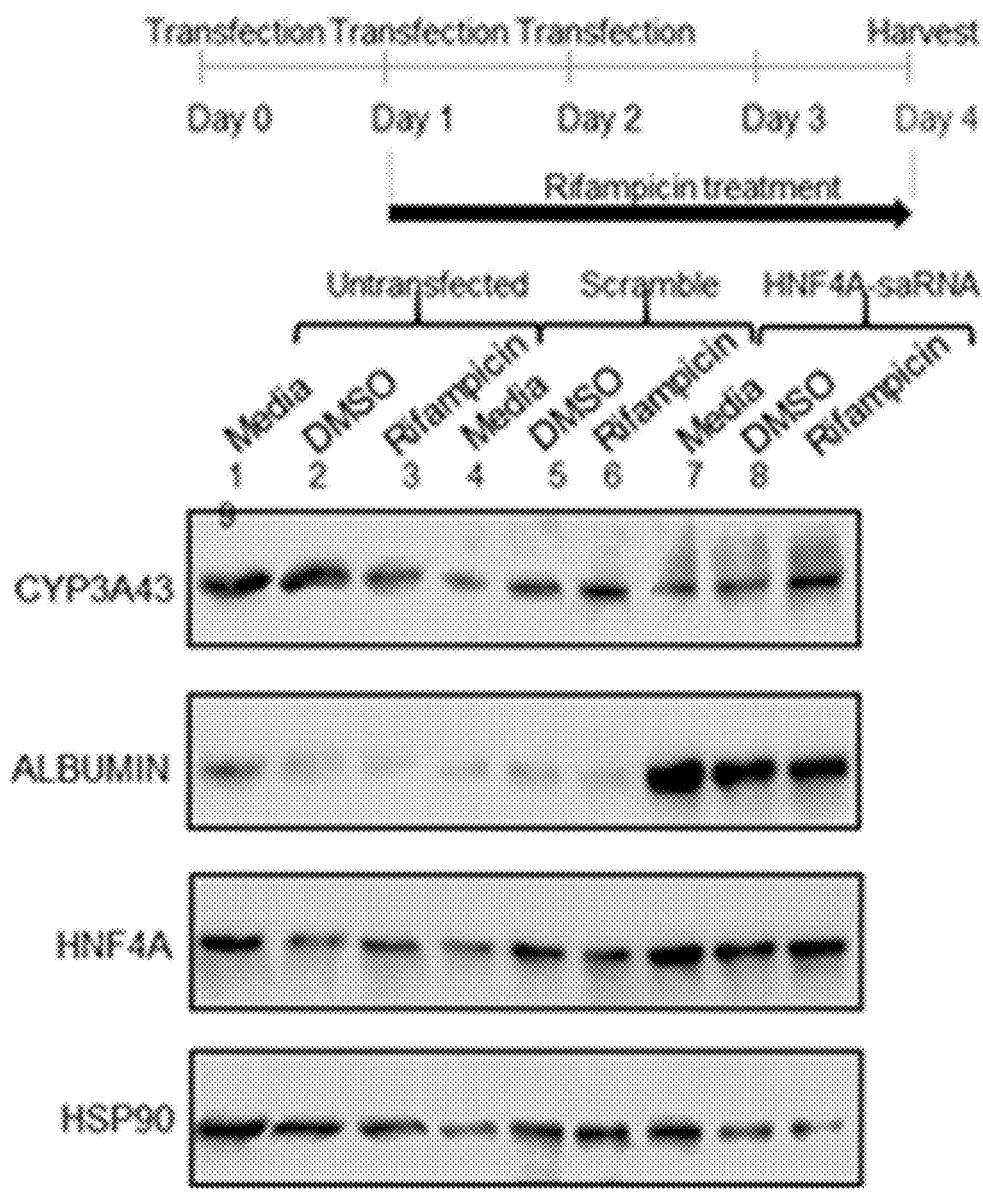
FIG. 12A shows Western blotting data showing HNF4a protein expression level changes. Top: schematic representation of transfection protocol and rifampicin treatment. Bottom: Protein extracts analyzed for Cytochrome P450
Figure 12B:
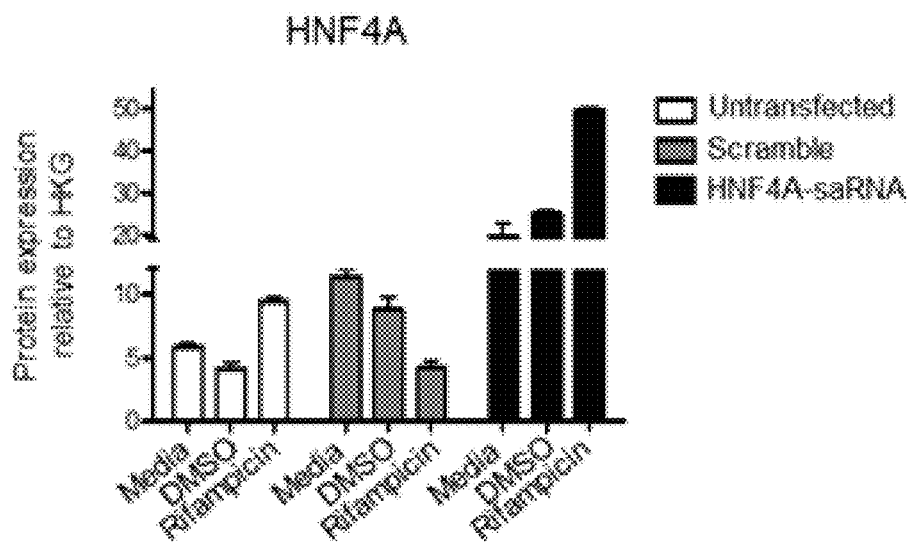
Figure 12C:
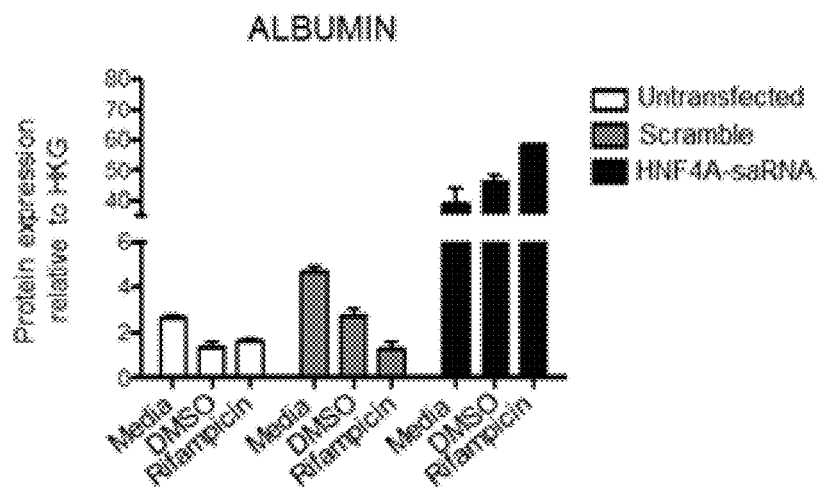
Figure 12D:
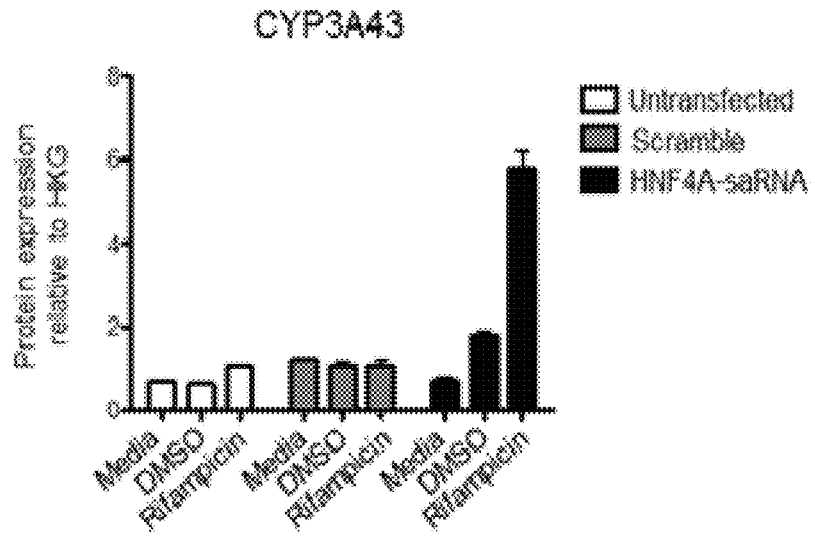

FIG. 12B-12D are quantifications of FIG. 12A Western blot. FIG. 12B shows HNF4a-saRNA upregulated HNF4a protein expression. FIG. 12C shows HNF4a-saRNA upregulated albumin protein expression. FIG. 12D shows HNF4a-saRNA upregulated CYP3A43 protein expression. Rifampicin (a CYP450 inducer) further enhanced the upregulations.

Figure 12E:
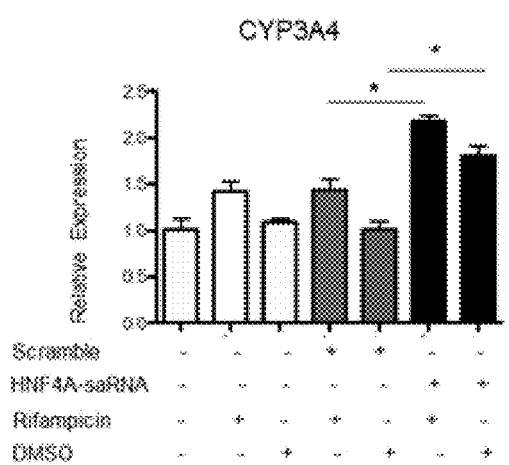
Figure 12F:
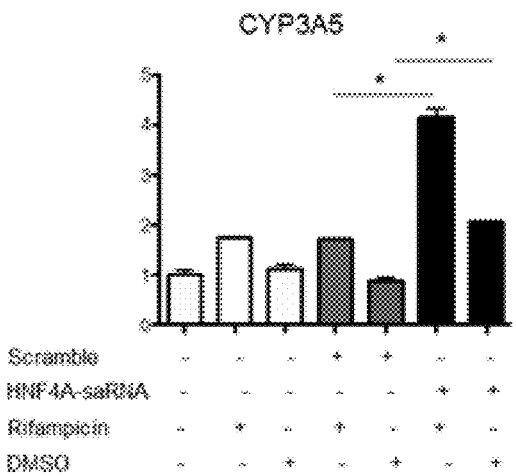
Figure 12G:
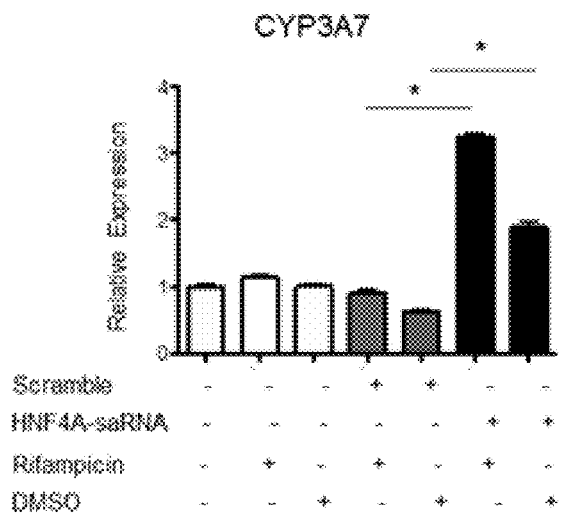

FIGS. 12E-12G Cytochrome p450 upregulation was measured in qPCR and upregulations of Cytochrome P450 Family 3 Subfamily A Member 4 (CYP3A4) (FIG. 12E), Cytochrome P450 Family 3 Subfamily A Member 5 (CYP3A5) (FIG. 12F) and Cytochrome P450 Family 3 Subfamily A Member 7 (CYP3A7) (FIG. 12G) were observed. HepG2 cells treated with DMSO or Rifampicin and transfected with sa-HNF4-RNA or Scramble-RNA. 72 h after second transfection cell were harvested and RNA extracted. CYP3A4, CYP3A5 and CYP3A7 were normalized to ACTIN. Asterisks denote significance as follows: *p<0.05 (one-tail t-test, 95% confidence).

Figure 12H:
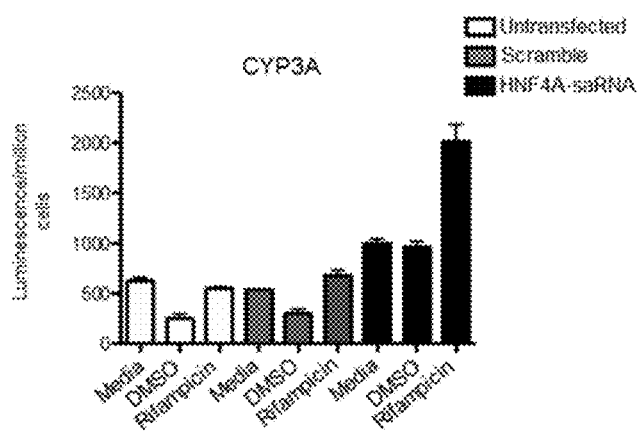

FIG. 12H shows luciferase assay data of HepG2 cells treated with DMSO or Rifampicin and transfected with HNF4A-saRNA or Scramble-RNA. The results demonstrate HNF4a-saRNA transfection increased cytochrome p450 activity.

Figure 13A:
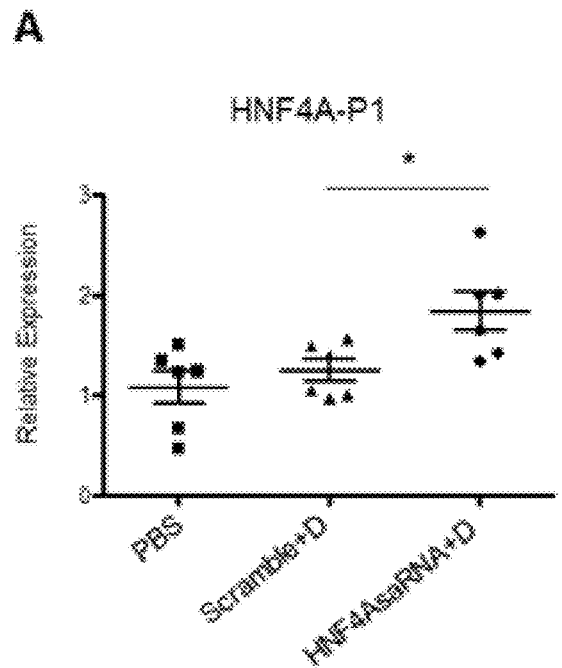
Figure 13B:
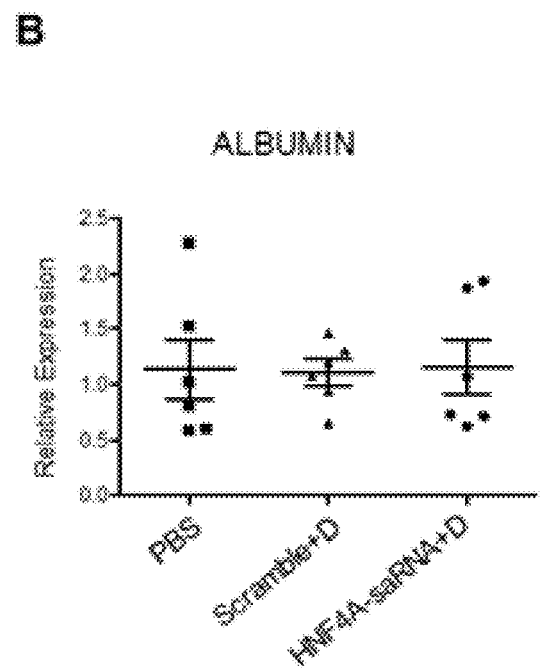
Figure 13C:
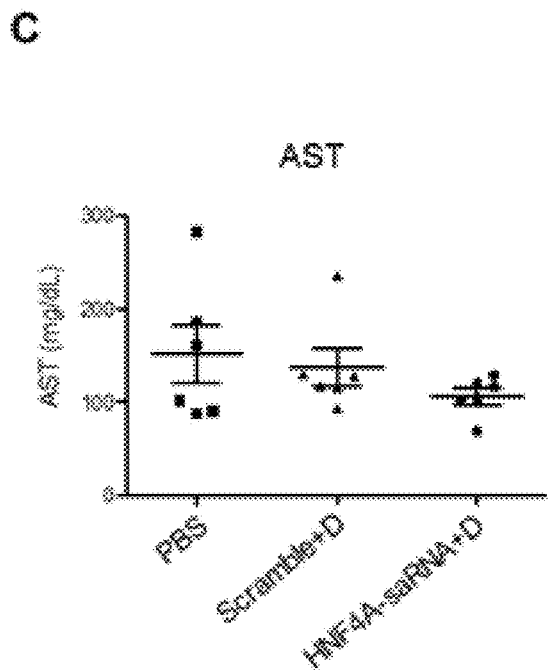
Figure 13D:
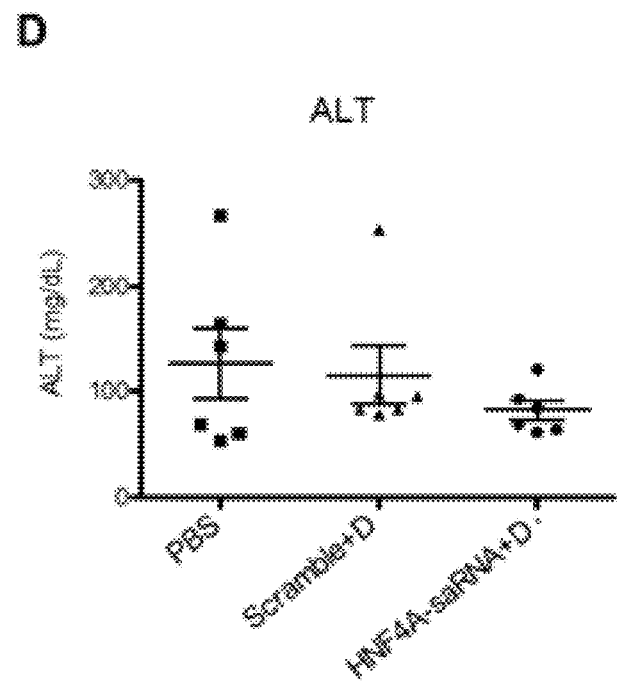
Figure 13E:
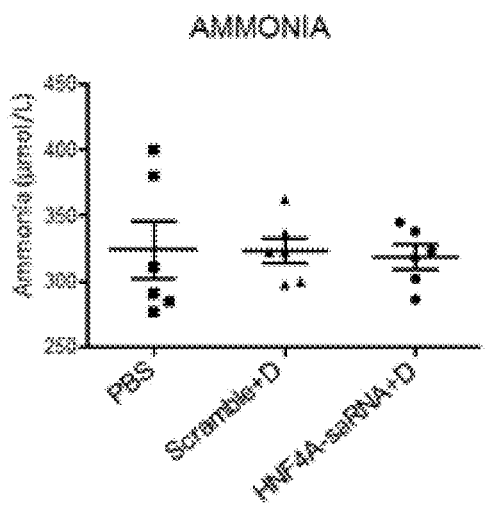
Figure 13F:
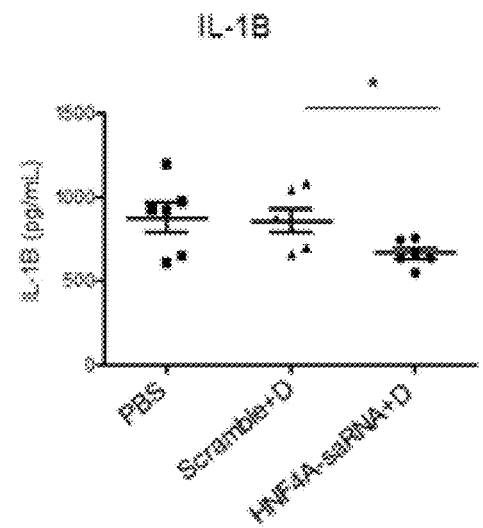
Figure 13G:
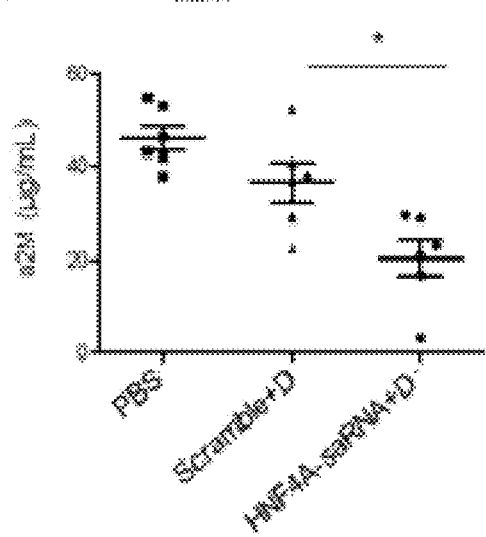
Figure 13H:
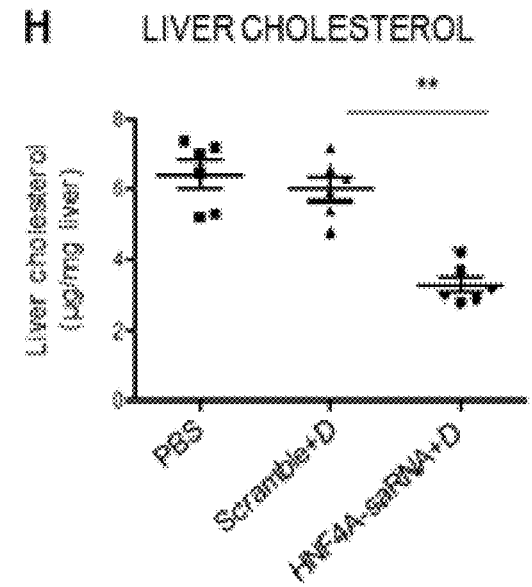
Figure 13I:
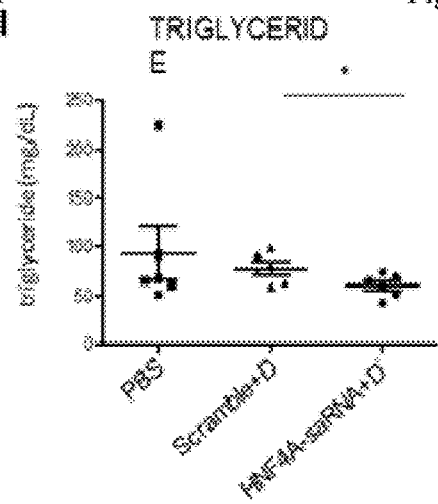
Figure 13J:
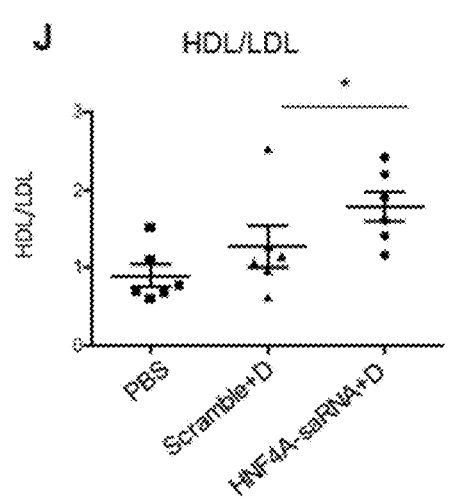

FIG. 13A-13J show level changes of HNF4a-P1 (FIG. 13A), albumin (FIG. 13B), AST (FIG. 13C), ALT (FIG. 13D), ammonia (FIG. 13E), IL-1B (FIG. 13F), α2M (FIG. 13G), liver cholesterol (FIG. 13H), liver triglyceride (FIG. 13I) and HDL/LDL (FIG. 13J). RNA extracted from liver tissue was analyzed for (A) HNF4A-P1 and (B) ALBUMIN expression. HNF4A-PR1 was normalized to HPRT. ALMUMIN was normalized to GAPDH. Serum levels of (C) aspartate aminotransferase (AST) (D) alanine aminotransferase (ALT), and (E) ammonia showed no significant change upon HNF4A-saRNA treatment. (F) Interleukin 1 beta (IL-1B) and (G) alpha-2 macroglobulin (A2M) showed a significant reduction. (H) Liver cholesterol, (I) triglyceride and (J) HDL/LDL changes upon HNF4A-saRNA treatment. Asterisks denote significance as follows: *p<0.05 (two-tail t-test, 95% confidence).

Figure 14:
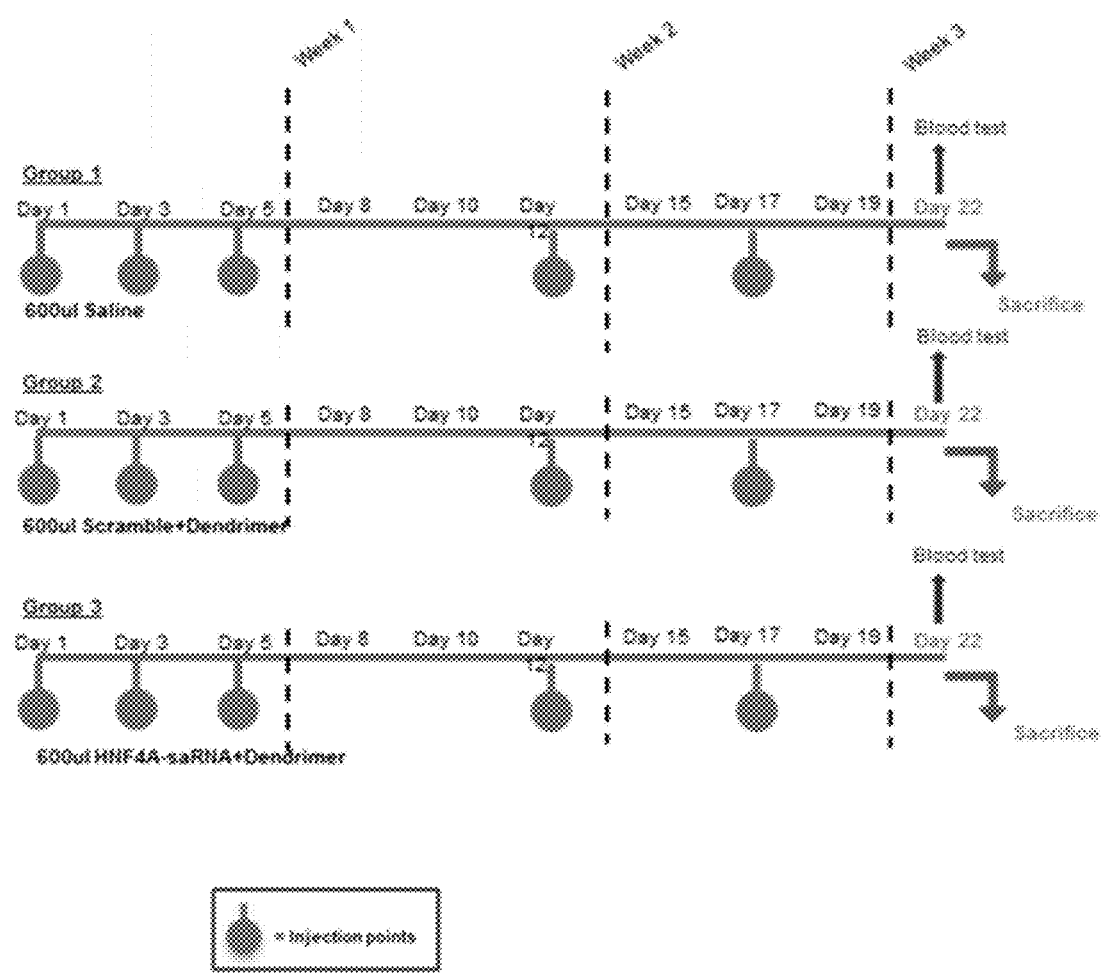

FIG. 14 is a schematic representation of animal treatment.

Figure 15A:
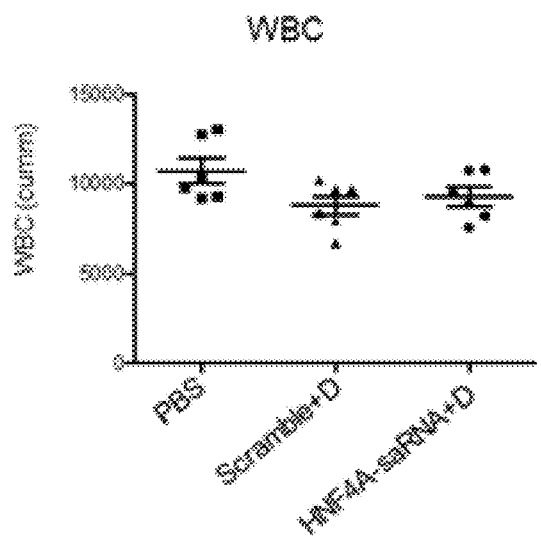
Figure 15B:
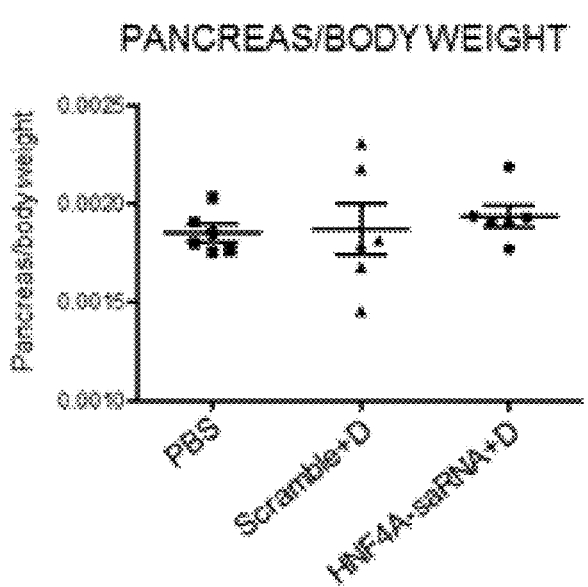
Figure 15C:
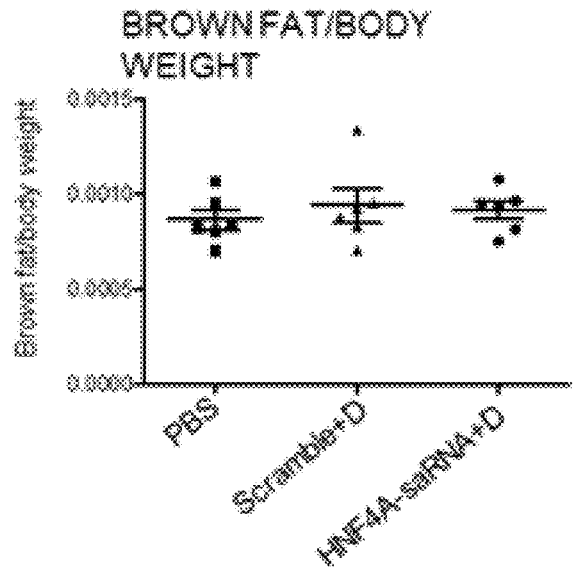

FIG. 15A-15C demonstrate that white blood cell (WBC) (FIG. 15A), pancreas body weight ratio (FIG. 15B), and brown fat body weight ratio (FIG. 15C) showed no significant change.

Figure 16A:
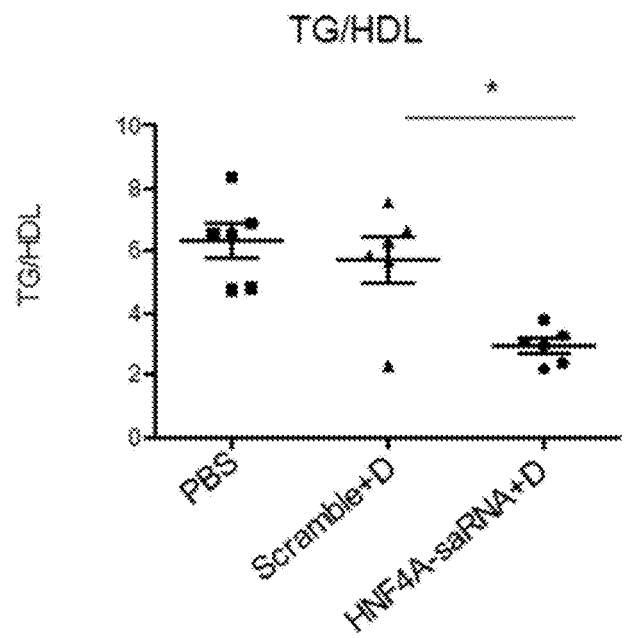

FIG. 16A shows TG/HDL ratio after treatment. Asterisks denote significance as follows: *p<0.05, **p<0.01 (two-tail t-test, 95% confidence).

Figure 16B:
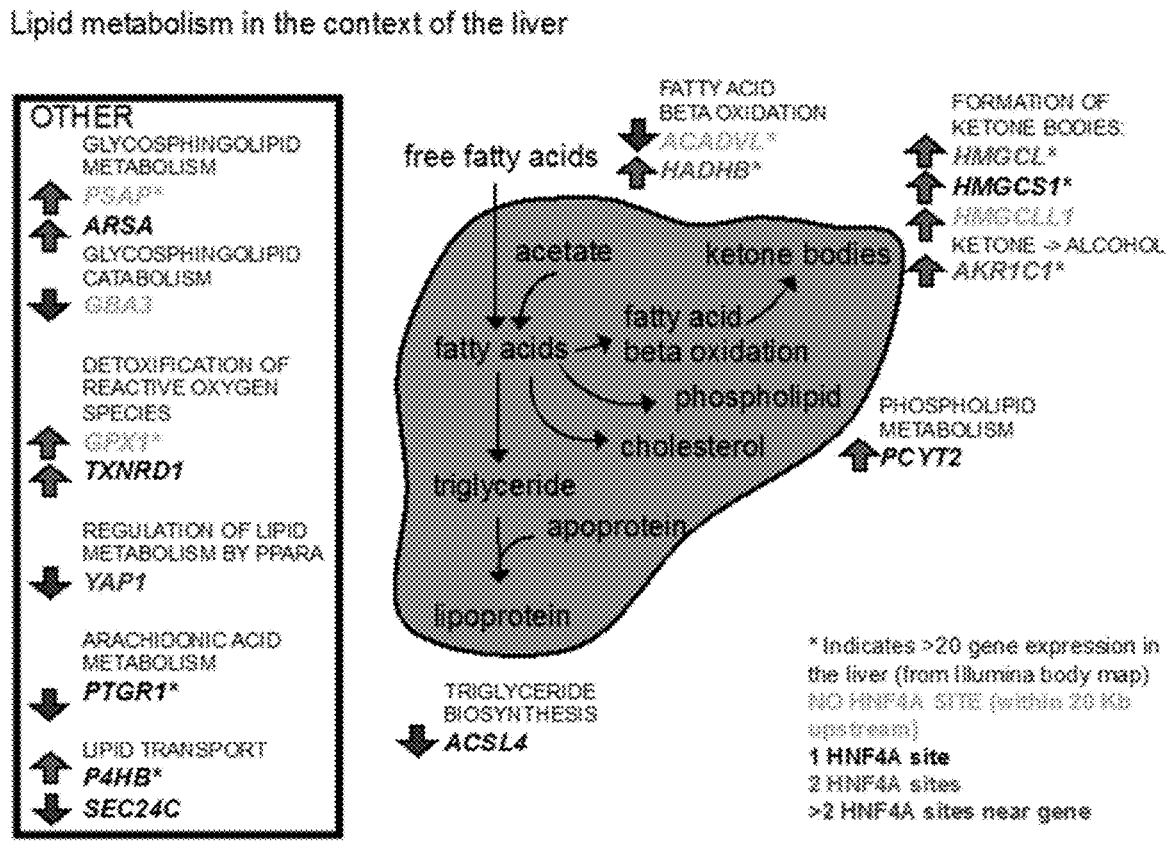

As shown in FIG. 16B, genes showing significant increase or decreases in expression in HNF4A-saRNA treated cells lines are depicted in the context of lipid metabolism in the liver. "Up" arrows indicate increases, and "down" arrows indicate decreases were observed in the expression of protein products of the genes. Asterisks note genes that have levels of expression >20 in the liver (according to the Illumina Body Map), and the colour of the gene names corresponding with the presence of HNF4a binding sites upstream of the gene.

Figure 17A:
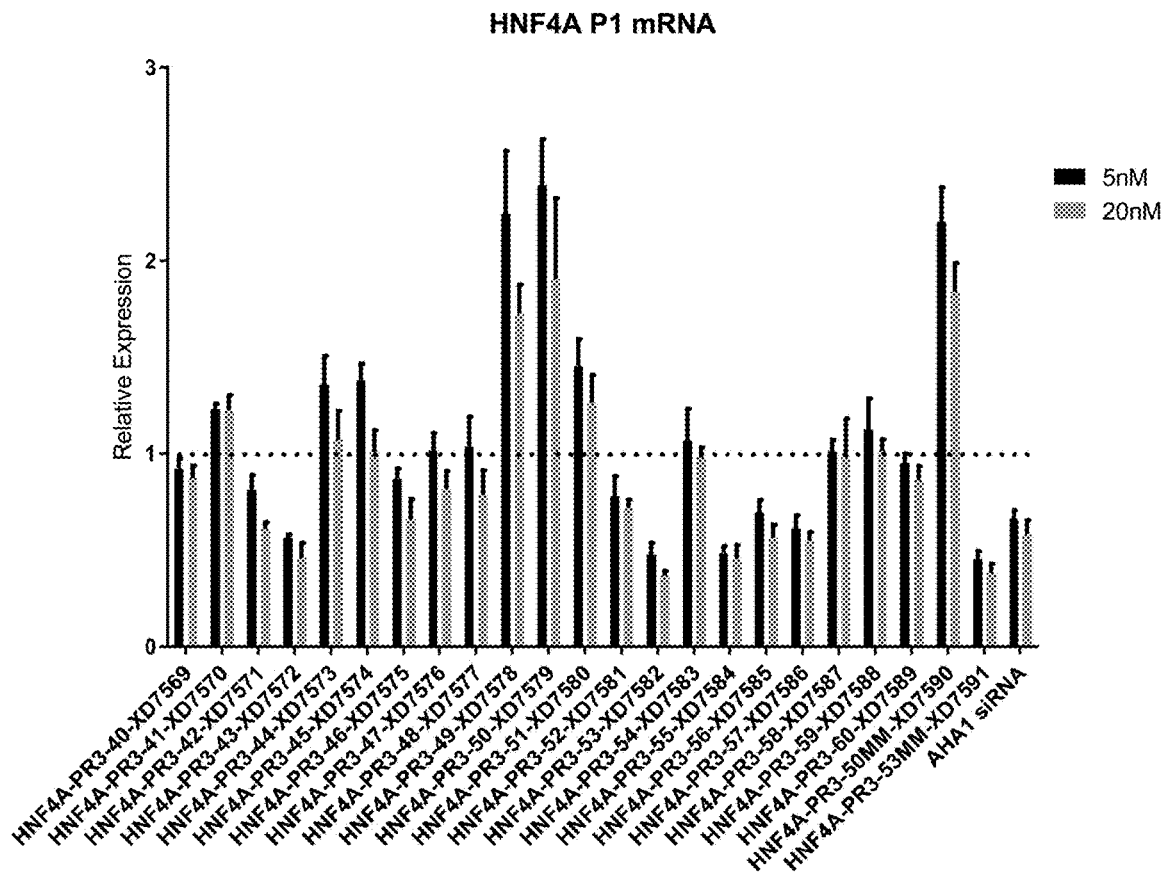
Figure 17B:
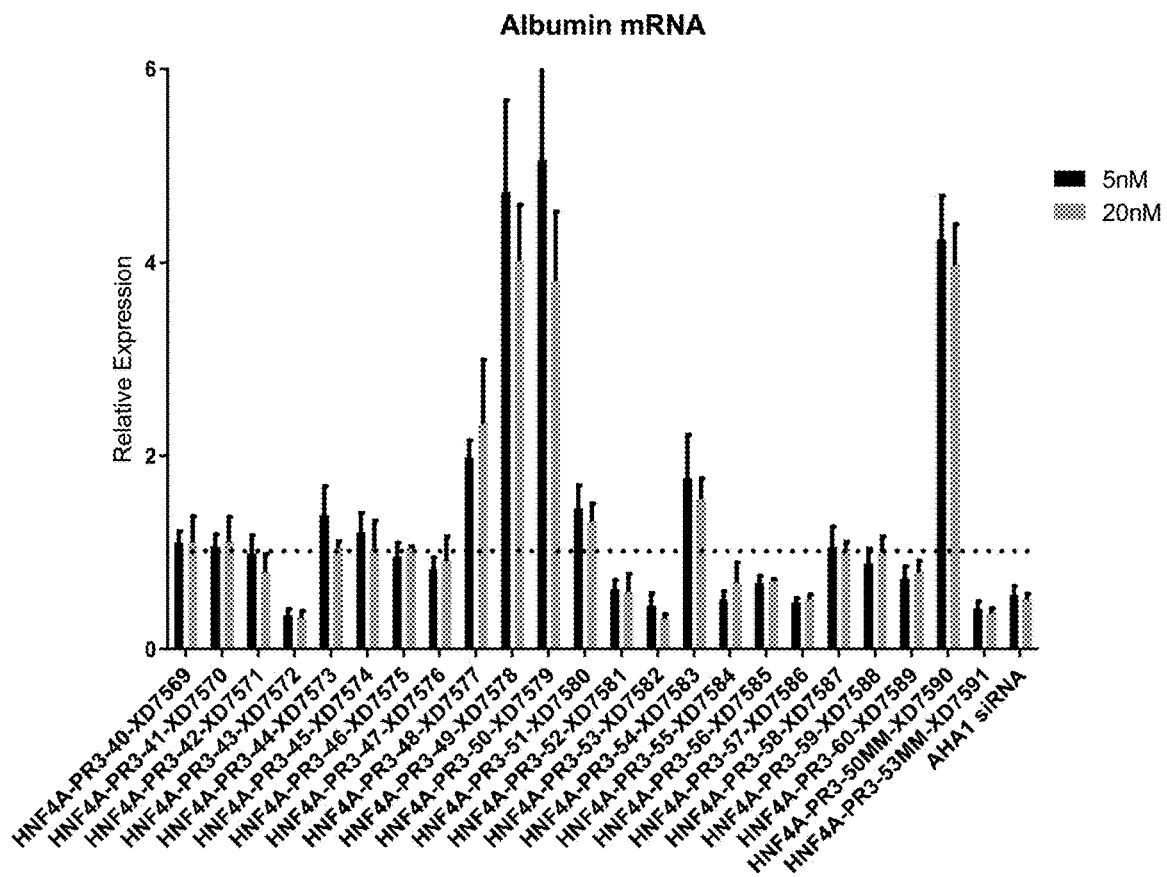

FIG. 17A shows HNF4a P1 mRNA changes in cells transfected with HNF4a-saRNAs. FIG. 17B shows albumin mRNA changes in cells transfected with HNF4a-saRNAs.

Figure 18A:
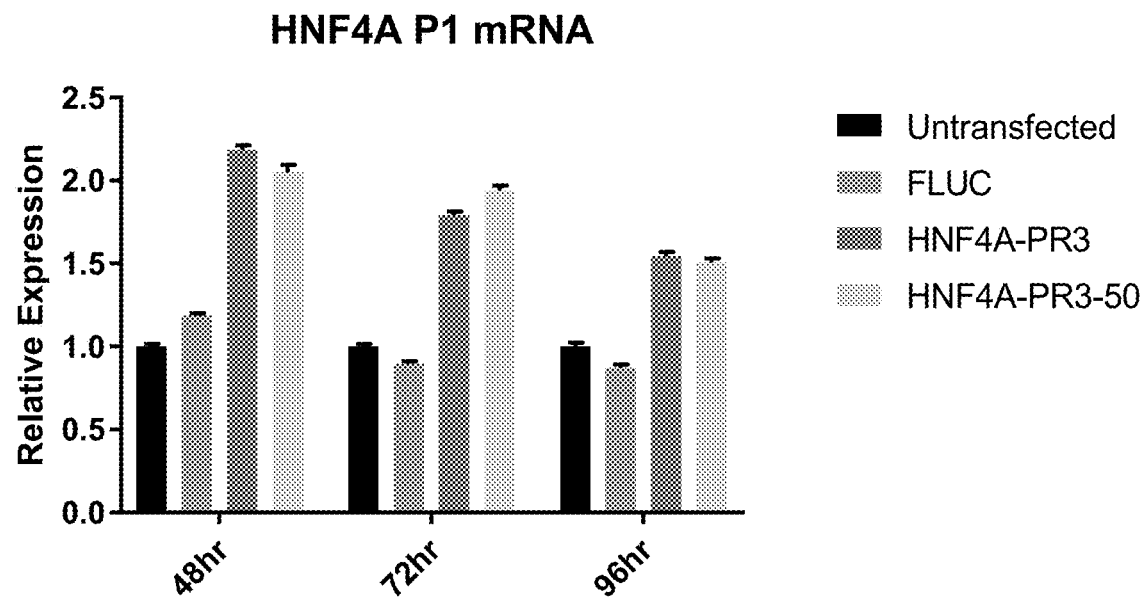
Figure 18B:
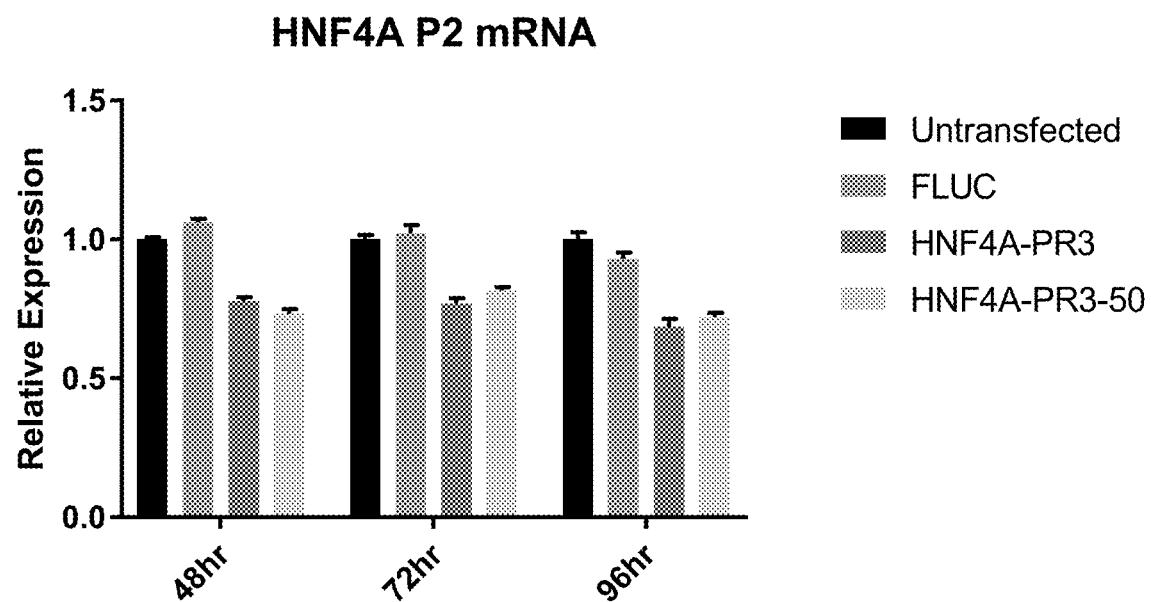
Figure 18C:
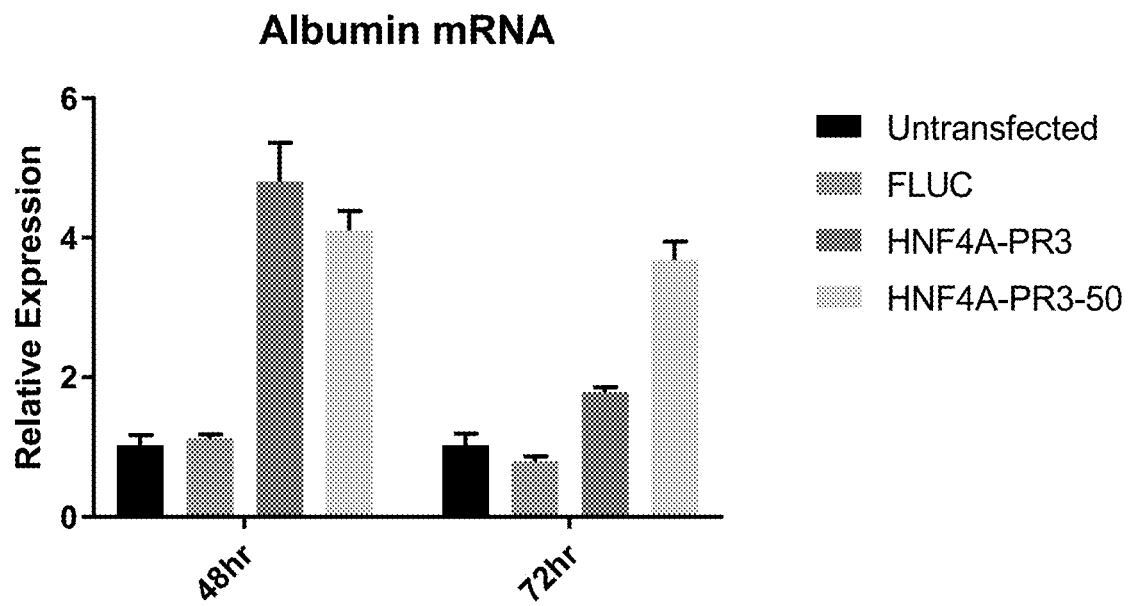

FIG. 18A shows HNF4a P1 mRNA levels are increased in cells transfected with PR3 or PR3-50. FIG. 18B shows HNF4a P2 mRNA levels are not increased in cells transfected with PR3 or PR3-50. FIG. 18C shows albumin mRNA levels are increased in cells transfected with PR3 or PR3-50.

Figure 19A:
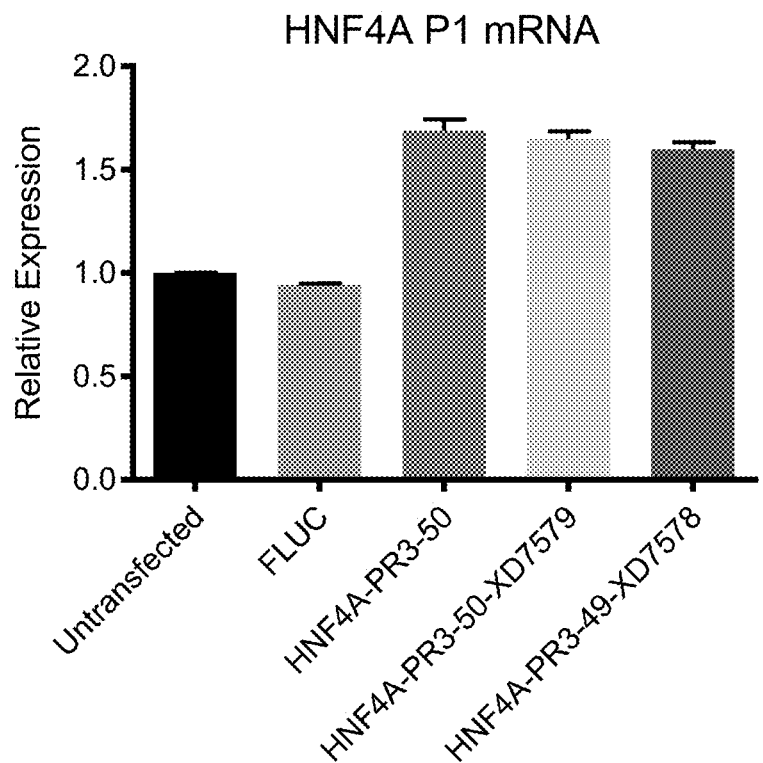
Figure 19B:
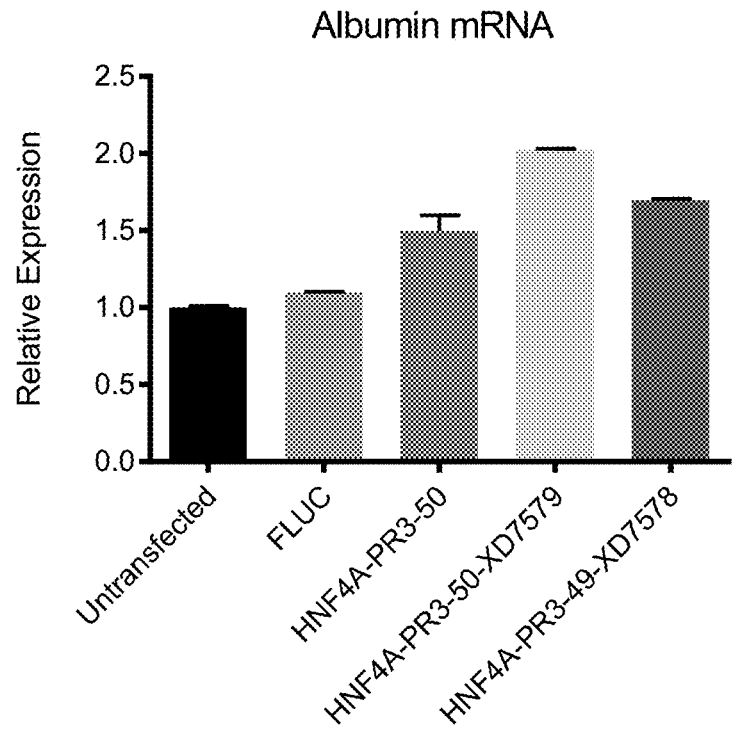

FIG. 19A shows HNF4a P1 mRNA levels are increased in cynomolgus monkey hepatocytes transfected with HNF4a-saRNAs. FIG. 19B shows albumin mRNA levels are increased in cynomolgus monkey hepatocytes transfected with HNF4a-saRNAs.

Figure 20A:
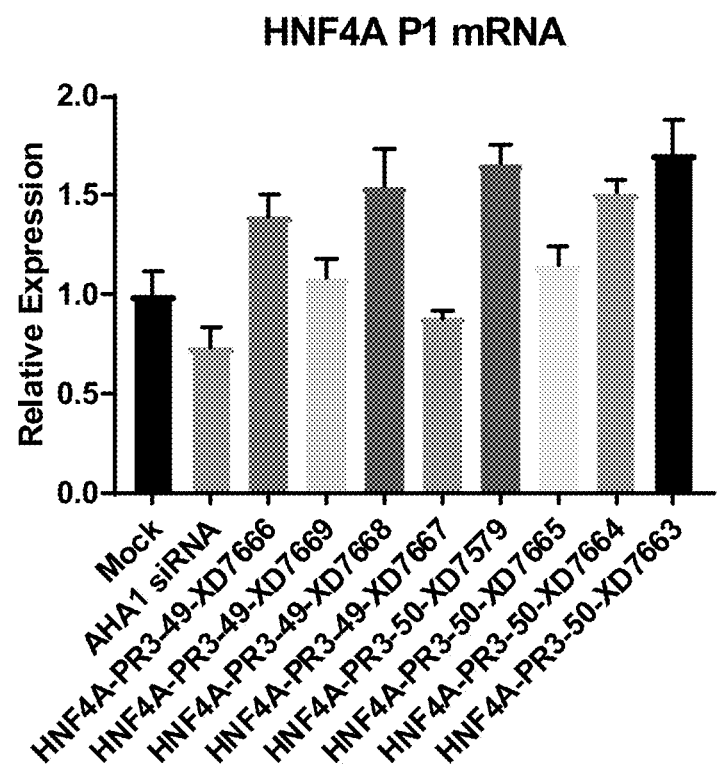
Figure 20B:
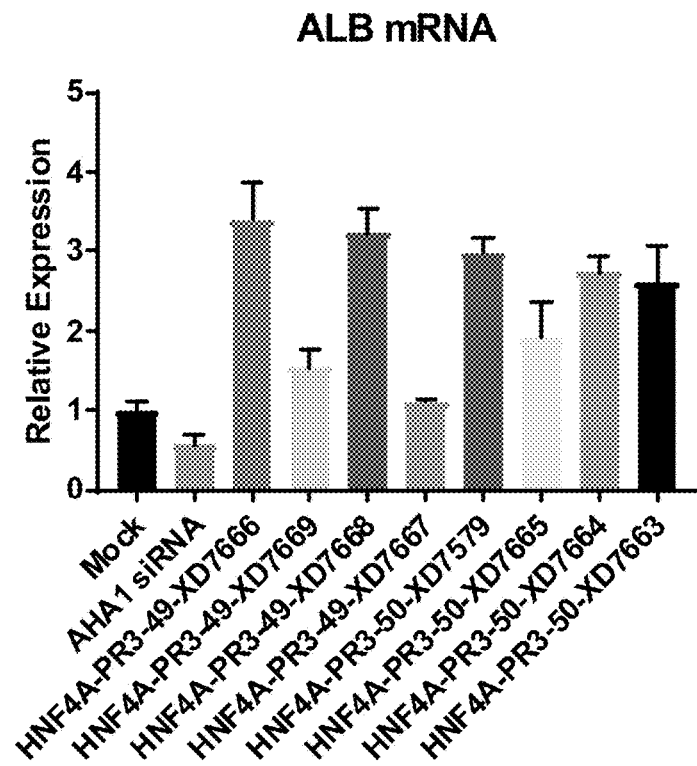
Figure 20C:
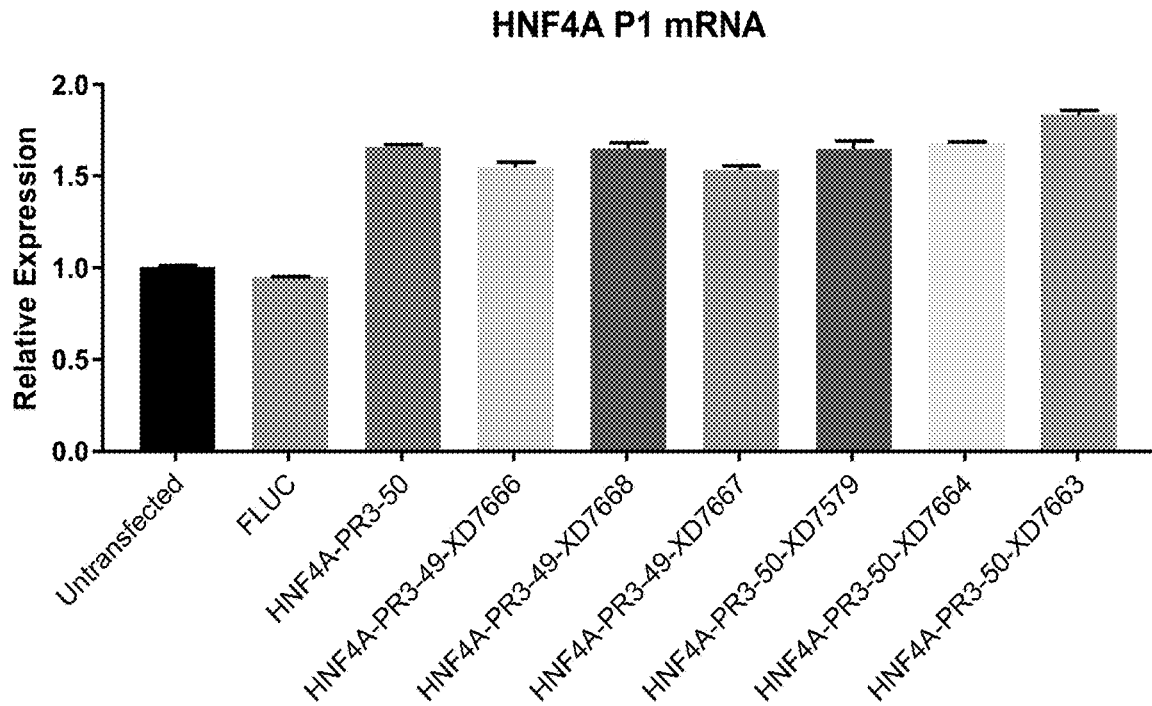

FIG. 20A and FIG. 20B show the results of a bDNA assay. HNF4a P1 mRNA and albumin mRNA changes were measured in HepG2 cells transfected with 50 nM PR3-49-XD7666, PR3-49-XD7669, PR3-49-XD7668, PR3-49-XD7667, PR3-50-XD7579, PR3-50-XD7665, PR3-50-XD7664, and PR3-50-XD7663 48 hours after seeding. FIG. 20C shows HNF4a P1 mRNA levels are increased in HepG2 cells transfected with PR3-50, PR3-50-XD7579, PR3-49-XD7666, PR3-50-XD7663, PR3-49-XD7667, PR3-50-XD7664 and PR3-49-XD7668.

Figure 21A:
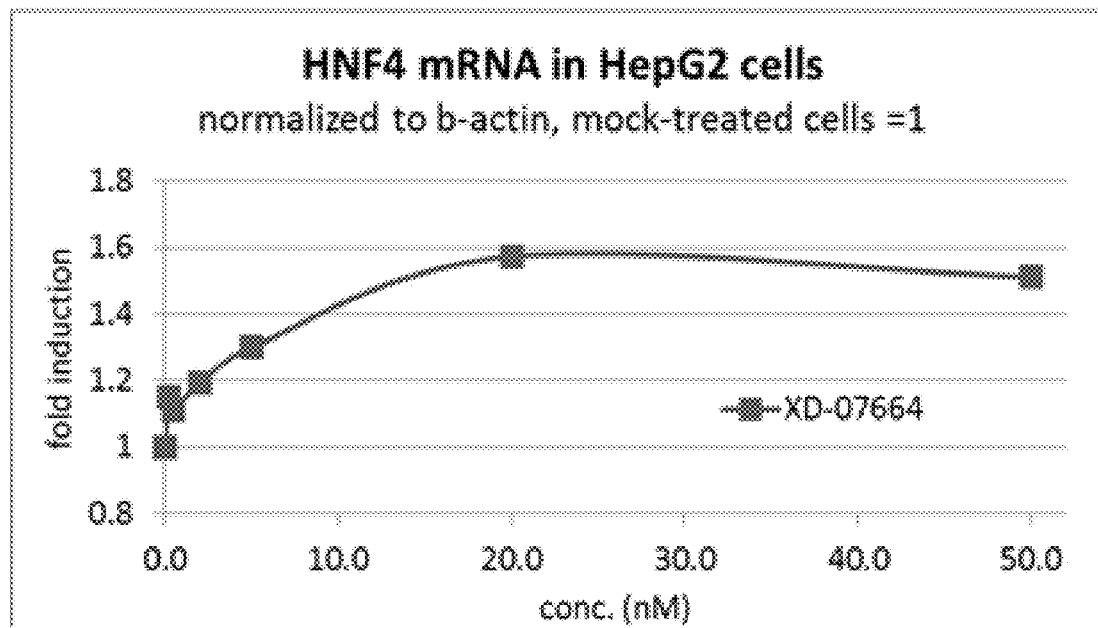
Figure 21B:
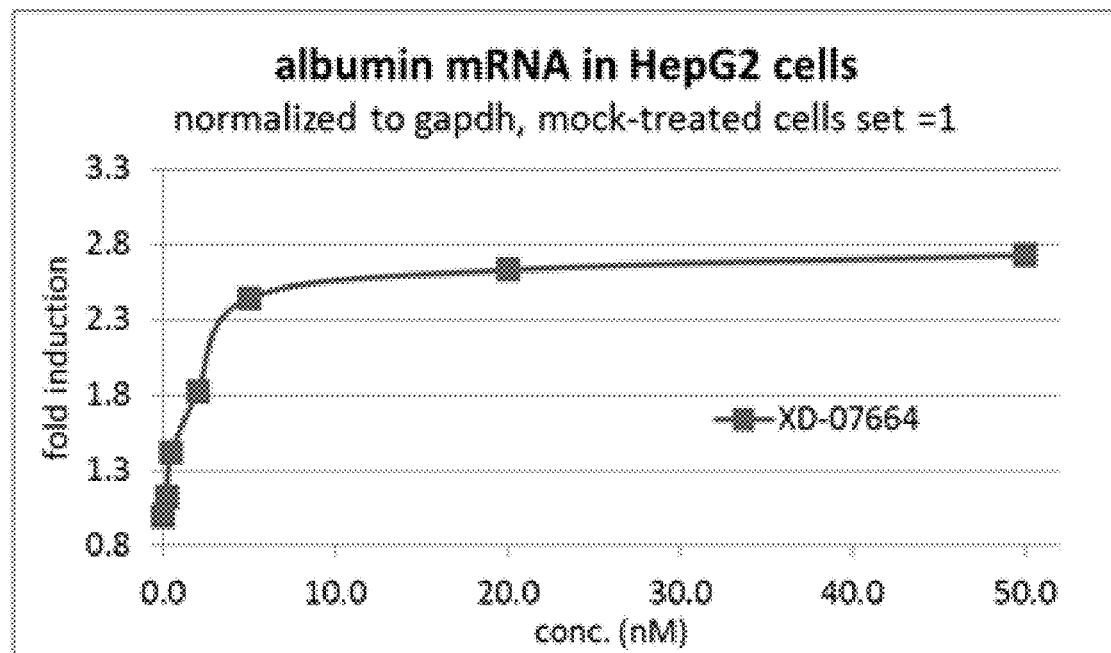

FIG. 21A-21B show gene induction efficacy of XD-07664 analyzed by dose-response experiments in HepG2 cells. FIG. 21A shows HNF4a mRNA fold changes. FIG. 21B shows albumin mRNA fold changes.

Figure 22:
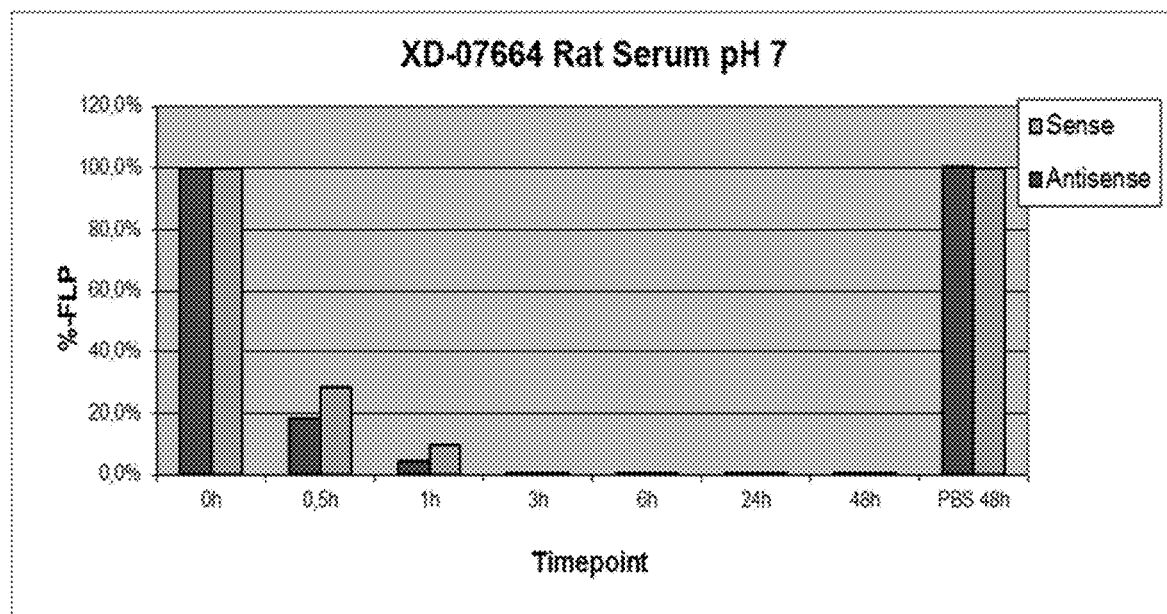

FIG. 22 shows results from stability studies of XD-07664 in neutral rat plasma.

Figure 23:
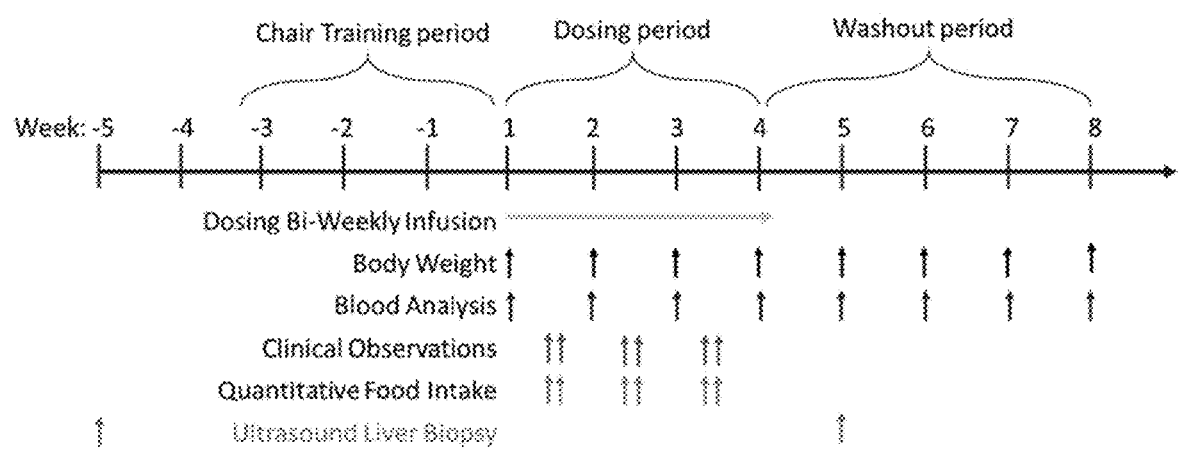

FIG. 23 shows the protocol to study the activity of PR3 formulated in NOV340 SMARTICLES® in dysmetabolic cynomolgus monkeys.

Figure 24A:
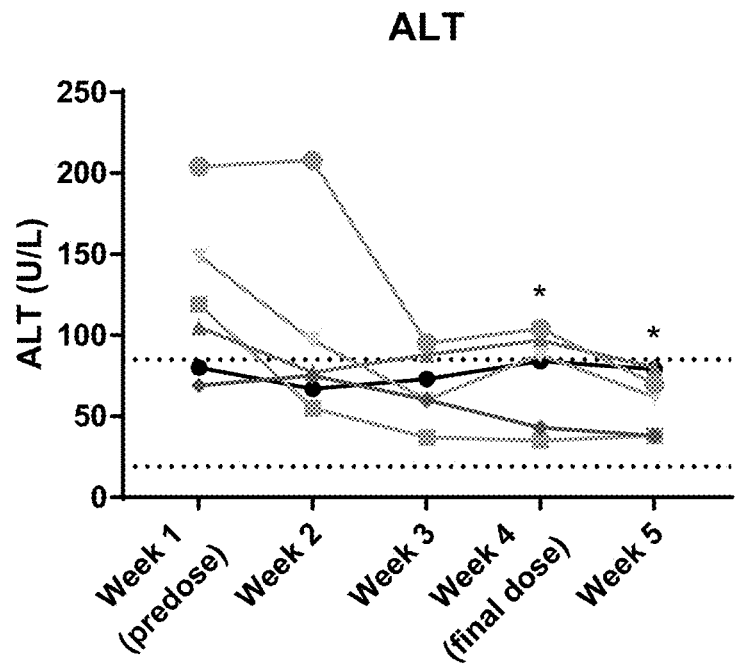
Figure 24B:
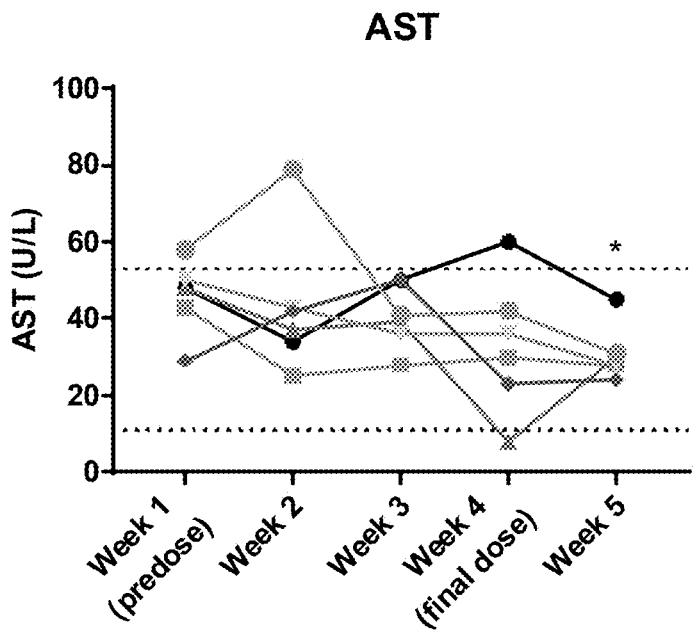
Figure 24C:
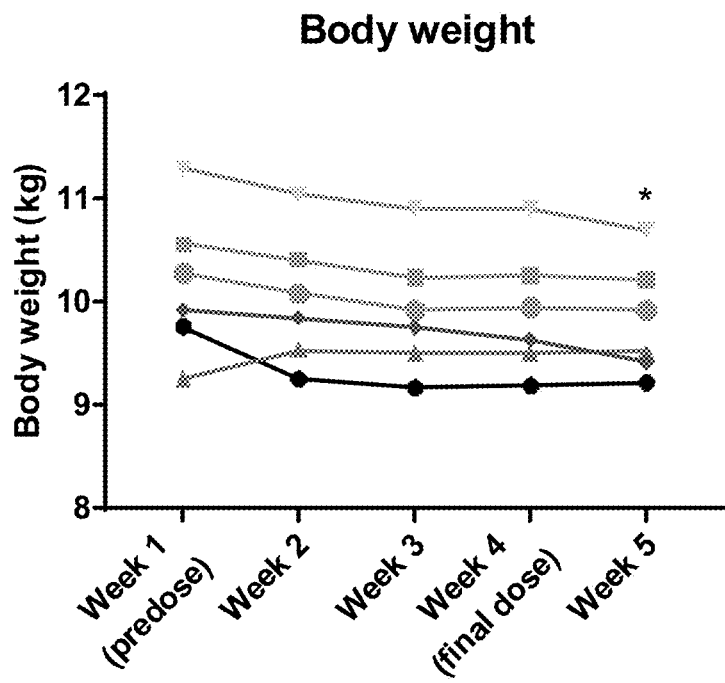
Figure 24D:
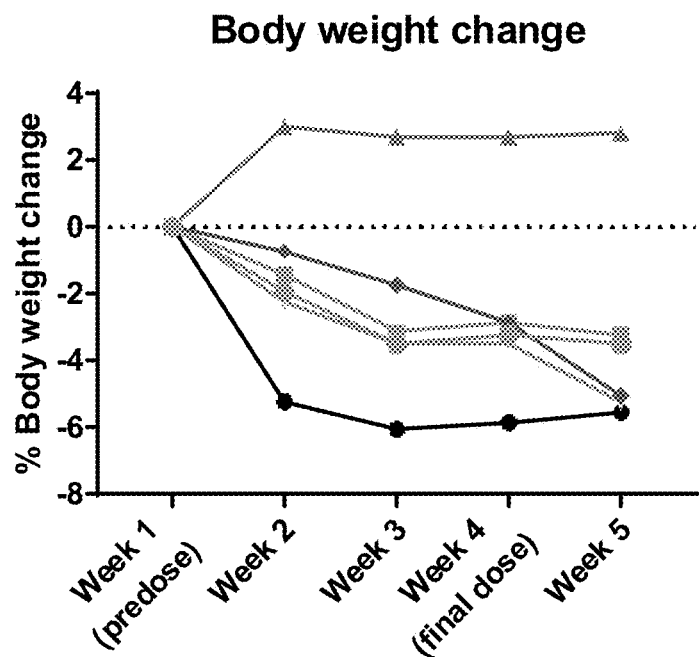

FIG. 24A-FIG. 24D shows liver enzyme levels and body weight changes of dysmetabolic cynomolgus monkeys after 4 weeks of dosing. FIG. 24A: ALT levels; FIG. 24B: AST levels; FIG. 24C: body weights; and FIG. 24D: body weight changes.

DETAILED DESCRIPTION

The present invention provides compositions, methods and kits for modulating HNF4a gene expression and/or function for therapeutic purposes. These compositions, methods and kits comprise nucleic acid constructs that target an HNF4a transcript.

HNF4a protein is known as a critical nuclear transcription factor. Modulating HNF4a gene has great potentials for therapeutic purposes. The present invention addresses this need by providing nucleic acid constructs targeting an HNF4a transcript, wherein the nucleic acid constructs may include single or double stranded DNA or RNA with or without modifications.

HNF4a gene as used herein is a double-stranded DNA comprising a coding strand and a template strand. It may also be referred to the target gene in the present application.

The terms "HNF4a transcript", "HNF4a target transcript" or "target transcript" in the context may be HNF4a mRNA encoding HNF4a protein. HNF4a mRNA is transcribed from the template strand of HNF4a gene and may exist in the mitochondria.

The antisense RNA of the HNF4a gene transcribed from the coding strand of the HNF4a gene is called a target antisense RNA transcript herein after. The target antisense RNA transcript may be a long non-coding antisense RNA transcript.

The terms "small activating RNA", "short activating RNA", or "saRNA" in the context of the present invention means a single-stranded or double-stranded RNA that upregulates or has a positive effect on the expression of a specific gene. The saRNA may be single-stranded of 14 to 30 nucleotides. The saRNA may also be double-stranded, each strand comprising 14 to 30 nucleotides. The gene is called the target gene of the saRNA. A saRNA that upregulates the expression of the HNF4a gene is called an "HNF4a-saRNA" and the HNF4a gene is the target gene of the HNF4a-saRNA.

In one embodiment, HNF4a-saRNA targeting an HNF4a target antisense RNA transcript upregulates HNF4a gene expression and/or function.

The terms "target" or "targeting" in the context mean having an effect on an HNF4a gene. The effect may be direct or indirect. Direct effect may be caused by complete or partial hybridization with the HNF4a target antisense RNA transcript. Indirect effect may be upstream or downstream.

HNF4a-saRNA may have a downstream effect on a biological process or activity. In such embodiments, HNF4a-saRNA may have an effect (either upregulating or downregulating) on a second, non-target transcript.

The term "gene expression" in the context may include the transcription step of generating HNF4a mRNA from HNF4a gene or the translation step generating HNF4a protein from HNF4a mRNA. An increase of HNF4a mRNA and an increase of HNF4a protein both indicate an increase or a positive effect of HNF4a gene expression.

By "upregulation" or "activation" of a gene is meant an increase in the level of expression of a gene, or levels of the polypeptide(s) encoded by a gene or the activity thereof, or levels of the RNA transcript(s) transcribed from the template strand of a gene above that observed in the absence of the saRNA of the present invention. The saRNA of the present invention may have a direct or indirect upregulating effect on the expression of the target gene.

I. Composition of the Invention

One aspect of the present invention provides pharmaceutical compositions comprising a saRNA that upregulates HNF4a gene, and at least one pharmaceutically acceptable carrier. Such a saRNA is referred herein after as "HNF4a-saRNA", or "saRNA of the present invention", used interchangeably in this application.

saRNA Design

HNF4a-saRNA upregulates HNF4a gene. In one embodiment, it is designed to be complementary to a target antisense RNA transcript of HNF4a gene, and it may exert its effect on HNF4a gene expression and/or function by downregulating the target antisense RNA transcript.

The term "complementary to" in the context means being able to hybridize with the target antisense RNA transcript under stringent conditions.

The term "sense" when used to describe a nucleic acid sequence in the context of the present invention means that the sequence has identity to a sequence on the coding strand of a gene. The term "antisense" when used to describe a nucleic acid sequence in the context of the present invention means that the sequence is complementary to a sequence on the coding strand of a gene.

It is to be understood that thymidine of the DNA is replaced by uridine in RNA and that this difference does not alter the understanding of the terms "antisense" or "complementarity".

The target antisense RNA transcript may be transcribed from a locus on the coding strand between up to 100, 80, 60, 40, 20 or 10 kb upstream of a location corresponding to the target gene's transcription start site (TSS) and up to 100, 80, 60, 40, 20 or 10 kb downstream of a location corresponding to the target gene's transcription stop site.

In one embodiment, the target antisense RNA transcript is transcribed from a locus on the coding strand located within +/−1 kb of the target gene's transcription start site.

In another embodiment, the target antisense RNA transcript is transcribed from a locus on the coding strand located within +/−500, +/−250 or +/−100 of the target gene's transcription start site.

In another embodiment, the target antisense RNA transcript is transcribed from a locus on the coding strand located +/−2000 nucleotides of the target gene's transcription start site.

In another embodiment, the locus on the coding strand is no more than 1000 nucleotides upstream or downstream from a location corresponding to the target gene's transcription start site.

In another embodiment, the locus on the coding strand is no more than 500 nucleotides upstream or downstream from a location corresponding to the target gene's transcription start site.

The term "transcription start site" (TSS) as used herein means a nucleotide on the template strand of a gene corresponding to or marking the location of the start of transcription. The TSS may be located within the promoter region on the template strand of the gene.

The term "transcription stop site" as used herein means a region, which can be one or more nucleotides, on the template strand of a gene, which has at least one feature such as, but not limited to, a region which encodes at least one stop codon of the target transcript, a region encoding a sequence preceding the 3'UTR of the target transcript, a region where the RNA polymerase releases the gene, a region encoding a splice site or an area before a splice site and a region on the template strand where transcription of the target transcript terminates.

The phrase "is transcribed from a particular locus" in the context of the target antisense RNA transcript of the invention means the transcription of the target antisense RNA transcript starts at the particular locus.

The target antisense RNA transcript is complementary to the coding strand of the genomic sequence of the target gene, and any reference herein to "genomic sequence" is shorthand for "coding strand of the genomic sequence".

The "coding strand" of a gene has the same base sequence as the mRNA produced, except T is replayed by U in the mRNA. The "template strand" of a gene is therefore complementary and antiparallel to the mRNA produced.

Thus, the target antisense RNA transcript may comprise a sequence which is complementary to a genomic sequence located between 100, 80, 60, 40, 20 or 10 kb upstream of the target gene's transcription start site and 100, 80, 60, 40, 20 or 10 kb downstream of the target gene's transcription stop site.

In one embodiment, the target antisense RNA transcript comprises a sequence which is complementary to a genomic sequence located between 1 kb upstream of the target gene's transcription start site and 1 kb downstream of the target gene's transcription stop site.

In another embodiment, the target antisense RNA transcript comprises a sequence which is complementary to a genomic sequence located between 500, 250 or 100 nucleotides upstream of the target gene's transcription start site and ending 500, 250 or 100 nucleotides downstream of the target gene's transcription stop site.

The target antisense RNA transcript may comprise a sequence which is complementary to a genomic sequence which includes the coding region of the HNF4a gene. The target antisense RNA transcript may comprise a sequence which is complementary to a genomic sequence that aligns with the target gene's promoter region on the template strand. Genes may possess a plurality of promoter regions, in which case the target antisense RNA transcript may align with one, two or more of the promoter regions. An online database of annotated gene loci may be used to identify the promoter regions of genes. The terms 'align' and 'alignment' when used in the context of a pair of nucleotide sequences mean the pair of nucleotide sequences are complementary to each other or have sequence identity with each other.

The region of alignment between the target antisense RNA transcript and the promoter region of the target gene may be partial and may be as short as a single nucleotide in length, although it may be at least 15 or at least 20 nucleotides in length, or at least 25 nucleotides in length, or at least 30, 35, 40, 45 or 50 nucleotides in length, or at least 55, 60, 65, 70 or 75 nucleotides in length, or at least 100 nucleotides in length. Each of the following specific arrangements is intended to fall within the scope of the term "alignment":

a) The target antisense RNA transcript and the target gene's promoter region are identical in length and they align (i.e. they align over their entire lengths).

b) The target antisense RNA transcript is shorter than the target gene's promoter region and aligns over its entire length with the target gene's promoter region (i.e. it aligns over its entire length to a sequence within the target gene's promoter region).

c) The target antisense RNA transcript is longer than the target gene's promoter region and the target gene's promoter region is aligned fully by it (i.e. the target gene's promoter region is aligns over its entire length to a sequence within the target antisense RNA transcript).

d) The target antisense RNA transcript and the target gene's promoter region are of the same or different lengths and the region of alignment is shorter than both the length of the target antisense RNA transcript and the length of the target gene's promoter region.

The above definition of "align" and "alignment" applies mutatis mutandis to the description of other overlapping, e.g., aligned sequences throughout the description. Clearly, if a target antisense RNA transcript is described as aligning with a region of the target gene other than the promoter region then the sequence of the target antisense RNA transcript aligns with a sequence within the noted region rather than within the promoter region of the target gene.

In one embodiment, the target antisense RNA transcript is at least 1 kb, or at least 2, 3, 4, 5, 6, 7, 8, 9 or 10, e.g., 20, 25, 30, 35 or 40 kb long.

In one embodiment, the target antisense RNA transcript comprises a sequence which is at least 75%, or at least 85%, or at least 90%, or at least 95% complementary along its full length to a sequence on the coding strand of the target gene.

The present invention provides saRNAs having a high degree of complementarity to a region within the target antisense RNA transcript. The saRNA will have no more than 5, or no more than 4 or 3, or no more than 2, or no more than 1, or no mismatches with the region within the target antisense RNA transcript to be targeted. In some embodiments, the saRNA down-regulates the target antisense RNA transcript. In some embodiments, the saRNA does not down-regulate the target antisense RNA transcript.

Figure 1:
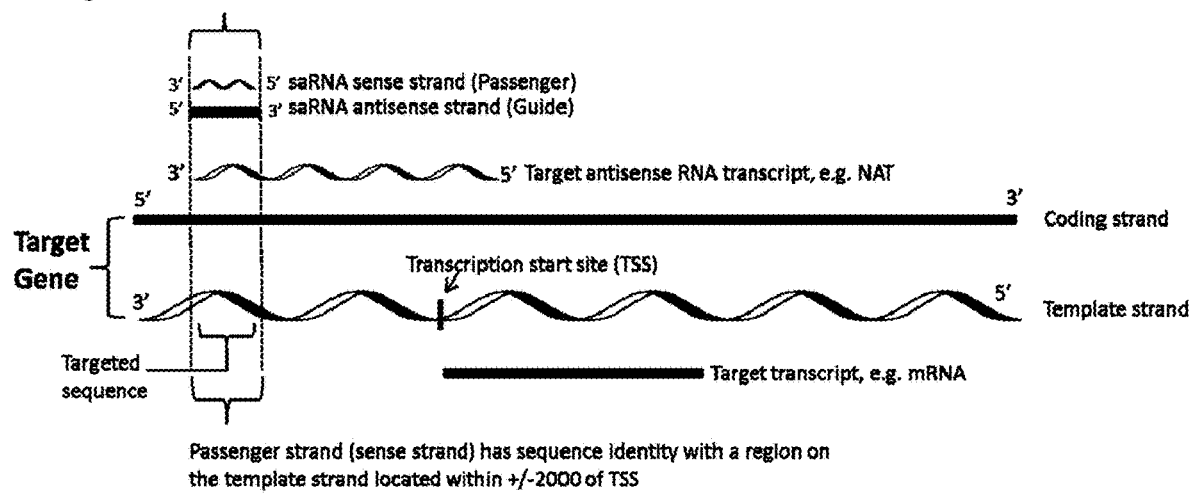
FIG. 1 is a schematic illustrating the relationships among the nucleic acid moieties involved in the function of saRNAs of the invention.

Referring to FIG. 1, as the target antisense RNA transcript has sequence identity with a region of the template strand of the target gene, the target antisense RNA transcript will be in part identical to a region within the template strand of the target gene allowing reference to be made either to the template strand of the gene or to a target antisense RNA transcript. The location at which the saRNA hybridizes or binds to the target antisense RNA transcript (and hence the same location on the template strand) is referred to as the "targeted sequence" or "target site". Not willing to be bound to any theory, the mechanism may be the following: saRNA in the presence AGO2 binds at the target site, leads to recruitment of RNA polymerase II and generation of an RNA induced transcriptional activation (RITA) complex, and then leads to new mRNA transcription as detailed in Li et al, *Cell Research* 26(3) 320-35 (2016), the contents of which are incorporated herein by reference in their entirety. The down-regulation of the target antisense RNA transcript is not required in the saRNA mechanism.

The antisense strand of the saRNA (whether single- or double-stranded) may be at least 80%, 90%, 95%, 98%, 99% or 100% identical with the reverse complement of the targeted sequence. Thus, the reverse complement of the antisense strand of the saRNA has a high degree of sequence identity with the targeted sequence. The targeted sequence may have the same length, i.e., the same number of nucleotides, as the saRNA and/or the reverse complement of the saRNA.

In some embodiments, the targeted sequence comprises at least 14 and less than 30 nucleotides.

In some embodiments, the targeted sequence has 19, 20, 21, 22, or 23 nucleotides.

In some embodiments, the location of the targeted sequence is situated within a promoter area of the template strand.

In some embodiments, the targeted sequence is located within a TSS (transcription start site) core of the template stand. A "TSS core" or "TSS core sequence" as used herein, refers to a region between 2000 nucleotides upstream and 2000 nucleotides downstream of the TSS (transcription start site). Therefore, the TSS core comprises 4001 nucleotides and the TSS is located at position 2001 from the 5' end of the TSS core sequence.

The HNF4a target gene has two transcription start sites from two promoters: the P1 promoter TSS is located 45455 nucleotides downstream of the P2 promoter TSS. The P1 promoter TSS core has a sequence of SEQ ID No. 1. The P2 promoter TSS core has a sequence of SEQ ID No. 2. HNF4a TSS core sequences are shown in the table below:

| Target Gene | Target transcript REF. ID No. | Protein encoded by target transcript | Nature of target transcript | Transcript TSS location | SEQ ID of TSS core |
|---|---|---|---|---|---|
| HNF4A | NM_000457 | NP_000448 | Coding | chr20: 44401255 plus strand | 1 |
| HNF4A | NM_001030003 | NP_001025174 | Coding | chr20: 44355800 plus strand | 2 |
| HNF4A | NM_001030004 | NP_001025175 | Coding | chr20: 44355800 plus strand | 2 |

| Target Gene | Target transcript REF. ID No. | Protein encoded by target transcript | Nature of target transcript | Transcript TSS location | SEQ ID of TSS core |
|---|---|---|---|---|---|
| HNF4A | NM_001258355 | NP_001245284 | Coding | chr20: 44401255 plus strand | 1 |
| HNF4A | NM_001287182 | NP_001274111 | Coding | chr20: 44355800 plus strand | 2 |
| HNF4A | NM_001287183 | NP_001274112 | Coding | chr20: 44355800 plus strand | 2 |
| HNF4A | NM_001287184 | NP_001274113 | Coding | chr20: 44355800 plus strand | 2 |
| HNF4A | NM_175914 | NP_787110 | Coding | chr20: 44355800 plus strand | 2 |
| HNF4A | NM_178849 | NP_849180 | Coding | chr20: 44401255 plus strand | 1 |
| HNF4A | NM_178850 | NP_849181 | Coding | chr20: 44401255 plus strand | 1 |

In some embodiments, the targeted sequence is located between 1000 nucleotides upstream and 1000 nucleotides downstream of the TSS.

In some embodiments, the targeted sequence is located between 500 nucleotides upstream and 500 nucleotides downstream of the TSS.

In some embodiments, the targeted sequence is located between 250 nucleotides upstream and 250 nucleotides downstream of the TSS.

In some embodiments, the targeted sequence is located between 100 nucleotides upstream and 100 nucleotides downstream of the TSS.

In some embodiments, the targeted sequence is located upstream of the TSS in the TSS core. The targeted sequence may be less than 2000, less than 1000, less than 500, less than 250, or less than 100 nucleotides upstream of the TSS.

In some embodiments, the targeted sequence is located downstream of the TSS in the TSS core. The targeted sequence may be less than 2000, less than 1000, less than 500, less than 250, or less than 100 nucleotides downstream of the TSS.

In some embodiments, the targeted sequence is located +/−50 nucleotides surrounding the TSS of the TSS core. In some embodiments, the targeted sequence substantially overlaps the TSS of the TSS core. In some embodiments, the targeted sequence overlap begins or ends at the TSS of the TSS core. In some embodiments, the targeted sequence overlaps the TSS of the TSS core by 1, 2, 3, 4, 5, 6, 7, 8, 9, 10, 11, 12, 13, 14, 15, 16, 17, 18 or 19 nucleotides in either the upstream or downstream direction.

The location of the targeted sequence on the template strand is defined by the location of the 5' end of the targeted sequence. The 5' end of the targeted sequence may be at any position of the TSS core and the targeted sequence may start at any position selected from position 1 to position 4001 of the TSS core. For reference herein, when the 5' most end of the targeted sequence from position 1 to position 2000 of the TSS core, the targeted sequence is considered upstream of the TSS and when the 5' most end of the targeted sequence is from position 2002 to 4001, the targeted sequence is considered downstream of the TSS. When the 5' most end of the targeted sequence is at nucleotide 2001, the targeted sequence is considered to be a TSS centric sequence and is neither upstream nor downstream of the TSS.

For further reference, for example, when the 5' end of the targeted sequence is at position 1600 of the TSS core, i.e., it is the 1600$^{th}$ nucleotide of the TSS core, the targeted sequence starts at position 1600 of the TSS core and is considered to be upstream of the TSS.

In one embodiment, the saRNA of the present invention may have two strands that form a duplex, one strand being a guide strand. The saRNA duplex is also called a double-stranded saRNA. A double-stranded saRNA or saRNA duplex, as used herein, is a saRNA that includes more than one, and preferably, two, strands in which interstrand hybridization can form a region of duplex structure. The two strands of a double-stranded saRNA are referred to as an antisense strand or a guide strand, and a sense strand or a passenger strand.

The antisense strand of a saRNA duplex, used interchangeably with antisense strand saRNA or antisense saRNA, has a high degree of complementarity to a region within the target antisense RNA transcript. The antisense strand may have no more than 5, or no more than 4 or 3, or no more than 2, or no more than 1, or no mismatches with the region within the target antisense RNA transcript or targeted sequence. Therefore, the antisense strand has a high degree of complementary to the targeted sequence on the template strand. The sense strand of the saRNA duplex, used interchangeably with sense strand saRNA or sense saRNA, has a high degree of sequence identity with the targeted sequence on the template strand. In some embodiments, the targeted sequence is located within the promoter area of the template strand. In some embodiments, the targeted sequence is located within the TSS core of the template stand.

The location of the antisense strand and/or sense strand of the saRNA duplex, relative to the targeted sequence is defined by making reference to the TSS core sequence. For example, when the targeted sequence is downstream of the TSS, the antisense saRNA and the sense saRNA start downstream of the TSS. In another example, when the targeted sequence starts at position 200 of the TSS core, the antisense saRNA and the sense saRNA start upstream of the TSS.

The relationships among the saRNAs, a target gene, a coding strand of the target gene, a template strand of the target gene, a target antisense RNA transcript, a target transcript, a targeted sequence/target site, and the TSS are shown in FIG. 1.

A "strand" in the context of the present invention means a contiguous sequence of nucleotides, including non-naturally occurring or modified nucleotides. Two or more strands may be, or each form a part of, separate molecules, or they may be connected covalently, e.g., by a linker such as a polyethyleneglycol linker. At least one strand of a saRNA may comprise a region that is complementary to a target antisense RNA. Such a strand is called an antisense or guide strand of the saRNA duplex. A second strand of a saRNA that comprises a region complementary to the antisense strand of the saRNA is called a sense or passenger strand.

A saRNA duplex may also be formed from a single molecule that is at least partly self-complementary forming a hairpin structure, including a duplex region. In such case, the term "strand" refers to one of the regions of the saRNA that is complementary to another internal region of the saRNA. The guide strand of the saRNA will have no more than 5, or no more than 4 or 3, or no more than 2, or no more than 1, or no mismatches with the sequence within the target antisense RNA transcript.

In some embodiments, the passenger strand of a saRNA may comprise at least one nucleotide that is not complementary to the corresponding nucleotide on the guide strand, called a mismatch with the guide strand. The mismatch with the guide strand may encourage preferential loading of the guide strand (Wu et al., *PLoS ONE*, vol. 6(12):e28580 (2011), the contents of which are incorporated herein by reference in their entirety). In one embodiment, the at least one mismatch with the guide strand may be at 3' end of the passenger strand. In one embodiment, the 3' end of the passenger strand may comprise 1-5 mismatches with the guide strand. In one embodiment, the 3' end of the passenger strand may comprise 2-3 mismatches with the guide strand. In one embodiment, the 3' end of the passenger strand may comprise 6-10 mismatches with the guide strand.

In one embodiment, an saRNA duplex may show efficacy in proliferating cells

A saRNA duplex may have siRNA-like complementarity to a region of a target antisense RNA transcript; that is, 100% complementarity between nucleotides 2-6 from the 5' end of the guide strand in the saRNA duplex and a region of the target antisense RNA transcript. Other nucleotides of the saRNA may, in addition, have at least 80%, 90%, 95%, 98%, 99% or 100% complementarity to a region of the target antisense RNA transcript. For example, nucleotides 7 (counted from the 5' end) until the 3' end of the saRNA may have least 80%, 90%, 95%, 98%, 99% or 100% complementarity to a region of the target antisense RNA transcript.

The terms "small interfering RNA" or "siRNA" in the context mean a double-stranded RNA typically 20-25 nucleotides long involved in the RNA interference (RNAi) pathway and interfering with or inhibiting the expression of a specific gene. The gene is the target gene of the siRNA. For example, siRNA that interferes the expression of APOA1 gene is called "APOA1-siRNA" and the APOA1 gene is the target gene. siRNA is usually about 21 nucleotides long, with 3' overhangs (e.g., 2 nucleotides) at each end of the two strands.

siRNA inhibits target gene expression by binding to and promoting the cleavage of one or more RNA transcripts of the target gene at specific sequences. Typically in RNAi the RNA transcripts are mRNA, so cleavage of mRNA results in the down-regulation of gene expression. In the present invention, not willing to be bound with any theory, one of the possible mechanisms is that saRNA of the present invention may modulate the target gene expression by binding to the target antisense RNA transcript. The target antisense RNA transcript may or may not be cleaved.

A double-stranded saRNA may include one or more single-stranded nucleotide overhangs. The term "overhang" or "tail" in the context of double-stranded saRNA and siRNA refers to at least one unpaired nucleotide that protrudes from the duplex structure of saRNA or siRNA. For example, when a 3'-end of one strand of an saRNA extends beyond the 5'-end of the other strand, or vice versa, there is a nucleotide overhang. An saRNA may comprise an overhang of at least one nucleotide; alternatively, the overhang may comprise at least two nucleotides, at least three nucleotides, at least four nucleotides, at least five nucleotides or more. A nucleotide overhang may comprise of consist of a nucleotide/nucleoside analog, including a deoxynucleotide/nucleoside. The overhang(s) may be on the sense strand, the antisense strand or any combination thereof. Furthermore, the nucleotide(s) of an overhang can be present on the 5' end, 3' end or both ends of either an antisense or sense strand of an saRNA. Where two oligonucleotides are designed to form, upon hybridization, one or more single-stranded overhangs, and such overhangs shall not be regarded as mismatches with regard to the determination of complementarity. For example, an saRNA comprising one oligonucleotide 19 nucleotides in length and another oligonucleotide 21 nucleotides in length, wherein the longer oligonucleotide comprises a sequence of 19 nucleotides that is fully complementary to the shorter oligonucleotide, can yet be referred to as "fully complementary" for the purposes described herein. The overhang nucleotide may be a natural or a non-natural nucleotide. The overhang may be a modified nucleotide as defined herein.

In one embodiment, the antisense strand of a double-stranded saRNA has a 1-10 nucleotide overhang at the 3' end and/or the 5' end. In one embodiment, the antisense strand of a double-stranded saRNA has 1-4 nucleotide overhang at its 3' end, or 1-2 nucleotide overhang at its 3' end. In one embodiment, the sense strand of a double-stranded saRNA has a 1-10 nucleotide overhang at the 3' end and/or the 5' end. In one embodiment, the sense strand of a double-stranded saRNA has 1-4 nucleotide overhang at its 3' end, or 1-2 nucleotide overhang at its 3' end. In one embodiment, both the sense strand and the antisense strand of a double-stranded saRNA have 3' overhangs. The 3' overhangs may comprise one or more uracils, e.g., the sequences UU or UUU. In one embodiment, one or more of the nucleotides in the overhang is replaced with a nucleoside thiophosphate, wherein the internucleoside linkage is thiophosphate. In one embodiment, the overhang comprises one or more deoxyribonucleoside, e.g., the sequence dTdT or dTdTdT. In one embodiments, the overhang comprises the sequence dT*dT, wherein '*' is a thiophosphate internucleoside linkage (sometimes referred to as 's'). In one embodiment, the overhang comprises at least one 2'-OMe modified U (referred to as u). In one embodiment, the overhang comprises u*u (also referred to as usu). In one embodiment, the overhang comprises uu. In one embodiment, the overhang comprises an inverted nucleotide or nucleoside, which is connected to a strand with reversed linkage (3'-3' or 5'-5' linkage). For example, the overhang may comprise an inverted dT, or an inverted abasic nucleoside. An inverted abasic nucleoside does not have a base moiety.

The skilled person will appreciate that it is convenient to define the saRNA of the present invention by reference to the target antisense RNA transcript or the targeted sequence, regardless of the mechanism by which the saRNA modulates the target gene expression. However, the saRNA of the present invention may alternatively be defined by reference to the target gene. The target antisense RNA transcript is complementary to a genomic region on the coding strand of the target gene, and the saRNA of the present invention is in turn complementary to a region of the target antisense RNA transcript, so the saRNA of the present invention may be defined as having sequence identity to a region on the coding strand of the target gene. All of the features discussed herein with respect to the definition of the saRNA of the present invention by reference to the target antisense RNA transcript apply mutatis mutandis to the definition of the saRNA of the present invention by reference to the target gene so any discussion of complementarity to the target antisense RNA transcript should be understood to include identity to the genomic sequence of the target gene. Thus, the saRNA of the present invention may have a high percent identity, e.g. at least 80%, 90%, 95%, 98% or 99%, or 100% identity, to a genomic sequence on the target gene. The genomic sequence may be up to 2000, 1000, 500, 250, or 100 nucleotides upstream or downstream of the target gene's transcription start site. It may align with the target gene's promoter region. Thus, the saRNA may have sequence identity to a sequence that aligns with the promoter region of the target gene.

In one embodiment, the existence of the target antisense RNA transcript does not need to be determined to design the saRNA of the present invention. In another word, the design of the saRNA does not require the identification of the target antisense RNA transcript. For example, the nucleotide sequence of the TSS core, i.e., the sequence in the region 2000 nucleotides upstream of the target gene's transcription start site to 2000 nucleotides downstream of the target gene's transcription start may be obtained by the genomic sequence of the coding strand of the target gene, by sequencing or by searching in a database. Targeted sequence within the TSS core starting at any position from position 1 to position 4001 of the TSS core on the template strand can be selected and can then be used to design saRNA sequences. As discussed above, the saRNA has a high degree of sequence identity with the reverse complement of the targeted sequence.

The saRNA sequence's off-target hit number in the whole genome, 0 mismatch (0 mm) hit number, and 1 mismatch (1 mm) hit number are then determined. The term "off-target hit number" refers to the number of other sites in the whole genome that are identical to the saRNA's targeted sequence on the template strand of the target gene. The term "0 mm hit number" refers to the number of known protein coding transcript other than the target transcript of the saRNA, the complement of which the saRNA may hybridize with or bind to with 0 mismatch. In another word, "0 mm hit number" counts the number of known protein coding transcript, other than the target transcript of the saRNA that comprises a region completely identical with the saRNA sequence. The term "1 mm hit number" refers to the number of known protein coding transcript other than the target transcript of the saRNA, the complement of which the saRNA may hybridize with or bind to with 1 mismatch. In another word, "1 mm hit number" counts the number of known protein coding transcript, other than the target transcript of the saRNA that comprises a region identical with the saRNA sequence with only 1 mismatch. In one embodiment, only saRNA sequences that have no off-target hit, no 0 mm hit and no 1 mm hit are selected. For those saRNA sequences disclosed in the present application, each has no off-target hit, no 0 mm hit and no 1 mm hit.

The method disclosed in US 2013/0164846 filed Jun. 23, 2011 (saRNA algorithm), the contents of which are incorporated herein by reference in their entirety, may also be used to design saRNA. The design of saRNA is also disclosed in U.S. Pat. Nos. 8,324,181 and 7,709,566 to Corey et al., US Pat. Pub. No. 2010/0210707 to Li et al., and Voutila et al., *Mol Ther Nucleic Acids*, vol. 1, e35 (2012), the contents of each of which are incorporated herein by reference in their entirety.

"Determination of existence" means either searching databases of ESTs and/or antisense RNA transcripts around the locus of the target gene to identify a suitable target antisense RNA transcript, or using RT PCR or any other known technique to confirm the physical presence of a target antisense RNA transcript in a cell.

In some embodiments, the saRNA of the present invention may be single or, double-stranded. Double-stranded molecules comprise a first strand and a second strand. If double-stranded, each strand of the duplex may be at least 14, or at least 18, e.g. 19, 20, 21 or 22 nucleotides in length. The duplex may be hybridized over a length of at least 12, or at least 15, or at least 17, or at least 19 nucleotides. Each strand may be exactly 19 nucleotides in length. Preferably, the length of the saRNA is less than 30 nucleotides since oligonucleotide duplex exceeding this length may have an increased risk of inducing the interferon response. In one embodiment, the length of the saRNA is 19 to 25 nucleotides. The strands forming the saRNA duplex may be of equal or unequal lengths.

In one embodiment, the saRNA of the present invention comprises a sequence of at least 14 nucleotides and less than 30 nucleotides which has at least 80%, 90%, 95%, 98%, 99% or 100% complementarity to the targeted sequence. In one embodiment, the sequence which has at least 80%, 90%, 95%, 98%, 99% or 100% complementarity to the targeted sequence is at least 15, 16, 17, 18 or 19 nucleotides in length, or 18-22 or 19 to 21, or exactly 19.

In some embodiments, the saRNA of the present invention is single-stranded and comprises at least 14 and less then 30 nucleotides. The strand may comprise 15, 16, 17, 18, 19, 20, 21 or 22 nucleotides in length. In one embodiment, the saRNA has a molecular weight or molar mass of between about 5000 Da to about 10000 Da, between about 6000 Da to about 8000 Da, or between 6500 Da to about 7500 Da.

In some embodiments, the saRNA of the present invention is double-stranded and each strand comprises at least 14 and less then 30 nucleotides. Each strand may comprise 15, 16, 17, 18, 19, 20, 21 or 22 nucleotides in length. In one embodiment, each strand of saRNA has a molecular weight or molar mass of between about 5000 Da to about 10000 Da, between about 6000 Da to about 8000 Da, or between 6500 Da to about 7500 Da.

The saRNA of the present invention may include a short 3' or 5' sequence which is not complementary to the target antisense RNA transcript. In one embodiment, such a sequence is at 3' end of the strand. The sequence may be 1-5 nucleotides in length, or 2 or 3. The sequence may comprise uracil, so it may be a 3' stretch of 2 or 3 uracils. The sequence may comprise one or more deoxyribonucleoside, such as dT. In one embodiment, one or more of the nucleotides in the sequence is replaced with a nucleoside thiophosphate, wherein the internucleoside linkage is thiophosphate. As a non-limiting example, the sequence comprises the sequence dT*dT, wherein * is a thiophosphate internucleoside linkage. This non-complementary sequence may be referred to as "tail". If a 3' tail is present, the strand may be longer, e.g., 19 nucleotides plus a 3' tail, which may be UU or UUU. Such a 3' tail shall not be regarded as mismatches with regard to determine complementarity between the saRNA and the target antisense RNA transcript.

Thus, the saRNA of the present invention may consist of (i) a sequence having at least 80% complementarity to a region of the target antisense RNA transcript; and (ii) a 3' tail of 1-5 nucleotides, which may comprise or consist of uracil residues. The saRNA will thus typically have complementarity to a region of the target antisense RNA transcript over its whole length, except for the 3' tail, if present. Any of the saRNA sequences disclosed in the present application may optionally include such a 3' tail. Thus, any of the saRNA sequences disclosed in the saRNA Tables and Sequence Listing may optionally include such a 3' tail. The saRNA of the present invention may further comprise Dicer or Drosha substrate sequences.

The saRNA of the present invention may contain a flanking sequence. The flanking sequence may be inserted in the 3' end or 5' end of the saRNA of the present invention. In one embodiment, the flanking sequence is the sequence of a miRNA, rendering the saRNA to have miRNA configuration and may be processed with Drosha and Dicer. In a non-limiting example, the saRNA of the present invention has two strands and is cloned into a microRNA precursor, e.g., miR-30 backbone flanking sequence.

The saRNA of the present invention may comprise a restriction enzyme substrate or recognition sequence. The restriction enzyme recognition sequence may be at the 3' end or 5' end of the saRNA of the present invention. Non-limiting examples of restriction enzymes include NotI and AscI.

In one embodiment, the saRNA of the present invention consists of two strands stably base-paired together. In some embodiments, the passenger strand may comprise at least one nucleotide that is not complementary to the corresponding nucleotide on the guide strand, called a mismatch with the guide strand. In one embodiment, the at least one mismatch with the guide strand may be at 3' end of the passenger strand. In one embodiment, the 3' end of the passenger strand may comprise 1-5 mismatches with the guide strand. In one embodiment, the 3' end of the passenger strand may comprise 2-3 mismatches with the guide strand. In one embodiment, the 3' end of the passenger strand may comprise 6-10 mismatches with the guide strand.

In some embodiments, the double-stranded saRNA may comprise a number of unpaired nucleotides at the 3' end of each strand forming 3' overhangs. The number of unpaired nucleotides forming the 3' overhang of each strand may be in the range of 1 to 5 nucleotides, or 1 to 3 nucleotides, or 2 nucleotides. The 3' overhang may be formed on the 3' tail mentioned above, so the 3' tail may be the 3' overhang of a double-stranded saRNA.

Thus, the saRNA of the present invention may be single-stranded and consists of (i) a sequence having at least 80% complementarity to a region of the target antisense RNA transcript; and (ii) a 3' tail of 1-5 nucleotides, which may comprise uracil residues. The saRNA of the present invention may have complementarity to a region of the target antisense RNA transcript over its whole length, except for the 3' tail, if present. As mentioned above, instead of "complementary to the target antisense RNA transcript" the saRNA of the present invention may also be defined as having "identity" to the coding strand of the target gene. The saRNA of the present invention may be double-stranded and consists of a first strand comprising (i) a first sequence having at least 80% complementarity to a region of the target antisense RNA transcript and (ii) a 3' overhang of 1-5 nucleotides; and a second strand comprising (i) a second sequence that forms a duplex with the first sequence and (ii) a 3' overhang of 1-5 nucleotides.

As described herein, the sequence for HNF4a gene is used to design HNF4a-saRNA. The sequence of a target antisense RNA transcript of HNF4a gene may be determined from the sequence of HNF4a gene for designing HNF4a-saRNA. However, the existence of such a target antisense RNA transcript does not need to be determined. Sequences of suitable HNF4a-saRNA of the present invention are provided in Table 1. Thus, provided is HNF4a-saRNA having a first strand comprising a sequence selected from SEQ ID Nos: 4, 6, 8, 10, 12, 14, 16, 18, 20, 22, 24, 26, 28, 30 and 32. Optionally, the HNF4a-saRNA may comprise a 3' tail at the 3' end of these sequences.

Single stranded HNF4a-saRNA only consists of a first strand, whereas double stranded HNF4a-saRNA also has a second strand. The single stranded HNF4a-saRNA comprises a sequence selected from the anti-sense strands in Table 1. The double-stranded HNF4a-saRNA comprises a first strand, wherein the first strand comprises a sequence selected from the anti-sense strands in Table 1, and a second strand, wherein the second strand comprises a sequence which is the corresponding sense strand in Table 1. The anti-sense and/or sense strands may comprise a 3' overhang. In one embodiment, the 3' overhang is mUmU (m refers to 2'-OMe modified).

TABLE 1

| | saRNA sequences | | | |
|---|---|---|---|---|
| ID | Sense strand (Passenger) 5'→3' | SEQ ID NO | Anti-sense strand (Guide) 5'→3' | SEQ ID NO |
| PR1 | GAGCUUUGGGCCCGUAAGA | 3 | UCUUACGGGCCCAAAGCUC | 4 |
| PR2 | GGUGGAUACGUUAAAGAGU | 5 | ACUCUUUAACGUAUCCACC | 6 |
| PR3 | CCCAGAAUGCCUGUGAUCA | 7 | UGAUCACAGGCAUUCUGGG | 8 |
| PR4 | CCGAUGUUCAGUUAUCAAU | 9 | AUUGAUAACUGAACAUCGG | 10 |
| BC1 | GAAGAUUGCUCGUGCAAAU | 11 | AUUUGCACGAGCAAUCUUC | 12 |
| BC2 | CAGAUAUGCUCCAGUGAUG | 13 | CAUCACUGGAGCAUAUCUG | 14 |
| PR38 | AUACCACUCGAACACACAU | 15 | AUGUGUGUUCGAGUGGUAU | 16 |
| PR106 | UACUCAGUAAUUUACCCUC | 17 | GAGGGUAAAUUACUGAGUA | 18 |
| PR25 | UCAUAUCAGCAACAUGUCC | 19 | GGACAUGUUGCUGAUAUGA | 20 |
| PR39 | ucucCUGACAUCAAAUCUA | 21 | UAGAUUUGAUGUCAGGAGA | 22 |

TABLE 1-continued saRNA sequences

| ID | Sense strand (Passenger) 5'→3' | SEQ ID NO | Anti-sense strand (Guide) 5'→3' | SEQ ID NO |
|---|---|---|---|---|
| PR94 | UCACUCACUCCUAAUUCAC | 23 | GUGAAUUAGGAGUGAGUGA | 24 |
| PR55 | AGACAUAACCGCAUUUCUC | 25 | GAGAAAUGCGGUUAUGUCU | 26 |
| PR257 | AACACACCAGAGAUAGCAA | 27 | UUGCUAUCUCUGGUGUGUU | 28 |
| PR196 | UCGAUCCCGGCUAUUCCUC | 29 | GAGGAAUAGCCGGGAUCGA | 30 |
| PR263 | UUUGGCACUCAACUUUGGG | 31 | CCCAAAGUUGAGUGCCAAA | 32 |

The saRNA of the present invention may be produced by any suitable method, for example synthetically or by expression in cells using standard molecular biology techniques which are well-known to a person of ordinary skill in the art. For example, the saRNA of the present invention may be chemically synthesized or recombinantly produced using methods known in the art.

Chemical Modifications of saRNA

Herein, in saRNA, the terms "modification" or, as appropriate, "modified" refer to structural and/or chemical modifications with respect to A, G, U or C ribonucleotides. Nucleotides in the saRNA of the present invention may comprise non-standard nucleotides, such as non-naturally occurring nucleotides or chemically synthesized nucleotides or deoxynucleotides. The saRNA of the present invention may include any useful modification, such as to the sugar, the nucleobase, or the internucleoside linkage (e.g. to a linking phosphate/to a phosphodiester linkage/to the phosphodiester backbone). One or more atoms of a pyrimidine nucleobase may be replaced or substituted with optionally substituted amino, optionally substituted thiol, optionally substituted alkyl (e.g., methyl or ethyl), or halo (e.g., chloro or fluoro). In certain embodiments, modifications (e.g., one or more modifications) are present in each of the sugar and the internucleoside linkage. Modifications according to the present invention may be modifications of ribonucleic acids (RNAs) to deoxyribonucleic acids (DNAs), threose nucleic acids (TNAs), glycol nucleic acids (GNAs), peptide nucleic acids (PNAs), locked nucleic acids (LNAs) or hybrids thereof.

In one embodiment, the saRNAs of the present invention may comprise at least one modification described herein.

In another embodiment, the saRNA is a saRNA duplex and the sense strand and antisense sequence may independently comprise at least one modification. As a non-limiting example, the sense sequence may comprise a modification and the antisense strand may be unmodified. As another non-limiting example, the antisense sequence may comprise a modification and the sense strand may be unmodified. As yet another non-limiting example, the sense sequence may comprise more than one modification and the antisense strand may comprise one modification. As a non-limiting example, the antisense sequence may comprise more than one modification and the sense strand may comprise one modification.

The saRNA of the present invention can include a combination of modifications to the sugar, the nucleobase, and/or the internucleoside linkage. These combinations can include any one or more modifications described herein or in International Application Publication WO2013/052523 filed Oct. 3, 2012, in particular Formulas (Ia)-(Ia-5), (Ib)-(If), (IIa)-(IIp), (IIb-1), (IIb-2), (IIc-1)-(IIc-2), (IIn-1), (IIn-2), (IVa)-(IV1), and (IXa)-(IXr)), the contents of which are incorporated herein by reference in their entirety.

The saRNA of the present invention may or may not be uniformly modified along the entire length of the molecule. For example, one or more or all types of nucleotide (e.g., purine or pyrimidine, or any one or more or all of A, G, U, C) may or may not be uniformly modified in the saRNA of the invention. In some embodiments, all nucleotides X in a saRNA of the invention are modified, wherein X may be any one of nucleotides A, G, U, C, or any one of the combinations A+G, A+U, A+C, G+U, G+C, U+C, A+G+U, A+G+C, G+U+C or A+G+C.

Different sugar modifications, nucleotide modifications, and/or internucleoside linkages (e.g., backbone structures) may exist at various positions in a saRNA. One of ordinary skill in the art will appreciate that the nucleotide analogs or other modification(s) may be located at any position(s) of a saRNA such that the function of saRNA is not substantially decreased. The saRNA of the present invention may contain from about 1% to about 100% modified nucleotides (either in relation to overall nucleotide content, or in relation to one or more types of nucleotide, i.e. any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%).

In some embodiments, the modification may be on the ribose ring. The 2'-OH group on the ribose may be substituted to protect saRNA against ribonucleases. For example, the 2'-OH group may be substituted with 2'-O-methyl (2'-OMe), 2'-fluoro (2'-F), 2'-O-methoxyethyl (2'-O-MOE), 2'-O-allyl (2'-O-allyl), etc.

In some embodiments, the modifications include bicyclic derivatives of the nucleotides (LNA, ENA, CLNA, CENA, AENA etc.), acyclic nucleotides (UNA, PNA, etc.) or nucleotides containing pyranose ring (ANA, HNA) instead of ribose.

In some embodiments, the modification may be on the backbone to increase nuclease resistance of the saRNA. Non-limiting examples include the replacement of phosphate group (PO) with phosphorothioate (PS) or boranophosphonate (PB) groups, the replacement of the 3',5'-phosphodiester bond with 2',5'-bond or the amide bond instead of the ester bond, etc.

In some embodiments, the modification may be on the nucleobases. For example, uridine (U) may be replaced with pseudouridine (ψ), 2-thiouridine (s2U), dihydrouridine (D), 5-bromo-U, 5-iodo-U, etc. Purine may be replaced with 2,6-diaminopurine.

In some embodiments, the modification may be at the termini of saRNA. Any termini modification may be used to increase nuclease resistance, to facilitate asymmetric RISC assembly, to help saRNA accumulation in cells, and to enable saRNA detection. For example, fluorescence labels and biotin may be attached to a terminus of saRNA. In another example, inverted deoxyribose may be employed at a terminus of saRNA.

In some embodiments, the saRNA of the present invention may be modified to be a spherical nucleic acid (SNA) or a circular nucleic acid. The terminals of the saRNA of the present invention may be linked by chemical reagents or enzymes, producing spherical saRNA that has no free ends. Spherical saRNA is expected to be more stable than its linear counterpart and to be resistant to digestion with RNase R exonuclease. Spherical saRNA may further comprise other structural and/or chemical modifications with respect to A, G, U or C ribonucleotides.

In some embodiments, the saRNA of the present invention may comprise inverted dT modifications. The inverted modification may be at 5' terminus or 3' terminus. In some embodiments, the 2'-OH of a nucleotide is substituted with -OMe, referred to as 2'-OMe. In some embodiments, the 2'-OH of a nucleotide is substituted with -F, referred to as 2'-F. In some embodiments, there is phosphorothioate linkage between nucleotides. In some embodiments, the saRNA of the present invention may comprise abasic modifications.

The saRNA of the present invention may comprise a combination of modifications. The saRNA may comprise at least 2, 3, 4, 5, 6, 7, 8, 9, 10, 11, 12, 13, 14, 15, 16, 17, 18, 19, or 20 modifications. For example, the saRNA may comprise alternating 2'-F and 2'-OMe modifications. In some embodiments, the saRNA may be modified across its whole length.

Any suitable modification to render the sense strand inactive and/or to reduce off-targets, which does not interfere with guide strand activity, may be used.

saRNA Conjugates and Combinations

Conjugation may result in increased stability and/or half life and may be particularly useful in targeting the saRNA of the present invention to specific sites in the cell, tissue or organism. The saRNA of the present invention can be designed to be conjugated to other polynucleotides, dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases, proteins, e.g., glycoproteins, or peptides, e.g., molecules having a specific affinity for a co-ligand, or antibodies e.g., an antibody, that binds to a specified cell type such as a cancer cell, endothelial cell, or bone cell, hormones and hormone receptors, non-peptidic species, such as lipids, lectins, carbohydrates, vitamins, cofactors, or a drug. Suitable conjugates for nucleic acid molecules are disclosed in International Publication WO 2013/090648 filed Dec. 14, 2012, the contents of which are incorporated herein by reference in their entirety.

According to the present invention, HNF4a-saRNA may be administered with, or further encode one or more of RNAi agents, small interfering RNAs (siRNAs), small hairpin RNAs (shRNAs), long non-coding RNAs (lncRNAs), enhancer RNAs, enhancer-derived RNAs or enhancer-driven RNAs (eRNAs), microRNAs (miRNAs), miRNA binding sites, antisense RNAs, ribozymes, catalytic DNA, tRNA, RNAs that induce triple helix formation, aptamers or vectors, and the like to achieve different functions. The one or more RNAi agents, small interfering RNAs (siRNAs), small hairpin RNAs (shRNAs), long non-coding RNAs (lncRNA), microRNAs (miRNAs), miRNA binding sites, antisense RNAs, ribozymes, catalytic DNA, tRNA, RNAs that induce triple helix formation, aptamers or vectors may comprise at least one modification or substitution. In some embodiments, the modification is selected from a chemical substitution of the nucleic acid at a sugar position, a chemical substitution at a phosphate position and a chemical substitution at a base position. In other embodiments, the chemical modification is selected from incorporation of a modified nucleotide; 3' capping; conjugation to a high molecular weight, non-immunogenic compound; conjugation to a lipophilic compound; and incorporation of phosphorothioate into the phosphate backbone. In a preferred embodiment, the high molecular weight, non-immunogenic compound is polyalkylene glycol, and more preferably is polyethylene glycol (PEG).

In one embodiment, HNF4a-saRNA may be attached to a transgene so it can be co-expressed from an RNA polymerase II promoter. In a non-limiting example, HNF4a-saRNA is attached to green fluorescent protein gene (GFP).

In one embodiment, HNF4a-saRNA may be attached to a DNA or RNA aptamer, thereby producing HNF4a-saRNA-aptamer conjugate. Aptamers are oligonucleotides or peptides with high selectivity, affinity and stability. They assume specific and stable three-dimensional shapes, thereby providing highly specific, tight binding to target molecules. An aptamer may be a nucleic acid species that has been engineered through repeated rounds of in vitro selection or equivalently, SELEX (systematic evolution of ligands by exponential enrichment) to bind to various molecular targets such as small molecules, proteins, nucleic acids, and even cells, tissues and organisms. Nucleic acid aptamers have specific binding affinity to molecules through interactions other than classic Watson-Crick base pairing. Nucleic acid aptamers, like peptides generated by phage display or monoclonal antibodies (mAbs), are capable of specifically binding to selected targets and, through binding, block their targets' ability to function. In some cases, aptamers may also be peptide aptamers. For any specific molecular target, nucleic acid aptamers can be identified from combinatorial libraries of nucleic acids, e.g. by SELEX. Peptide aptamers may be identified using a yeast two hybrid system. A skilled person is therefore able to design suitable aptamers for delivering the saRNAs or cells of the present invention to target cells such as liver cells. DNA aptamers, RNA aptamers and peptide aptamers are contemplated. Administration of saRNA of the present invention to the liver using liver-specific aptamers is particularly preferred.

As used herein, a typical nucleic acid aptamer is approximately 10-15 kDa in size (20-45 nucleotides), binds its target with at least nanomolar affinity, and discriminates against closely related targets. Nucleic acid aptamers may be ribonucleic acid, deoxyribonucleic acid, or mixed ribonucleic acid and deoxyribonucleic acid. Aptamers may be single stranded ribonucleic acid, deoxyribonucleic acid or mixed ribonucleic acid and deoxyribonucleic acid. Aptamers may comprise at least one chemical modification.

A suitable nucleotide length for an aptamer ranges from about 15 to about 100 nucleotides (nt), and in various other preferred embodiments, 15-30 nt, 20-25 nt, 30-100 nt, 30-60 nt, 25-70 nt, 25-60 nt, 40-60 nt, 25-40 nt, 30-40 nt, any of 22, 23, 24, 25, 26, 27, 28, 29, 30, 31, 32, 33, 34, 35, 36, 37, 38, 39 or 40 nt or 40-70 nt in length. However, the sequence can be designed with sufficient flexibility such that it can accommodate interactions of aptamers with two targets at the distances described herein. Aptamers may be further modified to provide protection from nuclease and other enzymatic activities. The aptamer sequence can be modified by any suitable methods known in the art.

The HNF4a-saRNA-aptamer conjugate may be formed using any known method for linking two moieties, such as direct chemical bond formation, linkage via a linker such as streptavidin and so on.

In one embodiment, HNF4a-saRNA may be attached to an antibody. Methods of generating antibodies against a target cell surface receptor are well known. The saRNA molecules of the invention may be attached to such antibodies with known methods, for example using RNA carrier proteins. The resulting complex may then be administered to a subject and taken up by the target cells via receptor-mediated endocytosis.

In one embodiment, HNF4a-saRNA may be conjugated with lipid moieties such as a cholesterol moiety (Letsinger et al., Proc. Natl. Acid. Sci. USA, 1989, 86: 6553-6556), cholic acid (Manoharan et al., Biorg. Med. Chem. Let., 1994, 4:1053-1060), a thioether, e.g., beryl-5-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-Hphosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylamino-carbonyloxycholesterol moiety (Crooke et al., J. Pharmacol. Exp. Ther., 1996, 277:923-937), the content of each of which is herein incorporated by reference in its entirety.

In one embodiment, the saRNA of the present invention is conjugated with a ligand disclosed in US 20130184328 to Manoharan et al., the contents of which are incorporated herein by reference in their entirety. The conjugate has a formula of Ligand-[linker]$_{optional}$[tether]$_{optional}$-oligonucleotide agent. The oligonucleotide agent may comprise a subunit having formulae (I) disclosed by US 20130184328 to Manoharan et al., the contents of which are incorporated herein by reference in their entirety.

Representative U.S. patents that teach the preparation of such nucleic acid/lipid conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, the content of each of which is herein incorporated by reference in its entirety.

In on embodiment, the saRNA is conjugated with a carbohydrate ligand, such as any carbohydrate ligand disclosed in U.S. Pat. Nos. 8,106,022 and 8,828,956 to Manoharan et al. (Alnylam Pharmaceuticals), the contents of which are incorporated herein by reference in their entirety. For example, the carbohydrate ligand may be monosaccharide, disaccharide, trisaccharide, tetrasaccharide, oligosaccharide, or polysaccharide. These carbohydrate-conjugated RNA agents may target the parenchymal cells of the liver. In one embodiment, the saRNA is conjugated with more than one carbohydrate ligand, preferably two or three. In one embodiment, the saRNA is conjugated with one or more galactose moiety. In another embodiment, the saRNA is conjugated at least one (e.g., two or three or more) lactose molecules (lactose is a glucose coupled to a galactose). In another embodiment, the saRNA is conjugated with at least one (e.g., two or three or more) N-Acetyl-Galactosamine (GalNAc), N—Ac-Glucosamine (GluNAc), or mannose (e.g., mannose-6-phosphate). In one embodiment, the saRNA is conjugated with at least one mannose ligand, and the conjugated saRNA targets macrophages.

In another embodiment, the saRNA is conjugated with one or more oligonucleotides containing unmethylated cytosine-guanine (CpG) dinucleotides, referred to as CpG oligonucleotides. In one example, the CpG oligonucleotides are between 2 to 100 base pairs in size and contain a consensus mitogenic CpG motif represented by the formula:

wherein C and G are unmethylated, $X_1$, $X_2$, $X_3$ and $X_4$ are nucleotides and a GCG trinucleotide sequence is not present at or near the 5' and 3' ends. Examples of CpG oligonucleotides are described in U.S. Pat. No. 6,194,388 to Krieg et al. and U.S. Pat. No. 6,207,646 to Krieg et al., the contents of each of which are incorporated herein by reference in their entirety. Preferably the CpG oligonucleotides range between 8 and 40 base pairs in size. In addition, the CpG oligonucleotides are preferably stabilized oligonucleotides, particularly preferred are phosphorothioate stabilized oligonucleotides. The CpG oligonucleotides may be conjugated to the saRNA of the present invention by any linker and/or any method disclosed in WO 2012128785 to Jove et al. and US 20140128324 to Yu et al., the contents of each of which are incorporated herein by reference in the their entirety, such as using branching or bridging compounds, covalent constructs, click chemistry, etc.

The saRNA of the present invention may be provided in combination with other active ingredients known to have an effect in the particular method being considered. The other active ingredients may be administered simultaneously, separately, or sequentially with the saRNA of the present invention. In one embodiment, HNF4a-saRNA is administered with saRNA modulating a different target gene. Non-limiting examples include saRNA that modulates albumin, insulin or HNF4A genes. Modulating any gene may be achieved using a single saRNA or a combination of two or more different saRNAs. Non-limiting examples of saRNA that can be administered with HNF4a-saRNA of the present invention include saRNA modulating CEBPA disclosed in International Publication WO2015/075557, saRNA modulating albumin or HNF4A disclosed in International Publication WO 2012/175958 filed Jun. 20, 2012, saRNA modulating insulin disclosed in International Publications WO 2012/046084 and WO 2012/046085 both filed Oct. 10, 2011, saRNA modulating human progesterone receptor, human major vault protein (hMVP), E-cadherin gene, p53 gene, or PTEN gene disclosed in U.S. Pat. No. 7,709,456 filed Nov. 13, 2006 and US Pat. Publication US 2010/0273863 filed Apr. 23, 2010, and saRNAs targeting p21 gene disclosed in International Publication WO 2006/113246 filed Apr. 11, 2006, the contents of each of which are incorporated herein by reference in their entirety.

In one embodiment, HNF4a-saRNA is administered with one or more drugs that regulate metabolics, particularly liver function. In a non-limiting example, HNF4a-saRNA of the present invention is administered with drugs that decrease low density lipoprotein (LDL) cholesterol levels, such as statin, simvastatin, atorvastatin, rosuvastatin, ezetimibe, niacin, PCSK9 inhibitors, CETP inhibitors, clofibrate, fenofibric, tocotrienols, phytosterols, bile acid sequestrants, probucol, or a combination thereof. HNF4a-saRNA may also be administered with vanadium biguanide complexes disclosed in U.S. Pat. No. 6,287,586 to Orvig et al. In another example, HNF4a-saRNA may be administered with a composition disclosed in WO 201102838 to Rhodes, the contents of which are incorporated by reference in their entirety, to lower serum cholesterol. The composition comprises an antigen binding protein that selectively binds to and inhibits a PCSK9 protein; and an RNA effector agent which inhibits the expression of a PCSK9 gene in a cell. In yet another example, HNF4a-saRNA may be administered with an ABC1 polypeptide having ABC1 biological activity, or a nucleic acid encoding an ABC1 polypeptide having ABC1 activity to modulate cholesterol levels as described in EP1854880 to Brooks-Wilson et al., the contents of which are incorporated herein by reference in their entirety.

In another embodiment, HNF4a-saRNA of the present invention is administered with drugs that increase insulin sensitivity or treat type II diabetes mellitus, such as metformin, sulfonylurea, nonsulfonylurea secretagogues, α glucosidase inhibitors, thiazolidinediones, pioglitazone, rosiglitazone, glucagon-like peptide-1 analog, and dipeptidyl peptidase-4 inhibitors or a combination thereof. Other hepato-protective agents that may be administered in combination with the saRNA of the present invention are disclosed in Adams et al., *Postgraduate Medical Journal*, vol. 82, 315-322 (2006), the contents of which are incorporated herein by reference in their entirety.

Gankyrin and FXR Protein

The development of hepatocellular carcinoma (HCC) is a multistep process which involves progressive changes of gene expression leading to liver hyperproliferation and to liver cancer. During carcinogenesis of liver cancer, tumor suppressor proteins Rb, p53, hepatocyte nuclear factor 4α (HNF4α), and C/EBP-α are neutralized. The elimination of these proteins is mediated by a small subunit of 26S proteasome, gankyrin, which is activated by cancer. Wang et al. discloses that gankyrin interacts with S193-ph isoform of C/EBPα and targets it for ubiquitinproteasome system (UPS)-mediated degradation. Gankyrin level is elevated during the early stages of liver cancer development (Wang et al., *J. Clin. Invest*, vol. 120(7):2549-2562 (2010), the contents of which are incorporated herein by reference in their entireties). Inhibiting gankyrin, e.g., using siRNA of the gankyrin gene (also known as PSMD10 gene) and/or gankyrin inhibitors, may prevent and/or treat HCC.

Jiang et al. found that farnesoid X receptor (FXR), also known as bile acid receptor (BAR) or NR1H4, inhibits expression of gankyrin in quiescent livers by silencing the gankyrin promoter through HDAC1-C/EBPβ complexes (Jiang et al., *Hepatology*, vol. 57(3):1098-1106 (2013), the contents of which are incorporated herein by reference in their entireties). Deletion of FXR signaling in mice leads to de-repression of the gankyrin promoter and to spontaneous development of liver cancer at 12 months of age. Diethylnitrosoamine (DEN)-mediated liver cancer in wild-type mice also involves the reduction of FXR and activation of gankyrin. Examination of liver cancer in old mice and liver cancer in human patients revealed that FXR is reduced, while gankyrin is elevated during spontaneous development of liver cancer. Jiang et al. concluded that FXR prevents liver cancer by inhibiting the gankyrin promoter via C/EBPβ-HDAC1 complexes leading to subsequent protection of tumor suppressor proteins from degradation. Stabilization and nuclear translocation of FXR inhibits gankyrin. Activating FXR, e.g., using FXR agonists or activators, or activator of NR1H4 gene, may prevent and/or treat HCC.

HNF4a-saRNA of the present invention may be used in combination with one or more of therapeutic agents that down-regulate gankyrin or up-regulate FXR. The combination may have synergistic effect on preventing and/or treating HCC. In some embodiments, HNF4a-saRNA of the present invention may be used in combination with gankyrin-siRNA. Double-stranded Gankyrin-siRNA may be produced using the method disclosed by Higashitsuji et al. in the 'Inhibition of endogenous gene expression by RNAi' section (Higashitsuji et al., *Cancer Cell*, vol. 8:75-87 (2005), the contents of which are incorporated herein by reference in their entireties). In some embodiments, HNF4a-saRNA of the present invention may be used in combination with FXR agonists. Non-limiting examples of FXR agonists or activators include taurocholic acid, obeticholic acid (OCA), INT-767 (Intercept Pharmaceuticals), INT-777 (Intercept Pharmaceuticals), and any FXR agonist or activator disclosed in US Pat. App. No. 20140057886, U.S. Pat. Nos. 8,546,365, 7,932,244, US Pat. App. No. 20140100209, U.S. Pat. Nos. 8,445,472, 8,114,862, US Pat. App. No. 20140094443, U.S. Pat. Nos. 8,410,083, 8,796,249, US Pat. App. No. 20140024631, U.S. Pat. Nos. 8,377,916, 8,258, 267, 7,786,102, 7,138,390, 7,994,352, 7,858,608, 7,812,011, US Pat. App. No. 20140148428, and US Pat. App. No. 20060252670 (the contents of each of which are incorporated herein by reference in their entirety).

Formulation, Delivery, Administration, and Dosing

Pharmaceutical formulations may additionally comprise a pharmaceutically acceptable excipient, which, as used herein, includes, but is not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington: The Science and Practice of Pharmacy, 21$^{st}$ Edition, A. R. Gennaro, Lippincott, Williams & Wilkins, Baltimore, MD, 2006; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition.

In some embodiments, compositions are administered to humans, human patients or subjects. For the purposes of the present disclosure, the phrase "active ingredient" generally refers to HNF4a-saRNA to be delivered as described herein.

Although the descriptions of pharmaceutical compositions provided herein are principally directed to pharmaceutical compositions which are suitable for administration to humans, it will be understood by the skilled artisan that such compositions are generally suitable for administration to any other animal, e.g., to non-human animals, e.g. non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as poultry, chickens, ducks, geese, and/or turkeys.

In one embodiment, the efficacy of the formulated saRNA described herein may be determined in proliferating cells.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

In some embodiments, the formulations described herein may contain at least one saRNA. As a non-limiting example, the formulations may contain 1, 2, 3, 4 or 5 saRNAs with different sequences. In one embodiment, the formulation contains at least three saRNAs with different sequences. In one embodiment, the formulation contains at least five saRNAs with different sequences.

The saRNA of the invention can be formulated using one or more excipients to: (1) increase stability; (2) increase cell transfection; (3) permit the sustained or delayed release (e.g., from a depot formulation of the saRNA); (4) alter the biodistribution (e.g., target the saRNA to specific tissues or cell types); (5) increase the translation of encoded protein in vivo; and/or (6) alter the release profile of encoded protein in vivo. In addition to traditional excipients such as any and all solvents, dispersion media, diluents, or other liquid vehicles, dispersion or suspension aids, surface active agents, isotonic agents, thickening or emulsifying agents, preservatives, excipients of the present invention can include, without limitation, lipidoids, liposomes, lipid nanoparticles, polymers, lipoplexes, core-shell nanoparticles, peptides, proteins, cells transfected with saRNA (e.g., for transplantation into a subject), hyaluronidase, nanoparticle mimics and combinations thereof. Accordingly, the formulations of the invention can include one or more excipients, each in an amount that together increases the stability of the saRNA and/or increases cell transfection by the saRNA. Further, the saRNA of the present invention may be formulated using self-assembled nucleic acid nanoparticles. Pharmaceutically acceptable carriers, excipients, and delivery agents for nucleic acids that may be used in the formulation with the saRNA of the present invention are disclosed in International Publication WO 2013/090648 filed Dec. 14, 2012, the contents of which are incorporated herein by reference in their entirety.

In one embodiment, the saRNA of the present invention comprises two single RNA strands that are 21 nucleotides in length each that are annealed to form a double stranded HNF4a-saRNA as the active ingredient in the pharmaceutical composition.

In another embodiment, the saRNA of the present invention may be delivered with dendrimers. Dendrimers are highly branched macromolecules. In a preferred embodiment, the saRNA of the present invention is complexed with structurally flexible poly(amidoamine) (PAMAM) dendrimers for targeted in vivo delivery. Dendrimers have a high degree of molecular uniformity, narrow molecular weight distribution, specific size and shape characteristics, and a highly-functionalized terminal surface. The manufacturing process is a series of repetitive steps starting with a central initiator core. Each subsequent growth step represents a new generation of polymers with a larger molecular diameter and molecular weight, and more reactive surface sites than the preceding generation. PAMAM dendrimers are efficient nucleotide delivery systems that bear primary amine groups on their surface and also a tertiary amine group inside of the structure. The primary amine group participates in nucleotide binding and promotes their cellular uptake, while the buried tertiary amino groups act as a proton sponge in endosomes and enhance the release of nucleic acid into the cytoplasm. These dendrimers protect the saRNA carried by them from ribonuclease degradation and achieves substantial release of saRNA over an extended period of time via endocytosis for efficient gene targeting. The in vivo efficacy of these nanoparticles have previously been evaluated where biodistribution studies show that the dendrimers preferentially accumulate in peripheral blood mononuclear cells and live with no discernible toxicity (see Zhou et al., Molecular Ther. 2011 Vol. 19, 2228-2238, the contents of which are incorporated herein by reference in their entirety). PAMAM dendrimers may comprise a triethanolamine (TEA) core, a diaminobutane (DAB) core, a cystamine core, a diaminohexane (HEX) core, a diaminododecane (DODE) core, or an ethylenediamine (EDA) core. Preferably, PAMAM dendrimers comprise a TEA core or a DAB core.

In some embodiments, the concentration of saRNA in the pharmaceutical composition is between about 1 mg/mL to about 10 mg/mL, between about 2 mg/mL to about 5 mg/mL, or between about 2.5 mg/mL to about 3 mg/mL.

In some embodiments, the pH of the pharmaceutical composition is between about 6 to about 8 or between about 7 to about 8.

In some embodiments, the pharmaceutical composition has an impurity level of less than about 10%, less than about 8%, less than about 7%, less than about 6%, or less than about 5%.

In some embodiments, saRNA of the present is encapsulated in particles. The particles may be nanoparticles. Particle size (z-average) may be between about 50 nm to about 1000 nm, between about 100 nm to about 500 nm, or between about 100 nm to about 200 nm.

Lipidoids

The synthesis of lipidoids has been extensively described and formulations containing these compounds are particularly suited for delivery of oligonucleotides or nucleic acids (see Mahon et al., Bioconjug Chem. 2010 21:1448-1454; Schroeder et al., J Intern Med. 2010 267:9-21; Akinc et al., Nat Biotechnol. 2008 26:561-569; Love et al., Proc Natl Acad Sci USA. 2010 107:1864-1869; Siegwart et al., Proc Natl Acad Sci USA. 2011 108:12996-3001; all of which are incorporated herein in their entireties).

While these lipidoids have been used to effectively deliver double stranded small interfering RNA molecules in rodents and non-human primates (see Akinc et al., Nat Biotechnol. 2008 26:561-569; Frank-Kamenetsky et al., Proc Natl Acad Sci USA. 2008 105:11915-11920; Akinc et al., Mol Ther. 2009 17:872-879; Love et al., Proc Natl Acad Sci USA. 2010 107:1864-1869; Leuschner et al., Nat Biotechnol. 2011 29:1005-1010; all of which is incorporated herein in their entirety), the present disclosure describes their formulation and use in delivering saRNA. Complexes, micelles, liposomes or particles can be prepared containing these lipidoids and therefore, can result in an effective delivery of the saRNA following the injection of a lipidoid formulation via localized and/or systemic routes of administration. Lipidoid complexes of saRNA can be administered by various means including, but not limited to, intravenous, intramuscular, or subcutaneous routes.

In vivo delivery of nucleic acids may be affected by many parameters, including, but not limited to, the formulation composition, nature of particle PEGylation, degree of loading, oligonucleotide to lipid ratio, and biophysical parameters such as, but not limited to, particle size (Akinc et al., Mol Ther. 2009 17:872-879; the contents of which are herein incorporated by reference in its entirety). As an example, small changes in the anchor chain length of poly(ethylene glycol) (PEG) lipids may result in significant effects on in vivo efficacy. Formulations with the different lipidoids, including, but not limited to penta[3-(1-laurylaminopropionyl)]-triethylenetetramine hydrochloride (TETA-5LAP; aka 98N12-5, see Murugaiah et al., Analytical Biochemistry, 401:61 (2010); the contents of which are herein incorporated by reference in its entirety), C12-200 (including derivatives and variants), and MD1, can be tested for in vivo activity.

The lipidoid referred to herein as "98N12-5" is disclosed by Akinc et al., Mol Ther. 2009 17:872-879 and the contents of which is incorporated by reference in its entirety. (See FIG. 2)

The lipidoid referred to herein as "C12-200" is disclosed by Love et al., Proc Natl Acad Sci USA. 2010 107:1864-1869 (see FIG. 2) and Liu and Huang, Molecular Therapy. 2010 669-670 (see FIG. 2); the contents of both of which are herein incorporated by reference in their entirety. The lipidoid formulations can include particles comprising either 3 or 4 or more components in addition to the saRNA. As an example, formulations with certain lipidoids, include, but are not limited to, 98N12-5 and may contain 42% lipidoid, 48% cholesterol and 10% PEG (C14 alkyl chain length). As another example, formulations with certain lipidoids, include, but are not limited to, C12-200 and may contain 50% lipidoid, 10% disteroylphosphatidyl choline, 38.5% cholesterol, and 1.5% PEG-DMG.

In one embodiment, a saRNA formulated with a lipidoid for systemic intravenous administration can target the liver. For example, a final optimized intravenous formulation using saRNA and comprising a lipid molar composition of 42% 98N12-5, 48% cholesterol, and 10% PEG-lipid with a final weight ratio of about 7.5 to 1 total lipid to saRNA and a C14 alkyl chain length on the PEG lipid, with a mean particle size of roughly 50-60 nm, can result in the distribution of the formulation to be greater than 90% to the liver. (see, Akinc et al., Mol Ther. 2009 17:872-879; the contents of which are herein incorporated by reference in its entirety). In another example, an intravenous formulation using a C12-200 (see U.S. provisional application 61/175,770 and published international application WO2010129709, the contents of each of which is herein incorporated by reference in their entirety) lipidoid may have a molar ratio of 50/10/38.5/1.5 of C12-200/disteroylphosphatidyl choline/ cholesterol/PEG-DMG, with a weight ratio of 7 to 1 total lipid to nucleic acid and a mean particle size of 80 nm may be effective to deliver saRNA (see, Love et al., Proc Natl Acad Sci USA. 2010 107:1864-1869, the contents of which are herein incorporated by reference in its entirety). In another embodiment, an MD1 lipidoid-containing formulation may be used to effectively deliver saRNA to hepatocytes in vivo. The characteristics of optimized lipidoid formulations for intramuscular or subcutaneous routes may vary significantly depending on the target cell type and the ability of formulations to diffuse through the extracellular matrix into the blood stream. While a particle size of less than 150 nm may be desired for effective hepatocyte delivery due to the size of the endothelial fenestrae (see, Akinc et al., Mol Ther. 2009 17:872-879, the contents of which are herein incorporated by reference in its entirety), use of a lipidoid-formulated saRNA to deliver the formulation to other cells types including, but not limited to, endothelial cells, myeloid cells, and muscle cells may not be similarly size-limited. Use of lipidoid formulations to deliver siRNA in vivo to other non-hepatocyte cells such as myeloid cells and endothelium has been reported (see Akinc et al., Nat Biotechnol. 2008 26:561-569; Leuschner et al., Nat Biotechnol. 2011 29:1005-1010; Cho et al. Adv. Funct. Mater. 2009 19:3112-3118; 8$^{th}$ International Judah Folkman Conference, Cambridge, MA Oct. 8-9, 2010; the contents of each of which is herein incorporated by reference in its entirety). Effective delivery to myeloid cells, such as monocytes, lipidoid formulations may have a similar component molar ratio. Different ratios of lipidoids and other components including, but not limited to, disteroylphosphatidyl choline, cholesterol and PEG-DMG, may be used to optimize the formulation of saRNA for delivery to different cell types including, but not limited to, hepatocytes, myeloid cells, muscle cells, etc. For example, the component molar ratio may include, but is not limited to, 50% C12-200, 10% disteroylphosphatidyl choline, 38.5% cholesterol, and %1.5 PEG-DMG (see Leuschner et al., Nat Biotechnol 2011

29:1005-1010; the contents of which are herein incorporated by reference in its entirety). The use of lipidoid formulations for the localized delivery of nucleic acids to cells (such as, but not limited to, adipose cells and muscle cells) via either subcutaneous or intramuscular delivery, may not require all of the formulation components desired for systemic delivery, and as such may comprise only the lipidoid and saRNA.

Liposomes, Lipoplexes, and Lipid Nanoparticles

The saRNA of the invention can be formulated using one or more liposomes, lipoplexes, or lipid nanoparticles. In one embodiment, pharmaceutical compositions of saRNA include liposomes. Liposomes are artificially-prepared vesicles which may primarily be composed of a lipid bilayer and may be used as a delivery vehicle for the administration of nutrients and pharmaceutical formulations. Liposomes can be of different sizes such as, but not limited to, a multilamellar vesicle (MLV) which may be hundreds of nanometers in diameter and may contain a series of concentric bilayers separated by narrow aqueous compartments, a small unicellular vesicle (SUV) which may be smaller than 50 nm in diameter, and a large unilamellar vesicle (LUV) which may be between 50 and 500 nm in diameter. Liposome design may include, but is not limited to, opsonins or ligands in order to improve the attachment of liposomes to unhealthy tissue or to activate events such as, but not limited to, endocytosis. Liposomes may contain a low or a high pH in order to improve the delivery of the pharmaceutical formulations.

The formation of liposomes may depend on the physicochemical characteristics such as, but not limited to, the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimization size, polydispersity and the shelf-life of the vesicles for the intended application, and the batch-to-batch reproducibility and possibility of large-scale production of safe and efficient liposomal products.

In one embodiment, pharmaceutical compositions described herein may include, without limitation, liposomes such as those formed from 1,2-dioleyloxy-N,N-dimethyl-aminopropane (DODMA) liposomes, DiLa2 liposomes from Marina Biotech (Bothell, WA), 1,2-dilinoleyloxy-3-dimethylaminopropane (DLin-DMA), 2,2-dilinoleyl-4-(2-dimethylaminoethyl)[1,3]-dioxolane (DLin-KC2-DMA), and MC3 (US20100324120; the contents of which are herein incorporated by reference in its entirety) and liposomes which may deliver small molecule drugs such as, but not limited to, DOXIL® from Janssen Biotech, Inc. (Horsham, PA).

In one embodiment, pharmaceutical compositions described herein may include, without limitation, liposomes such as those formed from the synthesis of stabilized plasmid-lipid particles (SPLP) or stabilized nucleic acid lipid particle (SNALP) that have been previously described and shown to be suitable for oligonucleotide delivery in vitro and in vivo (see Wheeler et al. Gene Therapy. 1999 6:271-281; Zhang et al. Gene Therapy. 1999 6:1438-1447; Jeffs et al. Pharm Res. 2005 22:362-372; Morrissey et al., Nat Biotechnol. 2005 2:1002-1007; Zimmermann et al., Nature. 2006 441:111-114; Heyes et al. J Contr Rel. 2005 107:276-287; Semple et al. Nature Biotech. 2010 28:172-176; Judge et al. J Clin Invest. 2009 119:661-673; deFougerolles *Hum Gene Ther.* 2008 19:125-132; the contents of each of which are incorporated herein in their entireties). The original manufacture method by Wheeler et al. was a detergent dialysis method, which was later improved by Jeffs et al. and is referred to as the spontaneous vesicle formation method. The liposome formulations may be composed of 3 to 4 lipid components in addition to the saRNA. As an example a liposome can contain, but is not limited to, 55% cholesterol, 20% disteroylphosphatidyl choline (DSPC), 10% PEG-S-DSG, and 15% 1,2-dioleyloxy-N,N-dimethylaminopropane (DODMA), as described by Jeffs et al. In another example, certain liposome formulations may contain, but are not limited to, 48% cholesterol, 20% DSPC, 2% PEG-c-DMA, and 30% cationic lipid, where the cationic lipid can be 1,2-distearloxy-N,N-dimethylaminopropane (DSDMA), DODMA, DLin-DMA, or 1,2-dilinolenyloxy-3-dimethyl-aminopropane (DLenDMA), as described by Heyes et al. In another example, the nucleic acid-lipid particle may comprise a cationic lipid comprising from about 50 mol % to about 85 mol % of the total lipid present in the particle; a non-cationic lipid comprising from about 13 mol % to about 49.5 mol % of the total lipid present in the particle; and a conjugated lipid that inhibits aggregation of particles comprising from about 0.5 mol % to about 2 mol % of the total lipid present in the particle as described in WO2009127060 to Maclachlan et al, the contents of which are incorporated herein by reference in their entirety. In another example, the nucleic acid-lipid particle may be any nucleic acid-lipid particle disclosed in US2006008910 to Maclachlan et al., the contents of which are incorporated herein by reference in their entirety. As a non-limiting example, the nucleic acid-lipid particle may comprise a cationic lipid of Formula I, a non-cationic lipid, and a conjugated lipid that inhibits aggregation of particles.

In one embodiment, the saRNA may be formulated in a lipid vesicle which may have crosslinks between functionalized lipid bilayers.

In one embodiment, the liposome may contain a sugar-modified lipid disclosed in U.S. Pat. No. 5,595,756 to Bally et al., the contents of which are incorporated herein by reference in their entirety. The lipid may be a ganglioside and cerebroside in an amount of about 10 mol percent.

In one embodiment, the saRNA may be formulated in a liposome comprising a cationic lipid. The liposome may have a molar ratio of nitrogen atoms in the cationic lipid to the phosphates in the saRNA (N:P ratio) of between 1:1 and 20:1 as described in International Publication No. WO2013006825, the contents of which are herein incorporated by reference in its entirety. In another embodiment, the liposome may have a N:P ratio of greater than 20:1 or less than 1:1.

In one embodiment, the saRNA may be formulated in a lipid-polycation complex. The formation of the lipid-polycation complex may be accomplished by methods known in the art and/or as described in U.S. Pub. No. 20120178702, the contents of which are herein incorporated by reference in its entirety. As a non-limiting example, the polycation may include a cationic peptide or a polypeptide such as, but not limited to, polylysine, polyornithine and/or polyarginine and the cationic peptides described in International Pub. No. WO2012013326; herein incorporated by reference in its entirety. In another embodiment, the saRNA may be formulated in a lipid-polycation complex which may further include a neutral lipid such as, but not limited to, cholesterol or dioleoyl phosphatidylethanolamine (DOPE).

The liposome formulation may be influenced by, but not limited to, the selection of the cationic lipid component, the degree of cationic lipid saturation, the nature of the PEGylation, ratio of all components and biophysical parameters such as size. In one example by Semple et al. (Semple et al.

Nature Biotech. 2010 28:172-176; the contents of which are herein incorporated by reference in its entirety), the liposome formulation was composed of 57.1% cationic lipid, 7.1% dipalmitoylphosphatidylcholine, 34.3% cholesterol, and 1.4% PEG-c-DMA.

In some embodiments, the ratio of PEG in the lipid nanoparticle (LNP) formulations may be increased or decreased and/or the carbon chain length of the PEG lipid may be modified from C14 to C18 to alter the pharmacokinetics and/or biodistribution of the LNP formulations. As a non-limiting example, LNP formulations may contain 1-5% of the lipid molar ratio of PEG-c-DOMG as compared to the cationic lipid, DSPC and cholesterol. In another embodiment the PEG-c-DOMG may be replaced with a PEG lipid such as, but not limited to, PEG-DSG (1,2-Distearoyl-sn-glycerol, methoxypolyethylene glycol) or PEG-DPG (1,2-Dipalmitoyl-sn-glycerol, methoxypolyethylene glycol). The cationic lipid may be selected from any lipid known in the art such as, but not limited to, DLin-MC3-DMA, DLin-DMA, C12-200 and DLin-KC2-DMA.

In one embodiment, the saRNA may be formulated in a lipid nanoparticle such as the lipid nanoparticles described in International Publication No. WO2012170930, the contents of which are herein incorporated by reference in its entirety.

In one embodiment, the cationic lipid which may be used in formulations of the present invention may be selected from, but not limited to, a cationic lipid described in International Publication Nos. WO2012040184, WO2011153120, WO2011149733, WO2011090965, WO2011043913, WO2011022460, WO2012061259, WO2012054365, WO2012044638, WO2010080724, WO201021865 and WO2008103276, U.S. Pat. Nos. 7,893, 302, 7,404,969 and 8,283,333 and US Patent Publication No. US20100036115 and US20120202871; the contents of each of which is herein incorporated by reference in their entirety. In another embodiment, the cationic lipid may be selected from, but not limited to, formula A described in International Publication Nos. WO2012040184, WO2011153120, WO2011149733, WO2011090965, WO2011043913, WO2011022460, WO2012061259, WO2012054365 and WO2012044638; the contents of each of which is herein incorporated by reference in their entirety. In yet another embodiment, the cationic lipid may be selected from, but not limited to, formula CLI-CLXXIX of International Publication No. WO2008103276, formula CLI-CLXXIX of U.S. Pat. No. 7,893,302, formula CLI-CLXXXXII of U.S. Pat. No. 7,404,969 and formula I-VI of US Patent Publication No. US20100036115; the contents of each of which is herein incorporated by reference in their entirety. In yet another embodiment, the cationic lipid may be a multivalent cationic lipid such as the cationic lipid disclosed in U.S. Pat. No. 7,223,887 to Gaucheron et al., the contents of which are incorporated herein by reference in their entirety. The cationic lipid may have a positively-charged head group including two quaternary amine groups and a hydrophobic portion including four hydrocarbon chains as described in U.S. Pat. No. 7,223,887 to Gaucheron et al., the contents of which are incorporated herein by reference in their entirety. In yet another embodiment, the cationic lipid may be biodegradable as the biodegradable lipids disclosed in US20130195920 to Maier et al., the contents of which are incorporated herein by reference in their entirety. The cationic lipid may have one or more biodegradable groups located in a lipidic moiety of the cationic lipid as described in formula I-IV in US 20130195920 to Maier et al., the contents of which are incorporated herein by reference in their entirety. As a non-limiting example, the cationic lipid may be selected from (20Z,23Z)-N,N-dimethylnonacosa-20,23-dien-10-amine, (17Z,20Z)-N,N-dimemylhexacosa-17,20-dien-9-amine, (1Z,19Z)-N5N-dimethylpentacosa-16, 19-dien-8-amine, (13Z,16Z)-N,N-dimethyldocosa-13,16-dien-5-amine, (12Z,15Z)-N,N-dimethylhenicosa-12,15-dien-4-amine, (14Z,17Z)-N,N-dimethyltricosa-14,17-dien-6-amine, (15Z,18Z)-N,N-dimethyltetracosa-15,18-dien-7-amine, (18Z,21Z)-N,N-dimethylheptacosa-18,21-dien-10-amine, (15Z,18Z)-N,N-dimethyltetracosa-15,18-dien-5-amine, (14Z,17Z)-N,N-dimethyltricosa-14,17-dien-4-amine, (19Z,22Z)-N,N-dimeihyloctacosa-19,22-dien-9-amine, (18Z,21 Z)-N,N-dimethylheptacosa-18,21-dien-8-amine, (17Z,20Z)-N,N-dimethylhexacosa-17,20-dien-7-amine, (16Z,19Z)-N,N-dimethylpentacosa-16,19-dien-6-amine, (22Z,25Z)-N,N-dimethylhentriaconta-22,25-dien-10-amine, (21 Z,24Z)-N,N-dimethyltriaconta-21,24-dien-9-amine, (18Z)-N,N-dimetylheptacos-18-en-10-amine, (17Z)-N,N-dimethylhexacos-17-en-9-amine, (19Z,22Z)-N,N-dimethyloctacosa-19,22-dien-7-amine, N,N-dimethylheptacosan-10-amine, (20Z,23Z)-N-ethyl-N-methylnonacosa-20,23-dien-10-amine, 1-[(11Z,14Z)-1-nonylicosa-11,14-dien-1-yl]pyrrolidine, (20Z)-N,N-dimethylheptacos-20-en-10-amine, (15Z)-N,N-dimethyl eptacos-15-en-1 O-amine, (14Z)-N,N-dimethylnonacos-14-en-10-amine, (17Z)-N,N-dimethylnonacos-17-en-10-amine, (24Z)-N,N-dimethyltritriacont-24-en-10-amine, (20Z)-N,N-dimethylnonacos-20-en-1 O-amine, (22Z)-N,N-dimethyl-hentriacont-22-en-10-amine, (16Z)-N,N-dimethylpentacos-16-en-8-amine, (12Z,15Z)-N,N-dimethyl-2-nonylhenicosa-12,15-dien-1-amine, (13Z,16Z)-N,N-dimethyl-3-nonyldocosa-13,16-dien-1-amine, N,N-dimethyl-1-[(1S,2R)-2-octylcyclopropyl]eptadecan-8-amine, 1-[(1 S,2R)-2-hexylcyclopropyl]-N,N-dimethylnonadecan-10-amine, N,N-dimethyl-1-[(1S,2R)-2-octylcyclopropyl]nonadecan-10-amine, N,N-dimethyl-21-[(1S,2R)-2-octylcyclopropyl]henicosan-10-amine, N,N-dimethyl-1-[(1S,2S)-2-{[(1R,2R)-2-pentylcyclopropyl]methyl}cyclopropyl]nonadecan-10-amine,N,N-dimethyl-1-[(1S,2R)-2-octylcyclopropyl] hexadecan-8-amine, N,N-dimethyl-[(1R,2 S)-2-undecylcyclopropyl]tetradecan-5-amine, N,N-dimethyl-3-{7-[(1S,2R)-2-octylcyclopropyl]heptyl}dodecan-1-amine, 1-[(1R,2 S)-2-heptylcyclopropyl]-N,N-dimethyloctadecan-9-amine, 1-[(1S,2R)-2-decylcyclopropyl]-N,N-dimethylpentadecan-6-amine, N,N-dimethyl-1-[(1S,2R)-2-octylcyclopropyl]pentadecan-8-amine, R-N,N-dimethyl-1-[(9Z,12Z)-octadeca-9,12-dien-1-yloxy]-3-(octyloxy)propan-2-amine, S-N,N-dimethyl-1-[(9Z,12Z)-octadeca-9,12-dien-1-yloxy]-3-(octyloxy)propan-2-amine, 1-{2-[(9Z,12Z)-octadeca-9,12-dien-1-yloxy]-1-[(octyloxy)methyl] ethyl}pyrrolidine, (2S)-N,N-dimethyl-1-[(9Z,12Z)-octadeca-9,12-dien-1-yloxy]-3-[(5Z)-oct-5-en-1-yloxy] propan-2-amine, 1-{2-[(9Z,12Z)-octadeca-9,12-dien-1-yloxy]-1-[(octyloxy)methyl]ethyl}azetidine, (2S)-1-(hexyloxy)-N,N-dimethyl-3-[(9Z,12Z)-octadeca-9,12-dien-1-yloxy]propan-2-amine, (2S)-1-(heptyloxy)-N,N-dimethyl-3-[(9Z,12Z)-octadeca-9,12-dien-1-yloxy]propan-2-amine, N,N-dimethyl-1-(nonyloxy)-3-[(9Z,12Z)-octadeca-9,12-dien-1-yloxy]propan-2-amine, N,N-dimethyl-1-[(9Z)-octadec-9-en-1-yloxy]-3-(octyloxy) propan-2-amine; (2S)-N,N-dimethyl-1-[(6Z,9Z,12Z)-octadeca-6,9,12-trien-1-yloxy]-3-(octyloxy)propan-2-amine, (2S)-1-[(11Z,14Z)-icosa-11,14-dien-1-yloxy]-N,N-dimethyl-3-(pentyloxy)propan-2-amine, (2S)-1-(hexyloxy)-3-[(11Z,14Z)-icosa-11,14-dien-1-yloxy]-N,N-dimethyl-propan-2-amine, 1-[(11Z,14Z)-icosa-11,14-dien-1-yloxy]-

N,N-dimethyl-3-(octyloxy)propan-2-amine, 1-[(13Z,16Z)-docosa-13,16-dien-1-yloxy]-N,N-dimethyl-3-(octyloxy)propan-2-amine, (2S)-1-[(13Z,16Z)-docosa-13,16-dien-1-yloxy]-3-(hexyloxy)-N,N-dimethylpropan-2-amine, (2S)-1-[(13Z)-docos-13-en-1-yloxy]-3-(hexyloxy)-N,N-dimethylpropan-2-amine, 1-[(13Z)-docos-13-en-1-yloxy]-N,N-dimethyl-3-(octyloxy)propan-2-amine, 1-[(9Z)-hexadec-9-en-1-yloxy]-N,N-dimethyl-3-(octyloxy)propan-2-amine, (2R)-N,N-dimethyl-H(1-metoyloctyl)oxy]-3-[(9Z,12Z)-octadeca-9,12-dien-1-yloxy]propan-2-amine, (2R)-1-[(3,7-dimethyloctyl)oxy]-N,N-dimethyl-3-[(9Z,12Z)-octadeca-9,12-dien-1-yloxy]propan-2-amine, N,N-dimethyl-1-(octyloxy)-3-({8-[(1S,2S)-2-{[(1R,2R)-2-pentylcyclopropyl]methyl}cyclopropyl]octyl}oxy)propan-2-amine, N,N-dimethyl-1-{[8-(2-oclylcyclopropyl)octyl]oxy}-3-(octyloxy)propan-2-amine and (11E,20Z,23Z)-N,N-dimethylnonacosa-11,20,2-trien-10-amine or a pharmaceutically acceptable salt or stereoisomer thereof.

In one embodiment, the lipid may be a cleavable lipid such as those described in International Publication No. WO2012170889, the contents of which are herein incorporated by reference in its entirety.

In one embodiment, the nanoparticles described herein may comprise at least one cationic polymer described herein and/or known in the art.

In one embodiment, the cationic lipid may be synthesized by methods known in the art and/or as described in International Publication Nos. WO2012040184, WO2011153120, WO2011149733, WO2011090965, WO2011043913, WO2011022460, WO2012061259, WO2012054365, WO2012044638, WO2010080724 and WO201021865; the contents of each of which is herein incorporated by reference in their entirety.

In one embodiment, the LNP formulations of the saRNA may contain PEG-c-DOMG at 3% lipid molar ratio. In another embodiment, the LNP formulations of the saRNA may contain PEG-c-DOMG at 1.5% lipid molar ratio.

In one embodiment, the pharmaceutical compositions of the saRNA may include at least one of the PEGylated lipids described in International Publication No. 2012099755, the contents of which is herein incorporated by reference in its entirety.

In one embodiment, the LNP formulation may contain PEG-DMG 2000 (1,2-dimyristoyl-sn-glycero-3-phophoethanolamine-N-[methoxy(polyethylene glycol)-2000). In one embodiment, the LNP formulation may contain PEG-DMG 2000, a cationic lipid known in the art and at least one other component. In another embodiment, the LNP formulation may contain PEG-DMG 2000, a cationic lipid known in the art, DSPC and cholesterol. As a non-limiting example, the LNP formulation may contain PEG-DMG 2000, DLin-DMA, DSPC and cholesterol. As another non-limiting example the LNP formulation may contain PEG-DMG 2000, DLin-DMA, DSPC and cholesterol in a molar ratio of 2:40:10:48 (see e.g., Geall et al., Nonviral delivery of self-amplifying RNA vaccines, PNAS 2012; PMID: 22908294; herein incorporated by reference in its entirety). As another non-limiting example, the saRNA described herein may be formulated in a nanoparticle to be delivered by a parenteral route as described in U.S. Pub. No. 20120207845; the contents of which are herein incorporated by reference in its entirety. The cationic lipid may be the cationic lipids disclosed in US20130156845 to Manoharan et al. and US 20130129785 to Manoharan et al., WO 2012047656 to Wasan et al., WO 2010144740 to Chen et al., WO 2013086322 to Ansell et al., or WO 2012016184 to Manoharan et al., the contents of each of which are incorporated herein by reference in their entirety.

In one embodiment, the saRNA of the present invention may be formulated with a plurality of cationic lipids, such as a first and a second cationic lipid as described in US20130017223 to Hope et al., the contents of which are incorporated herein by reference in their entirety. The first cationic lipid can be selected on the basis of a first property and the second cationic lipid can be selected on the basis of a second property, where the properties may be determined as outlined in US20130017223, the contents of which are herein incorporated by reference in its entirety. In one embodiment, the first and second properties are complementary.

In another embodiment, the saRNA may be formulated with a lipid particle comprising one or more cationic lipids and one or more second lipids, and one or more nucleic acids, wherein the lipid particle comprises a solid core, as described in US Patent Publication No. US20120276209 to Cullis et al., the contents of which are incorporated herein by reference in their entirety.

In one embodiment, the saRNA of the present invention may be complexed with a cationic amphiphile in an oil-in-water (o/w) emulsion such as described in EP2298358 to Satishchandran et al., the contents of which are incorporated herein by reference in their entirety. The cationic amphiphile may be a cationic lipid, modified or unmodified spermine, bupivacaine, or benzalkonium chloride and the oil may be a vegetable or an animal oil. As a non-limiting example, at least 10% of the nucleic acid-cationic amphiphile complex is in the oil phase of the oil-in-water emulsion (see e.g., the complex described in European Publication No. EP2298358 to Satishchandran et al., the contents of which are herein incorporated by reference in its entirety).

In one embodiment, the saRNA of the present invention may be formulated with a composition comprising a mixture of cationic compounds and neutral lipids. As a non-limiting example, the cationic compounds may be formula (I) disclosed in WO 1999010390 to Ansell et al., the contents of which are disclosed herein by reference in their entirety, and the neutral lipid may be selected from the group consisting of diacylphosphatidylcholine, diacylphosphatidylethanolamine, ceramide and sphingomyelin.

In one embodiment, the LNP formulation may be formulated by the methods described in International Publication Nos. WO2011127255 or WO2008103276, each of which are herein incorporated by reference in their entirety. As a non-limiting example, the saRNA of the present invention may be encapsulated in any of the lipid nanoparticle (LNP) formulations described in WO2011127255 and/or WO2008103276; the contents of each of which are herein incorporated by reference in their entirety.

In one embodiment, the LNP formulations described herein may comprise a polycationic composition. As a non-limiting example, the polycationic composition may be selected from formula 1-60 of US Patent Publication No. US20050222064; the contents of which are herein incorporated by reference in its entirety. In another embodiment, the LNP formulations comprising a polycationic composition may be used for the delivery of the saRNA described herein in vivo and/or in vitro.

In one embodiment, the LNP formulations described herein may additionally comprise a permeability enhancer molecule. Non-limiting permeability enhancer molecules are described in US Patent Publication No. US20050222064; the contents of which are herein incorporated by reference in its entirety.

In one embodiment, the pharmaceutical compositions may be formulated in liposomes such as, but not limited to, DiLa2 liposomes (Marina Biotech, Bothell, WA), SMARTICLES®/NOV340 (Marina Biotech, Bothell, WA), neutral DOPC (1,2-dioleoyl-sn-glycero-3-phosphocholine) based liposomes (e.g., siRNA delivery for ovarian cancer (Landen et al. Cancer Biology & Therapy 2006 5(12)1708-1713); the contents of which is herein incorporated by reference in its entirety) and hyaluronan-coated liposomes (Quiet Therapeutics, Israel). In some embodiments, the pharmaceutical compositions may be formulated with any amphoteric liposome disclosed in WO 2008/043575 to Panzner and U.S. Pat. No. 8,580,297 to Essler et al., the contents of which are incorporated herein by reference in their entirety. The amphoteric liposome may comprise a mixture of lipids including a cationic amphiphile, an anionic amphiphile and optional one or more neutral amphiphiles. The amphoteric liposome may comprise amphoteric compounds based on amphiphilic molecules, the head groups of which being substituted with one or more amphoteric groups. In some embodiments, the pharmaceutical compositions may be formulated with an amphoteric lipid comprising one or more amphoteric groups having an isoelectric point between 4 and 9, as disclosed in US 20140227345 to Essler et al., the contents of which are incorporated herein by reference in their entirety.

The nanoparticle formulations may be a carbohydrate nanoparticle comprising a carbohydrate carrier and a nucleic acid molecule (e.g., saRNA). As a non-limiting example, the carbohydrate carrier may include, but is not limited to, an anhydride-modified phytoglycogen or glycogen-type material, phtoglycogen octenyl succinate, phytoglycogen beta-dextrin, anhydride-modified phytoglycogen beta-dextrin. (See e.g., International Publication No. WO2012109121; the contents of which are herein incorporated by reference in its entirety).

Lipid nanoparticle formulations may be improved by replacing the cationic lipid with a biodegradable cationic lipid which is known as a rapidly eliminated lipid nanoparticle (reLNP). Ionizable cationic lipids, such as, but not limited to, DLinDMA, DLin-KC2-DMA, and DLin-MC3-DMA, have been shown to accumulate in plasma and tissues over time and may be a potential source of toxicity. The rapid metabolism of the rapidly eliminated lipids can improve the tolerability and therapeutic index of the lipid nanoparticles by an order of magnitude from a 1 mg/kg dose to a 10 mg/kg dose in rat. Inclusion of an enzymatically degraded ester linkage can improve the degradation and metabolism profile of the cationic component, while still maintaining the activity of the reLNP formulation. The ester linkage can be internally located within the lipid chain or it may be terminally located at the terminal end of the lipid chain. The internal ester linkage may replace any carbon in the lipid chain.

In one embodiment, the saRNA may be formulated as a lipoplex, such as, without limitation, the ATUPLEX™ system, the DACC system, the DBTC system and other siRNA-lipoplex technology from Silence Therapeutics (London, United Kingdom), STEMFECT™ from STEMGENT® (Cambridge, MA), and polyethylenimine (PEI) or pro-tamine-based targeted and non-targeted delivery of nucleic acids (Aleku et al. Cancer Res. 2008 68:9788-9798; Strumberg et al. Int J Clin Pharmacol Ther 2012 50:76-78; Santel et al., Gene Ther 2006 13:1222-1234; Santel et al., Gene Ther 2006 13:1360-1370; Gutbier et al., Pulm Pharmacol. Ther. 2010 23:334-344; Kaufmann et al. Microvasc Res 2010 80:286-293 Weide et al. J Immunother. 2009 32:498-507; Weide et al. J Immunother. 2008 31:180-188; Pascolo Expert Opin. Biol. Ther. 4:1285-1294; Fotin-Mleczek et al., 2011 J. Immunother. 34:1-15; Song et al., Nature Biotechnol. 2005, 23:709-717; Peer et al., Proc Natl Acad Sci USA. 2007 6; 104:4095-4100; deFougerolles *Hum Gene Ther.* 2008 19:125-132; the contents of each of which are incorporated herein by reference in its entirety).

In one embodiment such formulations may also be constructed or compositions altered such that they passively or actively are directed to different cell types in vivo, including but not limited to hepatocytes, immune cells, tumor cells, endothelial cells, antigen presenting cells, and leukocytes (Akinc et al. Mol Ther. 2010 18:1357-1364; Song et al., Nat Biotechnol. 2005 23:709-717; Judge et al., J Clin Invest. 2009 119:661-673; Kaufmann et al., Microvasc Res 2010 80:286-293; Santel et al., Gene Ther 2006 13:1222-1234; Santel et al., Gene Ther 2006 13:1360-1370; Gutbier et al., Pulm Pharmacol. Ther. 2010 23:334-344; Basha et al., Mol. Ther. 2011 19:2186-2200; Fenske and Cullis, Expert Opin Drug Deliv. 2008 5:25-44; Peer et al., Science. 2008 319: 627-630; Peer and Lieberman, Gene Ther. 2011 18:1127-1133; the contents of each of which are incorporated herein by reference in its entirety). One example of passive targeting of formulations to liver cells includes the DLin-DMA, DLin-KC2-DMA and DLin-MC3-DMA-based lipid nanoparticle formulations which have been shown to bind to apolipoprotein E and promote binding and uptake of these formulations into hepatocytes in vivo (Akinc et al. Mol Ther. 2010 18:1357-1364; the contents of which is herein incorporated by reference in its entirety). Formulations can also be selectively targeted through expression of different ligands on their surface as exemplified by, but not limited by, folate, transferrin, N-acetylgalactosamine (GalNAc), and antibody targeted approaches (Kolhatkar et al., Curr Drug Discov Technol. 2011 8:197-206; Musacchio and Torchilin, *Front Biosci.* 2011 16:1388-1412; Yu et al., Mol Membr Biol. 2010 27:286-298; Patil et al., Crit Rev Ther Drug Carrier Syst. 2008 25:1-61; Benoit et al., Biomacromolecules. 2011 12:2708-2714; Zhao et al., Expert Opin Drug Deliv. 2008 5:309-319; Akinc et al., Mol Ther. 2010 18:1357-1364; Srinivasan et al., Methods Mol Biol. 2012 820:105-116; Ben-Arie et al., Methods Mol Biol. 2012 757:497-507; Peer 2010 J Control Release. 20:63-68; Peer et al., Proc Natl Acad Sci USA. 2007 104:4095-4100; Kim et al., Methods Mol Biol. 2011 721:339-353; Subramanya et al., Mol Ther. 2010 18:2028-2037; Song et al., Nat Biotechnol. 2005 23:709-717; Peer et al., Science. 2008 319:627-630; Peer and Lieberman, Gene Ther. 2011 18:1127-1133; the contents of each of which are incorporated herein by reference in its entirety).

In one embodiment, the saRNA is formulated as a solid lipid nanoparticle. A solid lipid nanoparticle (SLN) may be spherical with an average diameter between 10 to 1000 nm. SLN possess a solid lipid core matrix that can solubilize lipophilic molecules and may be stabilized with surfactants and/or emulsifiers. In a further embodiment, the lipid nanoparticle may be a self-assembly lipid-polymer nanoparticle (see Zhang et al., ACS Nano, 2008, 2 (8), pp 1696-1702; the contents of which are herein incorporated by reference in its entirety).

In one embodiment, the saRNA of the present invention can be formulated for controlled release and/or targeted delivery. As used herein, "controlled release" refers to a pharmaceutical composition or compound release profile that conforms to a particular pattern of release to effect a therapeutic outcome. In one embodiment, the saRNA may be encapsulated into a delivery agent described herein and/or known in the art for controlled release and/or targeted delivery. As used herein, the term "encapsulate" means to enclose, surround or encase. As it relates to the formulation of the compounds of the invention, encapsulation may be substantial, complete or partial. The term "substantially encapsulated" means that at least greater than 50, 60, 70, 80, 85, 90, 95, 96, 97, 98, 99, 99.9, 99.9 or greater than 99.999% of the pharmaceutical composition or compound of the invention may be enclosed, surrounded or encased within the delivery agent. "Partially encapsulated" means that less than 10, 10, 20, 30, 40 50 or less of the pharmaceutical composition or compound of the invention may be enclosed, surrounded or encased within the delivery agent. Advantageously, encapsulation may be determined by measuring the escape or the activity of the pharmaceutical composition or compound of the invention using fluorescence and/or electron micrograph. For example, at least 1, 5, 10, 20, 30, 40, 50, 60, 70, 80, 85, 90, 95, 96, 97, 98, 99, 99.9, 99.99 or greater than 99.99% of the pharmaceutical composition or compound of the invention are encapsulated in the delivery agent.

In another embodiment, the saRNA may be encapsulated into a lipid nanoparticle or a rapidly eliminated lipid nanoparticle and the lipid nanoparticles or a rapidly eliminated lipid nanoparticle may then be encapsulated into a polymer, hydrogel and/or surgical sealant described herein and/or known in the art. As a non-limiting example, the polymer, hydrogel or surgical sealant may be PLGA, ethylene vinyl acetate (EVAc), poloxamer, GELSITE® (Nanotherapeutics, Inc. Alachua, FL), HYLENEX® (Halozyme Therapeutics, San Diego CA), surgical sealants such as fibrinogen polymers (Ethicon Inc. Cornelia, GA), TISSELL® (Baxter International, Inc Deerfield, IL), PEG-based sealants, and COSEAL® (Baxter International, Inc Deerfield, IL).

In another embodiment, the lipid nanoparticle may be encapsulated into any polymer known in the art which may form a gel when injected into a subject. As another non-limiting example, the lipid nanoparticle may be encapsulated into a polymer matrix which may be biodegradable.

In one embodiment, the saRNA formulation for controlled release and/or targeted delivery may also include at least one controlled release coating. Controlled release coatings include, but are not limited to, OPADRY®, polyvinylpyrrolidone/vinyl acetate copolymer, polyvinylpyrrolidone, hydroxypropyl methylcellulose, hydroxypropyl cellulose, hydroxyethyl cellulose, EUDRAGIT RL®, EUDRAGIT RS® and cellulose derivatives such as ethylcellulose aqueous dispersions (AQUACOAT® and SURELEASE®).

In one embodiment, the controlled release and/or targeted delivery formulation may comprise at least one degradable polyester which may contain polycationic side chains. Degradable polyesters include, but are not limited to, poly(serine ester), poly(L-lactide-co-L-lysine), poly(4-hydroxy-L-proline ester), and combinations thereof. In another embodiment, the degradable polyesters may include a PEG conjugation to form a PEGylated polymer.

In one embodiment, the saRNA of the present invention may be formulated with a targeting lipid with a targeting moiety such as the targeting moieties disclosed in US20130202652 to Manoharan et al., the contents of which are incorporated herein by reference in their entirety. As a non-limiting example, the targeting moiety of formula I of US 20130202652 to Manoharan et al. may be selected in order to favor the lipid being localized with a desired organ, tissue, cell, cell type or subtype, or organelle. Non-limiting targeting moieties that are contemplated in the present invention include transferrin, anisamide, an RGD peptide, prostate specific membrane antigen (PSMA), fucose, an antibody, or an aptamer.

In one embodiment, the saRNA of the present invention may be encapsulated in a therapeutic nanoparticle. Therapeutic nanoparticles may be formulated by methods described herein and known in the art such as, but not limited to, International Pub Nos. WO2010005740, WO2010030763, WO2010005721, WO2010005723, WO2012054923, US Pub. Nos. US20110262491, US20100104645, US20100087337, US20100068285, US20110274759, US20100068286 and US20120288541 and U.S. Pat. Nos. 8,206,747, 8,293,276, 8,318,208 and 8,318,211; the contents of each of which are herein incorporated by reference in their entirety. In another embodiment, therapeutic polymer nanoparticles may be identified by the methods described in US Pub No. US20120140790, the contents of which are herein incorporated by reference in its entirety.

In one embodiment, the therapeutic nanoparticle may be formulated for sustained release. As used herein, "sustained release" refers to a pharmaceutical composition or compound that conforms to a release rate over a specific period of time. The period of time may include, but is not limited to, hours, days, weeks, months and years. As a non-limiting example, the sustained release nanoparticle may comprise a polymer and a therapeutic agent such as, but not limited to, the saRNA of the present invention (see International Pub No. 2010075072 and US Pub No. US20100216804, US20110217377 and US20120201859, the contents of each of which are herein incorporated by reference in their entirety).

In one embodiment, the therapeutic nanoparticles may be formulated to be target specific. As a non-limiting example, the therapeutic nanoparticles may include a corticosteroid (see International Pub. No. WO2011084518; the contents of which are herein incorporated by reference in its entirety). In one embodiment, the therapeutic nanoparticles may be formulated to be cancer specific. As a non-limiting example, the therapeutic nanoparticles may be formulated in nanoparticles described in International Pub No. WO2008121949, WO2010005726, WO2010005725, WO2011084521 and US Pub No. US20100069426, US20120004293 and US20100104655, the contents of each of which are herein incorporated by reference in their entirety.

In one embodiment, the nanoparticles of the present invention may comprise a polymeric matrix. As a non-limiting example, the nanoparticle may comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester) or combinations thereof.

In one embodiment, the therapeutic nanoparticle comprises a diblock copolymer. In one embodiment, the diblock copolymer may include PEG in combination with a polymer such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester) or combinations thereof.

As a non-limiting example, the therapeutic nanoparticle comprises a PLGA-PEG block copolymer (see US Pub. No. US20120004293 and U.S. Pat. No. 8,236,330, each of which is herein incorporated by reference in their entirety). In another non-limiting example, the therapeutic nanoparticle is a stealth nanoparticle comprising a diblock copolymer of PEG and PLA or PEG and PLGA (see U.S. Pat. No. 8,246,968 and International Publication No. WO2012166923, the contents of each of which are herein incorporated by reference in its entirety).

In one embodiment, the therapeutic nanoparticle may comprise a multiblock copolymer such as, but not limited to the multiblock copolymers described in U.S. Pat. Nos. 8,263,665 and 8,287,910; the contents of each of which are herein incorporated by reference in its entirety.

In one embodiment, the block copolymers described herein may be included in a polyion complex comprising a non-polymeric micelle and the block copolymer. (See e.g., U.S. Pub. No. 20120076836; the contents of which are herein incorporated by reference in its entirety).

In one embodiment, the therapeutic nanoparticle may comprise at least one acrylic polymer. Acrylic polymers include but are not limited to, acrylic acid, methacrylic acid, acrylic acid and methacrylic acid copolymers, methyl methacrylate copolymers, ethoxyethyl methacrylates, cyanoethyl methacrylate, amino alkyl methacrylate copolymer, poly(acrylic acid), poly(methacrylic acid), polycyanoacrylates and combinations thereof.

In one embodiment, the therapeutic nanoparticles may comprise at least one amine-containing polymer such as, but not limited to polylysine, polyethylene imine, poly(amidoamine) dendrimers, poly(beta-amino esters) (See e.g., U.S. Pat. No. 8,287,849; the contents of which are herein incorporated by reference in its entirety) and combinations thereof.

In one embodiment, the therapeutic nanoparticles may comprise at least one degradable polyester which may contain polycationic side chains. Degradable polyesters include, but are not limited to, poly(serine ester), poly(L-lactide-co-L-lysine), poly(4-hydroxy-L-proline ester), and combinations thereof. In another embodiment, the degradable polyesters may include a PEG conjugation to form a PEGylated polymer.

In another embodiment, the therapeutic nanoparticle may include a conjugation of at least one targeting ligand. The targeting ligand may be any ligand known in the art such as, but not limited to, a monoclonal antibody. (Kirpotin et al, Cancer Res. 2006 66:6732-6740; the contents of which are herein incorporated by reference in its entirety).

In one embodiment, the therapeutic nanoparticle may be formulated in an aqueous solution which may be used to target cancer (see International Pub No. WO2011084513 and US Pub No. US20110294717, the contents of each of which are herein incorporated by reference in their entirety).

In one embodiment, the saRNA may be encapsulated in, linked to and/or associated with synthetic nanocarriers. Synthetic nanocarriers include, but are not limited to, those described in International Pub. Nos. WO2010005740, WO2010030763, WO201213501, WO2012149252, WO2012149255, WO2012149259, WO2012149265, WO2012149268, WO2012149282, WO2012149301, WO2012149393, WO2012149405, WO2012149411, WO2012149454 and WO2013019669, and US Pub. Nos. US20110262491, US20100104645, US20100087337 and US20120244222, the contents of each of which are herein incorporated by reference in their entirety. The synthetic nanocarriers may be formulated using methods known in the art and/or described herein. As a non-limiting example, the synthetic nanocarriers may be formulated by the methods described in International Pub Nos. WO2010005740, WO2010030763 and WO201213501 and US Pub. Nos. US20110262491, US20100104645, US20100087337 and US2012024422, the contents of each of which are herein incorporated by reference in their entirety. In another embodiment, the synthetic nanocarrier formulations may be lyophilized by methods described in International Pub. No. WO2011072218 and U.S. Pat. No. 8,211,473; the contents of each of which are herein incorporated by reference in their entirety.

In one embodiment, the synthetic nanocarriers may contain reactive groups to release the saRNA described herein (see International Pub. No. WO20120952552 and US Pub No. US20120171229, the contents of each of which are herein incorporated by reference in their entirety).

In one embodiment, the synthetic nanocarriers may be formulated for targeted release. In one embodiment, the synthetic nanocarrier may be formulated to release the saRNA at a specified pH and/or after a desired time interval. As a non-limiting example, the synthetic nanoparticle may be formulated to release the saRNA after 24 hours and/or at a pH of 4.5 (see International Pub. Nos. WO2010138193 and WO2010138194 and US Pub Nos. US20110020388 and US20110027217, the contents of each of which is herein incorporated by reference in their entireties).

In one embodiment, the synthetic nanocarriers may be formulated for controlled and/or sustained release of the saRNA described herein. As a non-limiting example, the synthetic nanocarriers for sustained release may be formulated by methods known in the art, described herein and/or as described in International Pub No. WO2010138192 and US Pub No. 20100303850, the contents each of which is herein incorporated by reference in their entirety.

In one embodiment, the nanoparticle may be optimized for oral administration. The nanoparticle may comprise at least one cationic biopolymer such as, but not limited to, chitosan or a derivative thereof. As a non-limiting example, the nanoparticle may be formulated by the methods described in U.S. Pub. No. 20120282343; the contents of which are herein incorporated by reference in its entirety.

In one embodiment, the saRNA of the present invention may be formulated in a modular composition such as described in U.S. Pat. No. 8,575,123 to Manoharan et al., the contents of which are herein incorporated by reference in their entirety. As a non-limiting example, the modular composition may comprise a nucleic acid, e.g., the saRNA of the present invention, at least one endosomolytic component, and at least one targeting ligand. The modular composition may have a formula such as any formula described in U.S. Pat. No. 8,575,123 to Manoharan et al., the contents of which are herein incorporated by reference in their entirety.

In one embodiment, the saRNA of the present invention may be encapsulated in the lipid formulation to form a stable nucleic acid-lipid particle (SNALP) such as described in U.S. Pat. No. 8,546,554 to de Fougerolles et al., the contents of which are incorporated here by reference in their entirety. The lipid may be cationic or non-cationic. In one non-limiting example, the lipid to nucleic acid ratio (mass/mass ratio) (e.g., lipid to saRNA ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1, or 5:1, 6:1, 7:1, 8:1, 9:1, 10:1, or 11:1. In another example, the SNALP includes 40% 2,2-Dilinoleyl-4-dimethylaminoethyl-[1,3]-dioxolane (Lipid A), 10% dioleoylphosphatidylcholine (DSPC), 40% cholesterol, 10% polyethyleneglycol (PEG)-C-DOMG (mole percent) with a particle size of 63.0±20 nm and a 0.027 nucleic acid/lipid ratio. In another embodiment, the saRNA of the present invention may be formulated with a nucleic acid-lipid particle comprising an endosomal membrane destabilizer as disclosed in U.S. Pat. No. 7,189,705 to Lam et al., the contents of which are incorporated herein by reference in their entirety. As a non-limiting example, the endosomal membrane destabilizer may be a $Ca^{2+}$ ion.

In one embodiment, the saRNA of the present invention may be formulated with formulated lipid particles (FLiPs) disclosed in U.S. Pat. No. 8,148,344 to Akine et al., the contents of which are herein incorporated by reference in their entirety. Akine et al. teach that FLiPs may comprise at least one of a single or double stranded oligonucleotide, where the oligonucleotide has been conjugated to a lipophile and at least one of an emulsion or liposome to which the conjugated oligonucleotide has been aggregated, admixed or associated. These particles have surprisingly been shown to effectively deliver oligonucleotides to heart, lung and muscle disclosed in U.S. Pat. No. 8,148,344 to Akine et al., the contents of which are herein incorporated by reference in their entirety.

In some embodiments, the saRNA of the present invention may be delivered by a viral vector, such as adenoviruses or adeno associated virus (AAV) vectors. In one embodiment, the saRNA of the present invention may be delivered to a cell using a composition comprising an expression vector in a lipid formulation as described in U.S. Pat. No. 6,086,913 to Tam et al., the contents of which are incorporated herein by reference in their entirety. The composition disclosed by Tam is serum-stable and comprises an expression vector comprising first and second inverted repeated sequences from an adeno associated virus (AAV), a rep gene from AAV, and a nucleic acid fragment. The expression vector in Tam is complexed with lipids. In another embodiment, any AAV vector disclosed in US 20140249209 to Fox et al. may be used to delivered saRNA of the present invention.

In one embodiment, the saRNA of the present invention may be formulated with a lipid formulation disclosed in US 20120270921 to de Fougerolles et al., the contents of which are incorporated herein by reference in their entirety. In one non-limiting example, the lipid formulation may include a cationic lipid having the formula A described in US 20120270921, the contents of which are herein incorporated by reference in its entirety. In another non-limiting example, the compositions of exemplary nucleic acid-lipid particles disclosed in Table A of US 20120270921, the contents of which are incorporated herein by reference in their entirety, may be used with the saRNA of the present invention.

In one embodiment, the saRNA of the present invention may be fully encapsulated in a lipid particle disclosed in US 20120276207 to Maurer et al., the contents of which are incorporated herein by reference in their entirety. The particles may comprise a lipid composition comprising preformed lipid vesicles, a charged therapeutic agent, and a destabilizing agent to form a mixture of preformed vesicles and therapeutic agent in a destabilizing solvent, wherein said destabilizing solvent is effective to destabilize the membrane of the preformed lipid vesicles without disrupting the vesicles.

In one embodiment, the saRNA of the present invention may be formulated with a conjugated lipid. In a non-limiting example, the conjugated lipid may have a formula such as described in US 20120264810 to Lin et al., the contents of which are incorporated herein by reference in their entirety. The conjugate lipid may form a lipid particle which further comprises a cationic lipid, a neutral lipid, and a lipid capable of reducing aggregation.

In one embodiment, the saRNA of the present invention may be formulated in a neutral liposomal formulation such as disclosed in US 20120244207 to Fitzgerald et al., the contents of which are incorporated herein by reference in their entirety. The phrase "neutral liposomal formulation" refers to a liposomal formulation with a near neutral or neutral surface charge at a physiological pH. Physiological pH can be, e.g., about 7.0 to about 7.5, or, e.g., about 7.5, or, e.g., 7.0, 7.1, 7.2, 7.3, 7.4, or 7.5, or, e.g., 7.3, or, e.g., 7.4. An example of a neutral liposomal formulation is an ionizable lipid nanoparticle (iLNP). A neutral liposomal formulation can include an ionizable cationic lipid, e.g., DLin-KC2-DMA.

In one embodiment, the saRNA of the present invention may be formulated with a charged lipid or an amino lipid. As used herein, the term "charged lipid" is meant to include those lipids having one or two fatty acyl or fatty alkyl chains and a quaternary amino head group. The quaternary amine carries a permanent positive charge. The head group can optionally include an ionizable group, such as a primary, secondary, or tertiary amine that may be protonated at physiological pH. The presence of the quaternary amine can alter the pKa of the ionizable group relative to the pKa of the group in a structurally similar compound that lacks the quaternary amine (e.g., the quaternary amine is replaced by a tertiary amine) In some embodiments, a charged lipid is referred to as an "amino lipid." In a non-limiting example, the amino lipid may be amino lipids described in US20110256175 to Hope et al., the contents of which are incorporated herein by reference in their entirety. For example, the amino lipids may have the structure disclosed as structure (II), DLin-K-C2-DMA, DLin-K2-DMA, DLin-K6-DMA disclosed in US20110256175 to Hope et al., the contents of which are incorporated herein by reference in their entirety. In another example, the amino lipid may have the structure (I), (II), (III), or (IV), or 4-(R)-DUn-K-DMA (VI), 4-(S)-DUn-K-DMA (V) as described in WO2009132131 to Muthiah et al., the contents of which are incorporated herein by reference in their entirety. In another example, the charged lipid used in any of the formulations described herein may be any charged lipid described in EP2509636 to Manoharan et al., the contents of which are incorporated herein by reference in their entirety.

In one embodiment, the saRNA of the present invention may be formulated with an association complex containing lipids, liposomes, or lipoplexes. In a non-limiting example, the association complex comprises one or more compounds each having a structure defined by formula (I), a PEG-lipid having a structure defined by formula (XV), a steroid and a nucleic acid disclosed in U.S. Pat. No. 8,034,376 to Manoharan et al., the contents of which are incorporated herein by reference in their entirety. The saRNA may be formulated with any association complex described in U.S. Pat. No. 8,034,376, the contents of which are herein incorporated by reference in its entirety.

In one embodiment, the saRNA of the present invention may be formulated with reverse head group lipids. As a non-limiting example, the saRNA may be formulated with a zwitterionic lipid comprising a headgroup wherein the positive charge is located near the acyl chain region and the negative charge is located at the distal end of the head group, such as a lipid having structure (A) or structure (I) described in WO2011056682 to Leung et al., the contents of which are incorporated herein by reference in their entirety.

In one embodiment, the saRNA of the present invention may be formulated in a lipid bilayer carrier. As a non-limiting example, the saRNA may be combined with a lipid-detergent mixture comprising a lipid mixture of an aggregation-preventing agent in an amount of about 5 mol % to about 20 mol %, a cationic lipid in an amount of about 0.5 mol % to about 50 mol %, and a fusogenic lipid and a detergent, to provide a nucleic acid-lipid-detergent mixture; and then dialyzing said nucleic acid-lipid-detergent mixture against a buffered salt solution to remove said detergent and to encapsulate said nucleic acid in a lipid bilayer carrier and provide a lipid bilayer-nucleic acid composition, wherein said buffered salt solution has an ionic strength sufficient to encapsulate of from about 40% to about 80% of said nucleic acid, described in WO1999018933 to Cullis et al., the contents of which are incorporated herein by reference in their entirety.

In one embodiment, the saRNA of the present invention may be formulated in a nucleic acid-lipid particle capable of selectively targeting the saRNA to a heart, liver, or tumor tissue site. For example, the nucleic acid-lipid particle may comprise (a) a nucleic acid; (b) 1.0 mole % to 45 mole % of a cationic lipid; (c) 0,0 mole % to 90 mole % of another lipid; (d) 1,0 mole % to 10 mole % of a bilayer stabilizing component; (e) 0,0 mole % to 60 mole % cholesterol; and (f) 0,0 mole % to 10 mole % of cationic polymer lipid as described in EP1328254 to Cullis et al., the contents of which are incorporated herein by reference in their entirety. Cullis teaches that varying the amount of each of said cationic lipid, bilayer stabilizing component, another lipid, cholesterol, and cationic polymer lipid can impart tissue selectivity for heart, liver, or tumor tissue site, thereby identifying a nucleic acid-lipid particle capable of selectively targeting a nucleic acid to said heart, liver, or tumor tissue site.

Delivery

The present disclosure encompasses the delivery of saRNA for any of therapeutic, pharmaceutical, diagnostic or imaging by any appropriate route taking into consideration likely advances in the sciences of drug delivery. Delivery may be naked or formulated.

The saRNA of the present invention may be delivered to a cell naked. As used herein in, "naked" refers to delivering saRNA free from agents which promote transfection. For example, the saRNA delivered to the cell may contain no modifications. The naked saRNA may be delivered to the cell using routes of administration known in the art and described herein.

The saRNA of the present invention may be formulated, using the methods described herein. The formulations may contain saRNA which may be modified and/or unmodified. The formulations may further include, but are not limited to, cell penetration agents, a pharmaceutically acceptable carrier, a delivery agent, a bioerodible or biocompatible polymer, a solvent, and a sustained-release delivery depot. The formulated saRNA may be delivered to the cell using routes of administration known in the art and described herein.

The compositions may also be formulated for direct delivery to an organ or tissue in any of several ways in the art including, but not limited to, direct soaking or bathing, via a catheter, by gels, powder, ointments, creams, gels, lotions, and/or drops, by using substrates such as fabric or biodegradable materials coated or impregnated with the compositions, and the like. The saRNA of the present invention may also be cloned into a retroviral replicating vector (RRV) and transduced to cells.

Administration

The saRNA of the present invention may be administered by any route which results in a therapeutically effective outcome. These include, but are not limited to, enteral, gastroenteral, epidural, oral, transdermal, epidural (peridural), intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection, (into the base of the penis), intravaginal administration, intrauterine, extra-amniotic administration, transdermal (diffusion through the intact skin for systemic distribution), transmucosal (diffusion through a mucous membrane), insufflation (snorting), sublingual, sublabial, enema, eye drops (onto the conjunctiva), or in ear drops. In specific embodiments, compositions may be administered in a way which allows them cross the blood-brain barrier, vascular barrier, or other epithelial barrier. Routes of administration disclosed in International Publication WO 2013/090648 filed Dec. 14, 2012, the contents of which are incorporated herein by reference in their entirety, may be used to administer the saRNA of the present invention.

Dosage Forms

A pharmaceutical composition described herein can be formulated into a dosage form described herein, such as a topical, intranasal, intratracheal, or injectable (e.g., intravenous, intraocular, intravitreal, intramuscular, intracardiac, intraperitoneal, subcutaneous). Liquid dosage forms, injectable preparations, pulmonary forms, and solid dosage forms described in International Publication WO 2013/090648 filed Dec. 14, 2012, the contents of which are incorporated herein by reference in their entirety may be used as dosage forms for the saRNA of the present invention.

II. Methods of Use

One aspect of the present invention provides methods of using HNF4a-saRNA and pharmaceutical compositions comprising said HNF4a-saRNA and at least one pharmaceutically acceptable carrier. HNF4a-saRNA modulates HNF4a gene expression. In one embodiment, the expression of HNF4a gene is increased by at least 20, 30, 40%, more preferably at least 45, 50, 55, 60, 65, 70, 75%, even more preferably at least 80% in the presence of the saRNA of the present invention compared to the expression of HNF4a gene in the absence of the saRNA of the present invention. In a further preferable embodiment, the expression of HNF4a gene is increased by a factor of at least 2, 3, 4, 5, 6, 7, 8, 9, 10, more preferably by a factor of at least 15, 20, 25, 30, 35, 40, 45, 50, even more preferably by a factor of at least 60, 70, 80, 90, 100, in the presence of the saRNA of the present invention compared to the expression of HNF4a gene in the absence of the saRNA of the present invention.

Several splice variants of HNF4a are generated via two alternative promoters (proximal promoter P1 and distal promoter P2) and two distinct 3' splicing events. P1-driven HNF4a protein (HNF4a P1) and P2-driven HNF4a protein (HNF4a P2) play distinct functional roles. HNF4a P1 is reported to be down-regulated in cancer and HNF4a P2 is up-regulated (Vuong et al., *Molecular and Cellular Biology*, vol. 35:3471 (2015)). Vuong et al. found that HNF4a P1 suppresses the growth of tumors in colon cancer cell lines, while HNF4a P2 does not. HNF4a P1 upregulates genes involved in growth suppression and cell death and HNF4a P2 upregulates genes involved in cell proliferation and anti-apoptosis. Therefore, it is desirable to increase HNF4a P1 levels, not HNF4a P2 levels.

In some embodiments, the HNF4a-saRNA of the present application increases HNF4a P1 expression. In some embodiments, the HNF4a-saRNA of the present application does not increase HNF4a P2 expression.

In one embodiment, the increase in gene expression of the saRNA descried herein is shown in proliferating cells.

Metabolics Regulation

Hepatocytes are generally perceived as being important for maintenance of several vital functions. For example, they can regulate carbohydrate and lipid metabolism and detoxification of exogenous and endogenous compounds. HNF4a expressed in a variety of tissues where it plays an important role in the differentiation of many cell types.

Non-alcoholic fatty liver disease (NAFLD) is a major global health concern and affects 1 in 3 people in the United States. NAFLD is the build-up of extra fat (lipid) in liver cells that is not caused by excessive alcohol use. It is called a fatty liver (steatosis) if more than 5%-10% of the liver's weight is fat. NAFLD may progress to steatohepatitis, cirrhosis, and liver cancer. It is associated with metabolic disorders, such as metabolic syndrome, insulin resistance, type II diabetes, hyperlipidemia, hypertension, obesity, etc. Treatment methods include lowering low-density lipoprotein (LDL) cholesterol levels, improving insulin sensitivity, treating metabolic risk factors, weight loss and so on. [Adams et al., *Postgraduate Medical Journal*, vol. 82, 315-322 (2006); Musso et al., *Curr. Opin. Lipidol.*, vol. 22(6), 489-496 (2011), the contents of which are incorporated herein by reference in their entirety]

HNF4a protein plays an important role in regulating liver function and metabolics. In one embodiment, provided is a method of regulating liver metabolism genes in vitro and in vivo by treatment of HNF4a-saRNA of the present invention. Also provided is a method of regulating liver genes involved in NAFLD in vitro and in vivo by treatment of HNF4a-saRNA of the present invention. The genes include, but are not limited to sterol regulatory element-binding factor 1 (SREBF-1 or SREBF), cluster of differentiation 36 (CD36), acetyl-CoA carboxylase 2 (ACACB), apolipoprotein C-III (APOC3), microsomal triglyceride transfer protein (MTP), peroxisome proliferator-activated receptor gamma coactivator 1 alpha (PPARγ-CoA1α or PPARGC1A), low density lipoprotein receptor (LDLR), peroxisome proliferator-activated receptor gamma coactivator 1 beta (PPARγ-CoA1β or PERC), peroxisome proliferator-activated receptor gamma (PPARγ), acetyl-CoA carboxylase 1 (ACACA), carbohydrate-responsive element-binding protein (ChREBP or MLX1PL), peroxisome proliferator-activated receptor alpha (PPARα or PPARA), FASN (fatty acid synthase), diglyceride acyltransferase-2 (DGAT2), and mammalian target of rapamycin (mTOR).

A summary of NAFLD and IR genes that may be modulated with HNF4a-saRNA is shown in Table 2. Abbreviations in Table 2: NAFLD: non-alcoholic fatty liver disease; IR: insulin resistance; DNL: de novo lipogenesis; FA: fatty acid; TG: triglycerides; LPL: lipoprotein lipase; HP: hepatic lipase; CHOL: cholesterol.

TABLE 2

NAFLD and IR genes that may be modulated with HNF4a-saRNA

| Gene name | Mechanism | Function/encoded products - References | Deregulation in NAFLD | Deregulation in IR |
|---|---|---|---|---|
| CD36 | FAs uptake | Scavenger receptor, free FAs transporter in liver and adipose tissue; regulates adipose tissue apoptosis and inflammation | up | up |
| PPARγ | DNL | Activates genes involved in lipid storage and metabolism; required for lipid homeostasis; high expressed in adipose tissue and very low in the liver; implicated in adipocyte differentiation and insulin sensitivity | up | down |
| PPARγ-CoA 1β (PERC) | DNL | Transcriptional coactivator for SREBP-1; enhances lipogenesis and VLDL synthesis; highly expressed in brown fat and heart and induced in the liver during fasting; master regulator of mitochondrial biogenesis and oxidative metabolism, lipogenesis, and TG secretion | up | up |
| SREBP-1c | DNL | Transcription factor, induces genes involved in glucose utilization and FA synthesis; major mediator of insulin action on lipogenic genes; regulates adipogenesis | up | up |
| ChREBP (MLX1PL) | DNL | Transcription factors activated by glucose; induces glycolytic and lipogenic genes; major determinant of adipose tissue fatty acid synthesis and systemic insulin sensitivity | up | up |
| FAS | DNL | Enzyme that catalyzes the last step in FA biosynthesis | up | up |
| ACACA (ACC1) | DNL | Enzyme that catalyzes the synthesis of malonyl-CoA for the synthesis of FAs in the cytosol | up | up |
| ACACB (ACC2) | β-oxidation | Enzyme that catalyzes the synthesis of malonyl-CoA, which functions as inhibitor of mitochondrial β-oxidation | up | up |

TABLE 2-continued

NAFLD and IR genes that may be modulated with HNF4a-saRNA

| Gene name | Mechanism | Function/encoded products - References | Deregulation in NAFLD | Deregulation in IR |
|---|---|---|---|---|
| PPARα | β-oxidation | Activates the genes involved in the oxidation of FAs, major regulator of lipid metabolism in the liver; predominantly expressed in the liver; involved in the regulation of glucose homeostasis, insulin sensitivity, fat accumulation, and adipose tissue glucose use | down | down |
| PPARγ-CoA 1α | β-oxidation | Transcriptional co-activator that regulates mitochondrial biology and energy homeostasis; crucial role in mitochondrial biogenesis; interacts with PPARα to increase the mitochondrial β-oxidation of FAs | down | down |
| DGAT2 | TG synthesis | Enzyme that catalyzes the final reaction in the synthesis of TG | up | up |
| APOC3 | TG concentration | Protein that inhibits LPL and HP; involved in the regulation of plasma TG concentrations; pro-steatosic | up | up |
| LDLR | CHOL concentration | Low-density lipoprotein receptor; critical role in regulating blood CHOL levels; abundant in the liver, which is the organ responsible for removing most excess CHOL from the body | down | no change |
| MTP (MTTP1) | Lipoprotein assembly | Carrier of TG; central role in VLDL assembly; prevalently expressed in the liver | down | no change |
| mTOR | Adipose mass | Possible regulator of adipose tissue mass; central role in lipolysis, lipogenesis, and adipogenesis | up | up |

TABLE 2

NAFLD and IR genes that may be modulated with HNF4a-saRNA (continued)

| Gene name | Effects of Ezetimibe in the liver | Effects of HNF4a Liver | Effects of HNF4a WAT | Effects of HNF4a BAT |
|---|---|---|---|---|
| CD36 | minor down | down | down | down |
| PPARγ | up | up | no change | no change |
| PPARγ-CoA 1β (PERC) | up | up | down | up |
| SREBP-1c | up | down | down | down |
| ChREBP (MLX1PL) | up | down | up | up |
| FAS | down | down | minor up | up |
| ACACA (ACC1) | minor up | no change | down | up |
| ACACB (ACC2) | up | up | down | down |
| PPARα | up | up | down | up |
| PPARγ-CoA 1α | up | up | up | up |
| DGAT2 | minor down | minor down | down | up |
| APOC3 | down | down | up | down |
| LDLR | minor down | down | up | minor down |
| MTP (MTTP1) | up | down | up | down |
| mTOR | no change | no change | down | down |

In one embodiment of the present invention, provided is a method of lowering serum cholesterol level by treatment of HNF4a-saRNA of the present invention. The serum cholesterol level with HNF4a-saRNA reduces at least 25%, preferably 50%, more preferably 75% compared to serum cholesterol level with no treatment. Also provided is a method of lowering LDL and triglyceride levels in hepatocyte cells and increasing circulating levels of LDL in vivo by administering HNF4a-saRNA of the present invention. The circulation LDL level may increase at least by a factor of 2, preferably by a factor of 3, preferably by a factor of 4, preferably by a factor of 5, preferably by a factor of 10, and preferably by a factor of 15 compared to circulating LDL level in the absence of HNF4a-saRNA. The liver triglyceride level may be reduced by at least 10%, 20%, 30%, 40%, 50%, 60%, or 70% compared to the liver triglyceride level in the absence of HNF4a-saRNA. The liver LDL level may be reduced by at least 10%, 20%, 30%, 40%, 50%, 60%, or 70% compared to the liver LDL level in the absence of HNF4a-saRNA. Also provided is a method of lowering serum glucose levels in vivo by administering HNF4a-saRNA of the present invention. The serum glucose level may be reduced by at least 10%, 20%, 30%, 40%, 50%, 60%, or 70% compared to the serum glucose level in the absence of HNF4a-saRNA.

In one embodiment of the present invention, provided is a method of treating NAFLD and reducing fatty liver size by administering HNF4a-saRNA of the present invention to a patient in need thereof. The size of a fatty liver of a patient treated with HNF4a-saRNA is reduced by at least 10%, 20%, 30%, 40%, or 50% compared with a patient without treatment. Also provided is a method of reducing body weight and treating obesity by administering HNF4a-saRNA of the present invention to a patient in need thereof. The body weight of a patient treated with HNF4a-saRNA is lower than the body weight of a patient without treatment of HNF4a-saRNA by at least 10%, 20%, 30%, 40%, 50%, 60%, or 70%. HNF4a-saRNA of the present invention may be administered in a dose, 2 doses, 3 does or more. Also provided is a method of decreasing hepatic uptake of free fatty acids by treatment of HNF4a-saRNA of the present invention. Also provided is a method of reducing white adipose tissue (WAT) inflammation by treatment of HNF4a-saRNA of the present invention. Also provided is a method of reducing de novo lipogenesis by treatment of HNF4a- saRNA of the present invention. Also provided is a method of increasing beta-oxidation in the liver by treatment of HNF4a-saRNA of the present invention. Also provided is a method of increasing brown adipose tissue (BAT) in the liver by treatment of HNF4a-saRNA of the present invention. Also provided is a method of reducing hepatic lipid uptake by treatment of HNF4a-saRNA of the present invention. Also provided is a method of decreasing lipogenesis in WAT by treatment of HNF4a-saRNA of the present invention. Also provided is a method of decreasing lipid storage in liver by treatment of HNF4a-saRNA of the present invention. Also provided is a method of reducing lipid overload in the liver by treatment of HNF4a-saRNA of the present invention.

In another embodiment, HNF4a-saRNA of the present invention is used to increase liver function. In one non-limiting example, HNF4a-saRNA increases albumin gene expression and thereby increasing serum albumin and unconjugated bilirubin levels. The expression of albumin gene may be increased by at least 20, 30, 40%, more preferably at least 45, 50, 55, 60, 65, 70, 75%, even more preferably at least 80% in the presence of the saRNA of the present invention compared to the expression of albumin gene in the absence of the saRNA of the present invention. In a further preferable embodiment, the expression of albumin gene is increased by a factor of at least 2, 3, 4, 5, 6, 7, 8, 9, 10, more preferably by a factor of at least 15, 20, 25, 30, 35, 40, 45, 50, even more preferably by a factor of at least 60, 70, 80, 90, 100, in the presence of the saRNA of the present invention compared to the expression of albumin gene in the absence of the saRNA of the present invention. In another non-limiting example, HNF4a-saRNA decreases the amount of alanine transaminase (ALT), aspartate aminotransferase (AST), gamma glutamyl transpeptidase (GGT), alphafectoprotein (AFP) and hepatocyte growth factor (HGF). The amount of ALT, AST, GGT, AFP, or HGF may be decreased by at least 20, 30, 40%, more preferably at least 45, 50, 55, 60, 65, 70, 75%, even more preferably at least 80% in the presence of the saRNA of the present invention compared to the amount of any of ALT, AST, GGT, AFP, or HGF in the absence of the saRNA of the present invention.

Surgical Care

Hepatectomy, surgical resection of the liver or hepatic tissue might cause liver failure, reduced production of albumin and coagulation factors. Proper surgical care after hepatectomy is needed. In some embodiments, HNF4a-saRNA of the present invention is used for surgical care after hepatectomy to promote liver regeneration and increase survival rate. In some embodiments, HNF4a-saRNA of the present invention is used for treating liver failure, liver fibrosis, or acute liver failure.

Hyperproliferation Disorders

In one embodiment of the invention, HNF4a-saRNA of the present invention is used to reduce cell proliferation of hyperproliferative cells. Examples of hyperproliferative cells include cancerous cells, e.g., carcinomas, sarcomas, lymphomas and blastomas. Such cancerous cells may be benign or malignant. Hyperproliferative cells may result from an autoimmune condition such as rheumatoid arthritis, inflammatory bowel disease, or psoriasis. Hyperproliferative cells may also result within patients with an oversensitive immune system coming into contact with an allergen. Such conditions involving an oversensitive immune system include, but are not limited to, asthma, allergic rhinitis, eczema, and allergic reactions, such as allergic anaphylaxis. In one embodiment, tumor cell development and/or growth is inhibited. In a preferred embodiment, solid tumor cell proliferation is inhibited. In another preferred embodiment, metastasis of tumor cells is prevented. In another preferred example, undifferentiated tumor cell proliferation is inhibited.

Inhibition of cell proliferation or reducing proliferation means that proliferation is reduced or stops altogether. Thus, "reducing proliferation" is an embodiment of "inhibiting proliferation". Proliferation of a cell is reduced by at least 20%, 30% or 40%, or preferably at least 45, 50, 55, 60, 65, 70 or 75%, even more preferably at least 80, 90 or 95% in the presence of the saRNA of the invention compared to the proliferation of said cell prior to treatment with the saRNA of the invention, or compared to the proliferation of an equivalent untreated cell. In embodiments wherein cell proliferation is inhibited in hyperproliferative cells, the "equivalent" cell is also a hyperproliferative cell. In preferred embodiments, proliferation is reduced to a rate comparable to the proliferative rate of the equivalent healthy (non-hyperproliferative) cell. Alternatively viewed, a preferred embodiment of "inhibiting cell proliferation" is the inhibition of hyperproliferation or modulating cell proliferation to reach a normal, healthy level of proliferation.

In one non-limiting example, HNF4a-saRNA is used to reduce the proliferation of leukemia and lymphoma cells. Preferably, the cells include Jurkat cells (acute T cell lymphoma cell line), K562 cells (erythroleukemia cell line), U373 cells (glioblastoma cell line), and 32Dp210 cells (myeloid leukemia cell line).

In another non-limiting example, HNF4a-saRNA is used to reduce the proliferation of ovarian cancer cells, liver cancer cells, pancreatic cancer cells, breast cancer cells, prostate cancer cells, rat liver cancer cells, and insulinoma cells. Preferably, the cells include PEO1 and PEO4 (ovarian cancer cell line), HepG2 (hepatocellular carcinoma cell line), Panc1 (human pancreatic carcinoma cell line), MCF7 (human breast adenocarcinoma cell line), DU145 (human metastatic prostate cancer cell line), rat liver cancer cells, and MING (rat insulinoma cell line).

In one embodiment, the saRNA of the present invention is used to treat hyperproliferative disorders. Tumors and cancers represent a hyperproliferative disorder of particular interest, and all types of tumors and cancers, e.g. solid tumors and haematological cancers are included. Examples of cancer include, but not limited to, cervical cancer, uterine cancer, ovarian cancer, kidney cancer, gallbladder cancer, liver cancer, head and neck cancer, squamous cell carcinoma, gastrointestinal cancer, breast cancer, prostate cancer, testicular cancer, lung cancer, non-small cell lung cancer, non-Hodgkin's lymphoma, multiple myeloma, leukemia (such as acute lymphocytic leukemia, chronic lymphocytic leukemia, acute myelogenous leukemia, and chronic myelogenous leukemia), brain cancer (e.g. astrocytoma, glioblastoma, medulloblastoma), neuroblastoma, sarcomas, colon cancer, rectum cancer, stomach cancer, anal cancer, bladder cancer, endometrial cancer, plasmacytoma, lymphomas, retinoblastoma, Wilm's tumor, Ewing sarcoma, melanoma and other skin cancers. The liver cancer may include, but not limited to, cholangiocarcinoma, hepatoblastoma, hemangiosarcoma, or hepatocellular carcinoma (HCC). HCC is of particular interest.

Primary liver cancer is the fifth most frequent cancer worldwide and the third most common cause of cancer-related mortality. HCC represents the vast majority of primary liver cancers [El-Serag et al., *Gastroenterology*, vol. 132(7), 2557-2576 (2007), the contents of which are disclosed herein in their entirety]. HCC is influenced by the interaction of several factors involving cancer cell biology, immune system, and different aetiologies (viral, toxic and generic). The majority of patients with HCC develop malignant tumors from a background of liver cirrhosis. Currently most patients are diagnosed at an advanced stage and therefore the 5 year survival for the majority of HCC patients remains dismal. Surgical resection, loco-regional ablation and liver transplantation are currently the only therapeutic options which have the potential to cure HCC. However, based on the evaluation of individual liver function and tumor burden only about 5-15% of patients are eligible for surgical intervention. The present invention utilizes HNF4a-saRNA to modulate the expression of HNF4a gene and treat liver cirrhosis and HCC.

The method of the present invention may reduce tumor volume by at least 10, 20, 30, 40, 50, 60, 70, 80 or 90%. Preferably, the development of one or more new tumors is inhibited, e.g. a subject treated according to the invention develops fewer and/or smaller tumors. Fewer tumors means that he develops a smaller number of tumors than an equivalent subject over a set period of time. For example, he develops at least 1, 2, 3, 4 or 5 fewer tumors than an equivalent control (untreated) subject. Smaller tumor means that the tumors are at least 10, 20, 30, 40, 50, 60, 70, 80 or 90% smaller in weight and/or volume than tumors of an equivalent subject. The method of the present invention reduces tumor burden by at least 10, 20, 30, 40, 50, 60, 70, 80 or 90%.

The set period of time may be any suitable period, e.g. 1, 2, 3, 4, 5, 6, 7, 8, 9 or 10 months or years.

In one non-limiting example, provided is a method of treating an undifferentiated tumor, comprising contacting a cell, tissue, organ or subject with HNF4a-saRNA of the present invention. Undifferentiated tumors generally have a poorer prognosis compared to differentiated ones. As the degree of differentiation in tumors has a bearing on prognosis, it is hypothesized that the use of a differentiating biological agent could be a beneficial anti-proliferative drug. Undifferentiated tumors that may be treated with HNF4a-saRNA include undifferentiated small cell lung carcinomas, undifferentiated pancreatic adenocarcinomas, undifferentiated human pancreatic carcinoma, undifferentiated human metastatic prostate cancer, and undifferentiated human breast cancer.

In one embodiment, HNF4a-saRNA is used to regulate oncogenes and tumor suppressor genes. Preferably, the expression of the oncogenes may be down-regulated. The expression of the oncogenes reduces by at least 20, 30, 40%, more preferably at least 45, 50, 55, 60, 65, 70, 75, 80, 85, 90, 95% in the presence of HNF4a-saRNA of the invention compared to the expression in the absence of HNF4a-saRNA of the invention. In a further preferable embodiment, the expression of the oncogenes is reduced by a factor of at least 2, 3, 4, 5, 6, 7, 8, 9, 10, more preferably by a factor of at least 15, 20, 25, 30, 35, 40, 45, 50, even more preferably by a factor of at least 60, 70, 80, 90, 100, in the presence of HNF4a-saRNA of the invention compared to the expression in the absence of HNF4a-saRNA of the invention. Preferably, the expressions of tumor suppressor genes may be inhibited. The expression of the tumor suppressor genes increase by at least 20, 30, 40%, more preferably at least 45, 50, 55, 60, 65, 70, 75, 80, 85, 90, 95%, even more preferably at least 100% in the presence of HNF4a-saRNA of the invention compared to the expression in the absence of HNF4a-saRNA of the invention. In a further preferable embodiment, the expression of tumor suppressor genes is increased by a factor of at least 2, 3, 4, 5, 6, 7, 8, 9, 10, more preferably by a factor of at least 15, 20, 25, 30, 35, 40, 45, 50, even more preferably by a factor of at least 60, 70, 80, 90, 100 in the presence of HNF4a-saRNA of the invention compared to the expression in the absence of HNF4a-saRNA of the invention. Non-limiting examples of oncogenes and tumor suppressor genes include Bcl-2-associated X protein (BAX), BH3 interacting domain death agonist (BID), caspase 8 (CASP8), disabled homolog 2-interacting protein (DAB21P), deleted in liver cancer 1 (DLC1), Fas surface death receptor (FAS), fragile histidine triad (FHIT), growth arrest and DNA-damage-inducible-beta (GADD45B), hedgehog interacting protein (HHIP), insulin-like growth factor 2 (IGF2), lymphoid enhancer-binding factor 1 (LEF1), phosphatase and tensing homolog (PTEN), protein tyrosine kinase 2 (PTK2), retinoblastoma 1 (RB1), runt-related transcription factor 3 (RUNX3), SMAD family member 4 (SMAD4), suppressor of cytokine signaling (3SOCS3), transforming growth factor, beta receptor II (TGFBR2), tumor necrosis factor (ligand) superfamily, member 10 (TNF SF10), P53, disintegrin and metalloproteinase domain-containing protein 17 (ADAM17), v-akt murine thymoma viral oncogene homolog 1 (AKT1), angiopoietin 2 (ANGPT2), B-cell CLL/lymphoma 2 (BCL2), BCL2-like 1 (BCL2L1), baculoviral IAP repeat containing 2 (BIRC2), baculoviral IAP repeat containing 5 (BIRC5), chemokine (C—C motif) ligand 5 (CCLS), cyclin D1 (CCND1), cyclin D2 (CCND2), cadherin 1 (CDH1), cadherin 13 (CDH13), cyclin-dependent kinase inhibitor 1A (CDKN1A), cyclin-dependent kinase inhibitor 1B (CDKN1B), cyclin-dependent kinase inhibitor 2A (CDKN2A), CASP8 and FADD-like apoptosis regulator (CFLAR), catenin (cadherin-associated protein) beta 1 (CTNNB1), chemokine receptor 4 (CXCR4), E2F transcription factor 1 (E2F1), epidermal growth factor (EGF), epidermal growth factor receptor (EGFR), E1A binding protein p300 (EP300), Fas (TNFRSF6)-associated via death domain (FADD), fms-related tyrosine kinase 1 (FLT1), frizzled family receptor 7 (FZD7), glutathione S-transferase pi 1 (GSTP1), hepatocyte growth factor (HGF), Harvey rat sarcoma viral oncogene homolog (HRAS), insulin-like growth factor binding protein 1 (IGFBP1), insulin-like growth factor binding protein 3 (IGFBP3), insulin receptor substrate 1 (IRS1), integrin beta 1 (ITGB1), kinase insert domain receptor (KDR), myeloid cell leukemia sequence 1 (MCL1), met proto-oncogene (MET), mutS homolog 2 (MSH2), mutS homolog 3 (MSH3), metadherin (MTDH), v-myc avian myelocytomatosis viral oncogene homolog (MYC), nuclear factor of kappa light polypeptide gene enhancer in B-cells 1 (NFKB1), neuroblastoma RAS viral (v-ras) oncogene homolog (NRAS), opioid binding protein/cell adhesion molecule-like (OPCML), platelet-derived growth factor receptor, alpha polypeptide (PDGFRA), peptidylprolyl cis/trans isomerase, NIMA-interacting 1 (PIN1), prostaglandin-endoperoxide synthase 2 (PTGS2), PYD and CARD domain containing (PYCARD), ras-related C3 botulinum toxin substrate 1 (RAC1), Ras association (RalGDS/AF-6) domain family member 1 (RASSF1), reelin (RELN), ras homolog family member A (RHOA), secreted frizzled-related protein 2 (SFRP2), SMAD family member 7 (SMAD7), suppressor of cytokine signaling 1 (SOCS1), signal transducer and activator of transcription 3 (STAT3), transcription factor 4 (TCF4), telomerase reverse transcriptase (TERT), transforming growth factor alpha (TGFA), transforming growth factor beta 1 (TGFB1), toll-like receptor 4 (TLR4), tumor necrosis factor receptor superfamily member 10b (TNFRSF10B), vascular endothelial growth factor A (VEGFA), Wilms tumor 1 (WT1), X-linked inhibitor of apoptosis (XIAP), and Yes-associated protein 1 (YAP1).

In one embodiment, HNF4a-saRNA is used to regulate micro RNAs (miRNA or miR) in the treatment of hepatocellular carcinoma. MicroRNAs are small non-coding RNAs that regulate gene expression. They are implicated in important physiological functions and they may be involved in every single step of carcinogenesis. They typically have 21 nucleotides and regulate gene expression at the post transcriptional level via blockage of mRNA translation or induction of mRNA degradation by binding to the 3'-untranslated regions (3'-UTR) of said mRNA.

In tumors, regulation of miRNA expression affects tumor development. In HCC, as in other cancers, miRNAs function either as oncogenes or tumor suppressor genes influencing cell growth and proliferation, cell metabolism and differentiation, apoptosis, angiogenesis, metastasis and eventually prognosis. [Lin et al., *Biochemical and Biophysical Research Communications*, vol. 375, 315-320 (2008); Kutay et al., *J. Cell. Biochem.*, vol. 99, 671-678 (2006); Meng et al., *Gastroenterology*, vol. 133(2), 647-658 (2007), the contents of each of which are incorporated herein by reference in their entirety] HNF4a-saRNA of the present invention modulates HNF4a gene expression and/or function and also regulates miRNA levels in HCC cells. Non-limiting examples of miRNAs that may be regulated by HNF4a-saRNA of the present invention include hsa-let-7a-5p, hsa-miR-133b, hsa-miR-122-5p, hsa-miR-335-5p, hsa-miR-196a-5p, hsa-miR-142-5p, hsa-miR-96-5p, hsa-miR-184, hsa-miR-214-3p, hsa-miR-15a-5p, hsa-let-7b-5p, hsa-miR-205-5p, hsa-miR-181a-5p, hsa-miR-140-5p, hsa-miR-146b-5p, hsa-miR-34c-5p, hsa-miR-134, hsa-let-7g-5p, hsa-let-7c, hsa-miR-218-5p, hsa-miR-206, hsa-miR-124-3p, hsa-miR-100-5p, hsa-miR-10b-5p, hsa-miR-155-5p, hsa-miR-1, hsa-miR-150-5p, hsa-let-7i-5p, hsa-miR-27b-3p, hsa-miR-127-5p, hsa-miR-191-5p, hsa-let-7f-5p, hsa-miR-10a-5p, hsa-miR-15b-5p, hsa-miR-16-5p, hsa-miR-34a-5p, hsa-miR-144-3p, hsa-miR-128, hsa-miR-215, hsa-miR-193a-5p, hsa-miR-23b-3p, hsa-miR-203a, hsa-miR-30c-5p, hsa-let-7e-5p, hsa-miR-146a-5p, hsa-let-7d-5p, hsa-miR-9-5p, hsa-miR-181b-5p, hsa-miR-181c-5p, hsa-miR-20b-5p, hsa-miR-125a-5p, hsa-miR-148b-3p, hsa-miR-92a-3p, hsa-miR-378a-3p, hsa-miR-130a-3p, hsa-miR-20a-5p, hsa-miR-132-3p, hsa-miR-193b-3p, hsa-miR-183-5p, hsa-miR-148a-3p, hsa-miR-138-5p, hsa-miR-3'73-3p, hsa-miR-29b-3p, hsa-miR-135b-5p, hsa-miR-21-5p, hsa-miR-181d, hsa-miR-301a-3p, hsa-miR-200c-3p, hsa-miR-7-5p, hsa-miR-29a-3p, hsa-miR-210, hsa-miR-17-5p, hsa-miR-98-5p, hsa-miR-25-3p, hsa-miR-143-3p, hsa-miR-19a-3p, hsa-miR-18a-5p, hsa-miR-125b-5p, hsa-miR-126-3p, hsa-miR-27a-3p, hsa-miR-372, hsa-miR-149-5p, and hsa-miR-32-5p.

In one non-limiting example, the miRNAs are oncogenic miRNAs and are downregulated by a factor of at least 0.01, 0.02, 0.05, 0.1, 0.2, 0.3, 0.5, 1, 1.5, 2, 2.5, and 3, in the presence of HNF4a-saRNA of the invention compared to in the absence of HNF4a-saRNA. In another non-limiting example, the miRNAs are tumor suppressing miRNAs and are upregulated by a factor of at least 0.01, 0.02, 0.05, 0.1, 0.2, 0.3, 0.5, 1, more preferably by a factor of at least 2, 3, 4, 5, 6, 7, 8, 9, 10, more preferably by a factor of at least 15, 20, 25, 30, 35, 40, 45, 50, even more preferably by a factor of at least 60, 70, 80, 90, 100, in the presence of HNF4a-saRNA of the invention compared to in the absence of HNF4a-saRNA.

Stem Cell Regulation

In some embodiments of the present invention, HNF4a-saRNA is used to regulate self-renewal pluripotency factors and affect stem cell differentiation. Altering the phenotype of cells in order to express a protein of interest or to change a cell to a different cell phenotype has been used in different clinical, therapeutic and research settings. Altering a phenotype of a cell is currently accomplished by expressing protein from DNA or viral vectors. Currently there are studies being done to evaluate the use of human embryonic stem cells as a treatment option for various diseases such as Parkinson's disease and diabetes and injuries such as a spinal cord injury. Embryonic stem cells have the ability to grow indefinitely while maintaining Pluripotency to generate any differentiated cell type.

Many factors such as pluripotency factors, cell phenotype altering factors, transdifferentiation factors, differentiation factors and dedifferentiation factors, are utilized to alter cell phenotype, which is useful in the field of personal regenerative medicine, cell therapy and therapies for other diseases. For example, the self-renewal and pluripotency properties of stem cells are regulated by an array of genes, such as transcription factors and chromatin remodeling enzymes, in a core regulatory circuitry including OCT4, SOX2, NANOG, and KLF genes [Bourillot et al., *BMC Biology*, 8:125 (2010), the contents of which are incorporated herein by reference in their entirety]. This regulatory circuitry for self-regulatory networks also affects downstream genes. Oligonucleotides have been utilized to regulate the core regulatory circuitry. Xu et al. disclosed that miRNA-145 targets the 3'-UTR of OCT4, SOX2, and KLF4. Reducing miRNA-145 impairs differentiation and elevates OCT4, SOX2, and KLF4. [Xu et al., *Cell*, vol. 137, 1-12 (2009), the contents of which are incorporated herein by reference in their entirety]

In one embodiment, HNF4a-saRNA of the present invention is used to regulate self-renewal pluripotency genes. Non-limiting examples of pluripotency genes include SOX2, OCT4, cKit, KLF4, KLF2, KLF5, NANOG, CDX2, and SALL4. In one embodiment, the expression of the pluripotency gene is reduced by at least 20%, 30% or 40%, or preferably at least 45, 50, 55, 60, 65, 70 or 75%, even more preferably at least 80, 90 or 95%, in the presence of HNF4a-saRNA of the invention compared to in the absence of HNF4a-saRNA. In another embodiment, the expression of the pluripotency gene is increased by at least 20, 30, 40%, more preferably at least 45, 50, 55, 60, 65, 70, 75%, even more preferably at least 80%, in the presence of HNF4a-saRNA of the invention compared to in the absence of HNF4a-saRNA. In a preferable embodiment, the expression of the pluripotency gene is increased by a factor of at least 2, 3, 4, 5, 6, 7, 8, 9, 10, more preferably by a factor of at least 15, 20, 25, 30, 35, 40, 45, 50, even more preferably by a factor of at least 60, 70, 80, 90, 100, in the presence of HNF4a-saRNA of the invention compared to the expression in the absence of HNF4a-saRNA.

In one embodiment, HNF4a-saRNA is used to regulate epithelial-mesenchymal transition (EMT) of a cell. Some tumors contain cancer stem cells or cancer stem-like cells that can self-renew and maintain tumor-initiating capacity through differentiation into a different lineage of cancer cells. It has been demonstrated that EMT is associated with cancer stem-like cells, tumor aggressiveness and metastasis, and tumor recurrence. [Kong et al., *Cancers*, vol. 3(1), 716-729 (2011)] There are many factors that regulate EMT, including miRNAs such as miR-200 and miR-134, growth factors such as fibroblast growth factor (FGF), epidermal growth factor (EGF), platelet-derived growth factor (PDGF), as well as factors such as Notch-1 and Wnt signaling pathway.

III. Kits and Devices

Kits

The invention provides a variety of kits for conveniently and/or effectively carrying out methods of the present invention. Typically, kits will comprise sufficient amounts and/or numbers of components to allow a user to perform multiple treatments of a subject(s) and/or to perform multiple experiments.

In one embodiment, the kits comprising saRNA described herein may be used with proliferating cells to show efficacy.

In one embodiment, the present invention provides kits for regulate the expression of genes in vitro or in vivo, comprising HNF4a-saRNA of the present invention or a combination of HNF4a-saRNA, saRNA modulating other genes, siRNAs, or miRNAs. The kit may further comprise packaging and instructions and/or a delivery agent to form a formulation composition. The delivery agent may comprise a saline, a buffered solution, a lipidoid, a dendrimer or any delivery agent disclosed herein. Non-limiting examples of genes include C/EBPα, other members of C/EBP family, albumin gene, alphafectoprotein gene, liver specific factor genes, growth factors, nuclear factor genes, tumor suppressing genes, pluripotency factor genes.

In one non-limiting example, the buffer solution may include sodium chloride, calcium chloride, phosphate and/or EDTA. In another non-limiting example, the buffer solution may include, but is not limited to, saline, saline with 2 mM calcium, 5% sucrose, 5% sucrose with 2 mM calcium, 5% Mannitol, 5% Mannitol with 2 mM calcium, Ringer's lactate, sodium chloride, sodium chloride with 2 mM calcium and mannose (See U.S. Pub. No. 20120258046; herein incorporated by reference in its entirety). In yet another non-limiting example, the buffer solutions may be precipitated or it may be lyophilized. The amount of each component may be varied to enable consistent, reproducible higher concentration saline or simple buffer formulations. The components may also be varied in order to increase the stability of saRNA in the buffer solution over a period of time and/or under a variety of conditions.

In another embodiment, the present invention provides kits to regulate the proliferation of cells, comprising HNF4a-saRNA of the present invention, provided in an amount effective to inhibit the proliferation of cells when introduced into said cells; optionally siRNAs and miRNAs to further regulate the proliferation of target cells; and packaging and instructions and/or a delivery agent to form a formulation composition.

In another embodiment, the present invention provides kits for reducing LDL levels in cells, comprising saRNA molecules of the present invention; optionally LDL reducing drugs; and packaging and instructions and/or a delivery agent to form a formulation composition.

In another embodiment, the present invention provides kits for regulating miRNA expression levels in cells, comprising HNF4a-saRNA of the present invention; optionally siRNAs, eRNAs and lncRNAs; and packaging and instructions and/or a delivery agent to form a formulation composition.

Devices

The present invention provides for devices which may incorporate HNF4a-saRNA of the present invention. These devices contain in a stable formulation available to be immediately delivered to a subject in need thereof, such as a human patient. Non-limiting examples of such a subject include a subject with hyperproliferative disorders such as cancer, tumor, or liver cirrhosis; and metabolics disorders such as NAFLD, obesity, high LDL cholesterol, or type II diabetes.

Non-limiting examples of the devices include a pump, a catheter, a needle, a transdermal patch, a pressurized olfactory delivery device, iontophoresis devices, multi-layered microfluidic devices. The devices may be employed to deliver HNF4a-saRNA of the present invention according to single, multi- or split-dosing regiments. The devices may be employed to deliver HNF4a-saRNA of the present invention across biological tissue, intradermal, subcutaneously, or intramuscularly. More examples of devices suitable for delivering oligonucleotides are disclosed in International Publication WO 2013/090648 filed Dec. 14, 2012, the contents of which are incorporated herein by reference in their entirety.

Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

About: As used herein, the term "about" means +/−10% of the recited value.

Administered in combination: As used herein, the term "administered in combination" or "combined administration" means that two or more agents, e.g., saRNA, are administered to a subject at the same time or within an interval such that there may be an overlap of an effect of each agent on the patient. In some embodiments, they are administered within about 60, 30, 15, 10, 5, or 1 minute of one another. In some embodiments, the administrations of the agents are spaced sufficiently close together such that a combinatorial (e.g., a synergistic) effect is achieved.

Amino acid: As used herein, the terms "amino acid" and "amino acids" refer to all naturally occurring L-alpha-amino acids. The amino acids are identified by either the one-letter or three-letter designations as follows: aspartic acid (Asp: D), isoleucine threonine (Thr:T), leucine (Leu:L), serine (Ser:S), tyrosine (Tyr:Y), glutamic acid (Glu:E), phenylalanine (Phe:F), proline (Pro:P), histidine (His:H), glycine (Gly:G), lysine (Lys:K), alanine (Ala:A), arginine (Arg:R), cysteine (Cys:C), tryptophan (Trp:W), valine (Val:V), glutamine (Gln:Q) methionine (Met:M), asparagines (Asn:N), where the amino acid is listed first followed parenthetically by the three and one letter codes, respectively.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization based connectivity sufficiently stable such that the "associated" entities remain physically associated.

Bifunctional: As used herein, the term "bifunctional" refers to any substance, molecule or moiety which is capable of or maintains at least two functions. The functions may affect the same outcome or a different outcome. The structure that produces the function may be the same or different.

Biocompatible: As used herein, the term "biocompatible" means compatible with living cells, tissues, organs or systems posing little to no risk of injury, toxicity or rejection by the immune system.

Biodegradable: As used herein, the term "biodegradable" means capable of being broken down into innocuous products by the action of living things.

Biologically active: As used herein, the phrase "biologically active" refers to a characteristic of any substance that has activity in a biological system and/or organism. For instance, a substance that, when administered to an organism, has a biological effect on that organism, is considered to be biologically active. In particular embodiments, the saRNA of the present invention may be considered biologically active if even a portion of the saRNA is biologically active or mimics an activity considered biologically relevant.

Cancer: As used herein, the term "cancer" in an individual refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within an individual, or may circulate in the blood stream as independent cells, such as leukemic cells.

Cell growth: As used herein, the term "cell growth" is principally associated with growth in cell numbers, which occurs by means of cell reproduction (i.e. proliferation) when the rate of the latter is greater than the rate of cell death (e.g. by apoptosis or necrosis), to produce an increase in the size of a population of cells, although a small component of that growth may in certain circumstances be due also to an increase in cell size or cytoplasmic volume of individual cells. An agent that inhibits cell growth can thus do so by either inhibiting proliferation or stimulating cell death, or both, such that the equilibrium between these two opposing processes is altered.

Cell type: As used herein, the term "cell type" refers to a cell from a given source (e.g., a tissue, organ) or a cell in a given state of differentiation, or a cell associated with a given pathology or genetic makeup.

Chromosome: As used herein, the term "chromosome" refers to an organized structure of DNA and protein found in cells.

Complementary: As used herein, the term "complementary" as it relates to nucleic acids refers to hybridization or base pairing between nucleotides or nucleic acids, such as, for example, between the two strands of a double-stranded DNA molecule or between an oligonucleotide probe and a target are complementary.

Condition: As used herein, the term "condition" refers to the status of any cell, organ, organ system or organism. Conditions may reflect a disease state or simply the physiologic presentation or situation of an entity. Conditions may be characterized as phenotypic conditions such as the macroscopic presentation of a disease or genotypic conditions such as the underlying gene or protein expression profiles associated with the condition. Conditions may be benign or malignant.

Controlled Release: As used herein, the term "controlled release" refers to a pharmaceutical composition or compound release profile that conforms to a particular pattern of release to effect a therapeutic outcome.

Cytostatic: As used herein, "cytostatic" refers to inhibiting, reducing, suppressing the growth, division, or multiplication of a cell (e.g., a mammalian cell (e.g., a human cell)), bacterium, virus, fungus, protozoan, parasite, prion, or a combination thereof.

Cytotoxic: As used herein, "cytotoxic" refers to killing or causing injurious, toxic, or deadly effect on a cell (e.g., a mammalian cell (e.g., a human cell)), bacterium, virus, fungus, protozoan, parasite, prion, or a combination thereof.

Delivery: As used herein, "delivery" refers to the act or manner of delivering a compound, substance, entity, moiety, cargo or payload.

Delivery Agent: As used herein, "delivery agent" refers to any substance which facilitates, at least in part, the in vivo delivery of a saRNA of the present invention to targeted cells.

Destabilized: As used herein, the term "destable," "destabilize," or "destabilizing region" means a region or molecule that is less stable than a starting, wild-type or native form of the same region or molecule.

Detectable label: As used herein, "detectable label" refers to one or more markers, signals, or moieties which are attached, incorporated or associated with another entity that is readily detected by methods known in the art including radiography, fluorescence, chemiluminescence, enzymatic activity, absorbance and the like. Detectable labels include radioisotopes, fluorophores, chromophores, enzymes, dyes, metal ions, ligands such as biotin, avidin, streptavidin and haptens, quantum dots, and the like. Detectable labels may be located at any position in the peptides, proteins or polynucleotides, e.g, saRNA, disclosed herein. They may be within the amino acids, the peptides, proteins, or polynucleotides located at the N- or C-termini or 5' or 3' termini as the case may be.

Encapsulate: As used herein, the term "encapsulate" means to enclose, surround or encase.

Engineered: As used herein, embodiments of the invention are "engineered" when they are designed to have a feature or property, whether structural or chemical, that varies from a starting point, wild type or native molecule.

Equivalent subject: As used herein, "equivalent subject" may be e.g. a subject of similar age, sex and health such as liver health or cancer stage, or the same subject prior to treatment according to the invention. The equivalent subject is "untreated" in that he does not receive treatment with a saRNA according to the invention. However, he may receive a conventional anti-cancer treatment, provided that the subject who is treated with the saRNA of the invention receives the same or equivalent conventional anti-cancer treatment.

Exosome: As used herein, "exosome" is a vesicle secreted by mammalian cells.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

Feature: As used herein, a "feature" refers to a characteristic, a property, or a distinctive element.

Formulation: As used herein, a "formulation" includes at least a saRNA of the present invention and a delivery agent.

Fragment: A "fragment," as used herein, refers to a portion. For example, fragments of proteins may comprise polypeptides obtained by digesting full-length protein isolated from cultured cells.

Functional: As used herein, a "functional" biological molecule is a biological molecule in a form in which it exhibits a property and/or activity by which it is characterized.

Gene: As used herein, the term "gene" refers to a nucleic acid sequence that comprises control and most often coding sequences necessary for producing a polypeptide or precursor. Genes, however, may not be translated and instead code for regulatory or structural RNA molecules.

A gene may be derived in whole or in part from any source known to the art, including a plant, a fungus, an animal, a bacterial genome or episome, eukaryotic, nuclear or plasmid DNA, cDNA, viral DNA, or chemically synthesized DNA. A gene may contain one or more modifications in either the coding or the untranslated regions that could affect the biological activity or the chemical structure of the expression product, the rate of expression, or the manner of expression control. Such modifications include, but are not limited to, mutations, insertions, deletions, and substitutions of one or more nucleotides. The gene may constitute an uninterrupted coding sequence or it may include one or more introns, bound by the appropriate splice junctions.

Gene expression: As used herein, the term "gene expression" refers to the process by which a nucleic acid sequence undergoes successful transcription and in most instances translation to produce a protein or peptide. For clarity, when reference is made to measurement of "gene expression", this should be understood to mean that measurements may be of the nucleic acid product of transcription, e.g., RNA or mRNA or of the amino acid product of translation, e.g., polypeptides or peptides. Methods of measuring the amount or levels of RNA, mRNA, polypeptides and peptides are well known in the art.

Genome: The term "genome" is intended to include the entire DNA complement of an organism, including the nuclear DNA component, chromosomal or extrachromosomal DNA, as well as the cytoplasmic domain (e.g., mitochondrial DNA).

Homology: As used herein, the term "homology" refers to the overall relatedness between polymeric molecules, e.g. between nucleic acid molecules (e.g. DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). In accordance with the invention, two polynucleotide sequences are considered to be homologous if the polypeptides they encode are at least about 50%, 60%, 70%, 80%, 90%, 95%, or even 99% for at least one stretch of at least about 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. In accordance with the invention, two protein sequences are considered to be homologous if the proteins are at least about 50%, 60%, 70%, 80%, or 90% identical for at least one stretch of at least about 20 amino acids.

The term "hyperproliferative cell" may refer to any cell that is proliferating at a rate that is abnormally high in comparison to the proliferating rate of an equivalent healthy cell (which may be referred to as a "control"). An "equivalent healthy" cell is the normal, healthy counterpart of a cell. Thus, it is a cell of the same type, e.g. from the same organ, which performs the same functions(s) as the comparator cell. For example, proliferation of a hyperproliferative hepatocyte should be assessed by reference to a healthy hepatocyte, whereas proliferation of a hyperproliferative prostate cell should be assessed by reference to a healthy prostate cell.

By an "abnormally high" rate of proliferation, it is meant that the rate of proliferation of the hyperproliferative cells is increased by at least 20, 30, 40%, or at least 45, 50, 55, 60, 65, 70, 75%, or at least 80%, as compared to the proliferative rate of equivalent, healthy (non-hyperproliferative) cells. The "abnormally high" rate of proliferation may also refer to a rate that is increased by a factor of at least 2, 3, 4, 5, 6, 7, 8, 9, 10, or by a factor of at least 15, 20, 25, 30, 35, 40, 45, 50, or by a factor of at least 60, 70, 80, 90, 100, compared to the proliferative rate of equivalent, healthy cells.

The term "hyperproliferative cell" as used herein does not refer to a cell which naturally proliferates at a higher rate as compared to most cells, but is a healthy cell. Examples of cells that are known to divide constantly throughout life are skin cells, cells of the gastrointestinal tract, blood cells and bone marrow cells. However, when such cells proliferate at a higher rate than their healthy counterparts, then they are hyperproliferative.

Hyperproliferative disorder: As used herein, a "hyperproliferative disorder" may be any disorder which involves hyperproliferative cells as defined above. Examples of hyperproliferative disorders include neoplastic disorders such as cancer, psoriatic arthritis, rheumatoid arthritis, gastric hyperproliferative disorders such as inflammatory bowel disease, skin disorders including psoriasis, Reiter's syndrome, Pityriasis rubra pilaris, and hyperproliferative variants of the disorders of keratinization.

The skilled person is fully aware of how to identify a hyperproliferative cell. The presence of hyperproliferative cells within an animal may be identifiable using scans such as X-rays, MM or CT scans. The hyperproliferative cell may also be identified, or the proliferation of cells may be assayed, through the culturing of a sample in vitro using cell proliferation assays, such as MTT, XTT, MTS or WST-1 assays. Cell proliferation in vitro can also be determined using flow cytometry.

Identity: As used herein, the term "identity" refers to the overall relatedness between polymeric molecules, e.g., between oligonucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research,* 12(1), 387 (1984)), BLASTP, BLASTN, and FASTA Altschul, S. F. et al., *J. Molec. Biol.,* 215, 403 (1990)).

Inhibit expression of a gene: As used herein, the phrase "inhibit expression of a gene" means to cause a reduction in the amount of an expression product of the gene. The expression product can be an RNA transcribed from the gene (e.g., an mRNA) or a polypeptide translated from an mRNA transcribed from the gene. Typically a reduction in the level of an mRNA results in a reduction in the level of a polypeptide translated therefrom. The level of expression may be determined using standard techniques for measuring mRNA or protein.

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe or cell or tissue thereof).

Isolated: As used herein, the term "isolated" refers to a substance or entity that has been separated from at least some of the components with which it was associated (whether in nature or in an experimental setting). Isolated substances may have varying levels of purity in reference to the substances from which they have been associated. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. Substantially isolated: By "substantially isolated" is meant that the compound is substantially separated from the environment in which it was formed or detected. Partial separation can include, for example, a composition enriched in the compound of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof. Methods for isolating compounds and their salts are routine in the art.

Label: The term "label" refers to a substance or a compound which is incorporated into an object so that the substance, compound or object may be detectable.

Linker: As used herein, a linker refers to a group of atoms, e.g., 10-1,000 atoms, and can be comprised of the atoms or groups such as, but not limited to, carbon, amino, alkylamino, oxygen, sulfur, sulfoxide, sulfonyl, carbonyl, and imine. The linker can be attached to a modified nucleoside or nucleotide on the nucleobase or sugar moiety at a first end, and to a payload, e.g., a detectable or therapeutic agent, at a second end. The linker may be of sufficient length as to not interfere with incorporation into a nucleic acid sequence. The linker can be used for any useful purpose, such as to form saRNA conjugates, as well as to administer a payload, as described herein. Examples of chemical groups that can be incorporated into the linker include, but are not limited to, alkyl, alkenyl, alkynyl, amido, amino, ether, thioether, ester, alkylene, heteroalkylene, aryl, or heterocyclyl, each of which can be optionally substituted, as described herein. Examples of linkers include, but are not limited to, unsaturated alkanes, polyethylene glycols (e.g., ethylene or propylene glycol monomeric units, e.g., diethylene glycol, dipropylene glycol, triethylene glycol, tripropylene glycol, tetraethylene glycol, or tetraethylene glycol), and dextran polymers and derivatives thereof. Other examples include, but are not limited to, cleavable moieties within the linker, such as, for example, a disulfide bond (—S—S—) or an azo bond (—N═N—), which can be cleaved using a reducing agent or photolysis. Non-limiting examples of a selectively cleavable bond include an amido bond can be cleaved for example by the use of tris(2-carboxyethyl)phosphine (TCEP), or other reducing agents, and/or photolysis, as well as an ester bond can be cleaved for example by acidic or basic hydrolysis.

Metastasis: As used herein, the term "metastasis" means the process by which cancer spreads from the place at which it first arose as a primary tumor to distant locations in the body. Metastasis also refers to cancers resulting from the spread of the primary tumor. For example, someone with breast cancer may show metastases in their lymph system, liver, bones or lungs.

Modified: As used herein "modified" refers to a changed state or structure of a molecule of the invention. Molecules may be modified in many ways including chemically, structurally, and functionally. In one embodiment, the saRNA molecules of the present invention are modified by the introduction of non-natural nucleosides and/or nucleotides.

Naturally occurring: As used herein, "naturally occurring" means existing in nature without artificial aid.

Nucleic acid: The term "nucleic acid" as used herein, refers to a molecule comprised of one or more nucleotides, i.e., ribonucleotides, deoxyribonucleotides, or both. The term includes monomers and polymers of ribonucleotides and deoxyribonucleotides, with the ribonucleotides and/or deoxyribonucleotides being bound together, in the case of the polymers, via 5' to 3' linkages. The ribonucleotide and deoxyribonucleotide polymers may be single or double-stranded. However, linkages may include any of the linkages known in the art including, for example, nucleic acids comprising 5' to 3' linkages. The nucleotides may be naturally occurring or may be synthetically produced analogs that are capable of forming base-pair relationships with naturally occurring base pairs. Examples of non-naturally occurring bases that are capable of forming base-pairing relationships include, but are not limited to, aza and deaza pyrimidine analogs, aza and deaza purine analogs, and other heterocyclic base analogs, wherein one or more of the carbon and nitrogen atoms of the pyrimidine rings have been substituted by heteroatoms, e.g., oxygen, sulfur, selenium, phosphorus, and the like.

Patient: As used herein, "patient" refers to a subject who may seek or be in need of treatment, requires treatment, is receiving treatment, will receive treatment, or a subject who is under care by a trained professional for a particular disease or condition.

Peptide: As used herein, "peptide" is less than or equal to 50 amino acids long, e.g., about 5, 10, 15, 20, 25, 30, 35, 40, 45, or 50 amino acids long.

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, PA, 1985, p. 1418, *Pharmaceutical Salts: Properties, Selection, and Use*, P. H. Stahl and C. G. Wermuth (eds.), Wiley-VCH, 2008, and Berge et al., *Journal of Pharmaceutical Science*, 66, 1-19 (1977), each of which is incorporated herein by reference in its entirety.

Pharmaceutically acceptable solvate: The term "pharmaceutically acceptable solvate," as used herein, means a compound of the invention wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

Pharmacologic effect: As used herein, a "pharmacologic effect" is a measurable biologic phenomenon in an organism or system which occurs after the organism or system has been contacted with or exposed to an exogenous agent. Pharmacologic effects may result in therapeutically effective outcomes such as the treatment, improvement of one or more symptoms, diagnosis, prevention, and delay of onset of disease, disorder, condition or infection. Measurement of such biologic phenomena may be quantitative, qualitative or relative to another biologic phenomenon. Quantitative measurements may be statistically significant. Qualitative measurements may be by degree or kind and may be at least 10%, 20%, 30%, 40%, 50%, 60%, 70%, 80%, 90% or more different. They may be observable as present or absent, better or worse, greater or less. Exogenous agents, when referring to pharmacologic effects are those agents which are, in whole or in part, foreign to the organism or system. For example, modifications to a wild type biomolecule, whether structural or chemical, would produce an exogenous agent. Likewise, incorporation or combination of a wild type molecule into or with a compound, molecule or substance not found naturally in the organism or system would also produce an exogenous agent. The saRNA of the present invention, comprises exogenous agents. Examples of pharmacologic effects include, but are not limited to, alteration in cell count such as an increase or decrease in neutrophils, reticulocytes, granulocytes, erythrocytes (red blood cells), megakaryocytes, platelets, monocytes, connective tissue macrophages, epidermal langerhans cells, osteoclasts, dendritic cells, microglial cells, neutrophils, eosinophils, basophils, mast cells, helper T cells, suppressor T cells, cytotoxic T cells, natural killer T cells, B cells, natural killer cells, or reticulocytes. Pharmacologic effects also include alterations in blood chemistry, pH, hemoglobin, hematocrit, changes in levels of enzymes such as, but not limited to, liver enzymes AST and ALT, changes in lipid profiles, electrolytes, metabolic markers, hormones or other marker or profile known to those of skill in the art.

Physicochemical: As used herein, "physicochemical" means of or relating to a physical and/or chemical property.

Preventing: As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Prodrug: The present disclosure also includes prodrugs of the compounds described herein. As used herein, "prodrugs" refer to any substance, molecule or entity which is in a form predicate for that substance, molecule or entity to act as a therapeutic upon chemical or physical alteration. Prodrugs may by covalently bonded or sequestered in some way and which release or are converted into the active drug moiety prior to, upon or after administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Preparation and use of prodrugs is discussed in T. Higuchi and V. Stella, "Prodrugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

Prognosing: As used herein, the term "prognosing" means a statement or claim that a particular biologic event will, or is very likely to, occur in the future.

Progression: As used herein, the term "progression" or "cancer progression" means the advancement or worsening of or toward a disease or condition.

Proliferate: As used herein, the term "proliferate" means to grow, expand or increase or cause to grow, expand or increase rapidly. "Proliferative" means having the ability to proliferate. "Anti-proliferative" means having properties counter to or inapposite to proliferative properties.

Protein: A "protein" means a polymer of amino acid residues linked together by peptide bonds. The term, as used herein, refers to proteins, polypeptides, and peptides of any size, structure, or function. Typically, however, a protein will be at least 50 amino acids long. In some instances the protein encoded is smaller than about 50 amino acids. In this case, the polypeptide is termed a peptide. If the protein is a short peptide, it will be at least about 10 amino acid residues long. A protein may be naturally occurring, recombinant, or synthetic, or any combination of these. A protein may also comprise a fragment of a naturally occurring protein or peptide. A protein may be a single molecule or may be a multi-molecular complex. The term protein may also apply to amino acid polymers in which one or more amino acid residues are an artificial chemical analogue of a corresponding naturally occurring amino acid.

Protein expression: The term "protein expression" refers to the process by which a nucleic acid sequence undergoes translation such that detectable levels of the amino acid sequence or protein are expressed.

Purified: As used herein, "purify," "purified," "purification" means to make substantially pure or clear from unwanted components, material defilement, admixture or imperfection.

Regression: As used herein, the term "regression" or "degree of regression" refers to the reversal, either phenotypically or genotypically, of a cancer progression. Slowing or stopping cancer progression may be considered regression.

Sample: As used herein, the term "sample" or "biological sample" refers to a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). A sample further may include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. A sample further refers to a medium, such as a nutrient broth or gel, which may contain cellular components, such as proteins or nucleic acid molecule.

Signal Sequences: As used herein, the phrase "signal sequences" refers to a sequence which can direct the transport or localization of a protein.

Single unit dose: As used herein, a "single unit dose" is a dose of any therapeutic administered in one dose/at one time/single route/single point of contact, i.e., single administration event.

Similarity: As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Split dose: As used herein, a "split dose" is the division of single unit dose or total daily dose into two or more doses.

Stable: As used herein "stable" refers to a compound that is sufficiently robust to survive isolation to a useful degree of purity from a reaction mixture, and preferably capable of formulation into an efficacious therapeutic agent.

Stabilized: As used herein, the term "stabilize", "stabilized," "stabilized region" means to make or become stable.

Subject: As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals such as mice, rats, rabbits, non-human primates, and humans) and/or plants.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantially equal: As used herein as it relates to time differences between doses, the term means plus/minus 2%.

Substantially simultaneously: As used herein and as it relates to plurality of doses, the term means within 2 seconds.

Suffering from: An individual who is "suffering from" a disease, disorder, and/or condition has been diagnosed with or displays one or more symptoms of a disease, disorder, and/or condition.

Susceptible to: An individual who is "susceptible to" a disease, disorder, and/or condition has not been diagnosed with and/or may not exhibit symptoms of the disease, disorder, and/or condition but harbors a propensity to develop a disease or its symptoms. In some embodiments, an individual who is susceptible to a disease, disorder, and/or condition (for example, cancer) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Sustained release: As used herein, the term "sustained release" refers to a pharmaceutical composition or compound release profile that conforms to a release rate over a specific period of time.

Synthetic: The term "synthetic" means produced, prepared, and/or manufactured by the hand of man. Synthesis of polynucleotides or polypeptides or other molecules of the present invention may be chemical or enzymatic.

Targeted Cells: As used herein, "targeted cells" refers to any one or more cells of interest. The cells may be found in vitro, in vivo, in situ or in the tissue or organ of an organism. The organism may be an animal, preferably a mammal, more preferably a human and most preferably a patient.

Therapeutic Agent: The term "therapeutic agent" refers to any agent that, when administered to a subject, has a therapeutic, diagnostic, and/or prophylactic effect and/or elicits a desired biological and/or pharmacological effect.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

Total daily dose: As used herein, a "total daily dose" is an amount given or prescribed in 24 hr period. It may be administered as a single unit dose.

Transcription factor: As used herein, the term "transcription factor" refers to a DNA-binding protein that regulates transcription of DNA into RNA, for example, by activation or repression of transcription. Some transcription factors effect regulation of transcription alone, while others act in concert with other proteins. Some transcription factor can both activate and repress transcription under certain conditions. In general, transcription factors bind a specific target sequence or sequences highly similar to a specific consensus sequence in a regulatory region of a target gene. Transcription factors may regulate transcription of a target gene alone or in a complex with other molecules.

Treating: As used herein, the term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

The phrase "a method of treating" or its equivalent, when applied to, for example, cancer refers to a procedure or course of action that is designed to reduce, eliminate or prevent the number of cancer cells in an individual, or to alleviate the symptoms of a cancer. "A method of treating" cancer or another proliferative disorder does not necessarily mean that the cancer cells or other disorder will, in fact, be completely eliminated, that the number of cells or disorder will, in fact, be reduced, or that the symptoms of a cancer or other disorder will, in fact, be alleviated. Often, a method of treating cancer will be performed even with a low likelihood of success, but which, given the medical history and estimated survival expectancy of an individual, is nevertheless deemed an overall beneficial course of action.

Tumor growth: As used herein, the term "tumor growth" or "tumor metastases growth", unless otherwise indicated, is used as commonly used in oncology, where the term is principally associated with an increased mass or volume of the tumor or tumor metastases, primarily as a result of tumor cell growth.

Tumor Burden: As used herein, the term "tumor burden" refers to the total Tumor Volume of all tumor nodules with a diameter in excess of 3 mm carried by a subject.

Tumor Volume: As used herein, the term "tumor volume" refers to the size of a tumor. The tumor volume in $mm^3$ is calculated by the formula: volume=(width)$^2$×length/2.

Unmodified: As used herein, "unmodified" refers to any substance, compound or molecule prior to being changed in any way. Unmodified may, but does not always, refer to the wild type or native form of a biomolecule. Molecules may undergo a series of modifications whereby each modified molecule may serve as the "unmodified" starting molecule for a subsequent modification.

Equivalents and Scope

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

The invention is further illustrated by the following non-limiting examples.

EXAMPLES

List of Abbreviations

| | |
|---|---|
| 2'OMe | Methyl modification at 2' OH position |
| bDNA | branched DNA |
| conc. | concentration |
| CDS | Coding sequence |
| ELISA | Enzyme linked immunosorbent assay |
| FCS | fetal calf serum |
| $EC_{50}$ | Concentration of half-maximal effect |
| HNF4A | Hepatocyte nuclear factor 4 alpha |
| HPLC | High pressure liquid chromatography |
| IL-6 | Interleukin-6 |
| INF-α | Interferon-α |
| miRNA | Micro RNA |
| MS | Mass spectrometry |
| n.a. | not applicable |
| PBMC | Peripheral blood mononuclear cells |
| PBS | Phosphate buffered saline |
| QC | Quality control |
| QG2.0 | QuantiGene 2.0 |
| RLU | relative light unit |
| RNA | ribonucleic acid |
| saRNA | small activating RNA |
| siRNA | Small interfering RNA |
| TNF-α | Tumor necrosis factor α |
| UTR | untranslated region |

Example 1. In Vitro Studies with HNF4a-saRNA

A panel of hepatocyte cell lines including HEPG2, HEP3B, PLCPRF5, and SNU475 were transfected with HNF4a-saRNA (PR3) and scramble control. HNF4a mRNA levels were measured.

| | |
|---|---|
| PR3 Sense sequence | CCCAGAAUGCCUGUGAUCA SEQ ID No. 7 |
| PR3 Antisense sequence | UGAUCACAGGCAUUCUGGG SEQ ID No. 8 |

The cells were seeded in 24-well dishes at 100,000 cells per well and were reverse transfected with 20 nM (f.c.) of each test item using Lipofectamine 2000. After an incubation period of 24 hours an additional forward transfection step was conducted with 20 nM (f.c.) of each test item using Lipofectamine 2000. Twenty-four hours after the second transfection, cells were lysed and collected to determine the HNF4a-mRNA levels by quantitative reverse transcription-PCR (qRT-PCR). As shown in FIG. 2A-2D, HNF4a-mRNA levels were increased by at least 75% in all cells transfected with HNF4a-saRNA.

In another study, a panel of cells including HEPG2, HEP3B, and PLCPRF5 were transfected with HNF4a-saRNA (PR3) and cell proliferations were measured. WST-1 assay (relative proliferation) results and absolute cell numbers were shown in FIG. 3A-3F. HNF4a-saRNA reduced cell proliferations in all cell lines, wherein the reduction in HEP3B and HEPG2 cell lines are more than in PLCPRF5 cells.

Additional HNF4a-saRNA sequences and gene walk sequences around PR3 are included in Table 3. Gene walk going +10/−10 nucleotides around PR3 produced PR3-40-XD7569, PR3-41-XD7570, PR3-42-XD7571, PR3-43-XD7572, PR3-44-XD7573, PR3-45-XD7574, PR3-46-XD7575, PR3-47-XD7576, PR3-48-XD7577, PR3-49-XD7578, PR3-50-XD7579, PR3-51-XD7580, PR3-52-XD7581, PR3-53-XD7582, PR3-54-XD7583, PR3-55-XD7584, PR3-56-XD7585, PR3-57-XD7586, PR3-58-XD7587, PR3-59-XD7588, and PR3-60-XD7589.

TABLE 3

Additional saRNA sequences

| ID | Sense strand (Passenger) 5'→3' | SEQ ID NO | Anti-sense strand (Guide) 5'→3' | SEQ ID NO |
|---|---|---|---|---|
| PR3 | CCCAGAAUGCCUGUGAUCA | 7 | UGAUCACAGGCAUUCUGGG | 8 |
| PR60 | AUUGACUUCUACCCUCAAUUU | 37 | AUUGAGGGUAGAAGUCAAUUU | 38 |
| PR13 | UGGGUGAAUUAAUGAGUGAUU | 39 | UCACUCAUUAAUUCACCCAUU | 40 |
| PR68 | CAGGGAUUUGGCUGUUUGUUU | 41 | ACAAACAGCCAAAUCCCUGUU | 42 |
| PR01 | GCCCGGUUAUCUUAUUGAUUU | 43 | AUCAAUAAGAUAACCGGGCUU | 44 |
| PR40 | GUGGAUACGUUAAAGAGUAUU | 45 | UACUCUUUAACGUAUCCACUU | 46 |
| PR53 | ACGCGUGUGUACAUAUAUAUU | 47 | UAUAUAUGUACACACGCGUUU | 48 |
| PR38-50 | AUACCACUCGAACACACAUuu | 49 | AUGUGUGUUCGAGUGGUAUuu | 50 |
| PR106-50 | UACUCAGUAAUUUACCCUCuu | 51 | GAGGGUAAAUUACUGAGUAuu | 52 |
| PR25-50 | UCAUAUCAGCAACAUGUCCuu | 53 | GGACAUGUUGCUGAUAUGAuu | 54 |
| PR39-50 | UCUCCUGACAUCAAAUCUAuu | 55 | UAGAUUUGAUGUCAGGAGAuu | 56 |
| PR94-50 | UCACUCACUCCUAAUUCACuu | 57 | GUGAAUUAGGAGUGAGUGAuu | 58 |
| PR55-50 | AGACAUAACCGCAUUUCUCuu | 59 | GAGAAAUGCGGUUAUGUCUuu | 60 |
| PR257-50 | AACACACCAGAGAUAGCAAuu | 61 | UUGCUAUCUCUGGUGUGUUuu | 62 |
| PR196-50 | UCGAUCCCGGCUAUUCCUCuu | 63 | GAGGAAUAGCCGGGAUCGAuu | 64 |
| PR263-50 | UUUGGCACUCAACUUUGGGuu | 65 | CCCAAAGUUGAGUGCCAAAuu | 66 |
| PR204-50 | AAAUGUCUGCACAGAAGGCuu | 67 | GCCUUCUGUGCAGACAUUUuu | 68 |
| PR147-50 | CUACAUCAAGACUUUACUUuu | 69 | AAGUAAAGUCUUGAUGUAGuu | 70 |
| PR358-50 | GAUUUGCUCACUCAUUAAUuu | 71 | AUUAAUGAGUGAGCAAAUCuu | 72 |
| PR183-50 | CACUUACUCAGUAAUUUACuu | 73 | GUAAAUUACUGAGUAAGUGuu | 74 |
| PR339-50 | GACUCCCAGCAGAUCUUCCuu | 75 | GGAAGAUCUGCUGGGAGUCuu | 76 |
| PR231-50 | AAUUCACCCACCCAUUCACuu | 77 | GUGAAUGGGUGGGUGAAUUuu | 78 |

TABLE 3-continued

Additional saRNA sequences

| ID | Sense strand (Passenger) 5'→3' | SEQ ID NO | Anti-sense strand (Guide) 5'→3' | SEQ ID NO |
|---|---|---|---|---|
| PR128-50 | AUCUUCCCAGAGGACGGUUuu | 79 | AACCGUCCUCUGGGAAGAUuu | 80 |
| PR160-50 | ACACUCACUCAUUAAUUGGuu | 81 | CCAAUUAAUGAGUGAGUGUuu | 82 |
| PR3-50 | CCCAGAAUGCCUGUGAUCAuu | 83 | UGAUCACAGGCAUUCUGGGuu | 84 |
| PR3-40-XE17569 | (invabasic)CUGUGAUCACUGUGCCUGGuu | 85 | UCAGGCACAGUGAUCACAGuu | 86 |
| PR3-41-XE17570 | (invabasic)CCUGUGAUCACUGUGCCUGuu | 87 | UAGGCACAGUGAUCACAGGuu | 88 |
| PR3-42-XE17571 | (invabasic)GCCUGUGAUCACUGUGCCUuu | 89 | UGGCACAGUGAUCACAGGCuu | 90 |
| PR3-43-XE17572 | (invabasic)UGCCUGUGAUCACUGUGCCuu | 91 | UGCACAGUGAUCACAGGCAuu | 92 |
| PR3-44-XE17573 | (invabasic)AUGCCUGUGAUCACUGUGCuu | 93 | UCACAGUGAUCACAGGCAUuu | 94 |
| PR3-45-XE17574 | (invabasic)AAUGCCUGUGAUCACUGUGuu | 95 | UACAGUGAUCACAGGCAUUuu | 96 |
| PR3-46-XE17575 | (invabasic)GAAUGCCUGUGAUCACUGUuu | 97 | UCAGUGAUCACAGGCAUUCuu | 98 |
| PR3-47-XE17576 | (invabasic)AGAAUGCCUGUGAUCACUGuu | 99 | UAGUGAUCACAGGCAUUCUuu | 100 |
| PR3-48-XE17577 | (invabasic)CAGAAUGCCUGUGAUCACUuu | 101 | UGUGAUCACAGGCAUUCUGuu | 102 |
| PR3-49-XE17578 | (invabasic)CCAGAAUGCCUGUGAUCACuu | 103 | UUGAUCACAGGCAUUCUGGuu | 104 |
| PR3-50-XE17579 | (invabasic)CCCAGAAUGCCUGUGAUCAuu | 105 | UGAUCACAGGCAUUCUGGGuu | 106 |
| PR3-51-XE17580 | (invabasic)ACCCAGAAUGCCUGUGAUCuu | 107 | UAUCACAGGCAUUCUGGGUuu | 108 |
| PR3-52-XE17581 | (invabasic)CACCCAGAAUGCCUGUGAUuu | 109 | UUCACAGGCAUUCUGGGUGuu | 110 |
| PR3-53-XE17582 | (invabasic)UCACCCAGAAUGCCUGUGAuu | 111 | UCACAGGCAUUCUGGGUGAuu | 112 |
| PR3-54-XE17583 | (invabasic)UUCACCCAGAAUGCCUGUGuu | 113 | UACAGGCAUUCUGGGUGAAuu | 114 |
| PR3-55-XE17584 | (invabasic)CUUCACCCAGAAUGCCUGUuu | 115 | UCAGGCAUUCUGGGUGAAGuu | 116 |

TABLE 3-continued

Additional saRNA sequences

| ID | Sense strand (Passenger) 5'→3' | SEQ ID NO | Anti-sense strand (Guide) 5'→3' | SEQ ID NO |
|---|---|---|---|---|
| PR3-56-XE17585 | (invabasic)CCUUCACCCAGAAUGCCUGuu | 117 | UAGGCAUUCUGGGUGAAGGuu | 118 |
| PR3-57-XE17586 | (invabasic)CCCUUCACCCAGAAUGCCUuu | 119 | UGGCAUUCUGGGUGAAGGGuu | 120 |
| PR3-58-XE17587 | (invabasic)UCCCUUCACCCAGAAUGCCuu | 121 | UGCAUUCUGGGUGAAGGGAuu | 122 |
| PR3-59-XE17588 | (invabasic)CUCCCUUCACCCAGAAUGCuu | 123 | UCAUUCUGGGUGAAGGGAGuu | 124 |
| PR3-60-XE17589 | (invabasic)CCUCCCUUCACCCAGAAUGuu | 125 | UAUUCUGGGUGAAGGGAGGuu | 126 |
| PR3-50MM-XE17590 | (invabasic)CCCAGAAUGCCUGUGAUCUuu | 127 | UGAUCACAGGCAUUCUGGGuu | 128 |
| PR3-53MM-XE17591 | (invabasic)UCACCCAGAAUGCCUGUGUuu | 120 | UCACAGGCAUUCUGGGUGAuu | 130 |
| PR3-49-XE17666 | (invabasic)CCAGAAUGCCUGUGAUCAAuu | 131 | UUGAUCACAGGCAUUCUGGuu | 132 |

When describing a sequence, lower case letters=2'-O-Methyl modified; f=2'-fluro modified; s=phosphorothioate linkage; invabasic=inverted abasic capped; invdT=inverted dT.

HepG2 cells were transfected with HNF4a-saRNAs in Table 3 using transfection protocol described above. HNF4a P1 mRNA levels were measured by qPCR using a reagent specific for HNF4a P1 transcript. As a downstream marker, albumin mRNA levels were also measured in cells transfected with HNF4a-saRNAs. HNF4a P1 mRNA changes are shown in Table 4 and also in FIG. 17A. Albumin mRNA changes are shown in FIG. 17B. The relative HNF4a P1 mRNA and albumin mRNA expressions in FIG. 17A and FIG. 17B were calculated by comparing with house keep gene beta-Actin.

Only PR3, PR3-50 (the same sequence as PR3 with a 3' uu tail), PR3-49-XD7578, and PR3-50-XD7579 (the same sequence as PR3 with 5' inverted abasic cap and a 3' uu tail) with increased HNF4a P1 expression by more than 2 folds.

TABLE 4

HNF4a P1 mRNA transcript fold changes

| ID | HNF4a P1 transcript fold change relative to untransfected |
|---|---|
| PR3 | 2.18 |
| PR60 | 1.15 |
| PR13 | 0.72 |
| PR68 | 1.19 |
| PR01 | 0.87 |
| PR40 | 0.82 |
| PR53 | 0.82 |
| PR38-50 | 1.01 |
| PR106-50 | 1.06 |
| PR25-50 | 1.00 |
| PR39-50 | 1.04 |
| PR94-50 | 0.72 |
| PR55-50 | 1.05 |
| PR257-50 | 0.79 |
| PR196-50 | 1.02 |
| PR263-50 | 0.81 |
| PR204-50 | 0.40 |
| PR147-50 | 0.89 |
| PR358-50 | 0.94 |
| PR183-50 | 0.59 |
| PR339-50 | 1.02 |
| PR231-50 | 0.72 |
| PR128-50 | 0.67 |
| PR160-50 | 0.45 |
| PR3-50 | 2.05 |
| PR3-40-XD7569 | 0.92 |
| PR3-41-XD7570 | 1.23 |
| PR3-42-XD7571 | 0.81 |
| PR3-43-XD7572 | 0.56 |
| PR3-44-XD7573 | 1.35 |
| PR3-45-XD7574 | 1.38 |
| PR3-46-XD7575 | 0.87 |
| PR3-47-XD7576 | 1.02 |
| PR3-48-XD7577 | 1.04 |
| PR3-49-XD7578 | 2.24 |
| PR3-50-XD7579 | 2.39 |
| PR3-51-XD7580 | 1.45 |
| PR3-52-XD7581 | 0.78 |
| PR3-53-XD7582 | 0.48 |
| PR3-54-XD7583 | 1.07 |
| PR3-55-XD7584 | 0.49 |
| PR3-56-XD7585 | 0.70 |

TABLE 4-continued

HNF4a P1 mRNA transcript fold changes

| ID | HNF4a P1 transcript fold change relative to untransfected |
|---|---|
| PR3-57-XD7586 | 0.61 |
| PR3-58-XD7587 | 1.01 |
| PR3-59-XD7588 | 1.12 |
| PR3-60-XD7589 | 0.95 |
| PR3-50MM-XD7590 | 2.20 |
| PR3-53MM-XD7591 | 0.45 |
| PR3-49-XD7666 | 1.55 |

FIG. 18A and FIG. 18B show both PR3 and PR3-50 (the same sequence as PR3 with a 3' uu tail) increase HNF4a P1 mRNA levels, but not HNF4a P2 mRNA levels. FIG. 18C shows the increase in HNF4a P1 mRNA leads to increased albumin mRNA levels.

PR3-50, PR3-50-XD7579, and PR3-49-XD7578 were shown to be active in cynomolgus monkey hepatocytes. HNF4a P1 mRNA and albumin mRNA changes are shown in FIG. 19A and FIG. 19B. The seed sequence is homologous in PR3-49-XD7578 to the human sequence, while PR3-50-XD7579 has a single mismatch at the end of the seed region which does not impact activity.

Example 2. HNF4a-saRNA in Metabolic Disorders

In rats, forced re-expression of the transcription factor HNF4A induces expression of the other hepatocyte-expressed transcription factors; restores functionality in terminally diseased hepatocytes isolated from CCl4-treated animals; and rapidly reverses fatal liver failure by restoring diseased hepatocytes (Nishikawa et al., J Clin Invest. 2015, 1533-1544, the contents of which are incorporated herein by reference in their entirety). In this study a high fat diet (HFD) rat model has been used in order to study the effect of HNF4A on the animal metabolism. Studies have revealed that high-fat diets promote hyperglycemia and whole-body insulin resistance, and numerous researchers have examined their effects on muscle and liver physiology as well as insulin signal transduction. Subsequently, it is generally accepted that high-fat diets (HFD) can be used to generate a valid rodent model for the metabolic syndrome with insulin resistance and compromised β-cell function.

The purpose of this study was to investigate whether activation of the endogenous HNF4, upon HNF4A-PR4+ dendrimers injection, would rescue the high fat diet phenotype. The end point of this study includes several markers of diabetes (Glucose, HbA1C, C-peptide and Insulin), obesity (organs weight and weight loss), inflammation (IL6, IL-1β, α2M, TNFα and WBC) and liver function (ALT, AST and Ammonia).

Materials and Methods

Test Item

The test item for this experiment was rrHNF4A-PR4 (rat specific). In addition, a non-targeting duplex, FLUC-500018 was used as a negative control. Sequences of RNA oligonucleotides:

| Identifier | Sequence | Notes |
|---|---|---|
| FLU C-500018 | Antisense: 5'-UCGAAGmUACUmUAGCGmUAAGdTsdT-3' (SEQ ID NO. 33)<br>Sense: 5'-mCmUmUAmCGmCmUGAGmUAmCmUmUmCGAdTsdT-3' (SEQ ID NO. 34) | Non-specific oligo control; SC |
| rrHNF4a-PR4 | Sense: 5'-UUCAUUAAGCCUUGAGACAmUmU-3' (SEQ ID NO. 35)<br>Antisense: 5'-UGUCUCAAGGCUUAAUGAAmUmU-3' (SEQ ID NO. 36) | Targeting oligo |

Critical Reagents

Dendrimer synthesis and characterization. The 5 ($G_5$) of triethanolamine-core PAMAM dendrimer was synthesized as previously described and characterized by IR, NMR, MS, and HPLC[3-7]. Dendrimer were stored at −20° C.

PBS (phosphate buffered saline) used for the injection was from UniRegion BioTech, Cat. No. UR-PBS001.

RNA Isolation. Total RNA was isolated with the RNeasy Mini Kit according to the manufacturer's protocol (Qiagen, Venlo, Netherlands).

Complementary DNA (cDNA) Synthesis. cDNA was synthesized using the Quantitect Reverse Transcription kit according to the manufacturer's protocol with 500 ng RNA in a 10 μL reaction (Qiagen).

Quantitative PCR. Quantitative PCR was performed with Taqman Fast Advanced Master (FAM) Mix (Life Technologies) and QuantiFast SYBR Green (Qiagen) on an Applied Biosystems 7900HT real-time PCR system (Life Technologies). Reactions were run in triplicate wells.

ELISA kits. The following ELISA kits have been used according to the manufacturer's protocol: Rat Insulin, Mercodia Cat. No. 10-1250-01; Rat IL-1 beta, RayBiotech Cat.No. ELR-IL1b; Rat Alpha-2-Macroglobulin, Cloud-Clone Cat.No. SEB017Ra; Rat Interleukin 6, Cloud-Clone Cat.No. SEA079Ra; and Rat TNF-a, BioLegend Cat.No. 438207.

Animals Husbandry

The animals used for this study were 6-8 weeks old Wistar male rats. In order to induce the HFD phonotype, the animals were fed for 16 weeks with high-fat diet consisting of 83% standard diet (LabDiet® Cat.No 5001), 15% lard oil (SIGMA Cat.No L0657) and 2% cholesterol (SIGMA Cat.No C8503). They were housed in group of 3 per cage in the vivarium for the duration of experiment. Standard controlled environment of 22±3° C., 50±20% humidity and night/dark cycle of 12 hours every day was maintained with 15-20 fresh air changes per hour.

Experimental Design

24 Rats (HFD) were divided in four groups, of 6 animals each. Group 1 (control) was sacrificed at day 1. Groups 2-3-4 were injected at day 1, 3, 5, 12 and 17. Group 2 was injected with 600 µl of PBS, group 3 with 600 µl scramble RNA+dendrimer (SC+D) and group 4 with 600 µl HNF4A-PR4 saRNA +dendrimer (HNF4+D) (Table 5). HNF4A-saRNA dose was calculated considering the average weight of a Wistar rat (300 mg) Blood samples were collected at day 22 prior to animal sacrifice. One day prior to administration, the samples were placed in the fridge overnight. On the morning of administration, the samples were removed from the fridge and allowed thaw at room temperature. Subsequently RNA oligos and dendrimers were mixed together and gently vortexed for 2-3 seconds. The mixture was incubated for 25 minutes at room temperature. 600 ul of bolus were then injected into each animal.

TABLE 5

Experimental Groups and Doses

| Group | Test Article | Dose (mg/Kg) | Regiment | No. of Animals |
|---|---|---|---|---|
| 1 (naive) | None | NA | NA | 6 |
| 2 (PBS) | PBS | NA | V, Day 1, 3, 5, 12, 17 | 6 |
| 3 (SC + D) | Non-specific oligo | 0.6 | V, Day 1, 3, 5, 12, 17 | 6 |
| 4 (HNF4a + D) | HNF4a-saRNA | 0.6 | V, Day 1, 3, 5, 12, 17 | 6 |

Data Evaluation

Data were analyzed using a non-parametric t test and a two-tailed p-value. HNF4+D was compared with SC+D. Only weight loss was calculated with a non-parametric t test and a one-tailed p-value. P-values lower than 0.05 were considered significant at 95% confidence interval.

Results and Discussion

Figure 4:
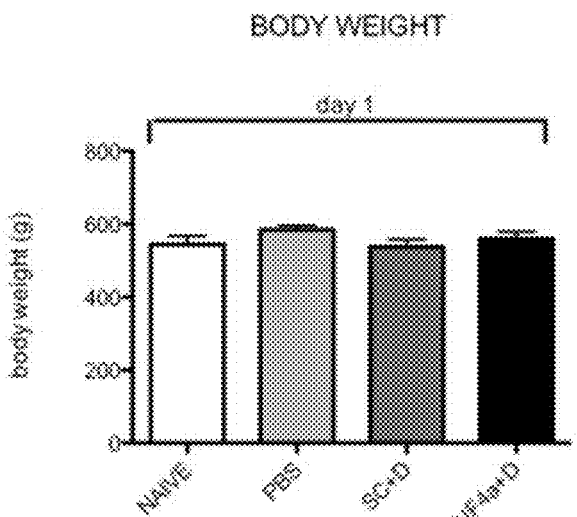
FIG. 4 shows body weight of rats in all groups before any treatment.

24 HFD rats were randomly divided in 4 groups. The body weight of the animal was measured prior to the start of the experiment (FIG. 4).

Figure 3A:
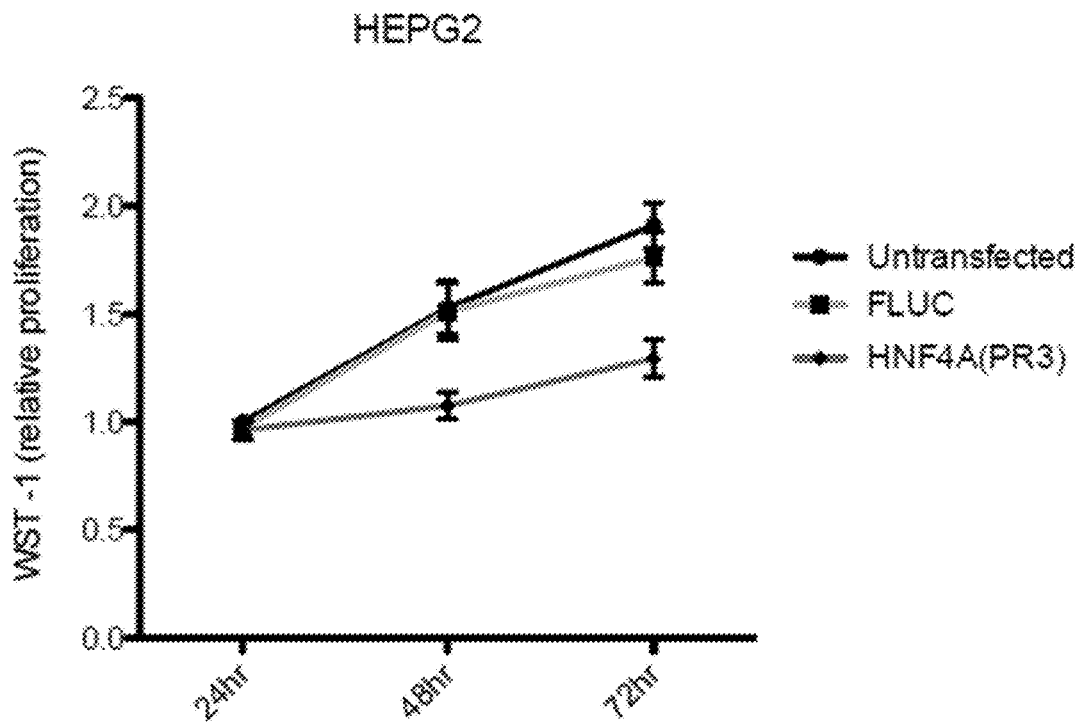
FIG. 3A-3F show WST-1 cell proliferation assay results and absolute cell numbers of HEPG2, HEP3B, and PLCPRF5 cell lines (untransfected, FLUC control transfected, or HNF4a-saRNA transfected).
Figure 3B:
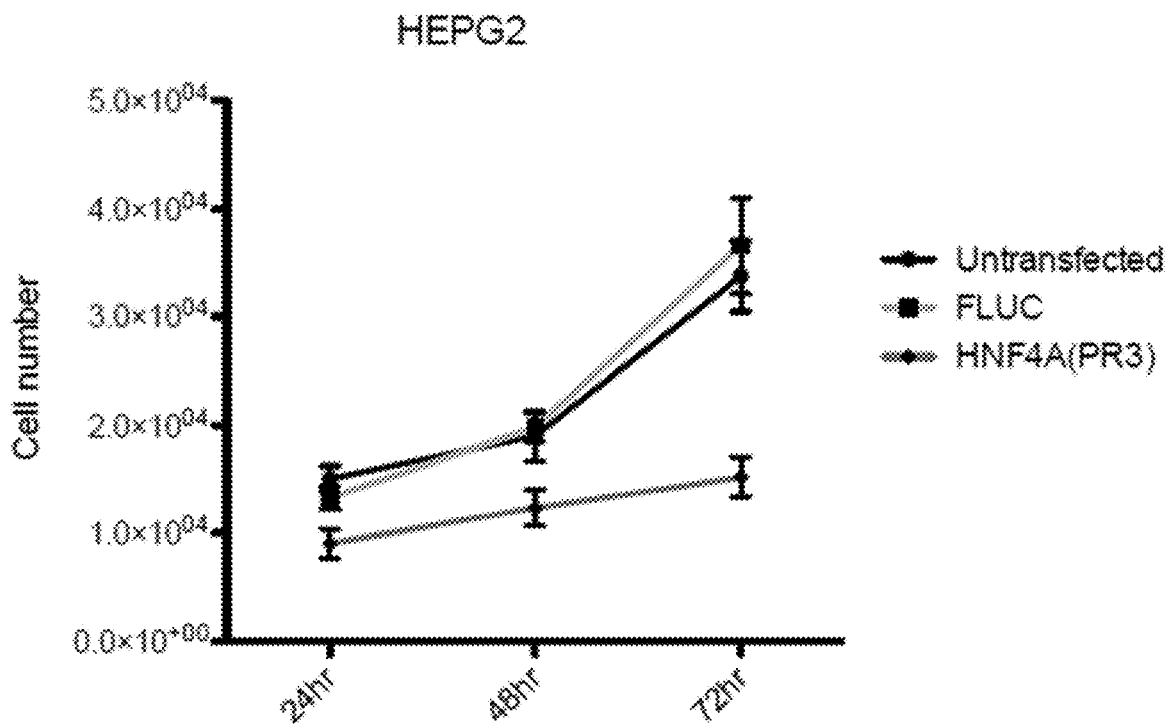
Figure 3C:
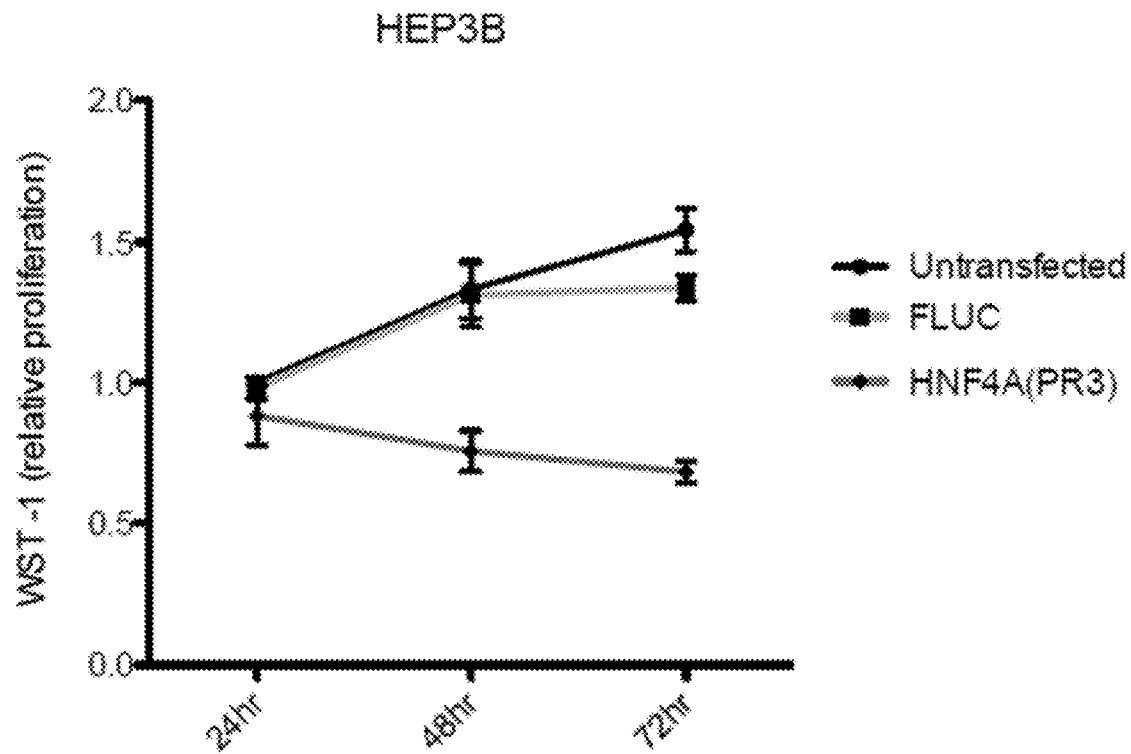
Figure 3D:
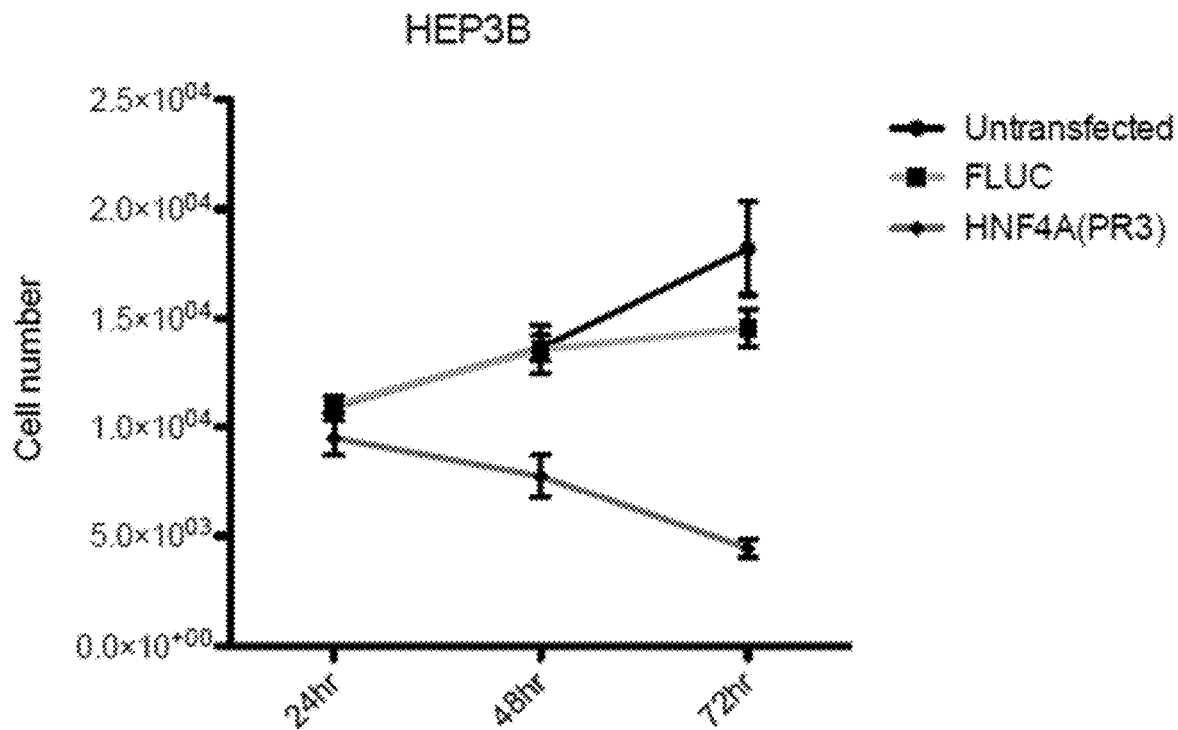
Figure 3E:
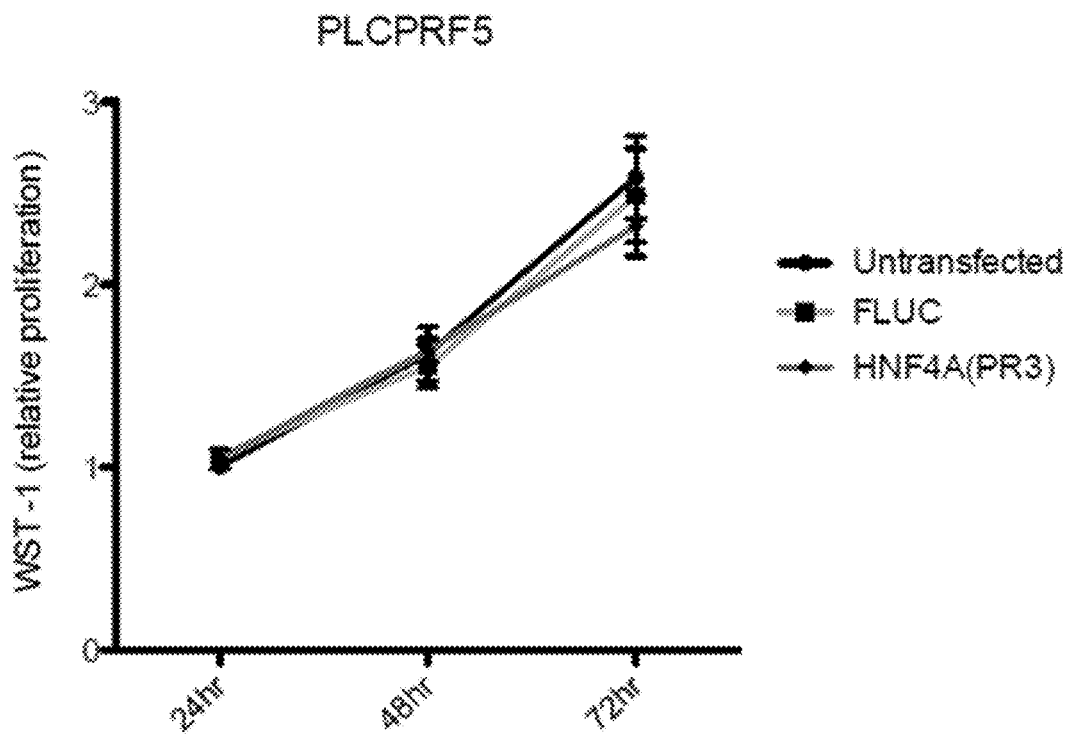
Figure 3F:
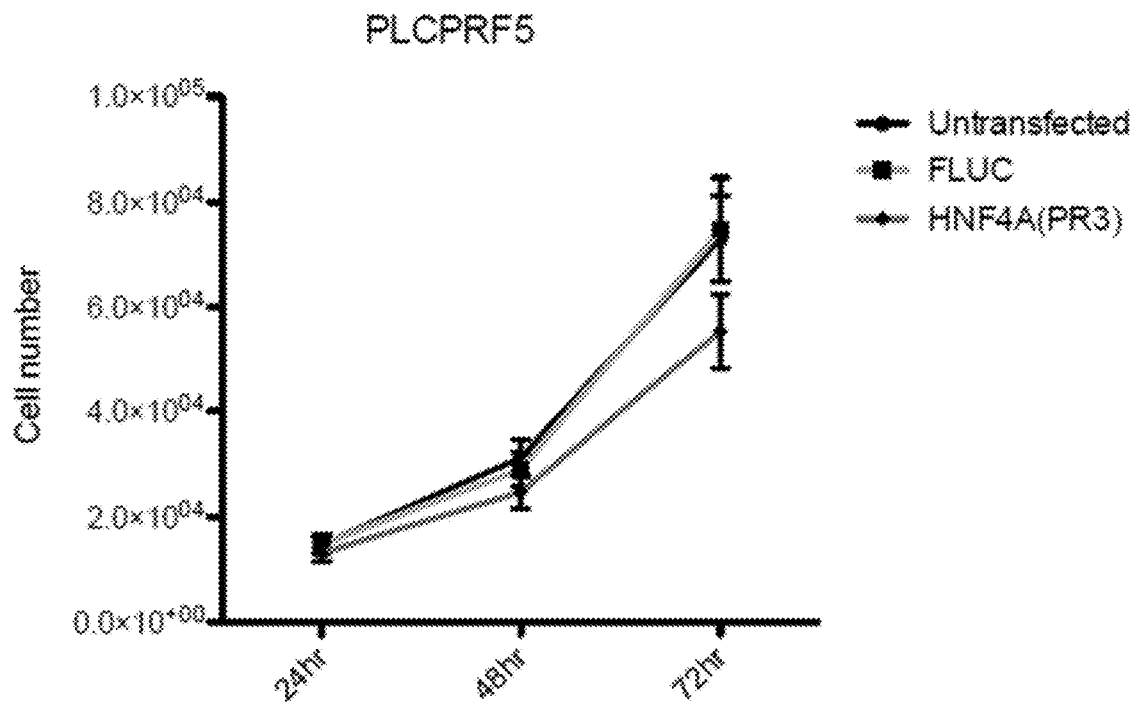

At completion of the treatment, HNF4A-saRNA+dendrimers (HNF4A+D) injected animals showed a significantly higher body weight loss (FIG. 5A) and a reduced liver weight-body weight ratio (FIG. 5B), similarly to a reduced white fat-body weight ratio (FIG. 3C). The pancreas-body weight ratio and brown fat-body weight ratio remained unchanged (FIGS. 3D and 3E). Such result suggests that HNF4A-saRNA reduces body weight and liver weight without affecting other organs such as pancreas and brown fat tissue. Instead, no significant reduction was observed in triglyceride, as well as in LDL, HDL, HDL/LDL ratio, and total cholesterol profile (FIGS. 6A, 6B, 6C, 6D and 6E). However, H & E staining showed fat content was reduced in the liver (FIG. 7A), specifically liver cholesterol (FIG. 7B), for HNF4A+D group. The reduction of liver cholesterol, compared to the unchanged total cholesterol indicates a specific action of HNF4A-saRNA in the liver.

Figure 8A:
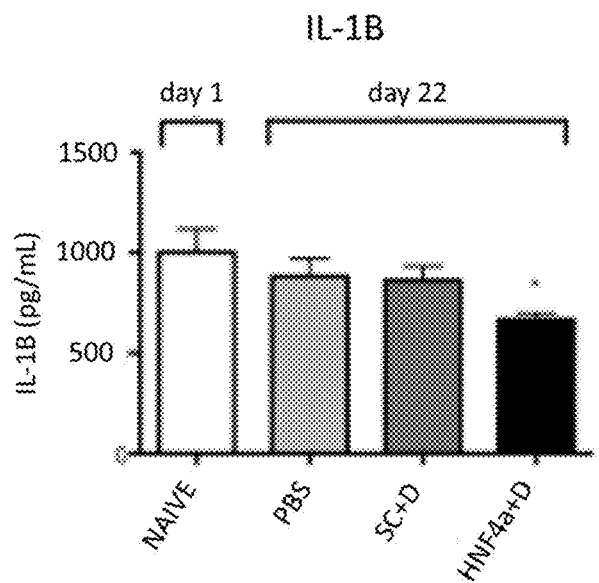
FIG. 8A-8E show inflammation marker levels in all groups: IL-1B (FIG. 8A), α2M (FIG. 8B), IL-6 (FIG. 8C), TNFα (FIG. 8D), and WBC (FIG. 8E).
Figure 8B:
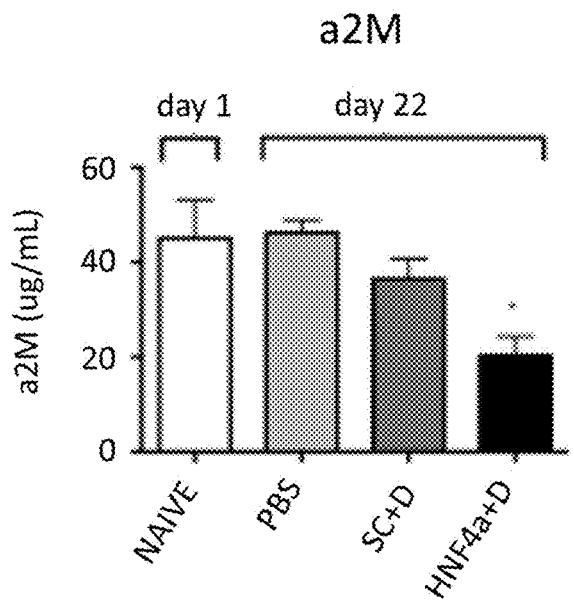
Figure 8C:
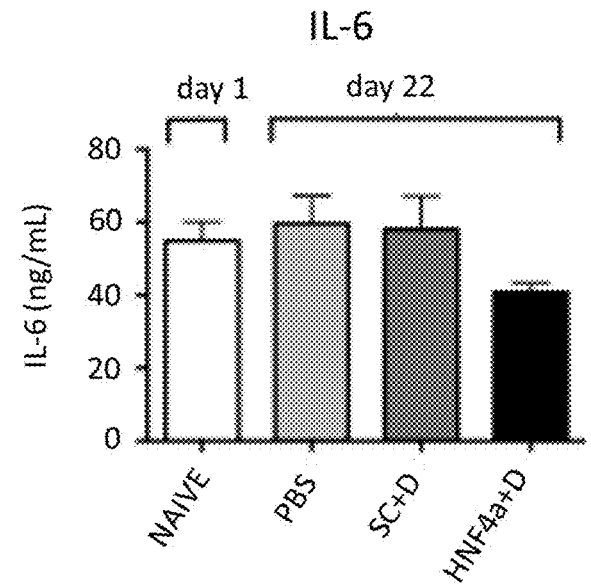
Figure 8D:
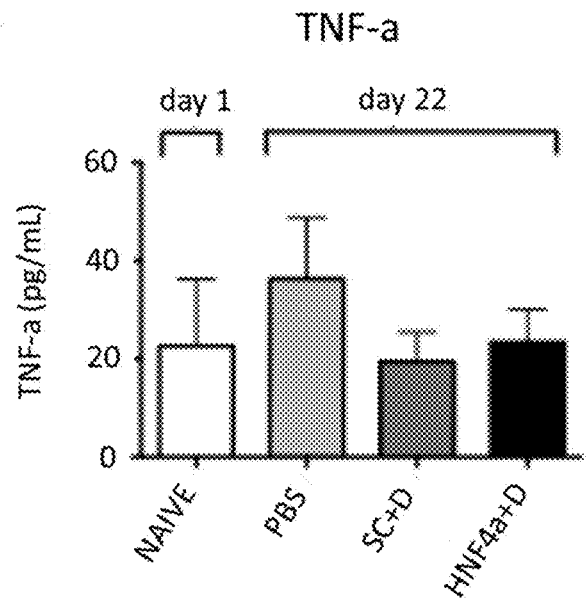
Figure 8E:
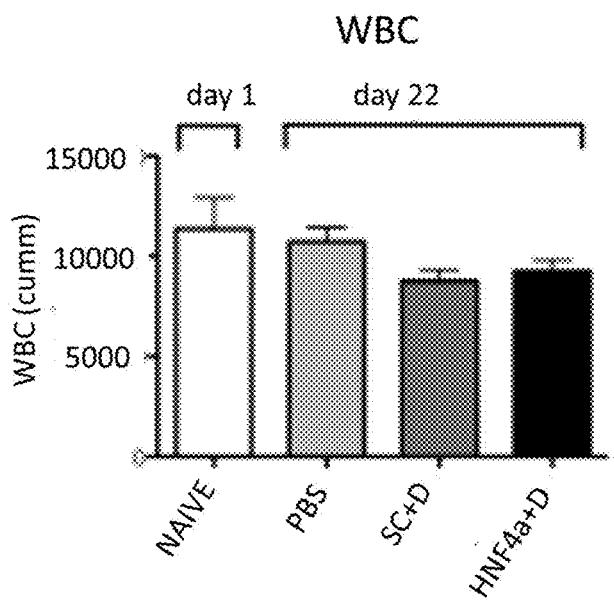
Figure 9A:
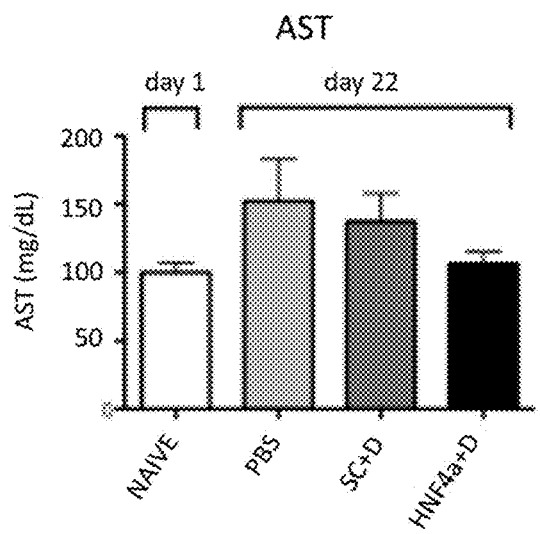
FIG. 9A-9C show liver function marker levels in all groups: ALT (FIG. 9A), AST (FIG. 9B), and ammonia (FIG. 9C).
Figure 9B:
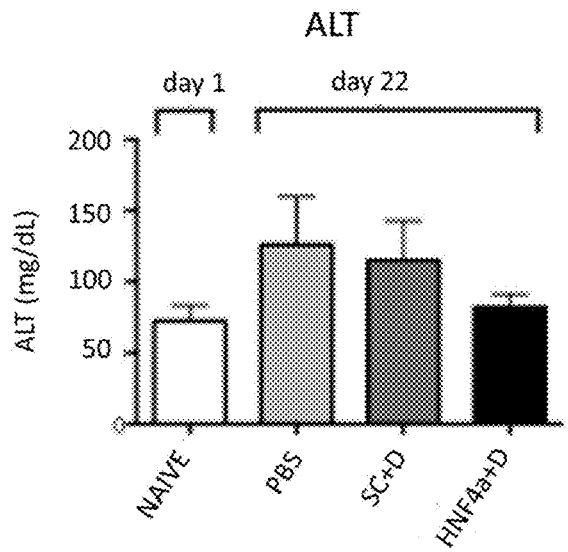
Figure 9C:
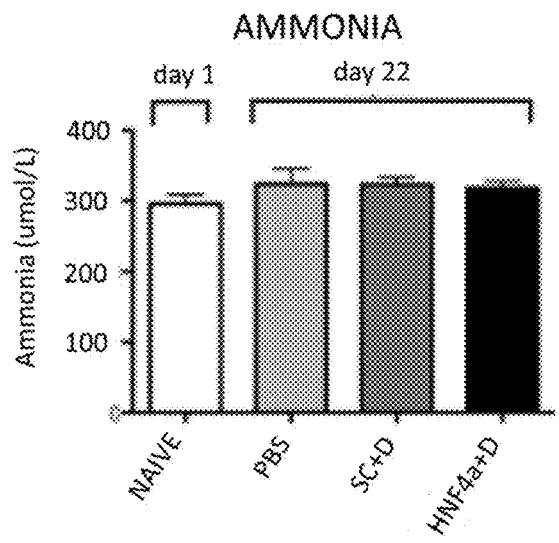
Figure 10A:
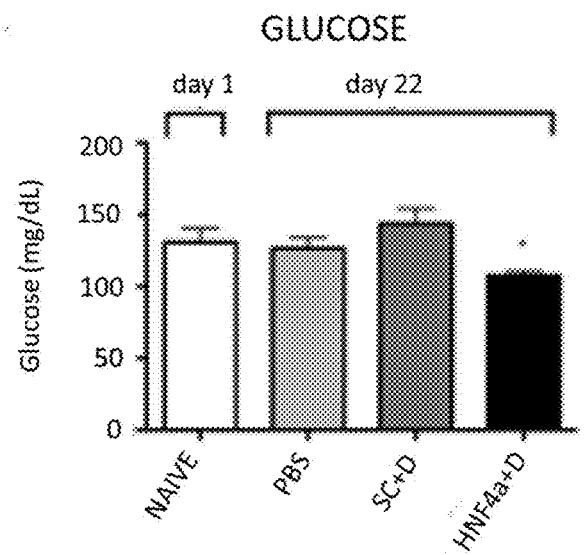
FIG. 10A-10D show diabetes marker levels in all groups: glucose (FIG. 10A), C-peptide (FIG. 10B), insulin (FIG. 10C) and HbA1C (FIG. 10D).
Figure 10B:
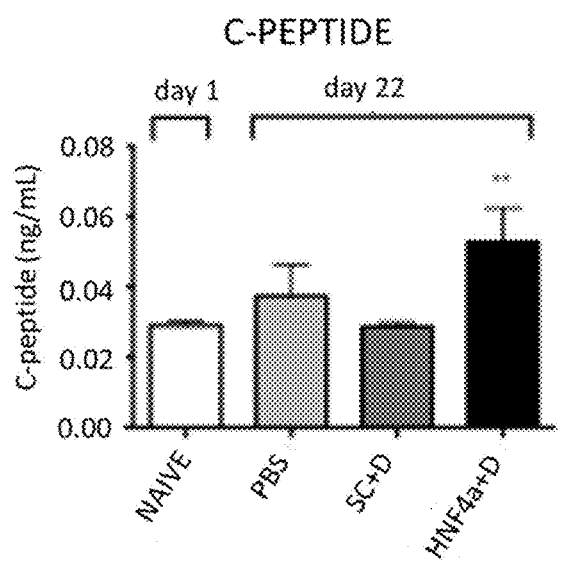
Figure 10C:
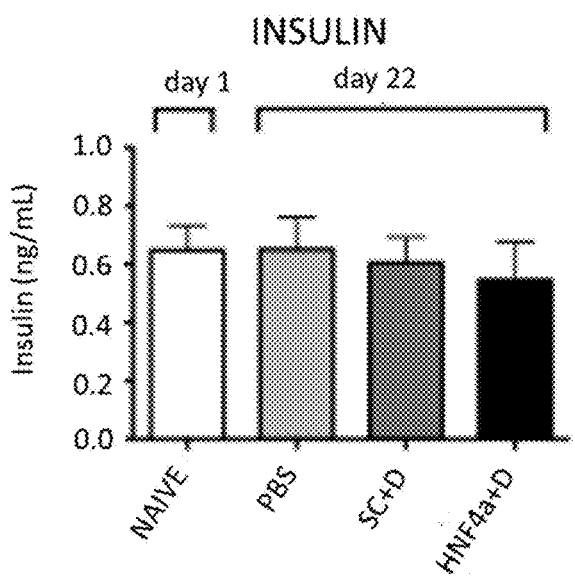
Figure 10D:
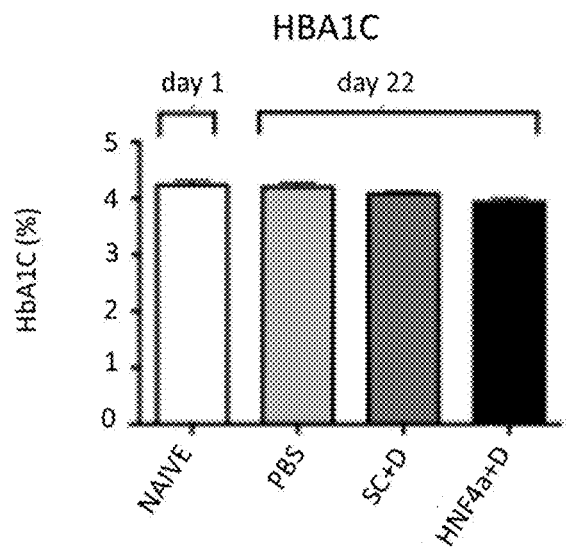

The markers of inflammation, such as interleukin 1 beta (IL-1B) were reduced by HNF4A compared with SC+D group (FIG. 8A), as well as alpha 2 macroglobulin ($\alpha$2M) levels, a marker of repair and remodeling during liver fibrosis (FIG. 8B). Interleukin 6 (IL-6), tumor necrosis factor alpha (TNF$\alpha$) and white blood cells (WBC) were unchanged (FIGS. 8C, 8D and 8E). Similarly, alanine transaminase (ALT), aspartate transaminase (AST) and Ammonia were unchanged (FIGS. 9A, 9B and 9C). Contradictory results were observed regarding the diabetic phenotype. Glucose levels were decreased (FIG. 10A); instead C-peptide was significantly increased in treated animals (FIG. 10B), while Insulin and HbA1C were unchanged (FIGS. 10C and 10D).

Figure 11A:
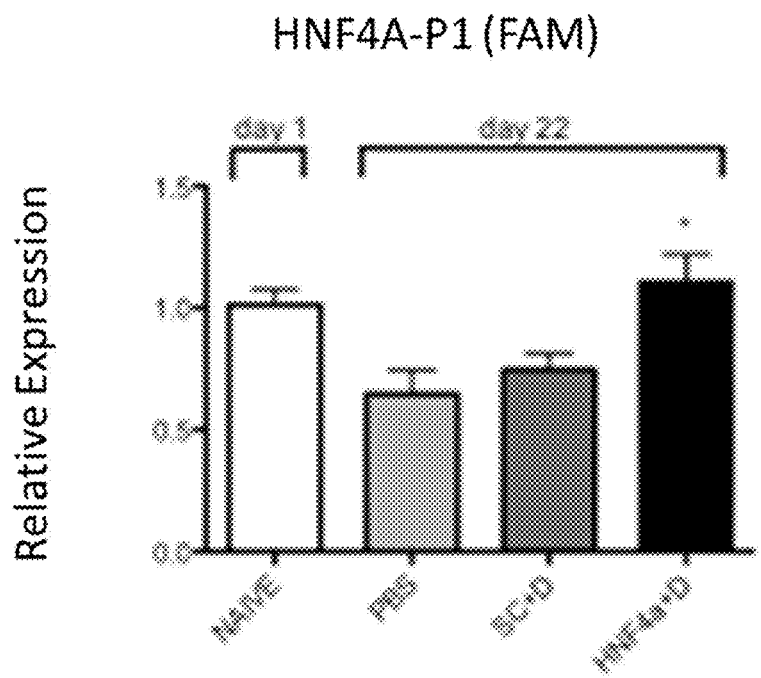
FIG. 11A-11C show the levels of HNF4-PR1 (promoter isoform 1) measured with FAM probe (FIG. 11A) and the overall transcript level (HNF4A-PR1/PR2, promoter isoforms 1 and 2) measured with both FAM (FIG. 11B) and SYBR (FIG. 11C) probes, of rats in all groups.
Figure 11B:
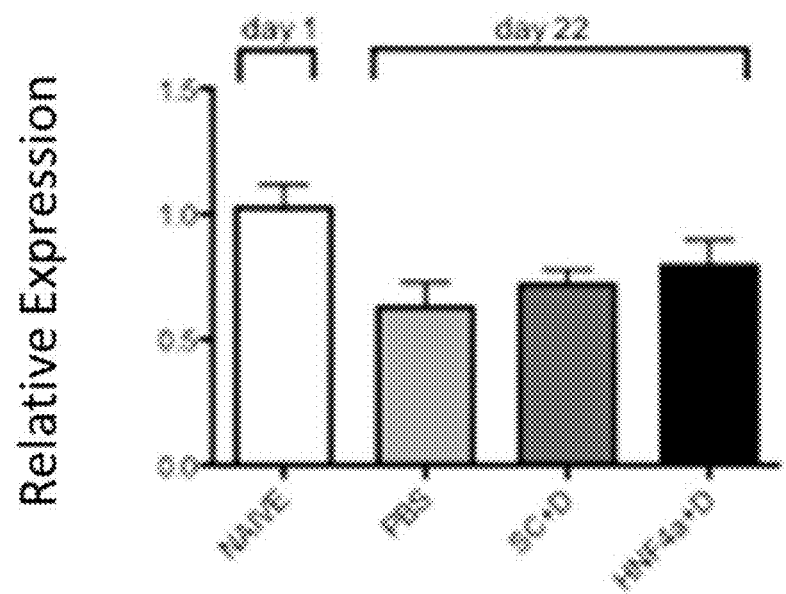
Figure 11C:
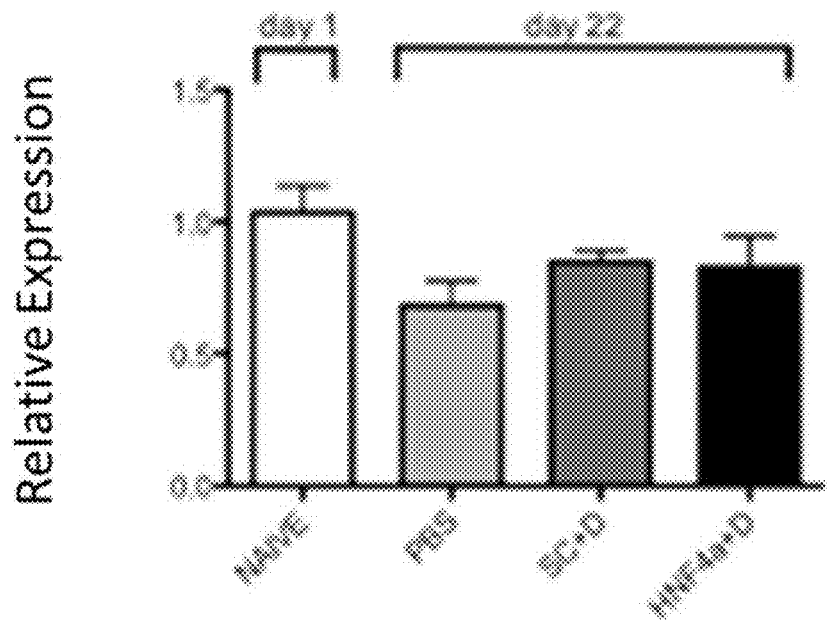

On the transcriptional level, HNF4-P1 (isoforms expressed from the P1 promoter) was significantly up regulated, however the overall transcript level (HNF4A-P1/P2, isoforms expressed from both P1 and P2 promoters), measured with both SYBR and FAM probes, remains unchanged (FIGS. 11A, 11B and 11C).

Conclusions

HNF4A-saRNA treatment seems to improve the HFD phenotype of the test animals. The higher body weight loss and the reduced ratio liver weight-body weight support this statement, together with the specific reduction of lipid cholesterol. Likewise, a reduction of the inflammation markers IL-1$\beta$ and $\alpha$2M and a reduction in glucose were detected. Moreover, TNF$\alpha$ was unchanged, indicating no toxicity at this level of the treatment.

In a further study, a further control group of non-HFD rats is added. This group provides the parameters of the healthy test animal. Blood samples are taken at several time points to define the best "window of action" of HNF4A.

Example 3. HNF4a-saRNA Treats Dyslipidemia and Promotes Favorable Metabolic Profile in a High Fat Diet (HFD) Fed Rat Model Methods Dendrimer-Based siRNA Delivery In Vivo The G5 dendrimer was synthesized starting with the triethanolamine core and following the iterative Michael addition and amidation as previously described. To form HNF4saRNA-coated G5 dendrimer-siRNA complexes, G5 was first mixed with saRNAs at N/P ([total terminal amines in G5]/[phosphates in saRNA]) ratio of 5 and kept at 37° C. for 30 min. The G5-saRNA complexes were then injected intravenously. rrHNF4a-PR4 was used in the study.

Animal Model, Experimental Design and Sample Collection

Eighteen male Wistar rats of 300±20 g body weight were obtained from the animal centre of the National Taiwan University. Rats were housed appropriately following a strict code of practice for the care and use of animals for scientific purposes. They were housed at (22±2° C.), with 65%-70% humidity in a light-controlled room in groups of three to four animals. The rats were fed a high-fat and high cholesterol diet (83% standard diet, 15% lard oil and 2% cholesterol) (LabDiet® Cat.No 5001, SIGMA Cat.No L0657, SIGMA Cat.No C8503). After 4 weeks, rats were randomised into 3 groups and injected via tail vein with either PBS, 0.6 mg/Kg of HNF-4$\alpha$ saRNA+dendrimer (HNF+D) or 0.6 mg/Kg of Scrambled saRNA+dendrimer (SC+D), in 600 µl of PBS final volume. After 16 weeks, blood samples were collected, animals were weighted and sacrificed. Livers and pancreas were removed and weighted. White and brown fat content were also evaluated. Liver, pancreas and fat weight are expressed in relation to the body weight.

Serum Biochemical Profiles

Serum levels of alanine aminotransferase (ALT), aspartate aminotransferase (AST), cholesterol, triglyceride (TG), high density lipoprotein (HDL), low density lipoprotein (LDL), ammonia, white blood cells (WBC), glucose, insulin, alpha-2 macroglobulin (A2M), interleukin 1 beta (IL-1 (3) and interleukin 6 (IL-6), were measured with VITROS 5.1 FS Chemistry Systems (Ortho-Clinical Diagnostics, Inc.). For lipid analysis, blood samples were collected for the determination of total and cholesterol and TG content using commercial kits (Sigma, MO, USA). Insulin resistance was evaluated through the TG/HDL ratio. A TG/HDL ratio ≥greater than 3 was considered as an index of insulin resistance. The following ELISA kits were used according to the manufacturer's protocol: 1). Rat Insulin, Mercodia Cat.No. 10-1250-01. 2). Rat IL-1 beta, RayBiotech Cat.No. ELR-IL 1b. 3). Rat Alpha-2-Macroglobulin, Cloud-Clone Cat.No. SEB017Ra. 4). Rat Interleukin 6, Cloud-Clone Cat.No. SEA079Ra. 5). Rat TNF-a, BioLegend Cat.No. 438207. 6). Rat Albumin, Bethyl Laboratories, Cat.No E110-125.

Liver Lipid Extraction and Quantification

For liver cholesterol measurement, 10 mg liver tissue were extracted with 200 ul of chloroform:Isopropanol:NP-40 (7:11:0.1). Cholesterol extracted from liver was quantified enzymatically using a Cholesterol/Cholesteryl Ester Quantitation Kit (K603-100; Biovision) following the manufacturer's instructions.

For triglycerides extraction, tissues (~100 mg) were homogenized in 1 ml water solution containing 5% NP-40. After a slow heat up to 80-100° C. in the water bath, sample were maintained in the water bath for 2-5 min or until the NP-40 became cloudy, then cooled down to room temperature. The heating was subsequently repeated. The samples were then centrifuged for 2 min at top speed in a microcentrifuge to remove any insoluble material. Triglycerides extracted from liver were quantified enzymatically using a Triglycerides Quantitation Kit (1(622-100; Biovision) following the manufacturer's instructions.

Histology

Samples from liver were fixed in 10% phosphate-buffered formalin, embedded in paraffin, and stained with haematoxylin-eosin (H & E).

Proteomics Analysis

Phosphoproteomics experiments were performed using mass spectrometry as previously reported (27). Briefly, cells were lysed in urea lysis buffer (8M urea, 10 mM $Na_3VO_4$, 50 mM NaF, 100 mM β-Glycerol phosphate and 25 mM $Na_2H_2P_2O_7$) and proteins reduced and alkylated by sequential addition of 1 mM DTT and 5 mM iodoacetamide. Immobilized trypsin was then added to digest proteins into peptides. After overnight incubation with trypsin, peptides were desalted by solid phase extraction (SPE) using OASIS HLB columns (Waters) in a vacuum manifold following manufacturer's guidelines with the exception that the elution buffer contained 1M glycolic acid. Phosphopeptides were enriched from the resulting peptide mixture using TiO2 chromatography as described by Larsen (28) with the modifications described by Montoya (29). TiO2 chromatographic media was added to the SPE eluted peptides and incubated 5 minutes with rotation. The TiO2 media was then packed in empty spin-tips and washed three times with 1M glycolic acid, 5% TFA. Phosphopeptides were eluted with 5% $NH_4OH$ and dried in a vacuum concentrator.

Dried phosphopeptide extracts were dissolved in 0.1% TFA and analysed by nanoflow LC-MS/MS in an LTQ-orbitrap as described before (27). Gradient elution was from 2% to 35% buffer B in 90 minutes with buffer A (0.1% formic acid in water and B was 0.1% formic acid in acetonitrile) being used to balance the mobile phase. MS/MS was acquired in multistage acquisition mode. MS raw files were converted into Mascot Generic Format using Mascot Distiller (version 1.2) and searched against the SwissProt database (2013.03 version) restricted to human entries using the Mascot search engine (version 2.3). Allowed mass windows were 10 ppm and 600 mmu for parent and fragment mass to charge values, respectively. Variable modifications included in searches were oxidation of methionine, pyro-glu (N-term) and phosphorylation of serine, threonine and tyrosine. Results were filtered to include those with a potential for false discovery rate less than 1% by comparing with searches against decoy databases. Quantification was performed by obtaining peak areas of extracted ion chromatographs (XICs) for the first three isotopes of each peptide ion using Pescal (31,32). Mass and retention time windows of XICs were 7 ppm and 1.5 minutes, respectively.

Transfection Reaction

For analyzing gene activation and protein expression, hepatocytes were seeded into 24-well plates at a density of $1\times10^5$ cells per well. Transfection was performed with lipofectamin 2000 HNF4A-saRNAs or scrambled saRNAs, were added to the cells at a final concentration of 50 nM, following the manufacture's instructions (Lifetechnologies, Cat number 11668019). The treatment was repeated 24 hours later and the cells were harvested at the 72-hour time point. All experiments with rifampicin were treated at a final concentration of 10 μM.

RNA Extraction

The total RNA was extracted for reverse transcription (QuantiFast® Reverse transcription, Qiagen) and target cDNA amplification by real-time PCR (QuantiFast® SYBR® Green Master mix). The cDNA probes used are listed below using QuantiTect® SYBR Probes from Qiagen.

Real-Time PCR Probes

Real-time PCR was performed with the following SYBR/FAM probes according to the manufacturer (Qiagen, Applied Biosystems):

| | | |
|---|---|---|
| ACTB_1_SG | QT00193473 | QIAGEN |
| ALB_1_SG | QT00189679 | QIAGEN |
| CEBPA_1_SG | QT00395010 | QIAGEN |
| HNF4A_1_SG | QT00188223 | QIAGEN |
| GAPD_1_SG | QT00199633 | QIAGEN |
| HNF4A-P1 | Rn 00696984ml | Applied Biosystems |
| HPRT | Rn 01526840ml | Applied Biosystems |

Protein Extraction for Western Blotting

The total protein was extracted using a conventional RIPA buffer (50 mM Tris-HCl, 150 mM sodium chloride, 1.0% Igepal, 0.5% sodium deoxycholate and 0.1% sodium dodecyl sulfate). The total protein content was then quantitated using a Bradford assay, following the manufacturer's instructions (Bio-Rad Bradford Assay). The total protein extracts were separated by SDS-PAGE and transferred onto PVDF membranes, then were probed with antibodies against HNF4A (Abeam, Cat number ab92378), CYP3A4 (Abeam, Cat number ab124921), Albumin (Abeam, Cat number ab131176) and HSP90 (Stressgene, Cat number SPA-846). The proteins of interest were detected with an HRP-conjugated secondary antibody (1:5000) and visualized with LI-COR Western Sure ECL substrate, according to the manufacturer's protocol.

Luciferase Assay

Luciferase assays were carried out according to the manufacturer's instructions (Promega p450-Glo, TB325).

Data Analysis

All values were represented as a mean±standard deviation (SD). Statistical comparison between groups was done using the Student T test, Confidence interval 95%; $p<0.05$ was considered to be statistically significant (SPSS version 17.0, IBM Corporation, Armonk, New York).

Results

Figure 2A:
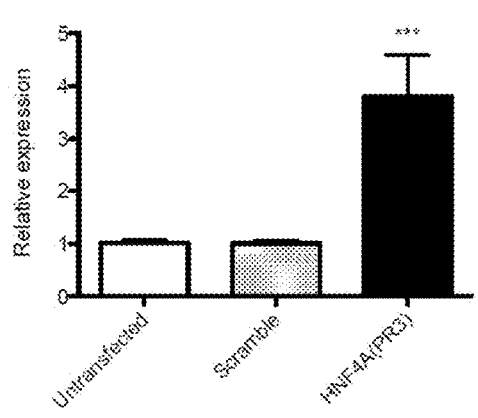
FIG. 2A-2D show HNF4a mRNA levels in hepatocyte cells transfected with HNF4a-saRNA.
Figure 2B:
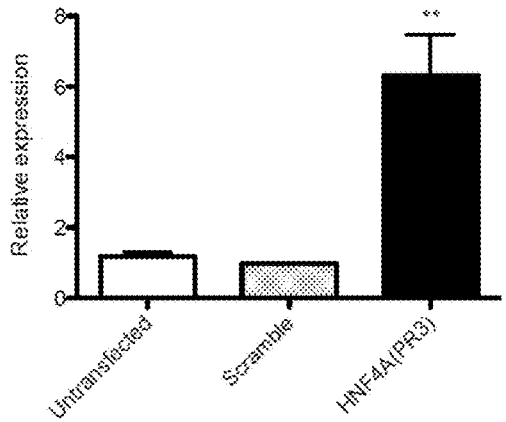
Figure 2C:
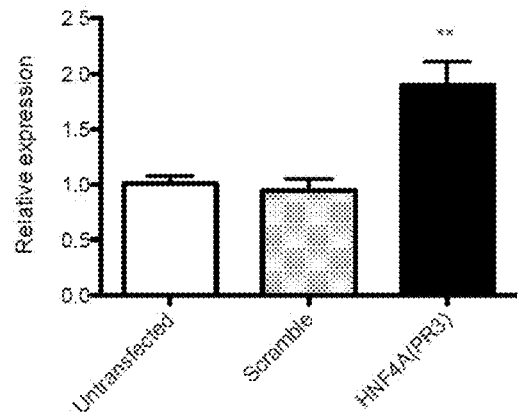
Figure 2D:
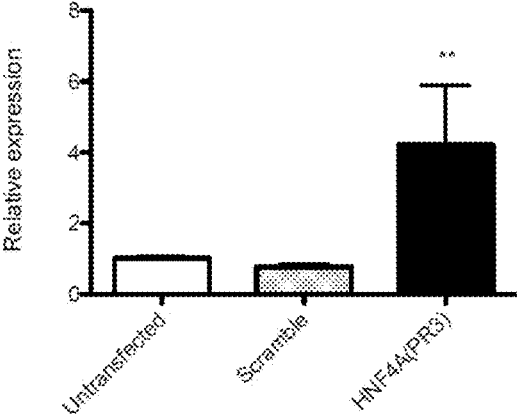

HNF4A-saRNA induced HNF-4α expression in HCC cells: To test for saRNA target activation of HNF-4α, the commonly used HepG2, Hep3B and PLCPRF5 HCC lines were transiently transfected with a mammalian specific saRNA. A non-specific dsRNA (Scramble), which does not have significant homology with any known human sequences, was used was used as a negative control. 50 nM of double stranded Scramble-RNA or HNF4A-saRNA were transfected into HepG2, Hep3B and PLCPRF5 cells. HNF-4α expression was evaluated 72 hours later. HNF-4α mRNA expression was significantly induced by HNF4A-saRNA in all the cell lines as demonstrated by quantitative RT-PCR analysis. HNF4A-saRNA caused a 3-fold increase in HNF-4α mRNA levels ($p<0.0001$) compared to untransfected in HepG2 cells (FIG. 2A); a 6-fold increase in Hep3B ($p=0.0022$) (FIG. 2B) and a 2 fold increase in PLCPRF5 cells ($p=0.0087$) (FIG. 2C). Scramble nucleotide did not cause an induction of HNF-4α mRNA levels (FIGS. 2A, 2B and 2C). HNF-4α expression at the protein level was verified by Western blotting (FIG. 12A). HNF4A-saRNA increased HNF-4α expression of 3-fold relative to untransfected control. In the presence of 10 μM rifampicin (a CYP450 inducer), HNF4A-saRNA enhanced the ability of HepG2 cells to further increase HNF-4α protein expression up to 5-fold change when the protein bands were quantified on a densitometry (FIG. 12B). HNF4A-saRNA induced a 15-fold increase in albumin, which was further augmented (35 fold) upon 10 μM rifampicin treatment (FIG. 12C). Protein expression of CYP3A43 increased 5.6 fold (FIG. 12D) when compared to untransfected HepG2 cells. HNF4A-saRNA transfection also increased cytochrome p450 activity as demonstrated by a luciferase assay (FIG. 12H). Cytochrome p450 upregulation was measured by qPCR where it was observed a significant 1.5 fold increase in CYP3A4 ($p=0.05$) (FIG. 12E); 2 fold increase in CYP3A5 ($p=0.05$) (FIG. 12F) and 3.6 fold increase CYP3A7 levels ($p=0.05$) (FIG. 12G).

HNF-4α increase the activity of signaling pathways and transcriptional factors known to promote metabolic regulation: Using mass spectrometry analysis of protein lysates from HNF4A-saRNA transfected HepG2, Hep3B and PLCPRF5 cell lines, the global protein expression and phosphoprotein changes that occurred downstream of HNF-4α expression were investigated.

Over-representation analysis of the genes that showed significant protein level changes in HNF4A-saRNA treated cell lines were enriched for pathways that regulate glucose transport, lipid metabolism and energy production. Increased protein expression in genes involved in fatty acid β-oxidation and ketogenesis was observed. The observed changes in liver triglyceride levels (FIG. 13I) concurrent to in vitro changes in mediators of lipid transport P4HB and SEC24C have also previously been documented in a high fat diet fed animal study where a decrease in fatty acid β-oxidation was proposed to contribute to hepatic lipid accumulation whilst ketogenesis was reported to prevent fatty liver injury and hyperglycemia. P4HB is involved in hepatic VLDL assembly and lipid homeostasis whilst SEC24C is the rate-limited step in transporting dietary fat across the intestinal absorptive cells. A reduction in protein expression of YAP1 and dephosphorylation at multiple sites was also observed across all HNF4A-saRNA treated cell lines. YAP1 is a downstream target of the Hippo signaling pathway, and is thought to play a role in organ size. Prolonged activation of YAP1 has been shown to lead to an increase in liver size in adult mice, an effect which was however reversible upon inhibition of YAP1 expression.

An increase in the expression of protein kinases in metabolic signaling pathways was also observed. These included glycogen synthase kinase-3 beta (GSK3β), and two isoforms of cAMP-dependent protein kinase A (PKA) regulatory subunits (PRKAR1A and PRKAR1B) as well as Cyclic AMP-responsive element-binding protein 1 (CREB1). Reduction of these factors are held accountable for the pathophysiological changes that cause non-alcoholic fatty liver disease.

Changes of gene expression for genes involved in the pathways after HNF4a-saRNA treatment are summarized in Tables 6A-6D:

TABLE 6A

Changes of gene expression for genes involved in Glucose Transport

| Gene Name | Protein ID | Expression Changes | | | Description |
|---|---|---|---|---|---|
| | | HEPG2 | HEP3B | PLCPRF5 | |
| TRIP10 | CIP4_HUMAN | increase | increase | increase | Thyroid Hormone Receptor Interactor 10, Cdc42-interacting protein 4 |

TABLE 6B

Changes of gene expression for genes involved in Lipid Metabolism

| Gene Name | Protein ID | Expression Changes | | | Description |
|---|---|---|---|---|---|
| | | HEPG2 | HEP3B | PLCPRF5 | |
| Sphingolipid metabolism | | | | | |
| ARSA | ARSA_HUMAN | increase | increase | increase | Arylsulfatase A |
| PSAP | SAP_HUMAN | increase | increase | increase | Prosaposin |
| Sphingolipid catabolism | | | | | |
| GBA3 | GBA3_HUMAN | decrease | decrease | no change | Glucosidase, Beta, Acid 3 |

TABLE 6B-continued

Changes of gene expression for genes involved in Lipid Metabolism

| Gene Name | Protein ID | HEPG2 | HEP3B | PLCPRF5 | Description |
|---|---|---|---|---|---|
| Fatty acid beta-oxidation | | | | | |
| HADHB | ECHB_HUMAN | increase | increase | increase | Trifunctional enzyme subunit beta, mitochondrial |
| ACADVL | ACADV_HUMAN | decrease | decrease | — | Very long-chain specific acyl-CoA dehydrogenase, mitochondrial |
| Ketogenesis | | | | | |
| HMGCL | HMGCL-HUMAN | increase | increase | increase | Hydroxymethylglutaryl_CoA lyase, mitochondrial |
| HMGCLL1 | HMGC2_HUMAN | increase | increase | increase | 3-hydroxymethyl-3-methylglutaryl-CoA lyase, cytoplasmic |
| HMGCS1 | HMGS1_HUMAN | increase | increase | increase | Hydroxymethylglutaryl-CoA synthase, cytoplasmic |
| AKR1C1 | AK1C1_HUMAN | increase | no change | increase | Aldo-keto reductase family 1 member C1 |
| Detoxification of relative oxygen species (ROS) | | | | | |
| GPX1 | GPX1_HUMAN | increase | increase | increase | Glutathione peroxidase 1 |
| TXNRD1 | TRXR1_HUMAN | increase | no change | increase | Thioredoxin reductase 1, cytoplasmic |
| Lipid transport | | | | | |
| PTGR1 | PTGR1_HUMAN | decrease | decrease | decrease | Prostaglandin reductase 1 |
| SEC24C | SC24C_HUMAN | decrease | decrease | decrease | Protein transport protein Sec24C |
| Other lipid-related | | | | | |
| YAP1 | YAP1_HUMAN | decrease | decrease | decrease | Yes Associated Protein 1, Yokie homolog |
| P4HB | PDIA1_HUMAN | no change | increase | increase | Protein disulfide-isomerase |
| PCYT2 | PCY2_HUMAN | increase | increase | increase | Ethanolamine-phosphate cytidylyltransferase |
| ACSL4 | ACSL4_HUMAN | decrease | decrease | decrease | Long-chain-fatty-acid-CoA ligase 4 |
| YAP1 phosphoproteomics | | | | | |
| YAP1 pS109 | | decrease | decrease | decrease | Yorkie homolog |
| YAP1 pS131 pD138 | | decrease | decrease | decrease | Yorkie homolog |
| YAP1 pS61 | | no change | decrease | decrease | Yorkie homolog |
| YAP1 seq: 107 – 124 + Phospho (ST) | | decrease | decrease | no change | Yorkie homolog |
| YAP1 seq: 125 – 161 + 2 Phospho (ST) | | decrease | no change | decrease | Yorkie homolog |
| YAP1 seq: 125 – 161 + Phospho (ST) | | decrease | decrease | decrease | Yorkie homolog |
| YAP1 seq: 162 – 181 + Phospho (ST) | | decrease | decrease | no change | Yorkie homolog |
| YAP1 seq: 59 – 76 + Phospho (ST) | | decrease | decrease | decrease | Yorkie homolog |

TABLE 6C

Changes of gene expression for genes involved in Metabolic Signaling

| Gene Name | Protein ID | HEPG2 | HEP3B | PLCPRF5 | Description |
|---|---|---|---|---|---|
| TRIM28 | KAP1_HUMAN | increase | increase | decrease | cAMP-dependent protein kinase type I-beta regulatory subunit |
| PRKAR1A | KAP0_HUMAN | increase | increase | increase | cAMP-dependent protein kinase type I-alpha regulatory subunit |

TABLE 6C-continued

Changes of gene expression for genes involved in Metabolic Signaling

| Gene Name | Protein ID | HEPG2 | HEP3B | PLCPRF5 | Description |
|---|---|---|---|---|---|
| GSK3B | GSK3B_HUMAN | increase | no change | increase | Glycogen synthase kinase-3 beta |
| CREB1 | CREB1_HUMAN | increase | increase | increase | Cyclic AMP-responsive element-binding protein 1 |
| ARPP19 pS62 | ARPP19 pS62 | increase | no change | increase | cAMP-regulated phophoprotein 19 |
| PRKAR1A pS83 | PRKAR1A pS83 | increase | increase | increase | cAMP-dependent protein kinase type I-alpha regulatory subunit |

TABLE 6D

Changes of gene expression for genes present in Reactome "lipid metabolism" pathways with significant changes in protein expression in HNF4a-saRNA treated cells

| Gene Name | Protein ID | HEPG2 | HEP3B | PLCPRF5 | Description |
|---|---|---|---|---|---|
| ABHD3 | ABHD3_HUMAN | no change | increase | increase | Abhydrolase domain-containing protein 3 |
| ACACB | ACACB_HUMAN | decrease | increase | increase | Acetyl-CoA carboxylase 2 |
| ACADM | ACADM_HUMAN | decrease | increase | increase | Medium-chain specific acyl-CoA dehydrogenase, mitochondrial |
| ACADVL | ACADVL_HUMAN | decrease | decrease | no change | Very long-chain specific acyl-CoA dehydrogenase, mitochondrial |
| ACOT2 | ACOT2_HUMAN | increase | decrease | decrease | Acyl-coenzyme A thioesterase 2, mitochondrial |
| ACSL4 | ACSL4_HUMAN | decrease | decrease | decrease | Long-chain-fatty-acid-CoA ligase 4 |
| AKR1C1 | AKR1C1_HUMAN | increase | no change | increase | Aldo-keto reductase family 1 member C1 |
| AKR1C2 | AKR1C2_HUMAN | increase | decrease | increase | Aldo-keto reductase family 1 member C2 |
| AKR1D1 | AKR1D1_HUMAN | decrease | decrease | increase | 3-oxo-5-beta-steroid 4-dehydrogenase |
| APOA2 | APOA2_HUMAN | increase | decrease | decrease | Apolipoprotein A-II |
| ARSA | ARSA_HUMAN | increase | increase | increase | Arylsulfatase A |
| ARSB | ARSB_HUMAN | increase | increase | decrease | Arylsulfatase B |
| ASAH1 | ASAH1_HUMAN | increase | decrease | decrease | Acid ceramidase |
| HADHB | ECHB_HUMAN | increase | increase | increase | Trifunctional enzyme subunit beta, mitochondrial |
| FDPS | FPPS_HUMAN | increase | increase | no change | Farnesyl pyrophosphate synthase |
| GBA3 | GBA3_HUMAN | decrease | decrease | no change | Gluosidase Beta Acid 3 |
| GPX1 | GPX1_HUMAN | increase | increase | increase | Glutathione peroxidase 1 |
| HMGCS1 | HMCS1_HUMAN | increase | increase | increase | Hydroxymethylglutaryl-CoA synthase, cytoplasmic |
| HMGCLL1 | HMGC2_HUMAN | increase | increase | increase | 3-hydroxymethyl-3-methylglutaryl-CoA lyase, cytoplasmic |
| HMGCL | HMGCL_HUMAN | increase | increase | increase | Hydroxymethylglutaryl-CoA lyase, mitochondrial |
| EPHX2 | HYES_HUMAN | increase | decrease | increase | Bifunctional epoxide hydrolase 2 |
| IDH1 | IDHC_HUMAN | increase | increase | decrease | Isocitrate dehydrogenase [NADP] cytoplasmic |
| LPIN3 | LPIN3_HUMAN | decrease | increase | increase | Lipin 3 |
| PIK3R2 | P85B_HUMAN | increase | decrease | increase | Phosphoinositide-3-Kinase, Regulatory Subunit 2 |
| PCYT1A | PCY1A_HUMAN | increase | increase | decrease | Choline-phosphate cytidylyltransferase |
| PCYT2 | PCY2_HUMAN | increase | increase | increase | Ethanolamine-phosphate |
| P4HB | PDIA1_HUMAN | no change | increase | increase | Protein disulfide-isomerase |

TABLE 6D-continued

Changes of gene expression for genes present in Reactome "lipid metabolism" pathways with significant changes in protein expression in HNF4a-saRNA treated cells

| Gene Name | Protein ID | Expression Changes | | | Description |
|---|---|---|---|---|---|
| | | HEPG2 | HEP3B | PLCPRF5 | |
| PLIN2 | PLIN2_HUMAN | increase | increase | decrease | Perilipin-2 |
| PPP1CB | PPIB_HUMAN | decrease | decrease | increase | Peptidyl-prolyl cis-trans isomerase B |
| PPT1 | PPT1_HUMAN | no change | decrease | increase | Peptidyl-prolyl cis-trans isomerase 1 |
| PTGR1 | PTGR1_HUMAN | decrease | decrease | decrease | Prostaglandin reductase 1 |
| PSAP | SAP_HUMAN | increase | increase | increase | Prosaposin |
| SEC23A | SC23A_HUMAN | increase | decrease | decrease | Protein transport protein Sec23A |
| SEC24C | SC24C_HUMAN | decrease | decrease | decrease | Protein transport protein Sec24C |
| TBL1X | TBL1X_HUMAN | decrease | decrease | increase | F-box-like/WD repeat-containing protein TBL1X |
| TXNRD1 | TRXR1_HUMAN | increase | increase | increase | Thioredoxin reductase 1, cytoplasmic |
| YAP1 | YAP1_HUMAN | decrease | decrease | decrease | Yorkie homolog |

HNF4A-saRNA-dendrimer treatment increases liver expression of HNF-4α: Since upregulation of HNF-4α by saRNA caused predicted changes in lipid and cholesterol metabolic pathways, the physiological effects of delivering therapeutic amounts of HNF4A-saRNA-dendrimer (0.6 mg/kg) or scrambled oligonucleotide control (Scramble-dendrimer) into a rat model sustained on a high fat diet (HFD) were investigated. 18 Wistar male rats (6-8 weeks old) were fed for 16 weeks with HFD. The animals were divided into three groups of 6 animals each. Groups 1-3 were injected at days 1, 3, 5, 12 and 17. The control Group 1 was injected with 600 µl of PBS; control Group 2 with 600 µl Scramble-dendrimer and experimental Group 3 with 600 µl HNF4A-saRNA-dendrimer. Blood samples were collected at day 22 prior to animal sacrifice for analysis and the liver lobes were biopsied for immediate total RNA extraction (FIG. 14).

To confirm target engagement of the saRNA in the liver samples, total RNA from tissue sections were analysed for HNF4A transcript expression using HNF4A-P1 promoter specific FAM-labelled probes. A 1.5-fold increase in HNF4A transcript was detected from the treated liver relative to scramble control (p=0.0411) (FIG. 13A). No change in albumin transcript levels were detected across each of the treatment groups suggesting that either there was no pathological requirement for albumin release from the animals or that steady state levels of albumin were simply maintained through a feedback regulation previously described in rats (Pietrangelo et al, J Clin. Invest, vol. 89:1755 (1992)) (FIG. 13B). No significant changes in liver function parameters (AST, ALT and ammonia) were observed indicating that HNF4A-saRNA-dendrimer injections caused no liver specific contra-indications (FIG. 13C, FIG. 13D and FIG. 13E). When circulating markers of inflammation were measured from the treated rats, a significant 1.3 fold reduction in IL-1B (p=0.0411) (FIG. 13F) was observed, suggesting a reduction in inflammation (Sgroi et al., PLoS ONE, vol. 6:e25442 (2011)), and 1.8 fold decrease in α2M (p=0.0260) (FIG. 13G), suggesting a decrease in at least one of the factors that contributes to insulin resistance. No abnormal changes in white blood cells were observed (FIG. 15A).

Figure 5A:
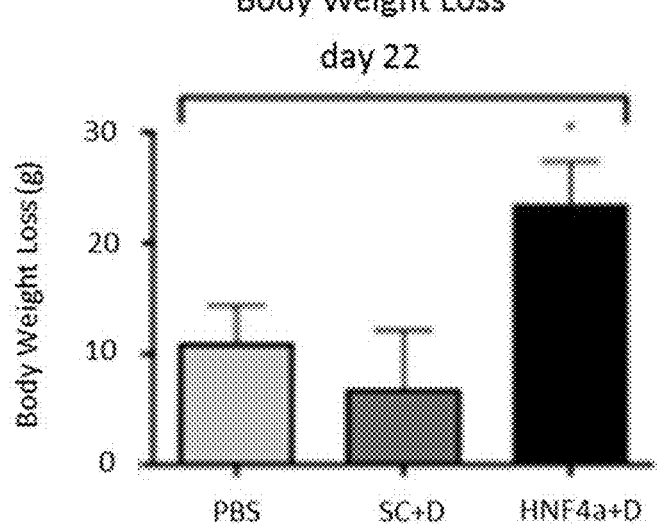
FIG. 5A-5E show body weight loss (FIG. 5A), liver/body weight ratio (FIG. 5B), white fat/body weight ratio (FIG. 5C), pancreas/body weight ratio (FIG. 5D), and brown fat/body weight ratio (FIG. 5E) of rats in all groups.
Figure 5B:
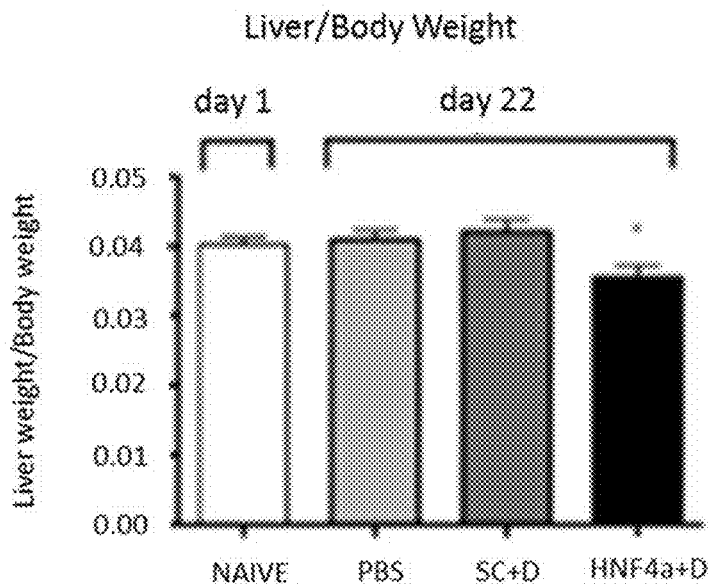
Figure 5C:
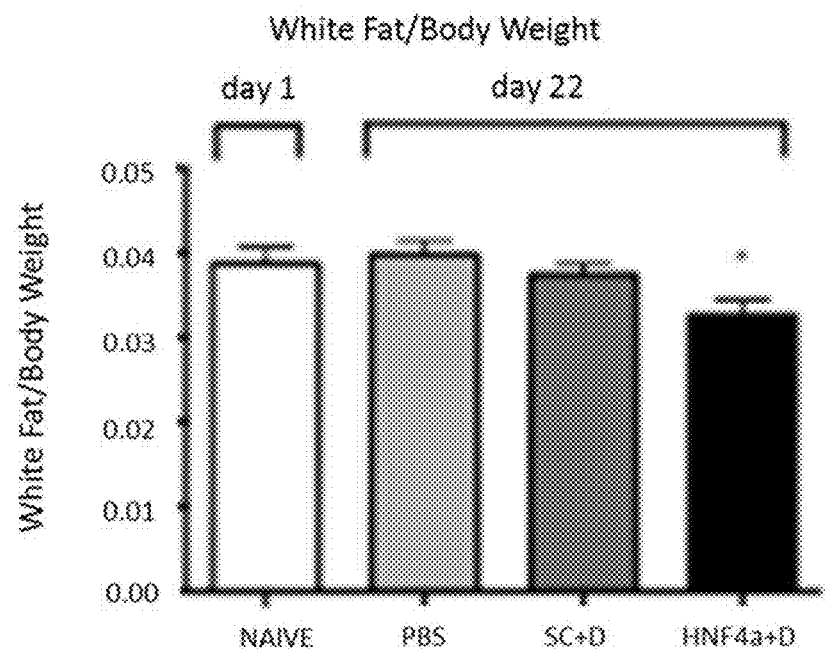
Figure 5D:
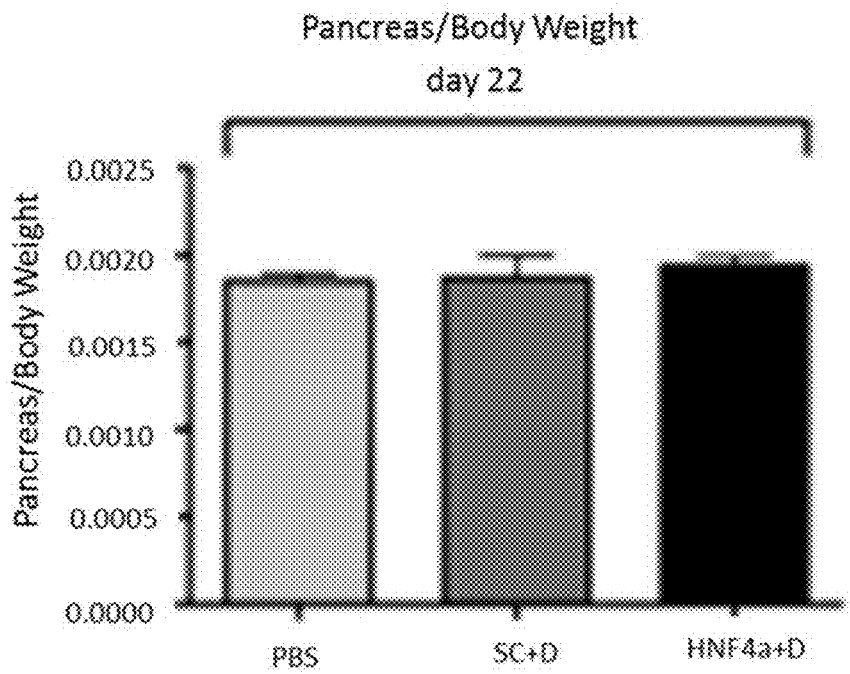
Figure 5E:
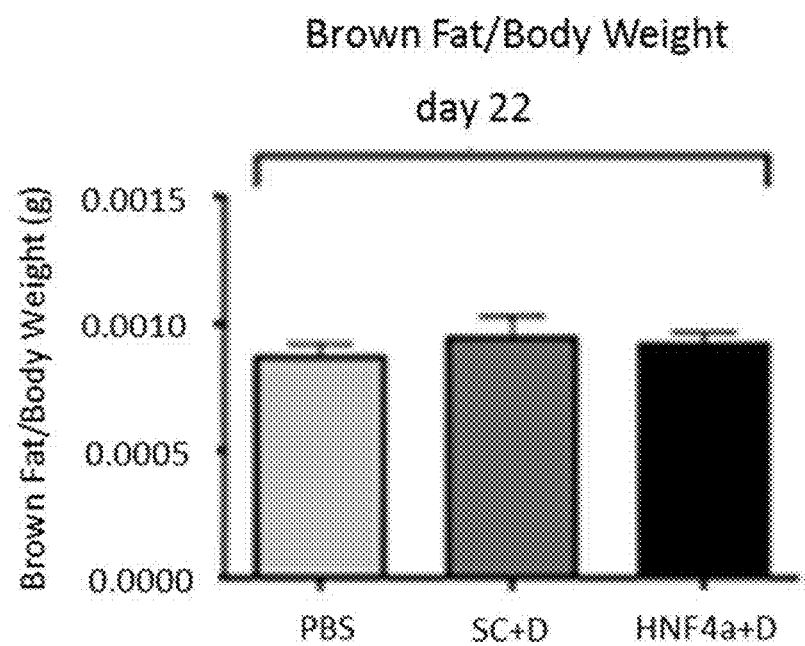
Figure 6A:
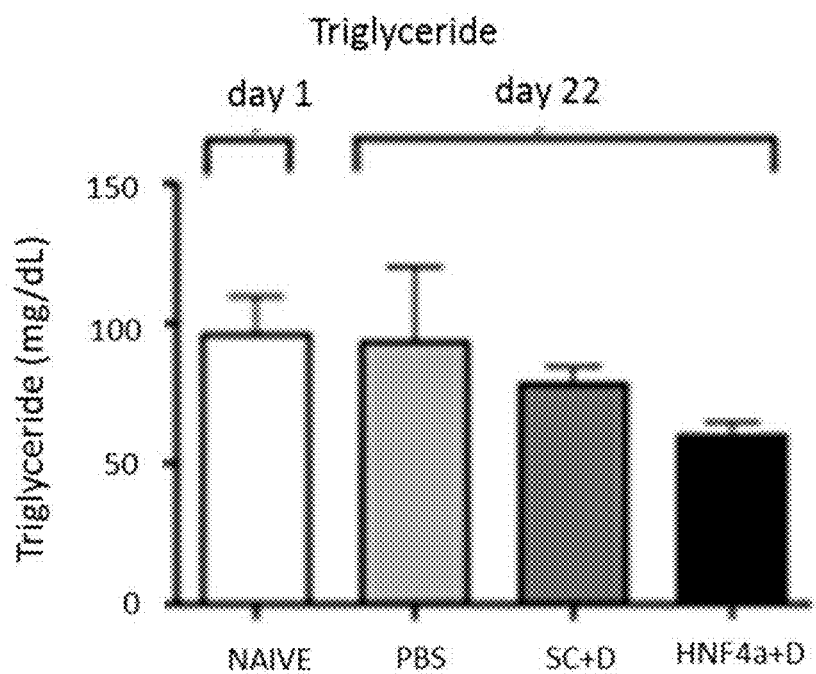
FIG. 6A-6E show triglyceride (FIG. 6A), HDL (FIG. 6B), LDL (FIG. 6C), HDL/LDL ratio (FIG. 6D), and total cholesterol (FIG. 6E) levels of rats in all groups.
Figure 6B:
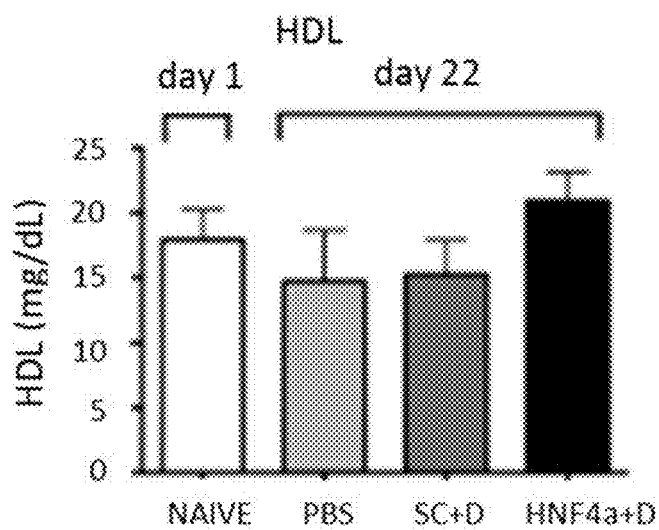
Figure 6C:
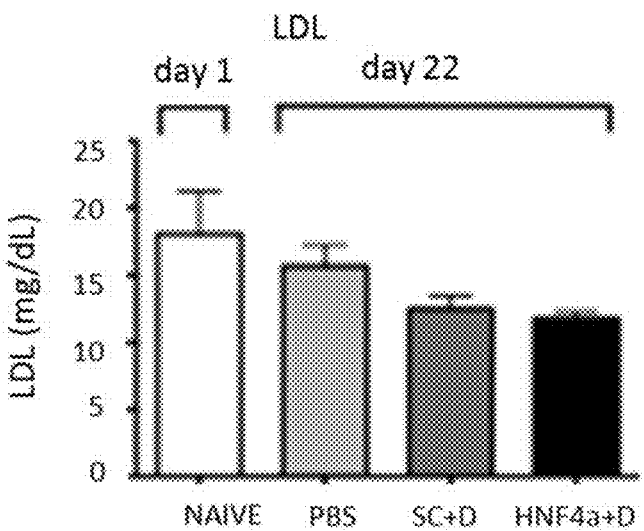
Figure 6D:
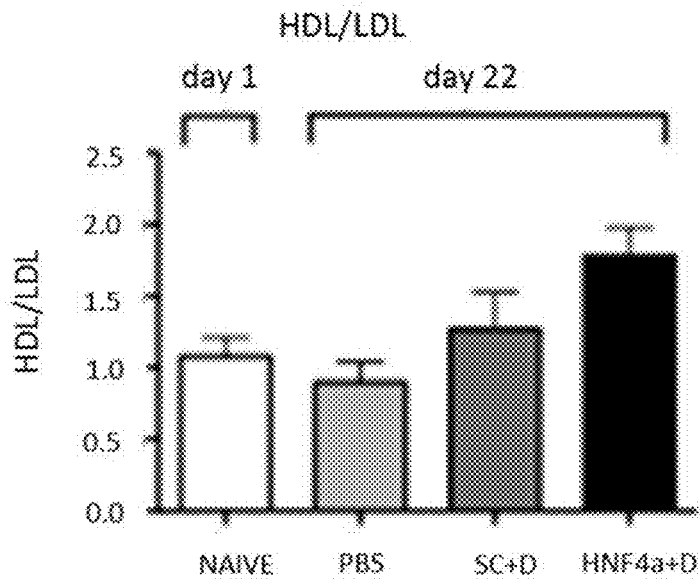
Figure 6E:
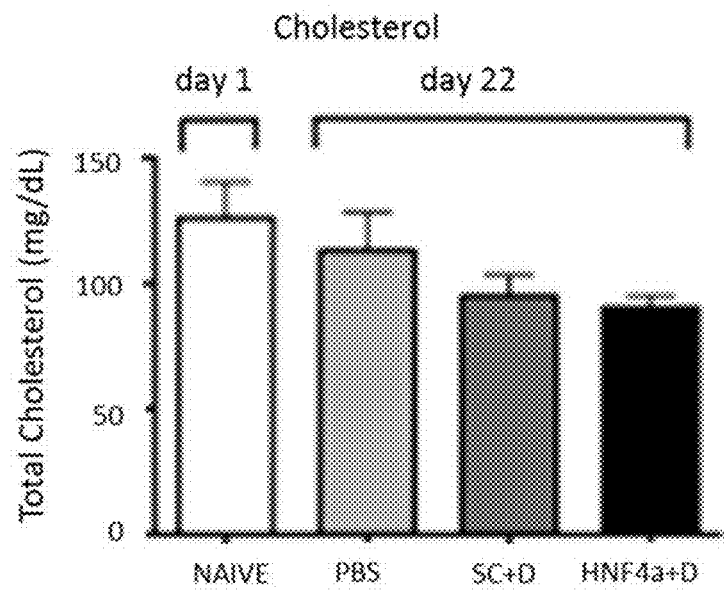
Figure 7A:
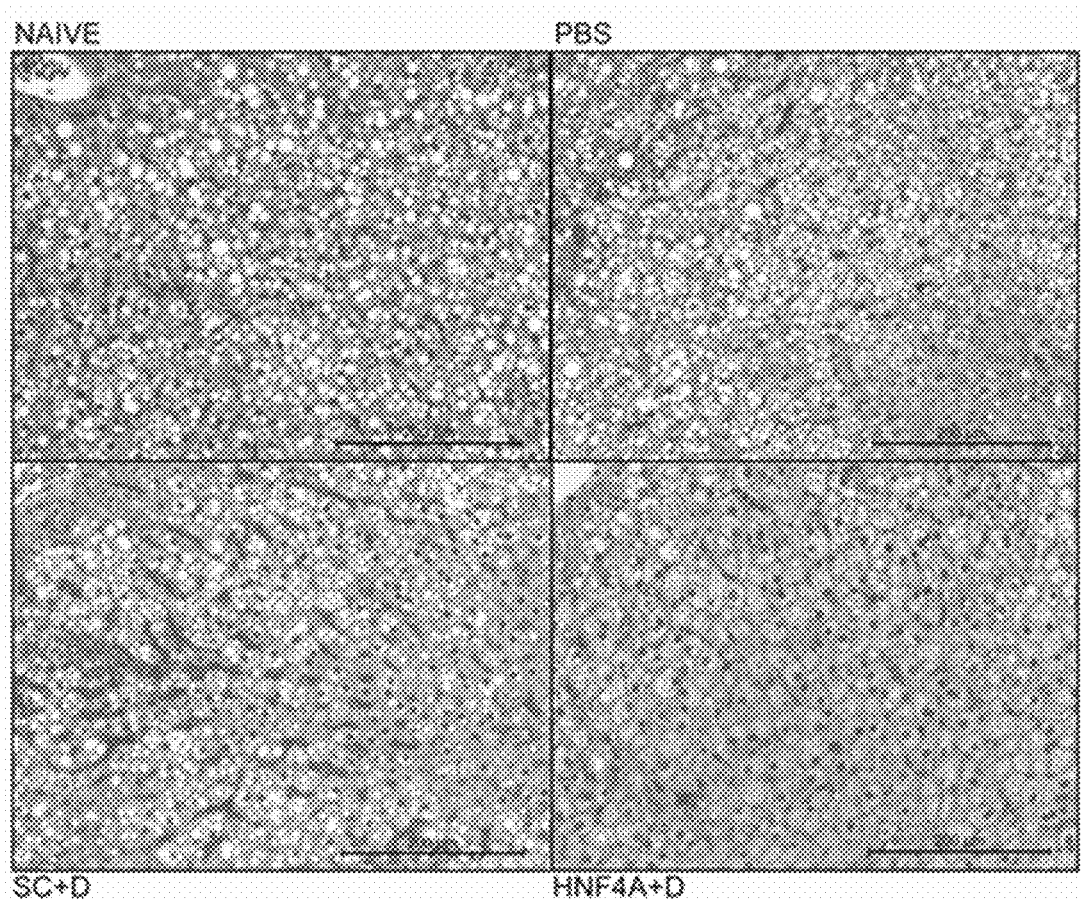
FIG. 7A shows H & E staining of fat content in all groups.
Figure 7B:
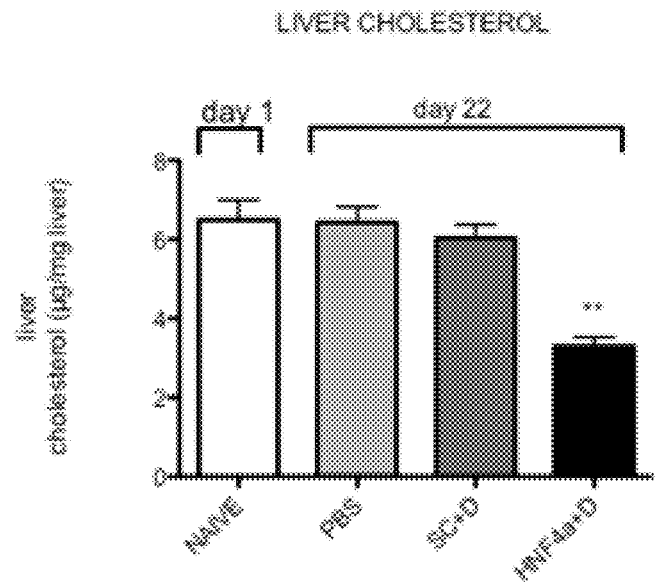
FIG. 7B shows liver cholesterol levels in all groups.

HNF-4α effect on serum lipid profile: HNF4A-saRNA-dendrimer treatment significantly reduced levels of liver cholesterol by over 40% (p=0.0022, FIG. 13H) in treated animals compared to the control groups despite the animals continuously being fed a high-fat diet. Furthermore, a 1.3 fold reduction in liver triglyceride (p=0.0388) (FIG. 13I), and 1.4 fold increase in HDL/LDL ratio in the treated animals (p=0.0465) were observed (FIG. 13J). Formalin-fix paraffin embedded (FFPE) tissue sections were processed and stained with haematoxylin & eosin for ultrastructural observation of fat deposits. H & E staining appeared more fulminant in the HNF4A-saRNA treated groups when compared to the control groups (PBS and Scramble) where punctate unstained areas were observed (FIG. 7A). Loss in total body weight was also significantly greater by 3.5 fold in the HNF4A-saRNA-dendrimer treated groups when compared to untreated control (p=0.0263) (FIG. 5A). The white adipose tissue to body weight and the liver to body weight ratio also showed a significant 1.15 fold decrease and 1.2-fold decrease respectively in the HNF4A-saRNA-dendrimer treated animals (p=0.0411 and p=0.0260, respectively) (FIG. 5C and FIG. 5B). No significant reduction in pancreas weight and brown fat content was noted (FIG. 15B and FIG. 15C).

HNF-4α normalized glucose homeostasis: HNF4A-saRNA-dendrimer treatment caused a significant 1.3 fold decrease in serum glucose levels when compared to the control groups (p=0.0129) (FIG. 10A). Circulating insulin level was not affected by HNF4A-saRNA (FIG. 10C) indicating that glucose clearance by pancreatic secretion of insulin was unlikely. Reducing IL-6 levels (FIG. 8C) and a 1.9 fold decrease in triglyceride/HDL ratio (p=0.0411) (FIG. 16A) suggests improved metabolic profile, which likely contributes to decreased insulin resistance following HNF4A-saRNA treatment.

In summary, nonalcoholic fatty liver disease (NAFLD) encompasses a wide spectrum of histology from asymptomatic hepatic steatosis to cirrhosis. In the absence of liver inflammation or fibrosis, most patients with NAFLD have simple steatosis. The progression of NAFLD to nonalcoholic steatohepatitis (NASH) is of great significance as it can evolve to cirrhosis, liver failure and hepatocellular carcinoma. Obesity, diabetes and insulin resistance are the crucial risk factors for the progression of NASH. It is therefore vital to understand the key factors that are central to lipid and glucose metabolism in order to prevent or manage progression of NASH. HNF4a is at the centre of a complex network of transcriptional control where its disruption has directly been linked to several human diseases including diabetes and steatosis. Insight into the transcription regulatory network of HNF4A highlights the importance of this transcription factor in regulating liver specific genes involved in glucose, cholesterol and fatty acid metabolism.

In this study, it is demonstrated the importance of resetting the transcriptional network of HNF4A with HNF4A-saRNA in a NAFLD rat model where triglyceride biosynthesis, phospholipid metabolism and arachidonic acid metabolism network were engaged (FIG. 16B).

Analysis of the gene expression changes caused by HNF4A-saRNA showed significant alteration to glucose transport and insulin resistance:

Glucose transport. Regulation of ARSA, PSAP, GBA3 and Cdc42 interacting protein 4 by HNF4A in hepatocytes suggested that more efficient glucose transport contributed to the decrease in glucose serum level in the HNF4A-saRNA treated animals.

Insulin resistance. Regulation of factors for lipid transport (P4HB and SEC24C), for lipid metabolism (YAP1) and oxidation of fatty acid (HADHB, ACADVL) by HNF4A-saRNA together with reduction in IL6; liver cholesterol, liver triglyceride (TG), HDL/LDL ratio and TG/HDL ratio all points towards HNF4A-saRNA induced increase in HNF4A reducing insulin resistance.

HNF4A-saRNA treatment in a model of fatty liver disease (HFD fed animal) caused changes in a collective network of factors that culminated in significant improvement in the metabolic profile. Currently, there are no single pharmacological agents that target steatosis or its progression to hepatitis. Most management entails a multi-targeted approach with several drugs and even surgery to treat the metabolic risk factors and improve insulin sensitivity.

It is demonstrated that activation of HNF4A by saRNA/nanoparticle conjugates may represent a new paradigm as a single agent in the treatment or management of fatty liver disease (e.g., dyslipidemia characterized by abnormally elevated cholesterol or fats (lipids) in the blood, and NAFLD) and insulin resistance.

Example 4. Chemical Modification of HNF4a-saRNAs

Chemical modifications were added to PR3-50-XD7579 and PR3-49-XD7666 (the same sequence as PR3-49-XD7578 but without mismatch), aimed at inhibiting immune stimulation and/or increasing stability. Fully stabilised saRNAs include PR3-50-XD7663 and PR3-49-XD7667. Immunosuppressive designs include PR3-50-XD7664 and PR3-49-XD7668. Other chemically modified designs include PR3-50-XD7665 and PR3-49-XD7669. Their sequences are included in Table 7.

TABLE 7

Sequences of chemically modified HNF4a-saRNAs

| ID | Sense strand (Passenger) 5'→3' | SEQ ID NO | Anti-sense strand (Guide) 5'→3' | SEQ ID NO |
|---|---|---|---|---|
| PR3-50-XD7663 | (NH2C6)sCfcCfaGfaAfUfGfcCfuGfuGfaUfcAfuu(invdT) | 133 | uGfaUfcAfcAfgGfcauUfcUfgGfgsusu | 134 |
| PR3-50-XD7664 | (invabasic)ccCaGAAUGcCUGuGAUCAuu | 135 | UGAUCACAGGCAUUCUGGGuu | 136 |
| PR3-50-XD7665 | (invabasic)cccAGAAuGccuGuGAucAu | 137 | UGAUcAcAGGcAUUCUGGGuu | 138 |
| PR3-49-XD7667 | (NH2C6)sCfcAfgAfaUfGfCfcUfgUfgAfuCfaAfu(invdT) | 139 | uUfgAfuCfaCfaGfgcaUfuCfuGfgsusu | 140 |
| PR3-49-XD7668 | (invabasic)ccAgAAUGCcUGUgAUCAAuu | 141 | UUGAUCACAGGCAUUCUGGuu | 142 |
| PR3-49-XD7669 | (invabasic)ccAGAAuGccuGugAucAAuu | 143 | UUGAUcAcAGGcAUUCUGGGuu | 144 |

The results of in vitro efficacy study in HepG2 cells are shown in Table 8. As shown in Table 8, fully stabilised and immunosuppressive designs increased HNF4a P1 mRNA levels by more than 50% and are active.

TABLE 8

HNF4a P1 transcript fold changes

| ID | HNF4a P1 transcript fold change relative to untransfected |
|---|---|
| PR3-50-XD7663 | 1.84 |
| PR3-50-XD7664 | 1.68 |
| PR3-50-XD7665 | 1.03 |
| PR3-49-XD7667 | 1.53 |
| PR3-49-XD7668 | 1.65 |
| PR3-49-XD7669 | 0.95 |

PR3-50-XD7665 and PR3-49-XD7669 have chemical modification patterns that permit retention of siRNA activity. According to Table 8, FIG. 20A and FIG. 20B, PR3-50-XD7665 and PR3-49-XD7669 did not show HNF4a upregulation or Albumin upregulation indicating differences in what modifications are tolerated for siRNA and saRNA.

The activities of the fully stabilised (PR3-50-XD7663 and PR3-49-XD7667) and immunosuppressive designs (PR3-50-XD7664 and PR3-49-XD7668) were compared with the parent sequences (PR3-50-XD7579, PR3-49-XD7666, and PR3-50) in HepG2 cells. As shown in FIG. 20C, the fully stabilised and immunosuppressive designs showed equivalent activity to PR3-50-XD7579, PR3-49-XD7666, and PR3-50.

Immune Stimulatory Activity Studies

The active HNF4a-saRNAs, PR3-50-XD7579 (also called XD-7579), PR3-50-XD7663 (also called XD-7663), PR3-50-XD7664 (also called XD-7664), PR3-50-XD7668 (also called XD-7668), were tested for immune stimulatory activity in human PBMCs. The assay included positive controls shown in Table 9.

PBMCs are isolated by ficoll gradient centrifugation from 2 independent donors; 100000 cells/well. The concentrations of the controls and test items were 100 nM and 300 nM for transfection; 0.5 and 1.5 µM for direct incubation. RNAiMax, 0.3 µl/well, was used as transfection control. Triplicate transfection was conducted. Incubation time was 24 h. 25 µl supernatant was taken for triplicate analysis using MSD platform (Meso scale diagnostics LLC, Rockville, USA), a multiplex ELISA system using electrochemiluminescence readout. A 3-plex assay for Interferon-α, Interleukin-6 and tumor-necrosis-factor-α was performed according to the manufacturer's instructions.

TABLE 9

Controls and test items in the immune stimulatory activity studies

| Controls: | XD-00366 | blunt end 25mer siRNA | |
|---|---|---|---|
| | XD-00367 | single overhang 21mer siRNA | positive controls |
| | ODN2216 | CpG Oligo | |
| | XD-03999 | 2'OMe modified siRNA | negative control |
| Test items: | XD-7579 | | |
| | XD-7663 | | |
| | XD-7664 | | |
| | XD-7668 | | |

All 4 HNF4a-saRNAs did not show evidence of immune stimulation while positive controls were active. IL6 levels are shown in Table 10-1. IFNa levels are shown in Table 10-2. TNFα levels are shown in Table 10-3.

TABLE 10-1

IL6 levels

| | | | IL6 (pg/ml) | | | |
|---|---|---|---|---|---|---|
| | | | mean | | SD | |
| | | | Donor A | Donor B | Donor A | Donor B |
| medium | | | 1.97 | 2.28 | 0.18 | 0.05 |
| RNAiMax | mock | | 1.43 | 2.19 | 0.28 | 0.24 |
| | XD-7579 | 100 nM | 1.90 | 2.21 | 0.32 | 0.13 |
| | | 300 nM | 1.75 | 2.34 | 0.21 | 0.24 |
| | XD-7663 | 100 nM | 1.52 | 1.96 | 0.46 | 0.29 |
| | | 300 nM | 1.75 | 2.30 | 0.30 | 0.26 |
| | XD-7664 | 100 nM | 2.00 | 1.85 | 0.15 | 0.42 |
| | | 300 nM | 1.99 | 2.20 | 0.06 | 0.16 |
| | XD-7668 | 100 nM | 1.86 | 2.16 | 0.15 | 0.48 |
| | | 300 nM | 1.94 | 2.09 | 0.02 | 0.18 |
| | XD-00366 | 100 nM | 40.12 | 25.53 | 7.43 | 4.70 |
| | | 300 nM | 48.32 | 62.13 | 1.43 | 33.96 |
| | XD-00367 | 100 nM | 27.61 | 12.79 | 8.50 | 4.74 |
| | | 300 nM | 35.51 | 21.16 | 2.70 | 1.22 |
| | XD-03999 | 100 nM | 1.62 | 1.95 | 0.35 | 0.19 |
| | | 300 nM | 2.30 | 4.68 | 0.15 | 4.16 |
| | mock | | 2.19 | 2.55 | 0.13 | 0.42 |
| direct | medium | | 1.75 | 1.99 | 0.42 | 0.03 |
| Incubation | XD-01024 | 500 nM | 30.11 | 22.66 | 3.02 | 2.78 |
| | | 1500 nM | 70.16 | 70.46 | 1.44 | 2.85 |
| | ODN2216 | 500 nM | 19.26 | 13.91 | 6.45 | 2.68 |
| | | 1500 nM | 28.68 | 18.78 | 9.94 | 1.19 |
| | poly IC | 20 µg/ml | 3915.26* | 5268.84* | 652.06* | 1221.89* |
| | ODN2216-5Me | 1500 nM | 1.70 | 3.62 | 0.20 | 1.88 |

*Above fit curve range.

TABLE 10-2

| | | | | IFNa levels | | | |
|---|---|---|---|---|---|---|---|
| | | | | IFNa (pg/ml) | | | |
| | | | | mean | | SD | |
| | | | | Donor A | Donor B | Donor A | Donor B |
| medium | | | | NaN | NaN | NaN | NaN |
| RNAiMax | mock | | | NaN | NaN | NaN | NaN |
| | XD-7579 | 100 | nM | NaN | NaN | NaN | NaN |
| | | 300 | nM | NaN | NaN | NaN | NaN |
| | XD-7663 | 100 | nM | NaN | NaN | NaN | NaN |
| | | 300 | nM | NaN | NaN | NaN | NaN |
| | XD-7664 | 100 | nM | NaN | NaN | NaN | NaN |
| | | 300 | nM | 0.12** | NaN | 0.03** | NaN |
| | XD-7668 | 100 | nM | NaN | NaN | NaN | NaN |
| | | 300 | nM | NaN | NaN | NaN | NaN |
| | XD-00366 | 100 | nM | 1313.10 | 716.15 | 338.16 | 113.80 |
| | | 300 | nM | 1720.97 | 1285.21 | 103.20 | 104.92 |
| | XD-00367 | 100 | nM | 754.60 | 281.76 | 195.20 | 84.09 |
| | | 300 | nM | 1010.05 | 549.34 | 166.29 | 51.35 |
| | XD-03999 | 100 | nM | NaN | NaN | NaN | NaN |
| | | 300 | nM | NaN | NaN | NaN | NaN |
| | mock | | | NaN | 3.60** | NaN | 3.73** |
| direct | medium | | | NaN | NaN | NaN | NaN |
| Incubation | XD-01024 | 500 | nM | 882.35 | 645.76 | 34.46 | 62.42 |
| | | 1500 | nM | 532.62 | 613.74 | 133.16 | 87.64 |
| | ODN2216 | 500 | nM | 819.73 | 397.09 | 314.15 | 80.92 |
| | | 1500 | nM | 551.61 | 429.74 | 154.62 | 136.39 |
| | poly IC | 20 | µg/ml | 2.81 | 7.66 | 0.72 | 1.30 |
| | ODN2216-5Me | 1500 | nM | NaN | NaN | NaN | NaN |

NaN = Below detection range.
**Below fit curve range.

TABLE 10-3

| | | | | TNFa levels | | | |
|---|---|---|---|---|---|---|---|
| | | | | TNFa (pg/ml) | | | |
| | | | | mean | | SD | |
| | | | | Donor A | Donor B | Donor A | Donor B |
| medium | | | | 0.51 | 0.80 | 0.12 | 0.14 |
| RNAiMax | mock | | | 0.83 | NaN | 0.24 | NaN |
| | XD-7579 | 100 | nM | 0.57 | NaN | 0.14 | NaN |
| | | 300 | nM | 0.46 | 0.97 | 0.15 | 0.30 |
| | XD-7663 | 100 | nM | 0.32** | 0.81** | 0.17** | 0.36** |
| | | 300 | nM | 0.52 | 0.97 | 0.17 | 0.05 |
| | XD-7664 | 100 | nM | NaN | 1.35 | NaN | 0.30 |
| | | 300 | nM | 0.56 | 1.30 | 0.16 | 0.23 |
| | XD-7668 | 100 | nM | 0.68 | NaN | 0.01 | NaN |
| | | 300 | nM | 0.60 | 0.90 | 0.21 | 0.30 |
| | XD-00366 | 100 | nM | 45.49 | 41.01 | 9.92 | 15.09 |
| | | 300 | nM | 43.28 | 74.96 | 6.59 | 3.08 |
| | XD-00367 | 100 | nM | 33.29 | 24.22 | 5.73 | 12.16 |
| | | 300 | nM | 34.41 | 29.05 | 9.16 | 3.83 |
| | XD-03999 | 100 | nM | 0.59 | 1.19 | 0.17 | 0.15 |
| | | 300 | nM | 0.29** | 1.71 | 0.04** | 1.44 |
| | mock | | | 0.73 | 1.19 | 0.43 | 0.50 |
| direct | medium | | | 0.58 | NaN | 0.34 | NaN |
| Incubation | XD-01024 | 500 | nM | 19.41 | 12.29 | 2.26 | 5.25 |
| | | 1500 | nM | 28.47 | 23.95 | 5.80 | 3.52 |
| | ODN2216 | 500 | nM | 12.27 | 6.59 | 4.29 | 0.40 |
| | | 1500 | nM | 11.19 | 7.57 | 0.80 | 1.07 |
| | poly IC | 20 | µg/ml | 399.18 | 1359.65 | 69.70 | 481.19 |
| | ODN2216-5Me | 1500 | nM | 1.37 | 2.13 | 0.34 | 0.40 |

NaN = Below detection range.
**Below fit curve range.

Example 5. Bioinformatics Analysis and In Vitro Studies of PR3-50-XD7664

PR3-50-XD7664 (also called XD-7664 or XD-07664) is a saRNA compound designed to upregulate the expression of the nuclear receptor HNF4A. Scope of this study was the characterization of XD-07664 with regard to gene activation activity, stability in serum, potential immunostimulatory side effects and potential off-target effects based on sequence.

Material and Methods

Test Item

XD-07664 is a 19mer double-stranded saRNA with an uu-overhang at the 3' end of both sense and antisense-strand. The sense strand is further modified with an inverted abasic residue at the 5' end and several 2'OMe modifications:

| Duplex-ID | Sense Sequence | Antisense Sequence |
|---|---|---|
| XD-07664 | (invabasic)ccCaGAAUGcCUGuGAUCAuu (SEQ ID No. 135) | UGAUCACAGGCAUUCUGGGuu (SEQ ID No. 136) |

UPPERCASE LETTER: RNA
lower case letter: 2'OMe modification

Oligonucleotide synthesis was performed on solid support following standard procedures. Oligonucleotides had to fulfill the following QC criteria before they were released for further testing: Single strand identity: +/−0.05% of calculated mass (by MS); Single strand purity: >85% full length oligonucleotide (by HPLC); Duplex purity: >90% by non-denaturing HPLC. Samples were stored refrigerated at 4° C. until use.

Cell Culture and saRNA-Transfection

HepG2 cells were purchased from ATCC (Rockville, MD, #HB-8065) and cultured under the conditions recommended by the provider (MEM with 10% FCS, 100 U/ml penicillin, 100 mg/ml streptomycin). For transfection, cells were plated directly into the transfection solution at a density of 15000 cells/well in a 96-well cell culture dish ("reverse transfection"). Lipofectamine 2000 (Life Technologies) was used as transfection reagent according to the manufacturer's protocol at 0.4 µL/well. All transfections were performed in quadruplicate. 24 h later, cells were provided with fresh medium and new transfection mix was added after one hour ("forward transfection"). After 48 h total incubation time, cells were lysed with 150 µl of lysis mixture (Quantigene 2.0 assay kit, Panomics/Affimetrix) diluted 1:3 with cell culture medium. Lysates were kept frozen until analysis.

mRNA Quantification

The branched DNA assay (Panomics/Affymetrix, Fremont, CA) was used for mRNA quantification, in the version Quantigene 2.0 for human HNF4A and albumin, and in the version Quantigene 1.0 for human β-actin. This hybridization-based assay system provides a chemo-luminescence readout. Probe sets were custom designed by Panomics.

The assay was performed according to the manufacturer's instructions: Briefly, lysates were hybridized over night with the respective probe set and subsequently processed for signal development. Signals were measured on a Victor Light luminescence reader (Perkin Elmer). For analysis of transfection experiments, luminescence units obtained for target genes were normalized to the housekeeper β-actin. Relative expression values obtained for transfection reagent only ("mock") treated cells were set as 1. Curve fitting of dose-response experiments and determination of $EC_{50}$ values were performed using XL-fit software (ID business solution limited).

Isolation of Human PBMCs from Buffy Coat of Healthy Donors

Peripheral blood mononuclear cells (PBMCs) were isolated by gradient centrifugation. Briefly, human buffy coat blood (obtained from Institute of Transfusion Medicine, Suhl, Germany) of three donors was fractionated by a Ficoll gradient (Sigma-Aldrich Chemie GmbH, Steinheim, Germany). The layer of white blood cells was aspirated, purified by a second gradient centrifugation and finally washed twice with cell culture medium (RPMI1640 without supplements). Viability and morphology of cells from all three donors were assessed by microscopy and PBMCs of two donors were nominated and used in subsequent experiments.

Assaying Immune Stimulation in PBMCs

For monitoring a potential immune stimulating activity of XD-07664, freshly isolated PBMCs from two healthy donors were seeded in regular 96-well tissue culture plates at a density of 100000 cells/well in 100 µl complete medium (RPMI1640 supplemented with standard concentrations of L-Glutamine and 10% FCS). Cells were transfected in triplicate with 100 nM and 300 nM test samples or control sequences using Lipofectamine RNAiMax (Thermo Fisher Scientific, #13778) as a transfection reagent according to the manufacturer's protocol. Transfection reagent alone was used as mock control. Additional controls were added directly at a concentration of 500 nM and 1500 nM without transfection. After 24 h incubation, supernatants were harvested and kept frozen until analysis.

| Compound | Description | application |
|---|---|---|
| XD-07664 | Test compound | transfection |
| XD-00366 | Blunt end 25mer siRNA, unmodified, positive control | transfection |
| XD-00367 | Single overhang 21mer siRNA, unmodified, positive control | transfection |
| XD-03999 | 2'OMe-modified siRNA, negative control | transfection |
| ODN2216 | CpG Oligo, positive control | direct incubation |
| ODN2216-5Me | CpG Oligo, 5-mC modified, negative control | direct incubation |
| XD-01024 | Cholesterol conjugated siRNA, unmodified, positive control | direct incubation |

MSD ELISA Analysis

Cytokine content in PBMC supernatants was measured using the MSD platform (Meso scale diagnostics LLC, Rockville, USA), a multiplex ELISA system using electro-chemiluminescence readout. A 3-plex assay for Interferon-α, Interleukin-6 and tumor-necrosis-factor-α was performed according to the manufacturer's instructions. MSD Discovery workbench 4.0 software was used for standard curve fitting and calculation of cytokine amounts.

Stability Analysis in Rat Serum

For determination of serum stability 5 µL of a 50 µM XD-07664 solution in PBS were mixed with 45 µL of neutral rat serum and incubated in serum for 0, 0.5, 1, 3, 6, 24 and 48 hours at 37° C. Incubation of 5 µL XD-07664 solution in 45 µl PBS served as control for unspecific degradation.

Incubation was stopped at the indicated time points by a proteinase K treatment to digest all present nucleases in the serum samples. After proteinase K treatment, the RNA is stable in the samples. Samples were subsequently analyzed by a generic AEX-HPLC method under denaturing conditions at elevated pH (11) and 40° C. on a Dionex DNA Pac PA200 column (4×250 mm).

Under these conditions the two single strands of XD-07664 are separated from each other and from the degradation products and could be evaluated as distinct peaks. An assignment of the two single strands was done by analysis of both reference single strands under same conditions. According to the reference single strands, the peaks were labelled with sense and antisense. For data evaluation only the peak area of the two single strands of XD-07664 were evaluated. Peak area at T=0 was set to 100% and all other time points were normalized to peak area at T=0 for rat serum. The data are then reported as % intact strand normalized to T=0.

Bioinformatics

The HNF4A-saRNA XD-07664 has a canonical siRNA duplex structure with a 19mer double-stranded region and a 2nt 3'-overhang on each strand. In consequence saRNA XD-07664 may show siRNA-like activity including potential off-target effects.

First potential off-target sites with full or partial complementarity to the sense and antisense strand of saRNA XD-07664, respectively, were predicted in human, rhesus monkey, cynomolgus monkey, mouse, and rat transcriptomes (NCBI Reference Database release 80, January 2017) using a proprietary algorithm. Because positions 1 and 19 as well as the UU 3'-overhang of a siRNA are not essential for the siRNA activity only the 17mer sequence from position 2 through 18 was considered for the prediction of potential off-target sites with up to 4 mismatches to the examined saRNA strand. Based on the number and the position of the mismatches a specificity score was calculated for each predicted off-target site. The specificity score for the most likely off-target site was assigned to the corresponding saRNA strand. In addition, the number of predicted off-target genes (off-target frequency) with 0, 1, 2, 3 or 4 mismatches was separately calculated for each saRNA strand.

Next potential seed-dependent, microRNA-like off-target effects were analyzed. siRNAs can function in a miRNA like manner via base-pairing of the seed-region (typically bases 2 through 7) with complementary sequences within the 3'-UTR of any mRNA molecule. Seed-region sequences of known miRNAs for which it is highly likely that functional miRNA target-sites exist were analyzed. This was accomplished by comparison of the seed-region (positions 2 through 7) of each saRNA strand with the seed-regions (positions 2 through 7) of known mature miRNAs from human, rhesus-monkey, rat, and mouse (miRBase release 21, June 2014). If applicable the seed-region identity and the name of the corresponding miRNA were tabulated for the sense and the antisense strand.

After that, listings with all predicted off-targets for all examined species and for both saRNA strands were created. Features of the predicted off-target sites were described in detail: strand orientation, accession number, gene ID, gene symbol, transcript description, sequence of off-target site, number and position of mismatches, location of target site (coordinates and region), indication of perfect seed match (timer seed for position 2-7, and 7mer seed for positions 2-8). In order to allow a more refined ranking the predicted off-target sites were then further classified based on the number of mismatches, the position of the mismatches and the location of the predicted target-sites in the 5'-UTR and CDS or the 3'-UTR. The classification ranges from class 1 (most likely off-targets) to class 11 (least likely off-targets), with the most likely off-targets having no or few mismatches and having a perfect match of the saRNA seed region with the 3'-UTR of the predicted off-target. Next a representative transcript was defined for each off-target site in order to reduce redundancy of the potential presence of the same target-site sequence in multiple transcripts or within the same transcript. Finally, the predicted off-targets were ranked according to the assigned off-target class.

In the last step, all predicted off-targets matched with up to 2 mismatches were identified and identical off-targets predicted for human and at least one other species were indicated. Homologous genes were identified for rhesus monkey, rat and mouse using the HomoloGene database at http://www.ncbi.nlm.nih.gov/homologene, Release 68. Gene Ids and gene symbols were updated using gene history data available at ftp://ftp.ncbi.nih.gov/gene/DATA/gene_history.gz (NCBI Gene DB, January, 2017). Homologous genes for cynomolgus monkey are not listed in the HomoloGene database. Therefore, they were identified by comparison of official gene symbols.

Results and Conclusions

Efficacy Studies

For determination of gene induction efficacy, XD-07664 was transfected into HepG2 cells in a 6 concentration dose-response experiment (50 nM, 20 nM, 5 nM, 2 nM, 0.5 nM and 0.2 nM). As readout, mRNA levels of HNF4A and its downstream target albumin were measured (see FIGS. 21A and 21B and Table 11). XLfit software was used for analysis of dose-response experiments and an $EC_{50}$ value (defined as the concentration at which half-maximal induction of HNF4A is obtained) of 3.01 nM was determined.

TABLE 11

HNF4a and albumin levels after XD-07664 treatment

| Conc. (nM) | HNF4a/β-actin XD-07664 | | Albumin/β-actin XD-07664 | |
|---|---|---|---|---|
| | Mean | SD | Mean | SD |
| Mock | 1.087 | 0.095 | 0.979 | 0.074 |
| 50.0 | 1.511 | 0.069 | 2.727 | 0.221 |
| 20.0 | 1.573 | 0.143 | 2.629 | 0.269 |
| 5.0 | 1.299 | 0.058 | 2.444 | 0.862 |
| 2.0 | 1.191 | 0.074 | 1.821 | 0.348 |
| 0.5 | 1.112 | 0.062 | 1.416 | 0.139 |
| 0.2 | 1.150 | 0.087 | 1.127 | 0.081 |
| 0.0 | 1.000 | 0.060 | 1.000 | 0.178 |

PBMC Assay

To monitor a potential immune-stimulatory effect, XD-07664 was transfected into seeded primary human PBMCs from two donors. For analysis, the cytokines Interferon-α, Interleukin-6 and TNF-α were measured on a MSD ELISA platform. As positive controls, 2 unmodified siRNAs, a CpG-oligonucleotide and an unmodified cholesterol-conjugated siRNA were used. 24 h after transfection of XD-07664, no significant secretion of any of the 3 cytokines was observed while all controls showed the expected response. In conclusion we can say that, under the conditions tested, XD-07664 did not show any undesired immune response.

Stability

In rat serum, the degradation of RNA is mainly induced by 3'-exonuclease depending on divalent cations. For XD-07664, the following observations were made (see FIG. 23; Table 12): XD-07664 is rapidly degraded in neutral rat serum and 72% degradation of the antisense and 82% of the sense peak was observed after 30 min of incubation at 37° C.; after 1 hour of incubation at 37° C. only 10% full-length product of the sense strand and 5% full-length product of the antisense strand were present; both strands are almost completely degraded after 3 hours of incubation at 37° C.

TABLE 12-1

Areas of the integrated sense and antisense signals at the indicated time points
XD-07664
Rat Serum pH 7
Area [mAU*min]

| Time point | Sense | Antisense |
|---|---|---|
| 48 h_PBS | 11.378 | 11.64 |
| 48 h | 0.0028 | 0.0039 |
| 24 h | 0.0379 | 0.0016 |
| 6 h | 0.0863 | 0.0244 |
| 3 h | 0.0608 | 0.0542 |
| 1 h | 1.1023 | 0.5179 |
| 0.5 h | 3.2030 | 2.1201 |
| 0 h | 11.3719 | 2.1201 |

TABLE 12-2

The corresponding percentage of intact strand normalized to T = 0
XD-07664
Rat Serum pH 7
Percentage of T = 0

| Time point | Sense | Antisense |
|---|---|---|
| 48 h_PBS | 100.1% | 100.3% |
| 48 h | 0.0% | 0.0% |
| 24 h | 0.3% | 0.0% |
| 6 h | 0.8% | 0.2% |
| 3 h | 0.5% | 0.5% |
| 1 h | 9.7% | 4.5% |
| 0.5 h | 28.2% | 18.3% |
| 0 h | 100.0% | 100.0% |

From the results, it can be concluded that without protection, e.g. by liposomal formulation, XD-07664 will be rapidly degraded in the circulation when used for in vivo applications.

Off-Target Analysis

Off-target analysis was carried out to address potential off-target effects of the saRNA compound XD-07664. Results are shown in Table 13-1 and Table 13-2. Off-target sites with up to 4 mismatches were predicted for both saRNA strands and various species and the off-target frequency was determined.

There are at least 2 mismatches of antisense strand with any other human transcript. There are at least 1 mismatch of sense strand with any other human transcript. 22 human off-targets were predicted to be matched with up to two mismatches by the antisense strand and 33 human off-targets were predicted to be matched with up to two mismatches by the sense strand. In both the antisense and sense strand, there were no human off-targets matched with zero mismatches and 6 off-targets were matched with 1 mismatch by the sense strand. Based on the analysis, saRNA XD-07664 is predicted to be specific in human, cynomolgus monkey, rat and mouse with the assumption that the sense strand is inactivated (due to the inverted abasic unit).

saRNA seed regions (2-7) of both saRNA XD-07664 strands are not identical to seed regions (2-7) of known miRNAs from human, rhesus monkey, rat, and mouse. This should avoid the saRNAs XD-07644 acting as a miRNA via functional miRNA target sites.

TABLE 13-1

Predicted siRNA-like specificity for
saRNA XD-07664 - antisense strand

| | Antisense strand | | | | | | |
|---|---|---|---|---|---|---|---|
| Species | miRNAs with seed regions (2-7) identical to see region (2-7) of siRNA strand | score | Off-target frequency classified by number of mismatches | | | | |
| | | | 0 | 1 | 2 | 3 | 4 |
| Human | — | 2 | 0 | 0 | 22 | 252 | 2408 |
| Rhesus monkey | — | 1 | 0 | 1 | 11 | 161 | 1587 |
| cynomolgus monkey | n.d. | 2 | 0 | 0 | 16 | 187 | 1778 |
| Mouse | — | 2 | 0 | 0 | 24 | 271 | 2373 |
| Rat | — | 2 | 0 | 0 | 27 | 228 | 2099 |

(n.d. - not determined, no data available)

TABLE 13-2

Predicted siRNA-like specificity
for saRNA XD-07664 - sense strand

| | Sense strand | | | | | | |
|---|---|---|---|---|---|---|---|
| Species | miRNAs with seed regions (2-7) identical to see region (2-7) of siRNA strand | score | Off-target frequency classified by number of mismatches | | | | |
| | | | 0 | 1 | 2 | 3 | 4 |
| Human | — | 1.9 | 0 | 6 | 27 | 247 | 2248 |
| Rhesus monkey | — | 1.9 | 0 | 2 | 20 | 181 | 1391 |
| cynomolgus monkey | n.d. | 1.9 | 0 | 2 | 23 | 176 | 1594 |
| Mouse | — | 2 | 0 | 0 | 14 | 258 | 2121 |
| Rat | — | 2 | 0 | 0 | 17 | 222 | 1930 |

(n.d. - not determined, no data available)

Example 6. Activity of PR3-50-XD7664 in Humanised Liver Mouse Model

The activity of PR3-50-XD7664 is demonstrated in a humanised liver mouse model in which human hepatocytes have been transplanted into mice to generate a humanised liver (for example, see Kim et al, *Transplantation Proceedings*, vol. 46:1186 (2014)). PR3-50-XD7664 encapsulated in a suitable formulation such as SMARTICLE® nanoparticles (described in Rodrigueza et al., *Cancer Chemother. Pharmacol*, vol. 74:151 (2014)) is administered systemically to the mice at a dose of 0.3-3 mg/kg on day 1 and day 3 with mice terminated at day 5. The impact of PR3-50-XD7664 is demonstrated by the measurement of human HNF4a mRNA by qPCR in the liver of the mice at day 5 and by measuring human serum albumin in the blood of mice at day 5. PR3-50-XD7664 causes an increased in human HNF4a mRNA in the liver of the mice and an increase in serum levels of human albumin.

Example 7. Activity of PR3-50-XD7664 in Dysmetabolic Cynomolgus Monkeys

The activity of PR3-50-XD07664 was demonstrated in cynomolgus monkeys that have developed diabetes and have Non-Alcoholic Fatty liver disease (for example, see Wang et al., *Journal of Diabetes and Metabolism*, 7, 1, 2016). Dysmetabolic cynomolgus monkeys were administered systemically with PR3-50-XD7664 encapsulated in NOV340 SMARTICLE® (Marina Biotech, Bothell, WA) nanoparticles at a dose of 3 mg/kg twice a week (D1/D3) for 4 weeks.

The lipid components of NOV340 SMARTICLE® nanoparticles are comprised of 1-palmitoyl-2-oleoyl-sn-glycero-3-phosphocholine (POPC), 1,2-dioleoyl-sn-glycero-3-phosphoethanolamine (DOPE), cholesteryl-hemi succinate (CHEMS), and 4-(2-aminoethyl)-morpholino-cholesterol hemisuccinate (MOCHOL). NOV340 consists of POPC, DOPE, CHEMS and MOCHOL in the molar ratio of 6:24:23:47. The nanoparticles are anionic at physiological pH, and their specific lipid ratio imparts a "pH-tunable" character and a charge to the liposomes, which changes depending upon the surrounding pH of the microenvironment to facilitate movement across physiologic membranes. SMARTICLES® nanoparticles are sized to avoid extensive immediate hepatic sequestration, with an average diameter of approximately about 50-about 150 nm, or about 100-about 120 nm, facilitating more prolonged systemic distribution and improved serum stability after i.v. injection leading to broader tissue distribution with high levels in liver, spleen and bone marrow reported.

The protocol of the study is shown in FIG. 23. "Week 1" is the predose levels on the day they received the first dose. "Week 5" is the timepoint at the end of the 4 weeks dosing schedule. Body weight, ALP, ALT, AST, triglyceride, cholesterol, bilirubin, blood albumin, HDL/LDL ratio and glucose levels of each animal were monitored. ALT levels of each animal measured in week 1 (predose), week 2, week 3, week 4, week 5 (after 4 weeks of dosing) were shown in FIG. 24A. AST levels of each animal were shown in FIG. 24B. The body weight and body weight change of each animal were shown in FIG. 24C and FIG. 24D. Each line in FIG. 24A-D represents changes in a single treated animal. Statistically significant reductions in ALT were seen in week 4, and statistically significant reductions in ALT, AST, and body weight were seen in week 5 using a paired t-test. Clinical observations were normal, suggesting that body weight loss was not due to toxicity.

OTHER EMBODIMENTS

It is to be understood that while the present disclosure has been described in conjunction with the detailed description thereof, the foregoing description is intended to illustrate and not limit the scope of the present disclosure, which is defined by the scope of the appended claims. Other aspects, advantages, and modifications are within the scope of the following claims.

---

The invention claimed is:

1. A method of up-regulating HNF4a gene in a cell comprising administering a synthetic isolated saRNA to the cell, wherein the saRNA comprises a strand comprising the sequence of SEQ ID NO: 136.

2. The method of claim 1, wherein the saRNA is single stranded.

3. The method of claim 1, wherein the saRNA is double-stranded and further comprises a sense strand.

4. The method of claim 3, wherein the sense strand comprises the sequence of SEQ ID NO: 135.

5. The method of claim 1, wherein HNF4a P1 mRNA is up-regulated.

6. The method of claim 1, wherein HNF4a P2 mRNA is not up-regulated.

7. The method of claim 1, wherein the cell is a hyper-proliferating cell.

8. The method of claim 7, wherein the cell is a cancer cell.

9. The method of claim 8, wherein the cell is a hepatocellular carcinoma (HCC) cell.

10. The method of claim 1, wherein the cell is a hepatocyte cell.

11. The method of claim 1, wherein HNF4a gene is up-regulated by at least 50%.

12. The method of claim 11, wherein HNF4a gene is up-regulated by a factor of at least 2.

* * * * *